(12) United States Patent
Huigens, III et al.

(10) Patent No.: US 11,130,764 B2
(45) Date of Patent: Sep. 28, 2021

(54) ANALOGS OF VINCAMINE AND USES THEREOF

(71) Applicant: University of Florida Research Foundation, Incorporated, Gainesville, FL (US)

(72) Inventors: Robert William Huigens, III, Williston, FL (US); Verrill M. Norwood, IV, Gainesville, FL (US); Hendrik Luesch, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/486,814

(22) PCT Filed: Feb. 1, 2018

(86) PCT No.: PCT/US2018/016515
§ 371 (c)(1),
(2) Date: Aug. 16, 2019

(87) PCT Pub. No.: WO2018/151951
PCT Pub. Date: Aug. 23, 2018

(65) Prior Publication Data
US 2019/0359622 A1 Nov. 28, 2019

Related U.S. Application Data

(60) Provisional application No. 62/502,108, filed on May 5, 2017, provisional application No. 62/460,470, filed on Feb. 17, 2017.

(51) Int. Cl.
*A61K 31/439* (2006.01)
*C07D 487/18* (2006.01)
(Continued)

(52) U.S. Cl.
CPC ......... *C07D 487/18* (2013.01); *C07D 401/04* (2013.01); *C07D 401/14* (2013.01);
(Continued)

(58) Field of Classification Search
None
See application file for complete search history.

(56) References Cited

U.S. PATENT DOCUMENTS

2010/0003324 A1 1/2010 Ellies et al.

FOREIGN PATENT DOCUMENTS

FR 2341585 A2 9/1977
RU 2397984 C1 8/2010

OTHER PUBLICATIONS

International Search Report and Written Opinion for Application No. PCT/US2018/016515, dated May 24, 2018.
(Continued)

*Primary Examiner* — Samantha L Shterengarts
(74) *Attorney, Agent, or Firm* — Wolf, Greenfield & Sacks, P.C.

(57) ABSTRACT

The present disclosure provides compounds of any one of Formulae (I'), (I), (IA), (II'), (II), (IIA), (IIIA), (III''), (III'), (III), (IIIA), (IV), (V'), (V), (VI), (VII), (VIII'), (VIII), (IX'), (IX), and (X). The compounds described herein may be useful in treating and/or preventing a broad range of diseases (e.g., proliferative disease (e.g., cancers (e.g., non-small cell lung cancer, or glioma), inflammatory diseases, autoimmune diseases), CNS disorder (e.g., drug addiction), metabolic disorder (e.g., diabetes), or infectious disease (e.g., bacterial infection or parasitic infection (e.g., malaria))). Also provided in the present disclosure are pharmaceutical compositions, methods of synthesis of a compound described herein, kits, methods, and uses including or using a compound described herein.

(Continued)

-continued
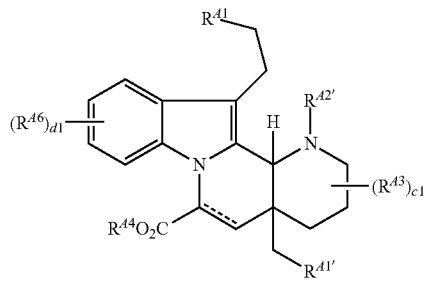
(II')
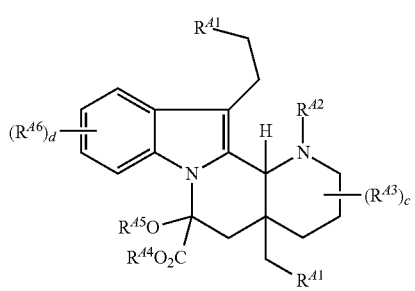
(II)
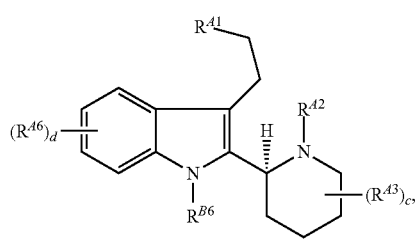
(IIA)
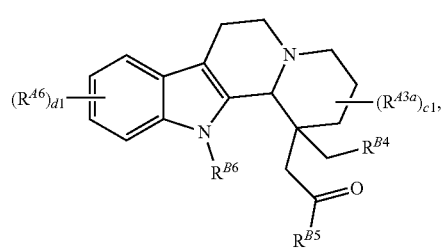
(III'')
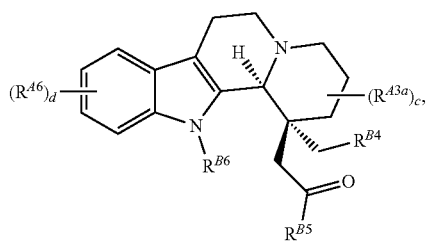
(III')
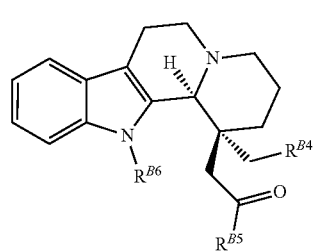
(III)
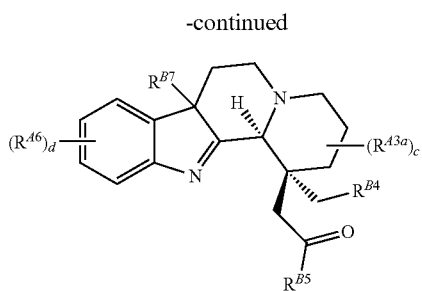
(IIIA)
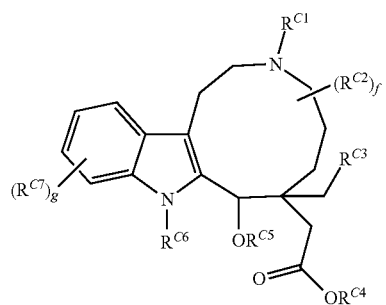
(IV)
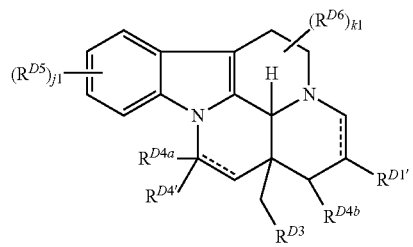
(V')
(V)
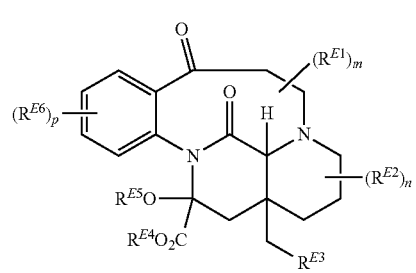
(VI)
(VII)

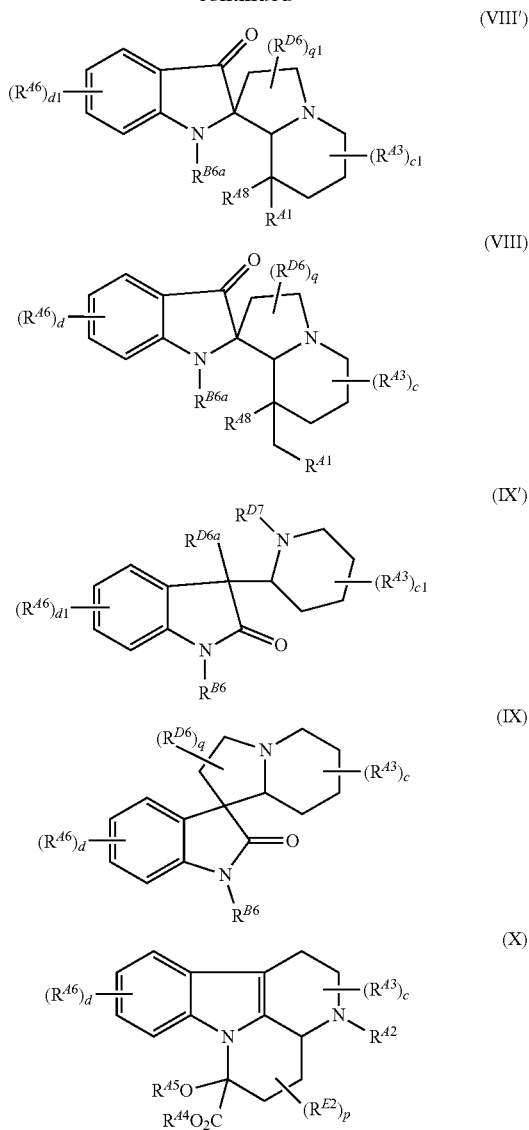

25 Claims, 27 Drawing Sheets

(51) Int. Cl.
C07D 401/04 (2006.01)
C07D 401/14 (2006.01)
C07D 471/14 (2006.01)
C07D 471/16 (2006.01)
C07D 471/20 (2006.01)
C07D 471/22 (2006.01)
C07D 487/04 (2006.01)
C07D 491/22 (2006.01)

(52) U.S. Cl.
CPC ......... C07D 471/14 (2013.01); C07D 471/16 (2013.01); C07D 471/20 (2013.01); C07D 471/22 (2013.01); C07D 487/04 (2013.01); C07D 491/22 (2013.01)

(56) References Cited

OTHER PUBLICATIONS

International Preliminary Report on Patentability for Application No. PCT/US2018/016515, dated Aug. 29, 2019.
Voskressensky et al., Synthesis of azecino[5,4-b]indoles and indolo[3,2-e][2]benzazonines via tandem transformation of hydrogenated indoloquinolizines and indolizines. Russian Chemical Bulletin. Jun. 2012;61(6):1231-41. Epub Mar. 16, 2013. doi: https://doi.org/10.1007/s11172-012-0167-6.
Woods et al., Synthesis of 15-methylene-eburnamonine from (+)-vincamine, evaluation of anticancer activity, and investigation of mechanism of action by quantitative NMR. Bioorg Med Chem Lett. Nov. 1, 2013;23(21):5865-9. doi: 10.1016/j.bmcl.2013.08.095. Epub Sep. 6, 2013.
PCT/US2018/016515, May 24, 2018, International Search Report and Written Opinion.
PCT/US2018/016515, Aug. 29, 2019, International Preliminary Report on Patentability.
Honty et al., Synthesis of vinca alkaloids and related compounds. Part LXVIII. Two diastereoisomeric A spidosperma-eburnea type bis-indoles: Their synthesis and structure revisited. Tetrahedron. 1993; 49(45): 10421-10426.
Kalaus et al., Synthesis of Vinca Alkaloids and Related Compounds XXXVI. Preparation of 1-Ethyl-1-hydroxyethyl-octahydroindolo[2,3-a]quinolizine Derivatives and Reactions of Their Mesylates with Cyanide Ion. Heterocycles. 1988;27:1179-1190.
Ma et al., Studies on the synthesis, structural characterization, Hirshfeld analysis and stability of apovincamine (API) and its co-crystal (terephthalic acid: Apovincamine = 1:2). J. Mol. Struct. Oct. 5, 2015;1097: 87-97.
Moldvai et al., Synthesis of Vinca Alkaloids and Related Compounds. Part LVIII. A Novel Formal Synthesis of (−)-Criocerine from (+)-Vincamine. Synthetic Comm. 1991;21:965-967.
Nemes et al., Synthesis of 18-hydroxyvincamines and epoxy-1,14-secovincamines; a new proof for the aspidospermane-eburnane rearrangement. Heterocycles. 2007;71(11):2347-2362.
Partial Supplementary European Search Report, dated Dec. 22, 2020, in connection with Application No. EP 18755061.1.
EP 18755061.1, Dec. 22, 2020, Partial Supplementary European Search Report.

| GPCR | V | V1a | V1p | V2a | V3a | V3b | V4a | V5a | Y | Therapy or Probe Use |
|---|---|---|---|---|---|---|---|---|---|---|
| CCR8 | 8 | 28 | 17 | 59 | 75 | 65 | 83 | 6 | 5 | Tumor Cell Metastasis |
| CHRM4 | -8 | 43 | 24 | 75 | 62 | 67 | 55 | 22 | 4 | Psychosis |
| CNR1 | 0 | 1 | 4 | 48 | 90 | 26 | 69 | 0 | 35 | Type-2 Diabetes |
| CNR2 | 11 | 17 | 2 | 60 | 100 | 39 | 51 | 13 | 20 | Cerebral Malaria, Bone Disorders |
| CXCR4 | 10 | 4 | -9 | 34 | 80 | 40 | 38 | -10 | 21 | Leukemia & Other Cancers |
| DRD2L | -10 | 98 | 0 | 15 | 6 | 11 | 15 | -5 | 102 | Non-small Cell Lung Carcinoma |
| FPR1 | 1 | 6 | 1 | 6 | 19 | 15 | 110 | 16 | -6 | Gliomas (CNS Cancers) |
| GPR119 | 3 | 2 | -2 | 30 | 86 | 35 | 66 | 5 | 8 | Insulin Release Probe |
| HCRTR2 | 9 | 8 | -4 | 80 | 26 | 10 | 29 | 16 | 9 | Heroin Dependence |
| HRH1 | 5 | 21 | 8 | 17 | 85 | 16 | 25 | -3 | 30 | Irritable Bowel Syndrome |
| NPSR1B | -15 | -27 | -17 | 30 | 81 | 24 | 76 | -10 | -3 | Cocaine Abuse |
| PRLHR (GPR10) | 3 | 18 | 26 | 59 | 84 | 70 | 82 | -7 | 1 | Opiod System & Obesity Probe |
| PTGIR | -3 | 41 | 22 | 75 | 97 | 84 | 76 | 22 | 8 | Tumor Angiogenesis |
| Hits (≥80%) | 0 | 6 | 0 | 1 | 8 | 1 | 4 | 0 | 7 | Out of 168 GPCRs |
| Hit Rate | 0.0% | 3.6% | 0.0% | 0.6% | 4.8% | 0.6% | 2.4% | 0.0% | 4.2% | Hit per 100 targets |

Figure 4B

9.) Synthesis of Vincamine Derivatives with Different Dipole Moments

10.) Results of Ring Distortion on Vincamine with Methyl Propiolate and Cyanogen Bromide 11.) Enamine Cleavage and Derivative Synthesis

ANALOGS OF VINCAMINE AND USES THEREOF

RELATED APPLICATIONS

This application is a national stage filing under 35 U.S.C. § 371 of international PCT application, PCT/US2018/016515, filed Feb. 1, 2018, which claims priority under 35 U.S.C. § 119(e) to U.S. Provisional Applications, U.S. Ser. No. 62/460,470, filed Feb. 17, 2017, and U.S. Ser. No. 62/502,108, filed May 5, 2017, each of which is incorporated herein by reference.

BACKGROUND OF THE INVENTION

New compounds based on or derived from vincamine may be useful as potential antibacterial, anticancer, or antimalarial agents. These compounds may also be useful in other therapeutic areas (e.g., metabolic disorders, CNS disorders, or infectious diseases). See FIG. 1 (depicting vincamine). Vincamine is an alkaloid with vasodilatory properties.

SUMMARY OF THE INVENTION

Described herein are compounds of Formulae (I'), (I), (IA), (II'), (II), (IIA), (III"), (III'), (IIIA), (III), (IV), (V'), (V), (VI), (VII), (VI'), (VIII), (IX'), (IX), and (X), which are derived from or based on vincamine. See FIG. 1 (depicting vincamine). The compounds described herein may be useful in treating and/or preventing a disease or condition, e.g., in treating and/or preventing a proliferative disease (e.g., cancers (e.g., non-small cell lung cancer, or glioma), inflammatory diseases, autoimmune diseases), CNS disorder (e.g., drug addiction), metabolic disorder (e.g., diabetes), or infectious disease (e.g., bacterial infection or parasitic infection (e.g., malaria)), in a subject in need thereof. The disclosed synthetic strategy is useful for rapidly creating and screening structurally diverse small molecules with various biological activities and for a variety of uses. Also provided are methods of preparing compounds of Formulae (I'), (I), (IA), (II'), (II), (IIA), (III"), (III'), (IIIA), (III), (IV), (V'), (V), (VI), (VII), (VIII'), (VIII), (IX'), (IX), and (X), and salts, solvates, hydrates, polymorphs, co-crystals, tautomers, stereoisomers, isotopically labeled derivatives, and prodrugs thereof, or mixtures thereof. Also provided are pharmaceutical compositions and kits including a compound described herein.

In one aspect, the present disclosure provides compounds of Formula (I'):

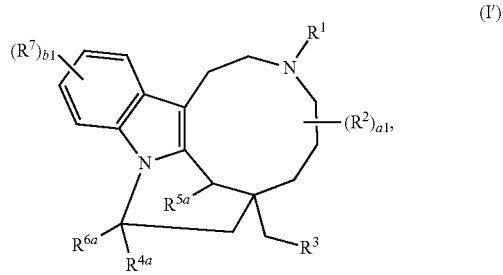

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^{4a}$, $R^{5a}$, $R^{6a}$, $R^7$, a1, and b1 are as defined herein.

In certain embodiments, the compound of Formula (I') is of Formula (I). In one aspect, the present disclosure provides compounds of Formula (I):

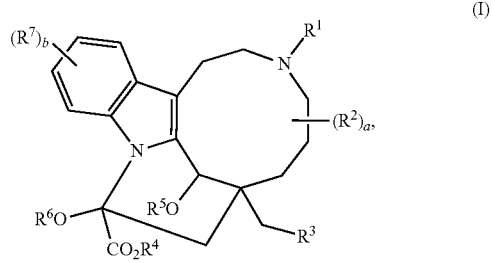

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, $R^5$, $R^6$, $R^7$, a, and b are as defined herein.

In one aspect, the present disclosure provides compounds of Formula (IA):

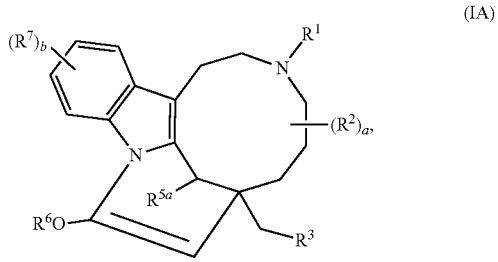

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^{5a}$, $R^6$, $R^7$, a, and b are as defined herein.

In certain embodiments, the compound of Formulae (I'), (I), or (IA) is of the formula:

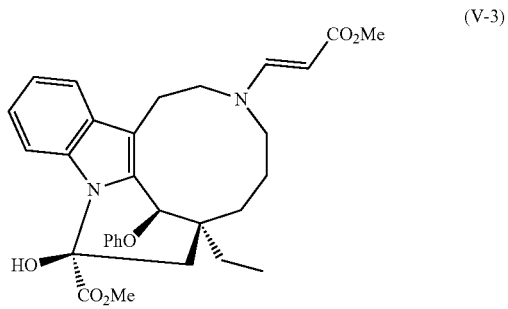

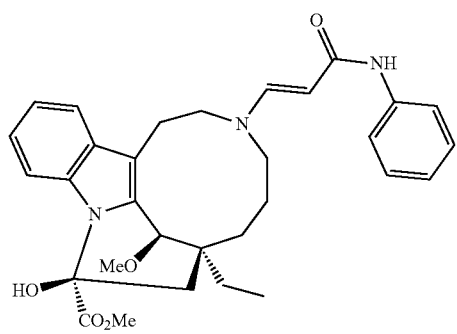 (V-4)
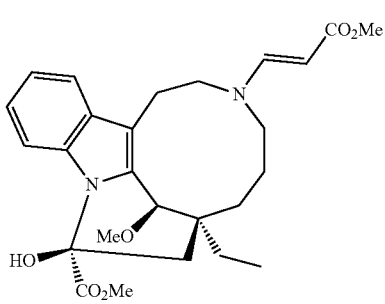 (V-18)
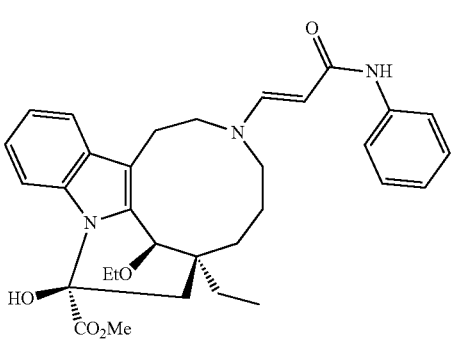 (V-20)
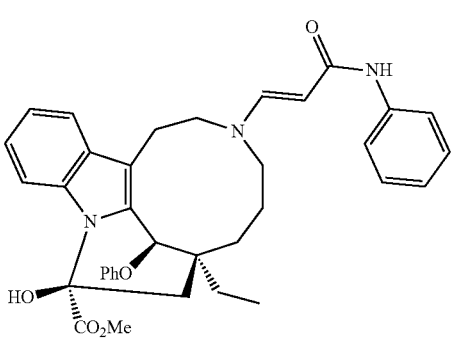 (V-21)
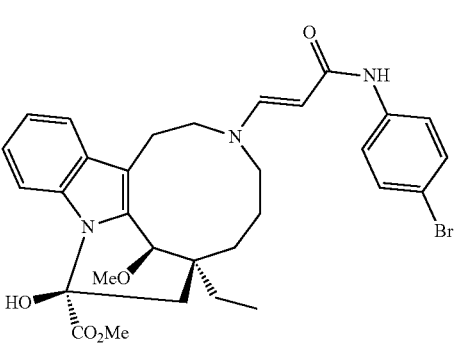 (V-22)
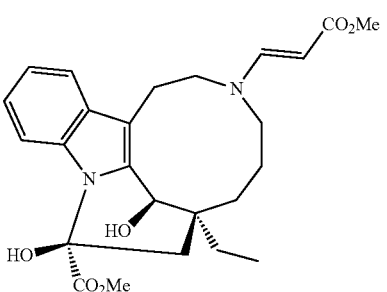 (V-27)
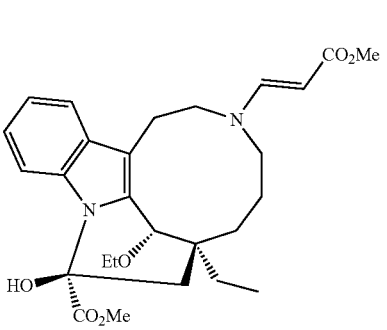 (V-28)
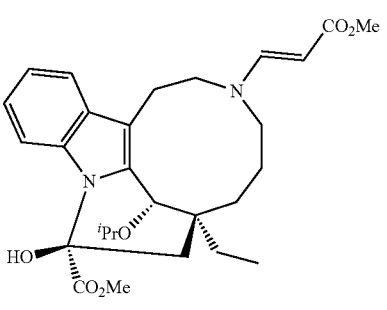 (V-29)
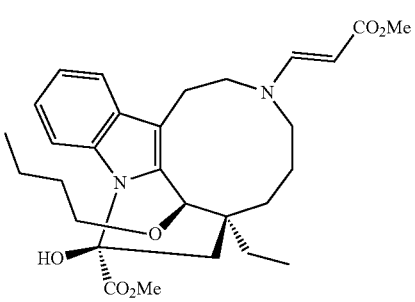 (V-30)
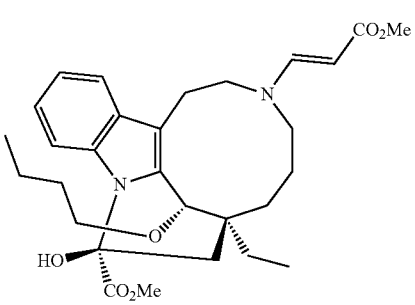 (V-31)

-continued
(V-46)
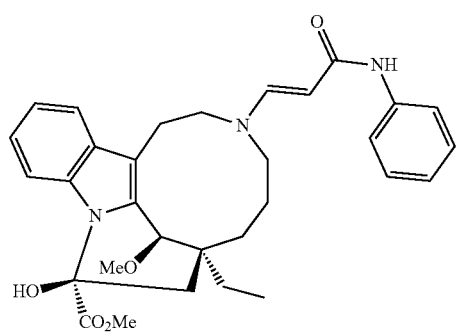
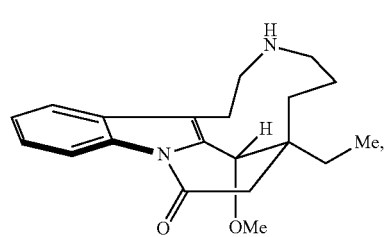
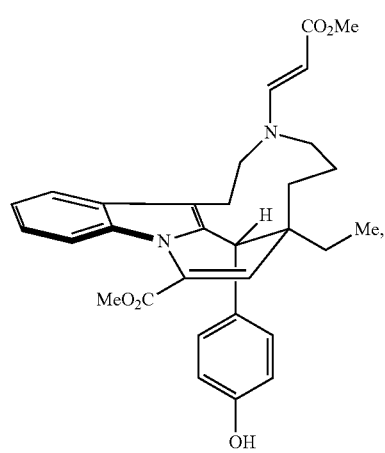
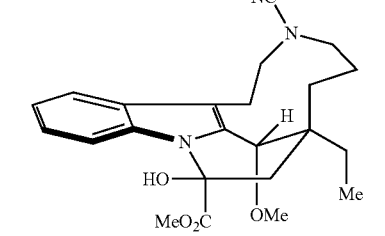
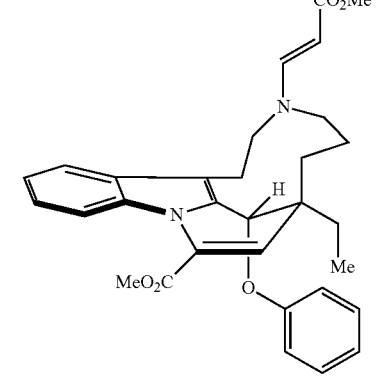
-continued
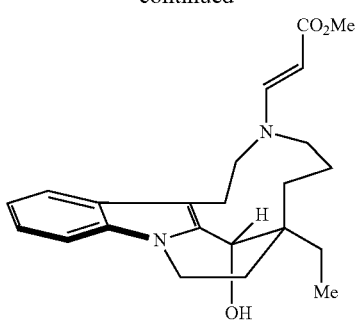
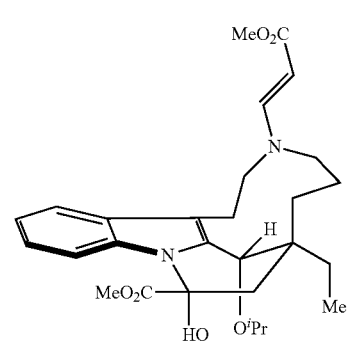
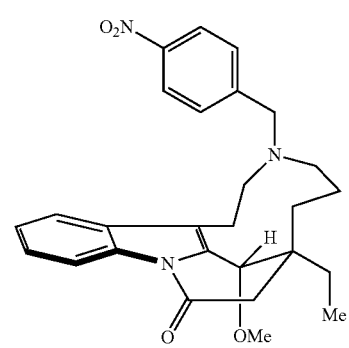
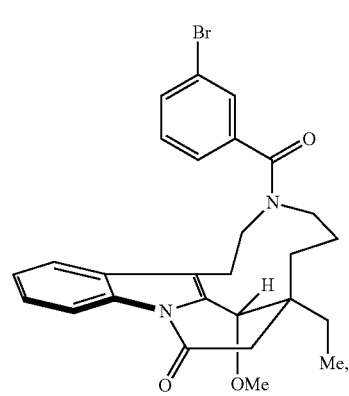
and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (II'):

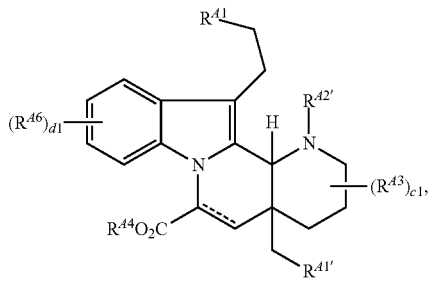

(II')

and pharmaceutically acceptable salts, solvates, hydrates, polymorphs, co-crystals, tautomers, stereoisomers, isotopically labeled derivatives, and prodrugs thereof, wherein $R^{A1}$, $R^{A1'}$, $R^{A2'}$, $R^{A3}$, $R^{A4}$, $R^{A6}$, c1, and d1 are as defined herein.

In certain embodiments, the compound of Formula (II') is of Formula (II). In one aspect, the present disclosure provides compounds of Formula (II):

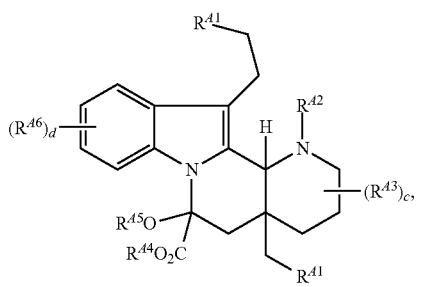

(II)

and pharmaceutically acceptable salts, solvates, hydrates, polymorphs, co-crystals, tautomers, stereoisomers, isotopically labeled derivatives, and prodrugs thereof, wherein $R^{A1}$, $R^{A2}$, $R^{A3}$, $R^{A4}$, $R^{A5}$, $R^{A6}$, c, and d are as defined herein.

In certain embodiments, the compound of Formula (II) is of Formula (I-i). In one aspect, the present disclosure provides compounds of Formula (II-i):

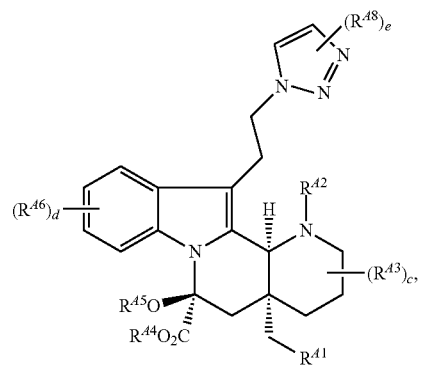

(II-i)

and pharmaceutically acceptable salts, solvates, hydrates, polymorphs, co-crystals, tautomers, stereoisomers, isotopically labeled derivatives, and prodrugs thereof, wherein $R^{A1}$, $R^{A2}$, $R^{A3}$, $R^{A4}$, $R^{A5}$, $R^{A6}$, $R^{A8}$, c, d, and e are as defined herein.

In certain embodiments, the compound of Formula (II) is of Formula (II-ii). In one aspect, the present disclosure provides compounds of Formula (II-ii):

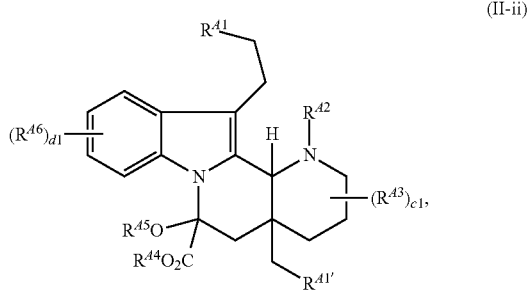

(II-ii)

and pharmaceutically acceptable salts, solvates, hydrates, polymorphs, co-crystals, tautomers, stereoisomers, isotopically labeled derivatives, and prodrugs thereof, wherein $R^{A1'}$, $R^{A1}$, $R^{A2}$, $R^{A3}$, $R^{A4}$, $R^{A5}$, $R^{A6}$, $R^{A8}$, c1, and d1 are as defined herein.

In one aspect, the present disclosure provides compounds of Formula (IIA):

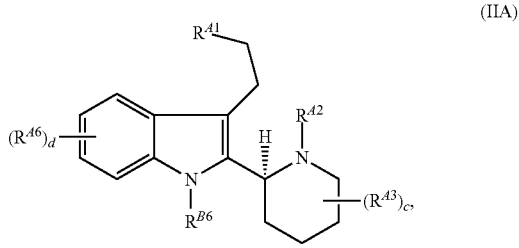

(IIA)

and pharmaceutically acceptable salts, solvates, hydrates, polymorphs, co-crystals, tautomers, stereoisomers, isotopically labeled derivatives, and prodrugs thereof, wherein $R^{A1}$, $R^{A2}$, $R^{A3}$, $R^{A6}$, $R^{B6}$, c, and d are as defined herein.

In certain embodiments, the compound of Formula (II'), (II), (II-i), (II-ii), or (IIA) is of the formula:

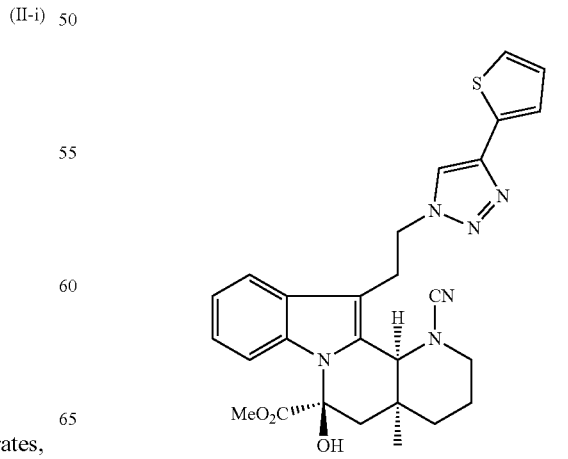

(V-35)
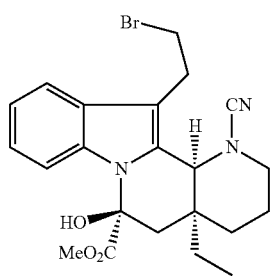
(V-36)
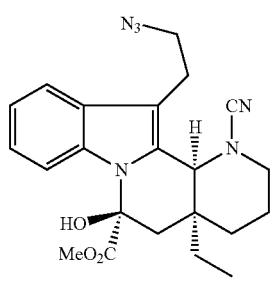
(V-38)
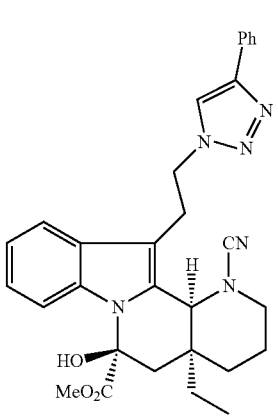
(V-39)
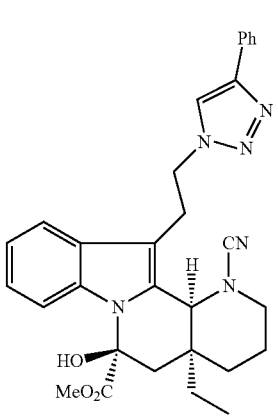
(V-40)
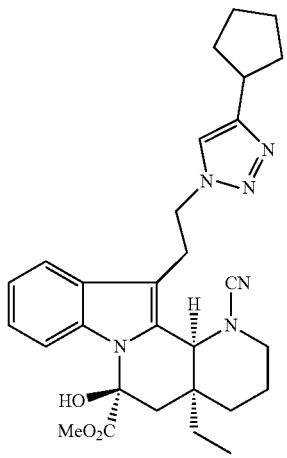
(V-41)
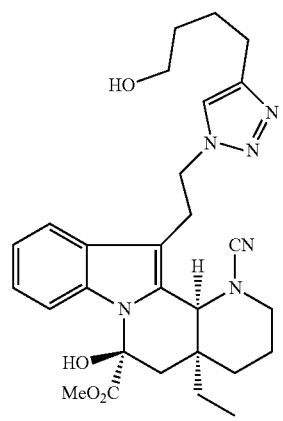
(V-42)
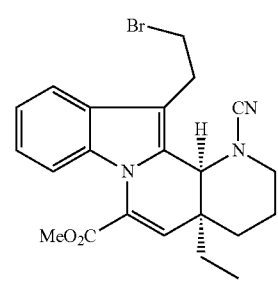
(V-43)
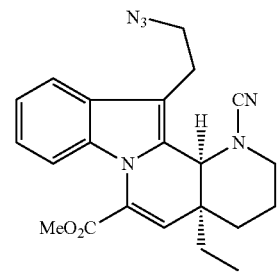

-continued

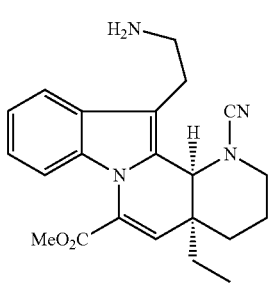
(V-44)

(V-45)

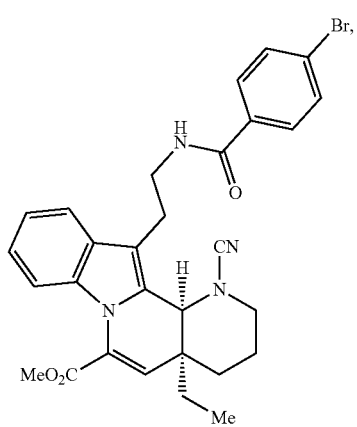
V4a and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (III″):

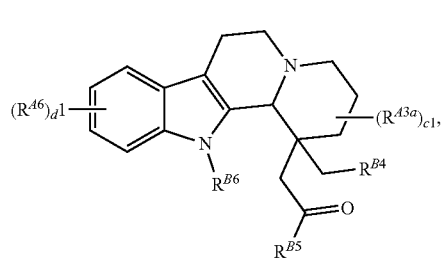
(III″)

and pharmaceutically acceptable salts, solvates, hydrates, polymorphs, co-crystals, tautomers, stereoisomers, isotopically labeled derivatives, and prodrugs thereof, wherein $R^{A3a}$, $R^{A6}$, $R^{B4}$, $R^{B5}$, $R^{B6}$, c1, and d1 are as defined herein.

In certain embodiments, the compound of Formula (III″) is of Formula (III). In one aspect, the present disclosure provides compounds of Formula (III):

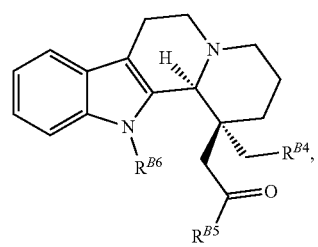
(III)

and pharmaceutically acceptable salts, solvates, hydrates, polymorphs, co-crystals, tautomers, stereoisomers, isotopically labeled derivatives, and prodrugs thereof, wherein $R^{B4}$, $R^{B5}$, and $R^{B6}$ are as defined herein.

In one aspect, the present disclosure provides compounds of Formula (IIIA):

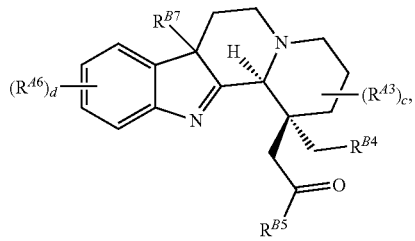
(IIIA)

and pharmaceutically acceptable salts, solvates, hydrates, polymorphs, co-crystals, tautomers, stereoisomers, isotopically labeled derivatives, and prodrugs thereof, wherein $R^{A3}$, $R^{A6}$, $R^{B4}$, $R^{B5}$, $R^{B7}$, c, and d are as defined herein.

In certain embodiments, the compound of Formula (III″), (III′), (III), or (IIIA) is of the formula:

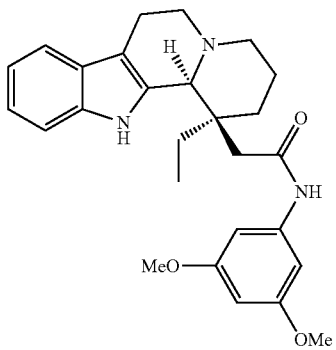
(V-5)

(V-8)
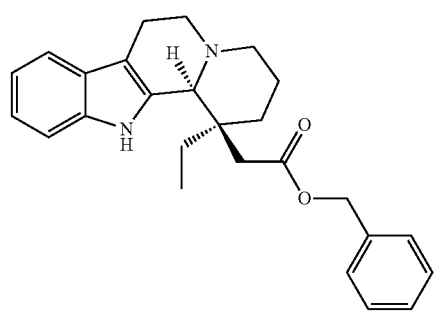
(V-9)
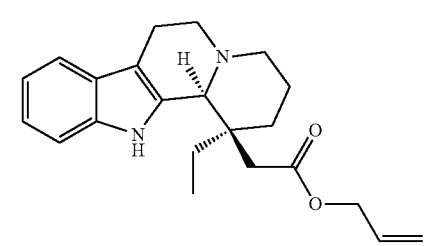
(V-10)
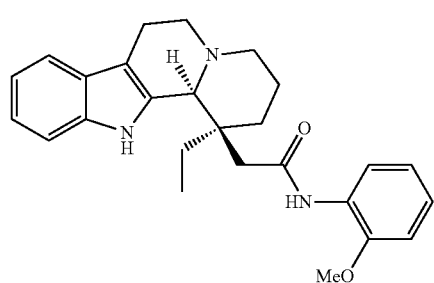
(V-11)
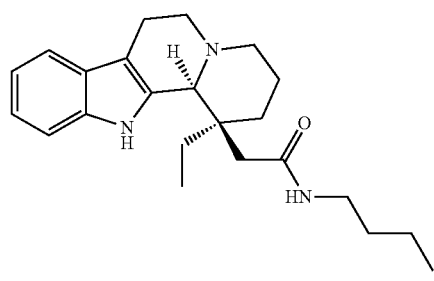
(V-19)
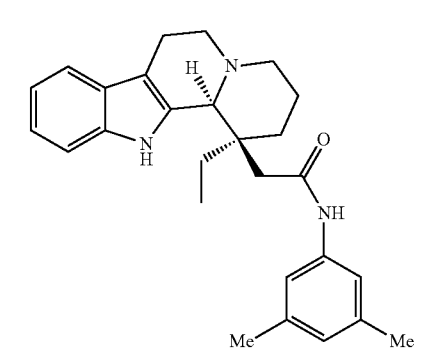
(V-23)
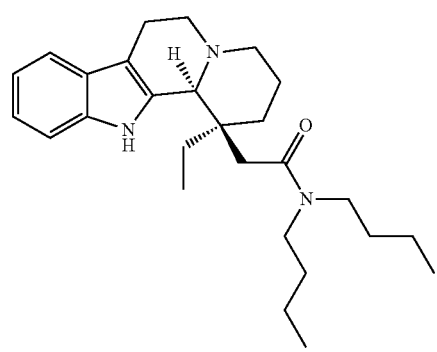
(V-24)
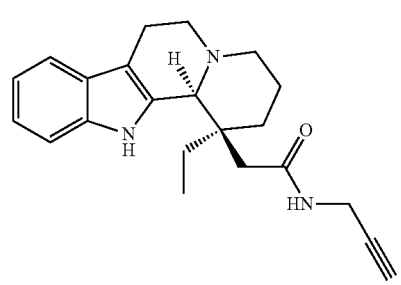
(V-25)
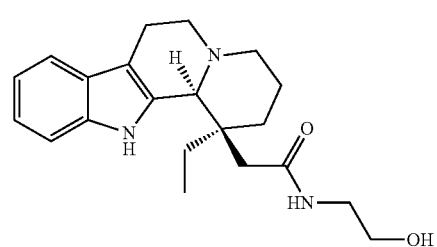
(V-26)
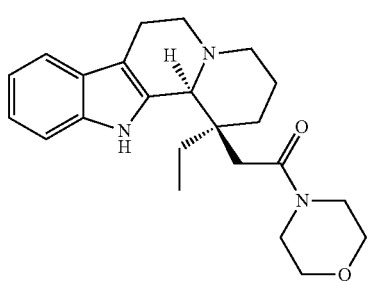
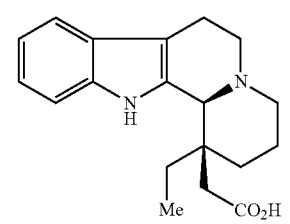
V1p
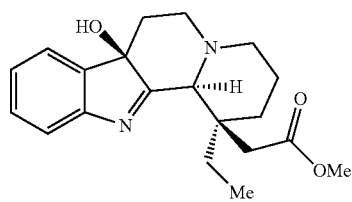

-continued

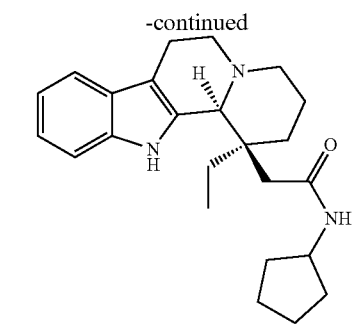

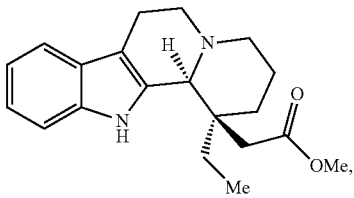

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (IV):

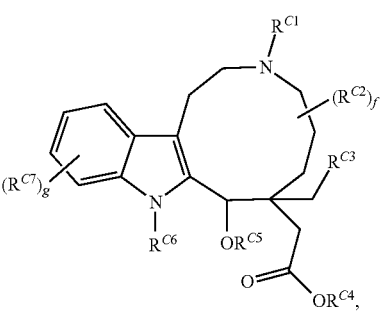

(IV)

and pharmaceutically acceptable salts, solvates, hydrates, polymorphs, co-crystals, tautomers, stereoisomers, isotopically labeled derivatives, and prodrugs thereof, wherein $R^{C1}$, $R^{C2}$, $R^{C3}$, $R^{C4}$, $R^{C5}$, $R^{C6}$, $R^{C7}$, f, and g are as defined herein.

In certain embodiments, the compound of Formula (IV) is of the formula:

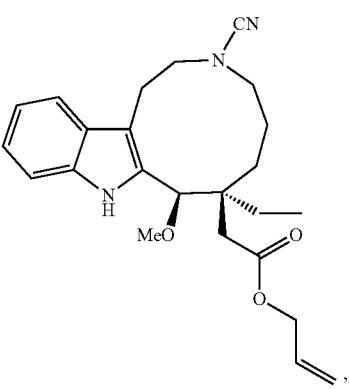

(V-7)

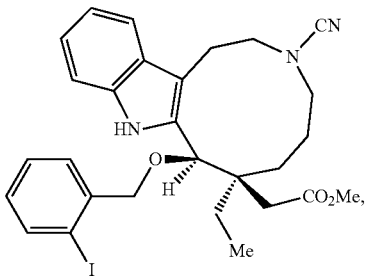

(V1o)

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (V'):

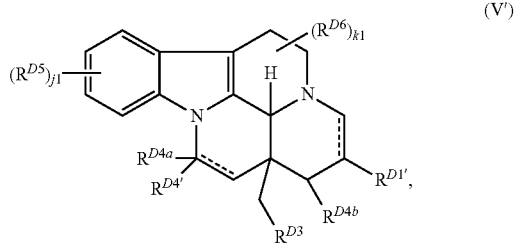

(V')

and pharmaceutically acceptable salts, solvates, hydrates, polymorphs, co-crystals, tautomers, stereoisomers, isotopically labeled derivatives, and prodrugs thereof, wherein $R^{D1}$, $R^{D3}$, $R^{D4'}$, $R^{D4a}$, $R^{D4b}$, $R^{D5}$, $R^{D6}$, j1, and k1 areas defined herein.

In certain embodiments, the compound of Formula (V') is of Formula (V). In one aspect, the present disclosure provides compounds of Formula (V):

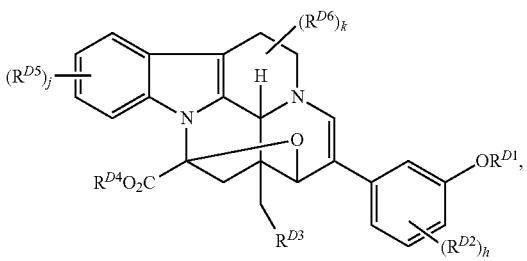

(V)

and pharmaceutically acceptable salts, solvates, hydrates, polymorphs, co-crystals, tautomers, stereoisomers, isotopically labeled derivatives, and prodrugs thereof, wherein $R^{D1}$, $R^{D2}$, $R^{D3}$, $R^{D4}$, $R^{D5}$, $R^{D6}$, j, and k are as defined herein.

In certain embodiments, the compound of Formulae (V') or (V) is of the formula:
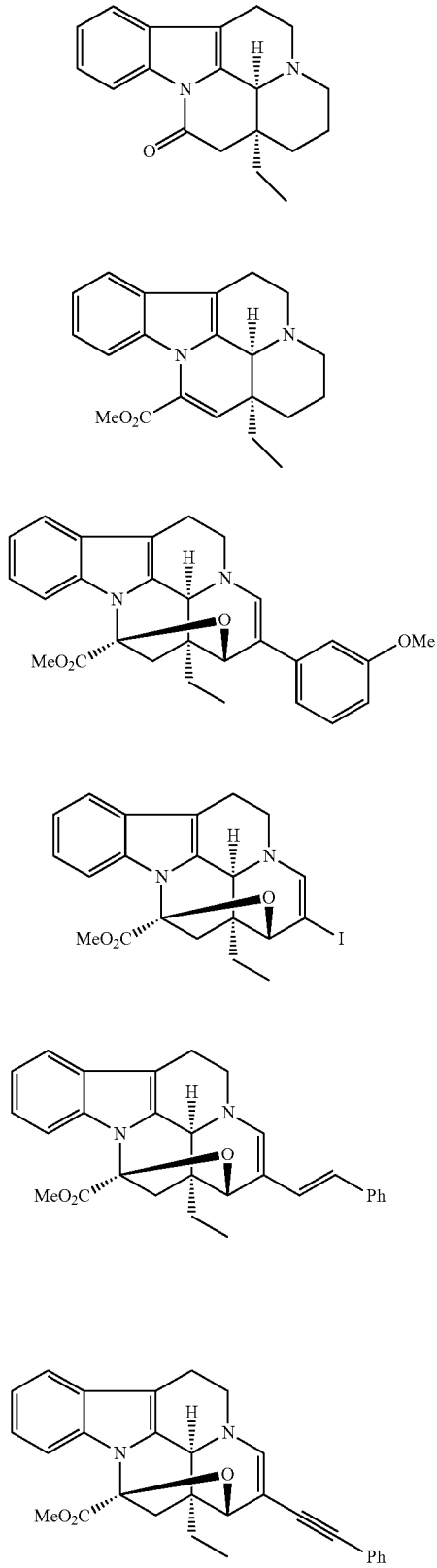
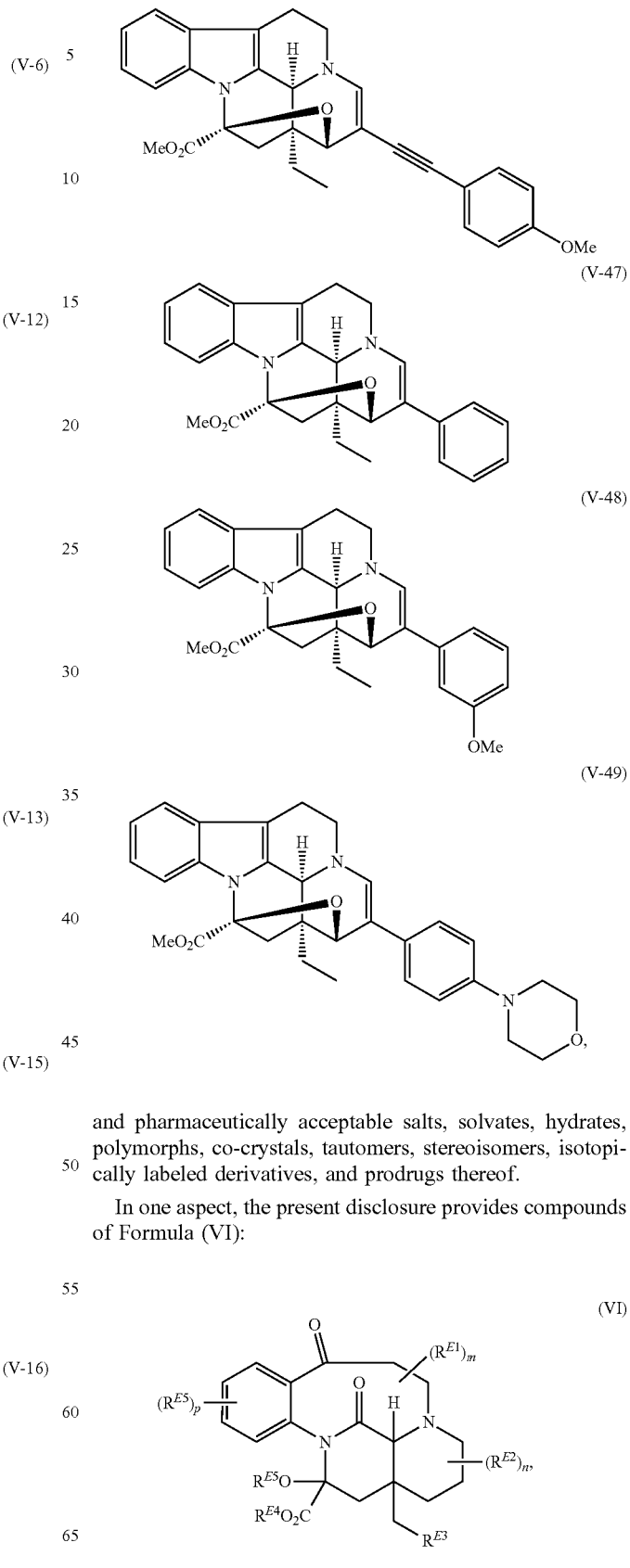
and pharmaceutically acceptable salts, solvates, hydrates, polymorphs, co-crystals, tautomers, stereoisomers, isotopically labeled derivatives, and prodrugs thereof.
In one aspect, the present disclosure provides compounds of Formula (VI):
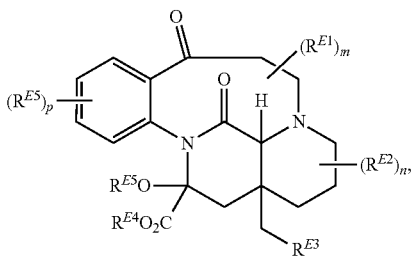

and pharmaceutically acceptable salts, solvates, hydrates, polymorphs, co-crystals, tautomers, stereoisomers, isotopically labeled derivatives, and prodrugs thereof, wherein $R^{E1}$, $R^{E2}$, $R^{E3}$, $R^{E4}$, $R^{E5}$, $R^{E}$, p, m, and n are as defined herein.

In certain embodiments, the compound of Formula (VI) is of the formula:

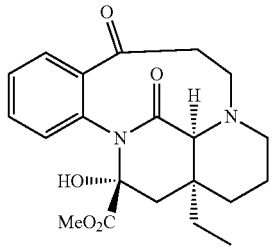 [SMILES: CC[C@@]12CCCN3CCC(=O)c4ccccc4N(C(=O)[C@@H]31)[C@](O)(C(=O)OC)C2]

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (VII):

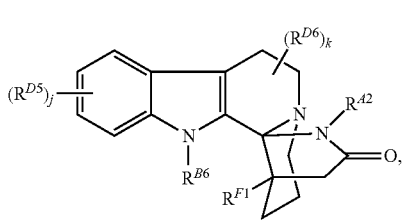

(VII)

and pharmaceutically acceptable salts, solvates, hydrates, polymorphs, co-crystals, tautomers, stereoisomers, isotopically labeled derivatives, and prodrugs thereof, wherein $R^{A2}$, $R^{F1}$, $R^{B6}$, $R^{D5}$, $R^{D6}$, j, and k are as defined herein.

In certain embodiments, the compound of Formula (VII) is of the formula:

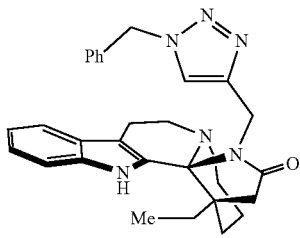

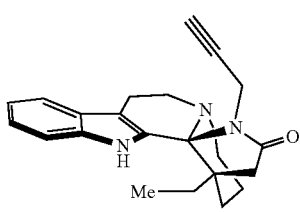

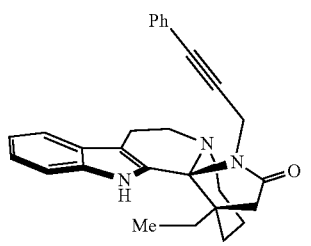

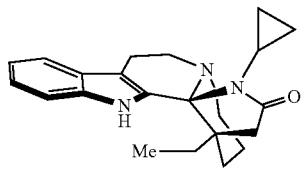

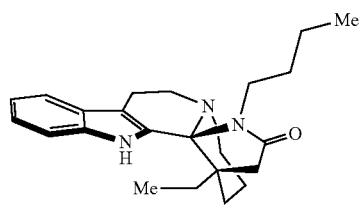

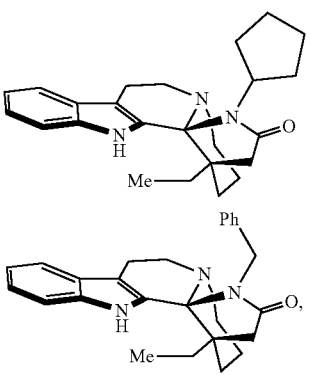

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (VIII'):

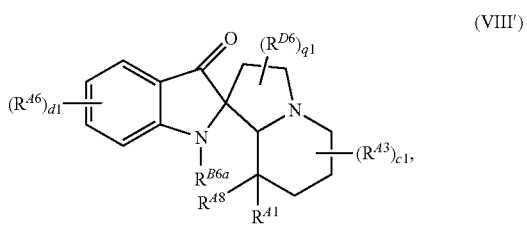

(VIII')

and pharmaceutically acceptable salts, solvates, hydrates, polymorphs, co-crystals, tautomers, stereoisomers, isotopically labeled derivatives, and prodrugs thereof, wherein $R^{A1z}$, $R^{A3}$, $R^{A6}$, $R^{A8}$, $R^{B6}$, $R^{D6}$, c, d1, and q1 are as defined herein.

In certain embodiments, the compound of Formula (VIII') is of Formula (VIII). In one aspect, the present disclosure provides compounds of Formula (VIII):

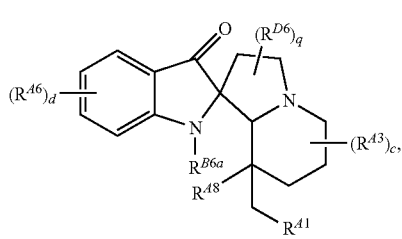

(VIII)

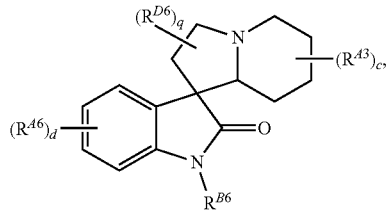

and pharmaceutically acceptable salts, solvates, hydrates, polymorphs, co-crystals, tautomers, stereoisomers, isotopically labeled derivatives, and prodrugs thereof, wherein $R^{A1}$, $R^{A3}$, $R^{A6}$, $R^{A8}$, $R^{B6a}$, $R^{D6}$, c, d, and q are as defined herein.

In certain embodiments, the compound of Formulae (V') or (V) is of the formula:

and pharmaceutically acceptable salts, solvates, hydrates, polymorphs, co-crystals, tautomers, stereoisomers, isotopically labeled derivatives, and prodrugs thereof, wherein $R^{A3}$, $R^{A6}$, $R^{B6}$, $R^{D6}$, c, d, and q are as defined herein.

In certain embodiments, the compound of Formulae (IX') or (IX) is of the formula:

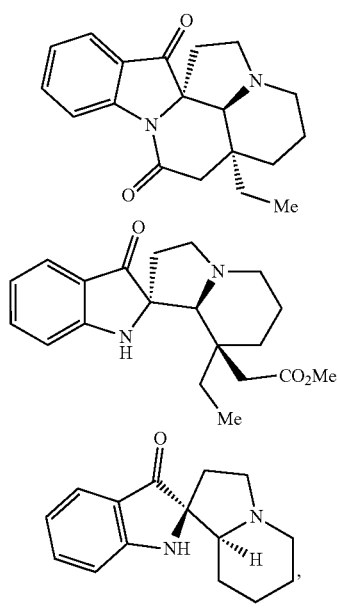

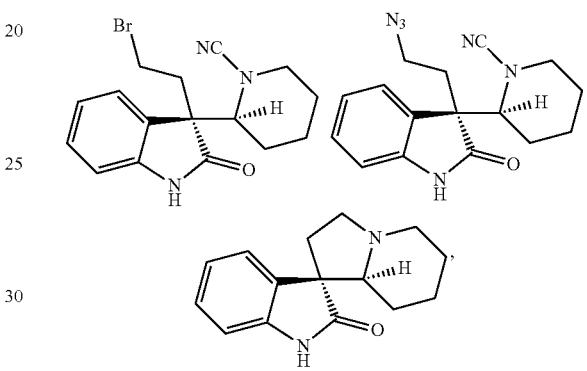

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (X):

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (IX'):

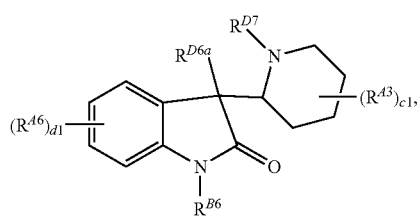

(X)

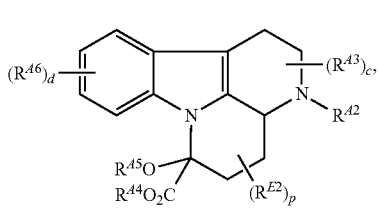

(IX')

and pharmaceutically acceptable salts, solvates, hydrates, polymorphs, co-crystals, tautomers, stereoisomers, isotopically labeled derivatives, and prodrugs thereof, wherein $R^{A2}$, $R^{A3}$, $R^{A4}$, $R^{A5}$, $R^{A6}$, $R^{E2}$, c, d, and p are as defined herein.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating and/or preventing a disease (e.g., a proliferative disease, CNS disorder, metabolic disorder, or infectious disease) in a subject in need thereof. In certain embodiments, the proliferative disease is cancer. In certain embodiments, the cancer is selected from the group consisting of pancreatic cancer, lung cancer (e.g., small cell lung cancer (SCLC), and and pharmaceutically acceptable salts, solvates, hydrates, polymorphs, co-crystals, tautomers, stereoisomers, isotopically labeled derivatives, and prodrugs thereof, wherein $R^{D7}$, $R^{A3}$, $R^{A6}$, $R^{B6a}$, $R^{D6a}$, c1, and d1 are as defined herein.

In certain embodiments, the compound of Formula (IX') is of Formula (IX). In one aspect, the present disclosure provides compounds of Formula (IX):

non-small cell lung cancer), prostate cancer, breast cancer, ovarian cancer, kidney cancer, liver cancer, Ewing's sarcoma, osteosarcoma, brain cancer, neuroblastoma, and colorectal cancer. In certain embodiments, the proliferative disease is a benign neoplasm or disease associated with angiogenesis. In certain embodiments, the disease is a CNS disorder (e.g., drug addiction, opioid (e.g., heroin) addiction). In certain embodiments, the proliferative disease is an infectious disease (e.g., malaria).

In another aspect, the present invention provides methods for treating and/or preventing a proliferative disease. Exemplary diseases which may be treated include cancer, benign neoplasms, diseases associated with angiogenesis, inflammatory diseases, CNS disorders, metabolic disorders, and infectious diseases.

The present invention provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional agent. The methods described herein may further include performing radiotherapy, immunotherapy, and/or transplantation on the subject.

In yet another aspect, the present invention provides compounds of Formulae (I'), (I), (IA), (II'), (II), (IIA), (III''), (IIIA), (III), (IV), (V'), (V), (VI), (VII), (VIII'), (VIII), (IX'), (IX), and (X), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a proliferative disease such as cancer or an infectious disease) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, Stereochemistry of Carbon Compounds (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-4}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —C$^A$H(C$^B$H$_2$C$^C$H$_3$)— includes only one carbon unit C$^A$. The term "C$_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

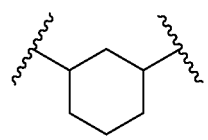 [SMILES: *C1CCCC(*)C1]

is a C$_3$ hydrocarbon chain. When a range of values is used, e.g., a C$_{1-6}$ hydrocarbon chain, the meaning of the range is as described herein. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C=C—CH$_2$—, and —C=C—CH=CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

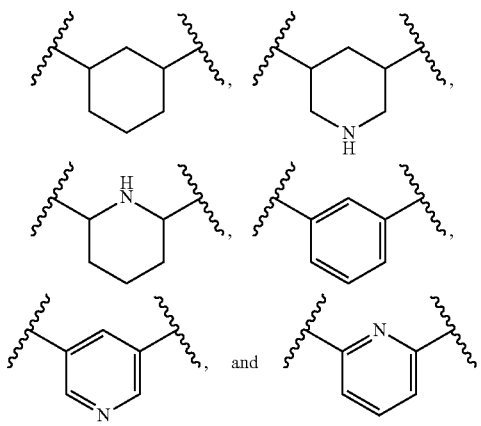

are all examples of a hydrocarbon chain. In contrast, in certain embodiments

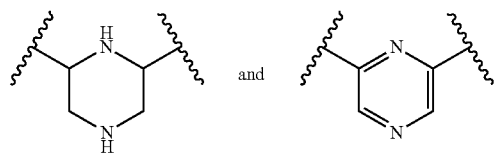 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("C$_{1-20}$ alkyl"). In some embodiments, an alkyl group has 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C), 3-pentanyl (C$_5$), amyl (C$_5$), neopentyl (C$_5$), 3-methyl-2-butanyl (C$_5$), tertiary amyl (C$_5$), and n-hexyl (C$_6$). Additional examples of alkyl groups include n-heptyl (C), n-octyl (C) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted C$_{1-10}$ alkyl (e.g., —CH$_3$). In certain embodiments, the alkyl group is substituted C$_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("C$_{1-8}$ haloalkyl"). In some embodiments, the haloalkyl moiety has 1 to 6 carbon atoms ("C$_{1-6}$ haloalkyl"). In some embodiments, the haloalkyl moiety has 1 to 4 carbon atoms ("C$_{1-4}$ haloalkyl"). In some embodiments, the haloalkyl moiety has 1 to 3 carbon atoms ("C$_{1-3}$ haloalkyl"). In some embodiments, the haloalkyl moiety has 1 to 2 carbon atoms ("C$_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —CF$_3$, —CF$_2$CF$_3$, —CF$_2$CF$_2$CF$_3$, —CCl$_3$, —CFCl$_2$, —CF$_2$Cl, and the like.

As used herein, "alkynyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ to alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and $_{ww}$ero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$-cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix-ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^+$, —P(OR$^{cc}$)$_3$$^+$X$^+$, —P(R$^{cc}$)$_4$, —P(OR$^{cc}$)$_4$, —OP(R$^{cc}$)$_2$, —OP(R$^{cc}$)$_3$$^+$X$^+$, —OP(OR$^{cc}$)$_2$, —OP(OR$^{cc}$)$_3$$^+$X$^+$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^+$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^c$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)

(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —C$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups, such as carbamate groups (e.g., —C(=O)OR$^{aa}$), include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups, such as sulfonamide groups (e.g., —S(=O)$_2$R$^{aa}$), include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —CO$_2R^{aa}$, —C(=O)N$(R^{bb})_2$, —C(=N$R^{bb}$)$R^{aa}$, —C(=N$R^{bb}$)O$R^{aa}$, —C(=N$R^{bb}$)N$(R^{bb})_2$, —S(=O)$R^{aa}$, —SO$_2R^{aa}$, —Si$(R^{aa})_3$, —P$(R^{cc})_2$, —P$(R^{cc})_3^+X^-$, —P(O$R^{cc}$)$_2$, —P(O$R^{cc}$)$_3^+X^-$, —P(=O)$(R^{aa})_2$, —P(=O)(O$R^{cc}$)$_2$, and —P(=O)(N$(R^{bb})_2$)$_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —CO$_2R$, —C(=O)N$(R^{bb})_2$, —C(=N$R^{bb}$)$R^{aa}$, —C(=N$R^{bb}$)O$R^{aa}$, —C(=N$R^{bb}$)N$(R^{bb})_2$, —S(=O)$R^{aa}$, —SO$_2R^{aa}$, —Si$(R^{aa})_3$, —P$(R^{cc})_2$, —P$(R^{cc})_3^+X^-$, —P(O$R^{cc}$)$_2$, —P(O$R^{cc}$)$_3^+X^-$, —P(=O)$(R^{aa})_2$, —P(=O)(O$R^{cc}$)$_2$, and —P(=O)(N$(R^{bb})_2$)$_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March's Advanced Organic Chemistry 6th ed. (501-502). Exemplary leaving groups include, but are not limited to, halo (e.g., chloro, bromo, iodo) and activated substituted hydroxyl groups (e.g., —OC(=O)$SR^{aa}$, —OC(=O)$R^{aa}$, —OCO$_2R^{aa}$, —OC(=O)N$(R^{bb})_2$, —OC(=N$R^{bb}$)$R^{aa}$, —OC(=N$R^{bb}$)O$R^{aa}$, —OC(=N$R^{bb}$)N$(R^{bb})_2$, —OS(=O)$R^{aa}$, —OSO$_2R^{aa}$, —OP$(R^{cc})_2$, —OP ($R^{cc}$)$_3$, —OP(=O)$_2R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I') and (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2H$_2$O) and hexahydrates (R.6H$_2$O)).

The term "tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formulae (I'), (I), (IA), (II'), (II), (IIA), (III''), (III'), (IIIA), (III), (IV), (V'), (V), (VI), (VII), (VIII'), (VIII), (IX'), (IX), and (X), become under physiological conditions the compounds of Formulae (I'), (I), (IA), (II'), (II), (IIA), (III''), (III'), (IIIA), (III), (IV), (V'), (V), (VI), (VII), (VIII'), (VIII), (IX'), (IX), and (X), which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formulae (I'), (I), (IA), (II'), (II), (IIA), (III''), (III'), (IIIA), (III), (IV), (V'), (V), (VI), (VII), (VIII'), (VIII), (IX'), (IX), and (X) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formulae (I'), (I), (IA), (II'), (II), (IIA), (III''), (III'), (IIIA), (III), (IV), (V'), (V), (VI), (VII), (VIII'), (VIII), (IX'), (IX), and (X) refers to an amount sufficient to elicit the desired biological response, i.e., treating the condition. As will be appreciated by those of ordinary skill in this art, the effective amount of a compound of Formulae (I'), (I), (IA), (II'), (II), (IIA), (III''), (III'), (IIIA), (III), (IV), (V'), (V), (VI), (VII), (VIII'), (VIII), (IX'), (IX), and (X) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formulae (I'), (I), (IA), (II'), (II), (IIA), (III''), (III'), (IIIA), (III), (IV), (V'), (V), (VI), (VII), (VIII'), (VIII), (IX'), (IX), and (X) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formulae (I'), (I), (IA), (II'), (II), (IIA), (III''), (III'), (IIIA), (III), (IV), (V'), (V), (VI), (VII), (VIII'), (VIII), (IX'), (IX), and (X) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multi-system inflammatory disease (NOMID), tumor necrosis factor (TNF) receptor-associated periodic syndrome (TRAPS), deficiency of the interleukin-1 receptor antagonist (DIRA), and Behçet's disease.

The term "central nervous system disorder" or "CNS disorder" refers to a disease of the central nervous system (brain, brainstem and cerebellum). Exemplary CNS disorders include, but are not limited to, neurotoxicity and/or neurotrauma, stroke, multiple sclerosis, spinal cord injury, epilepsy, a mental disorder, a sleep condition, a movement disorder, nausea and/or emesis, amyotrophic lateral sclerosis, Alzheimer's disease and drug addiction (e.g., opioid addiction (e.g., heroin addiction)).

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

An "infection" or "infectious disease" refers to an infection with a microorganism, such as a parasite, protozoa, fungus, bacteria, or virus. In certain embodiments, the infection is an infection with a protozoan parasite, i.e., a protozoan infection. In certain embodiments, the infection is an infection with a *Plasmodium falciparum, Plasmodium vivax, Plasmodium ovale, Plasmodium malariae*, or *Plasmodium knowlesi*. Various infections include, but are not limited to, skin infections, GI infections, urinary tract infections, genito-urinary infections, sepsis, blood infections, and systemic infections.

A "parasite" refers to an organism that lives on or in a host organism, may infect the host organism and obtains its food from or at the expense of its host. Exemplary parasites include protozoan parasites, helminth parasites (e.g., flatworms), and ectoparasites (e.g., ticks or fleas). Exemplary protozoan parasites include Sarcodina amoeba (e.g., *Entamoeba*); *Mastigophora flagellates*, (e.g., *Giardia, Leishmania*); *Ciliophora ciliates*, (e.g., *Balantidium*); and Sporozoa (e.g., *Plasmodium* and *Cryptosporidium*). Exemplary protozoan parasites include, but are not limited to, *Leishmania, Cryptosporidium* spp., *Giardia intestinalis, Trichomonas, Cyclospora cayetanensis*, and *Toxoplasma gondii*.

A "*Plasmodium*" refers to a protozoan parasite, which may infect host organisms, such as reptiles, birds, and mammals. In certain embodiments, a *Plasmodium* is *Plasmodium falciparum*. In certain embodiments, a *Plasmodium* is *Plasmodium vivax*. In certain embodiments, a *Plasmodium* is *Plasmodium ovale*. In certain embodiments, a *Plasmodium* is *Plasmodium malariae*. In certain embodiments, a *Plasmodium* is *Plasmodium knowlesi*.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D.C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, *Cannabis* dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

BRIEF DESCRIPTION OF THE DRAWINGS

The accompanying drawings, which constitute a part of this specification, illustrate several embodiments of the invention and together with the description, serve to explain the principles of the invention.

FIG. 4B. Effect of Exemplary Compounds (V, V1a, V1p, V2a, V3a, V3b, V4a, V5a, and Y) Against Certain G Protein-Coupled Receptors (GPCR's) and Exemplary Contemplated Therapy or Probe Use.

DETAILED DESCRIPTION OF CERTAIN EMBODIMENTS OF THE INVENTION

Figure 1:
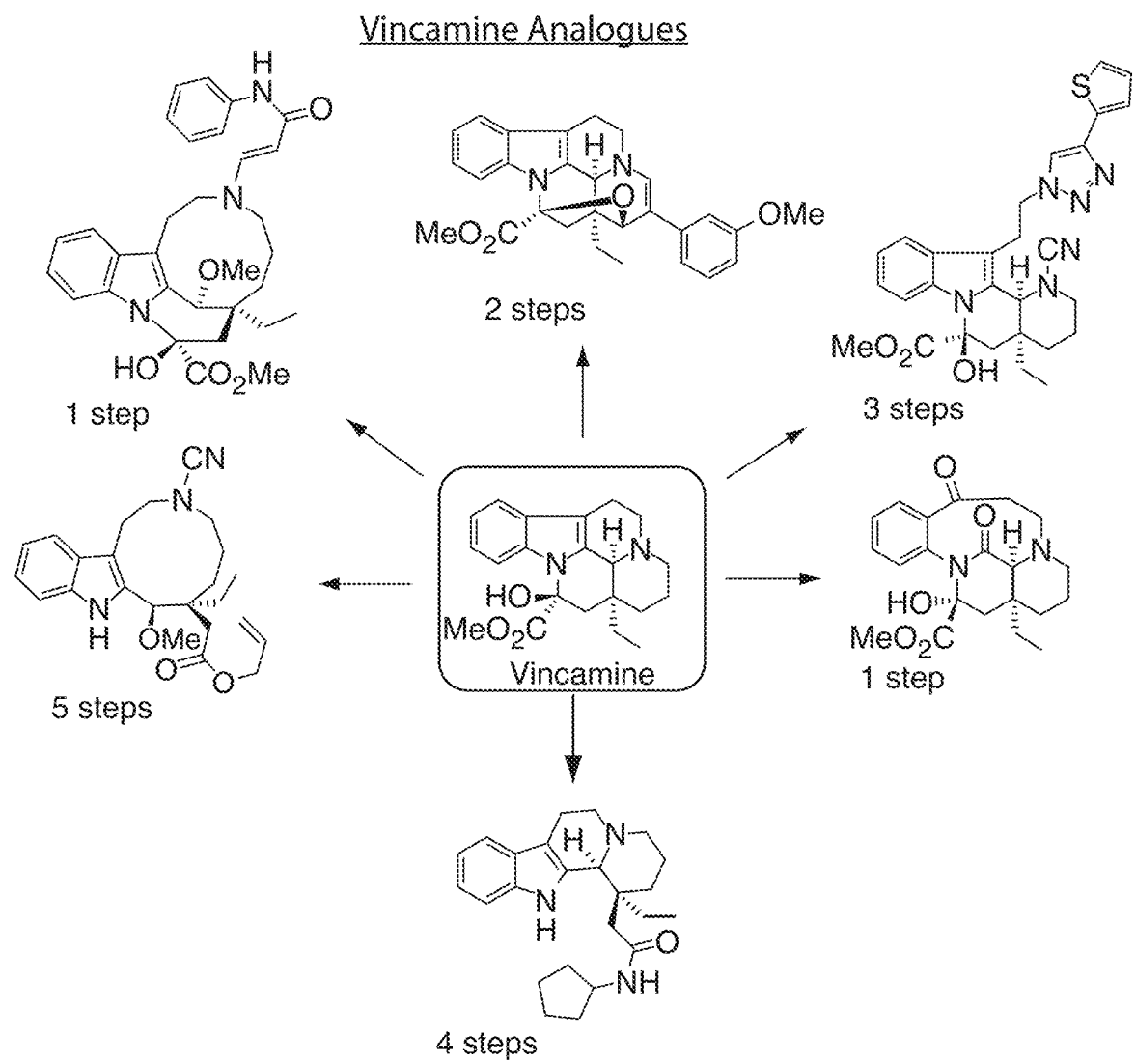
FIG. 1. Exemplary Synthetic Scheme Toward Diverse and Complex Small Molecules Derived from Vincamine.
Figure 2:
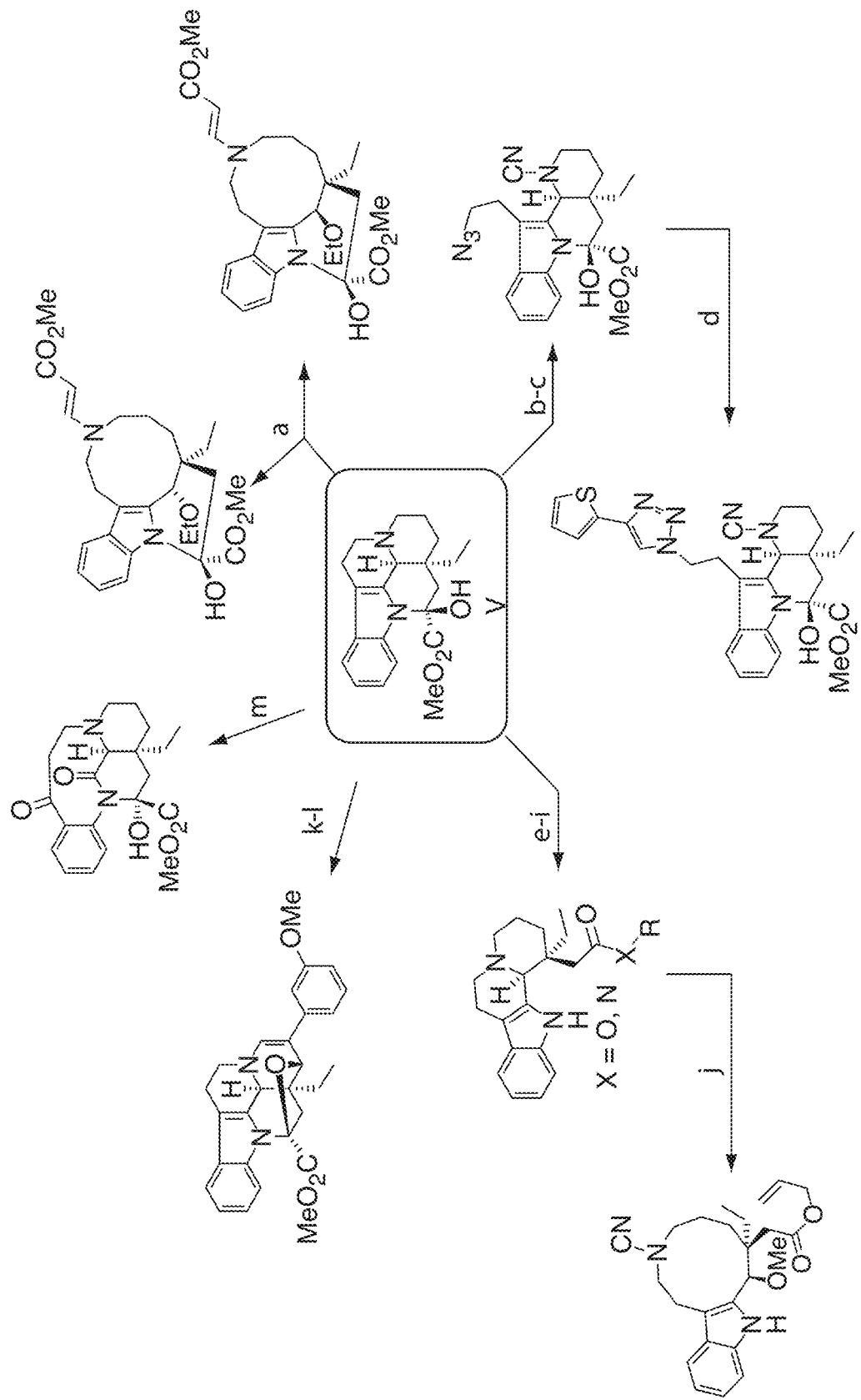
FIG. 2. Ring Distortion and Diversification of Vincamine. Conditions for the synthetic steps are as follows: a) Methyl Propiolate (1.5 eq), CH3CH2OH, reflux, 2 h; b) 3M CNBr (3.0 eq), DMF, μw, 100° C., 6 min; c) NaN3, DMF, μw, 100° C., 6 min; d) 2-ethynylthiophene (3.0 eq), CuSO4 (47 mol %), Sodium Ascorbate (1.5 eq), (t-BuOH:H2O) (2:1), DCM, 2.5 h; e) LAH (5.0 eq), THF, 0° C.-RT; f) NaIO4 (5.0 eq), (THF:H2O) (3:1), 2 h g) KOH (5.3 eq), (CH3CH2OH:H2O) (2:1) μw, 180° C., 10 min; h) X=N, methyl chloroformate (1.2 eq), cyclopentylamine (10 eq), Et3N (1.1 eq), cat. DMAP, DCM, 4 h; i) X=O, K2CO3 (2.0 eq), allyl bromide (1.2 eq), DMF, 2 h; j) 3.0M CNBr (2.0 eq), (CHCl3:CH3OH) (3:1), 5 h; k) 12 (4.1 eq), (sat. aq. NaHCO3:CHCl) (1:2), 2 h; 1) 3-methoxyphenylboronic acid (1.05 eq), Pd(OAc)2 (24 mol %), K2CO3 (3.0 eq), MeOH, 4 h; m) 40 μM Methylene Blue, CH3OH, 24 hours.
Figure 3:
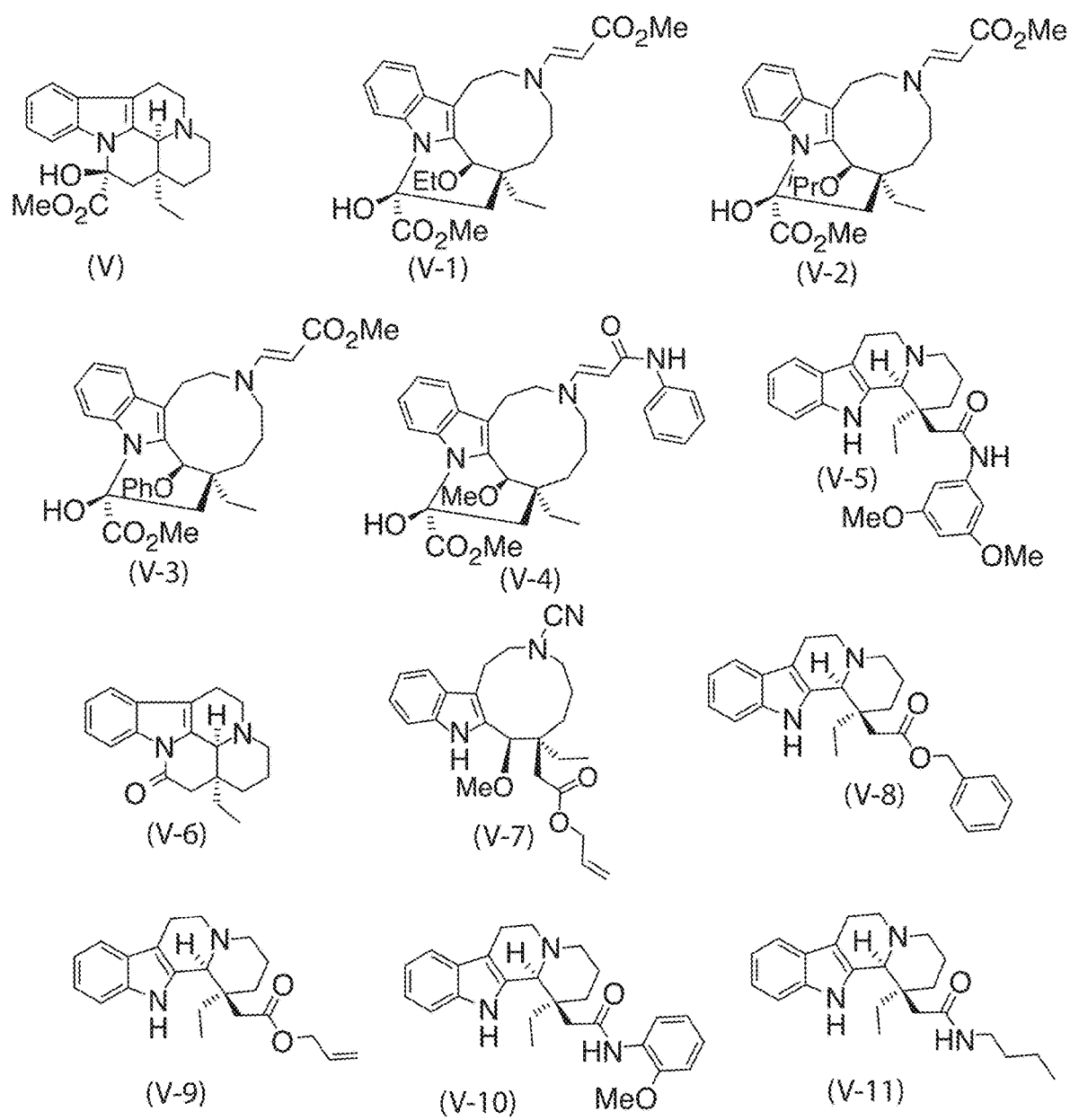
FIG. 3. Vincamine Analog Compound Library.
Figure 3:
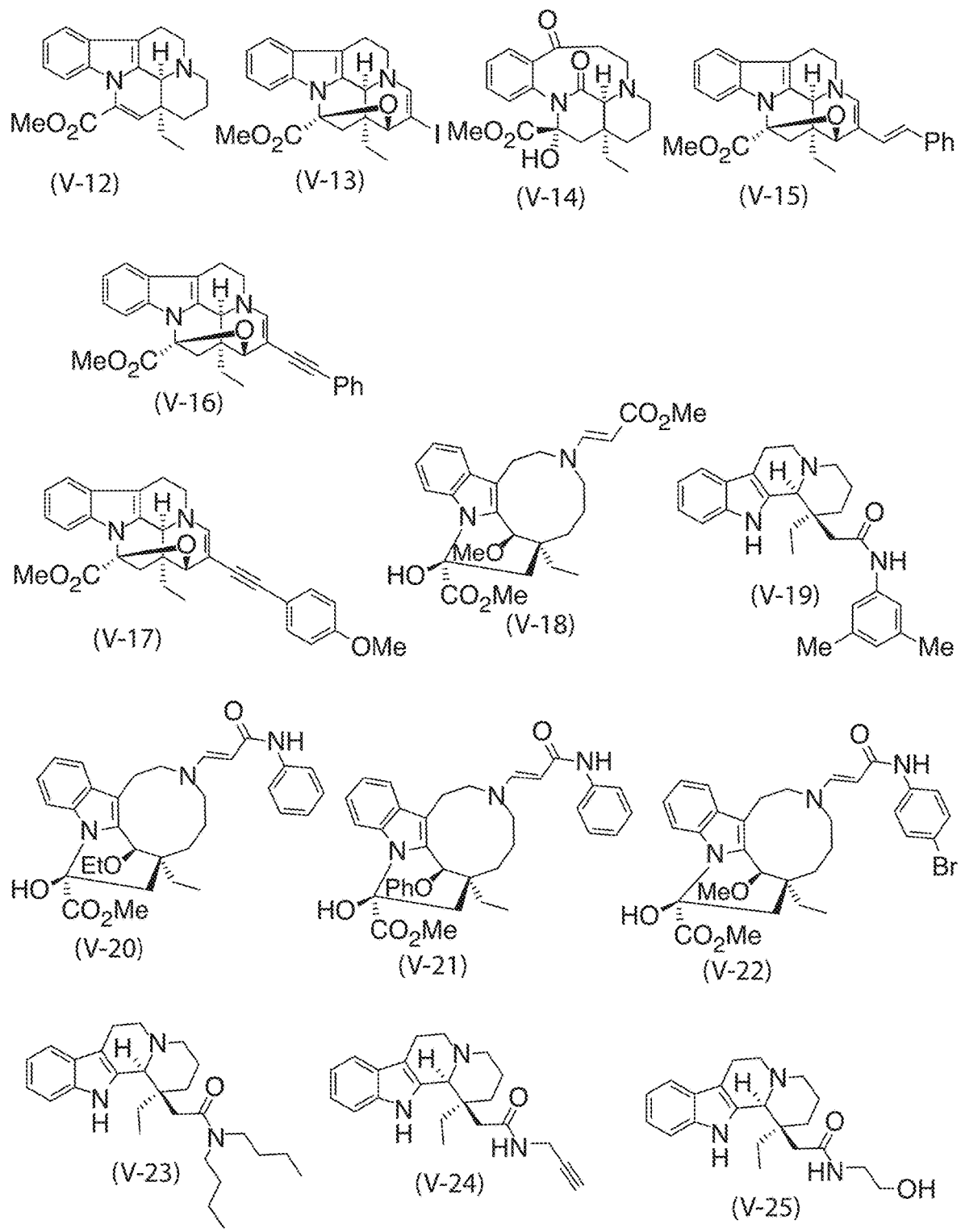
Figure 3:
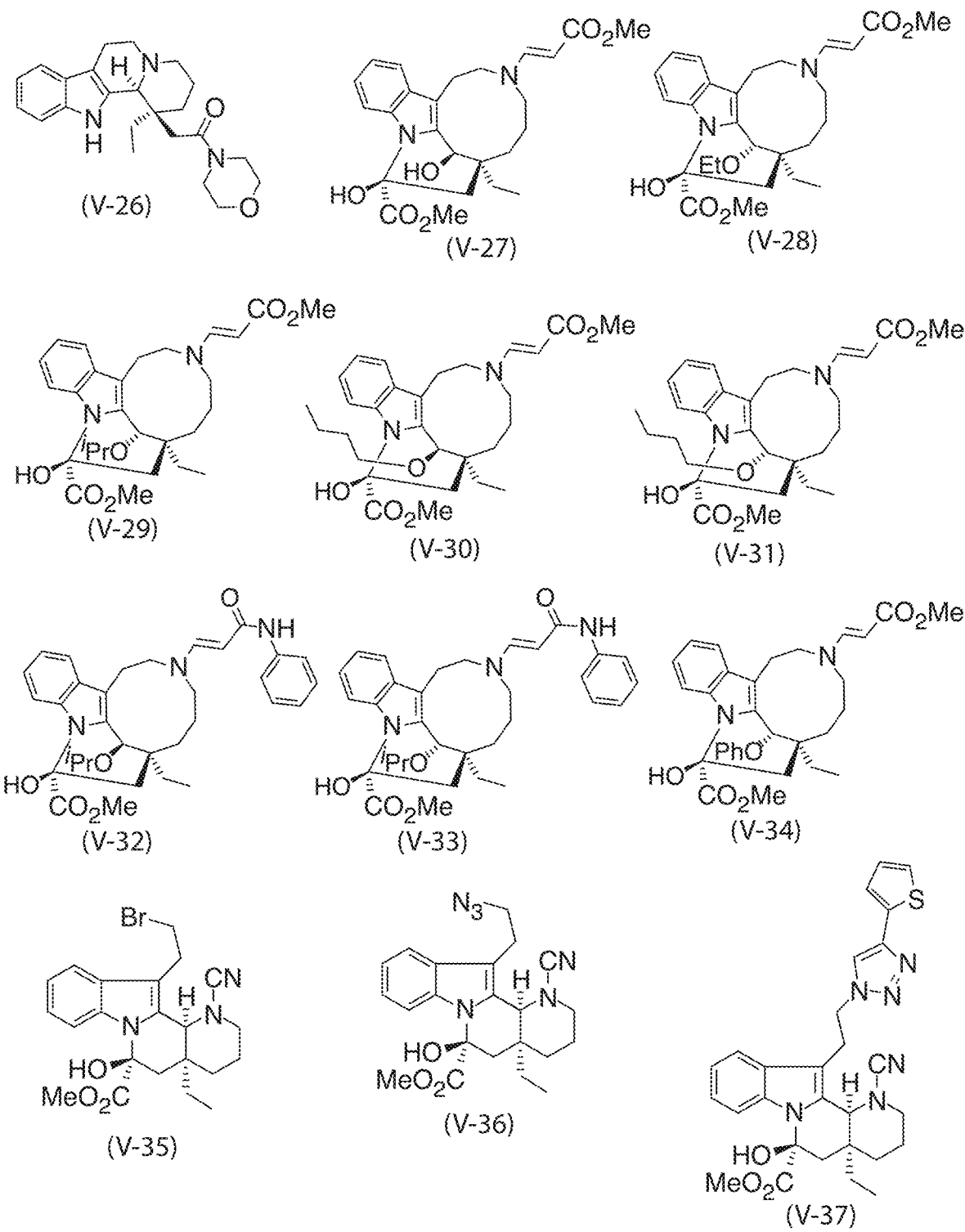
Figure 3:
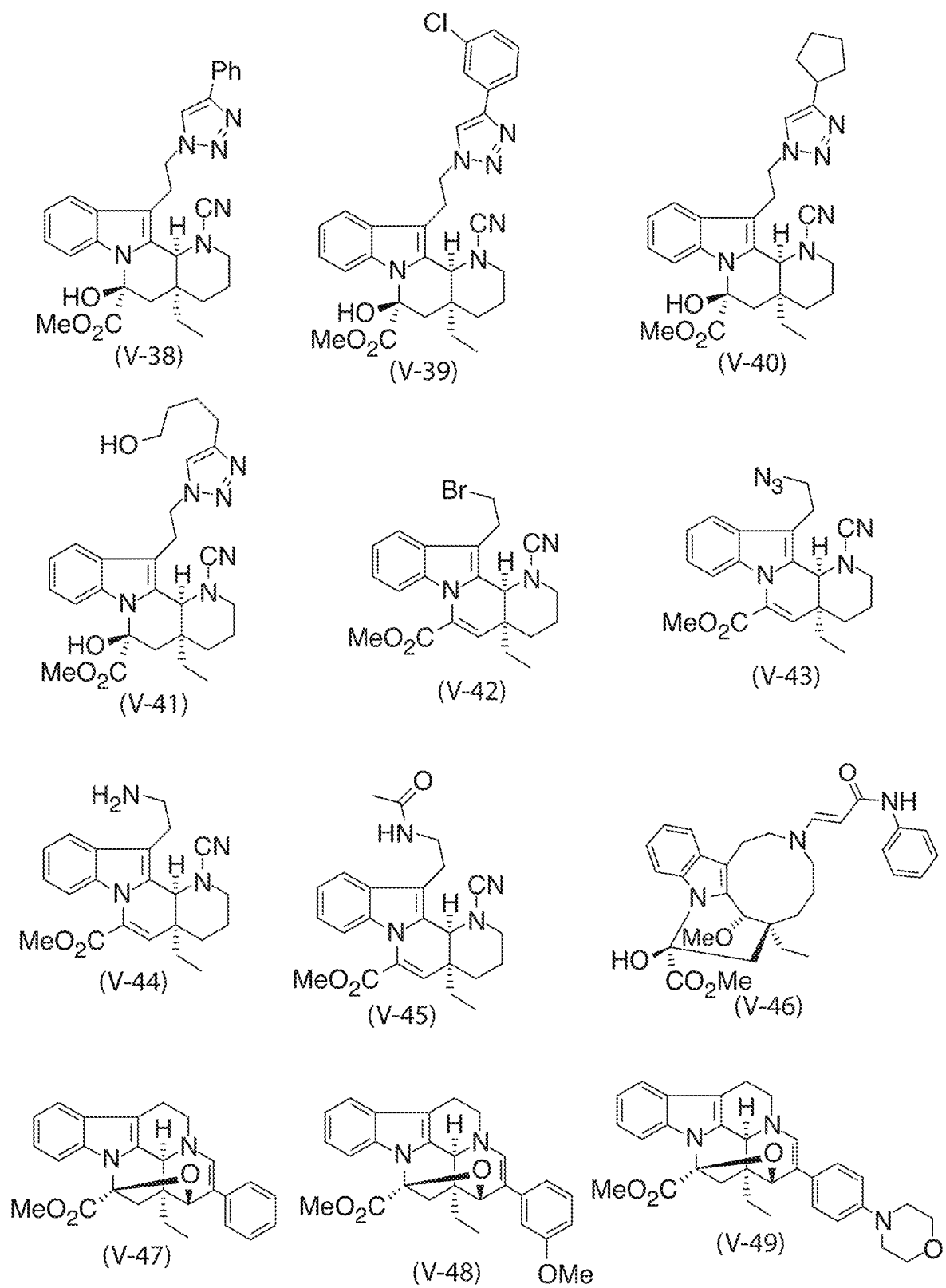
Figure 4:
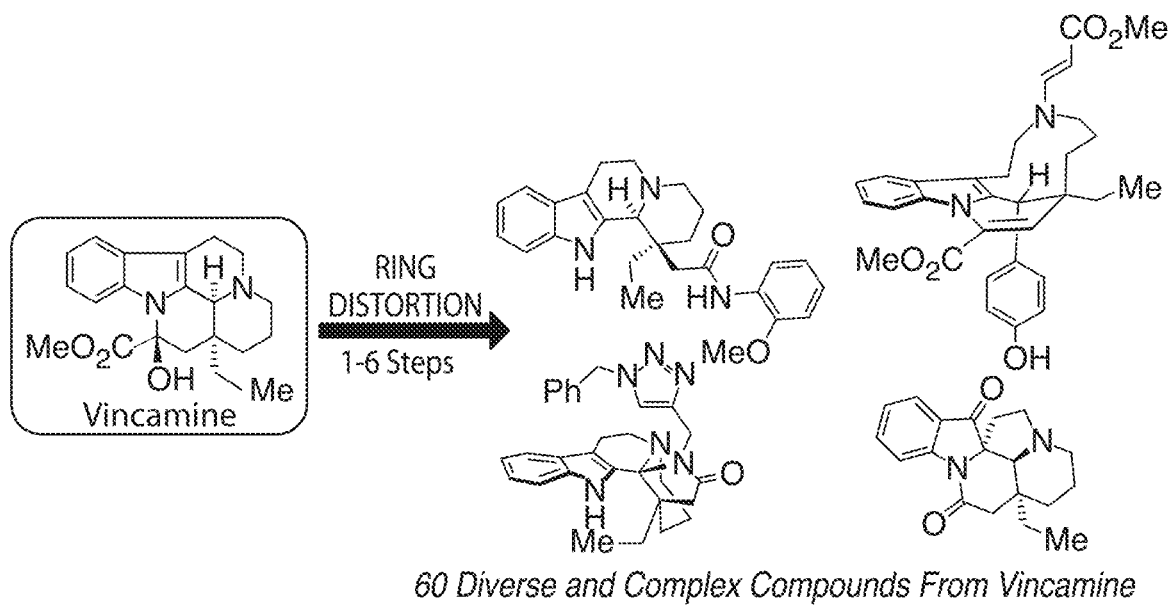
FIG. 4: High Throughput Screening and Compound Libraries. High Throughput Screening was conducted under standard conditions.
Figure 4:
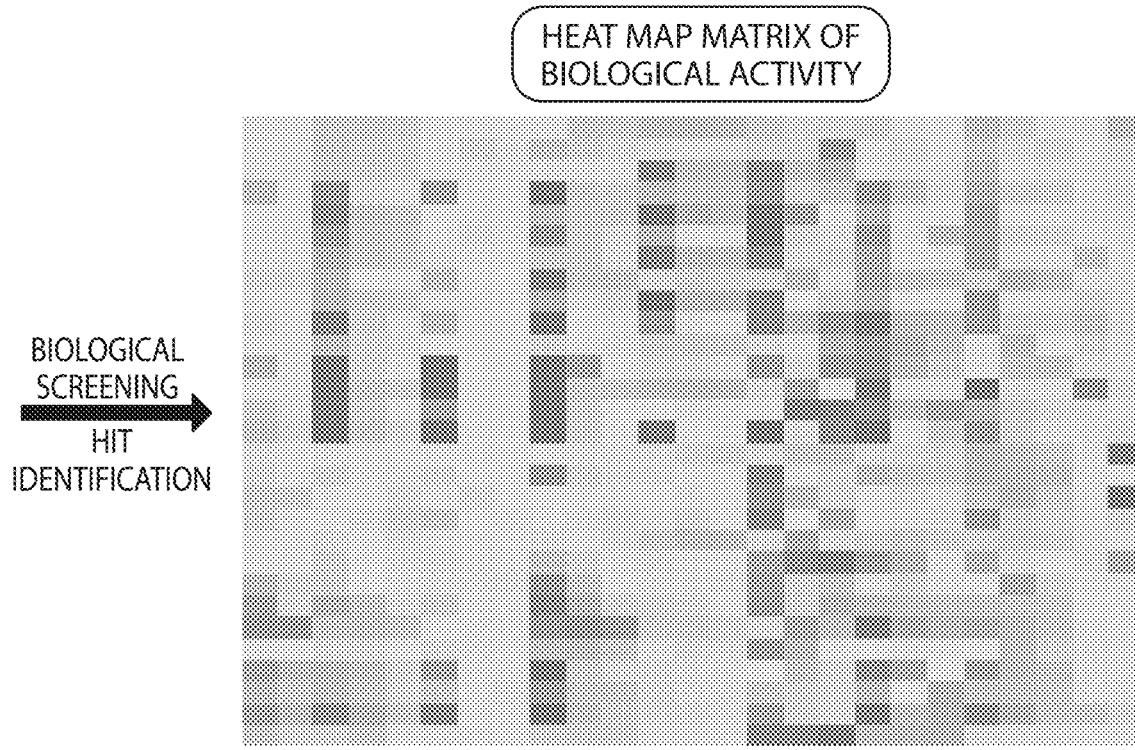
Figure 4A:
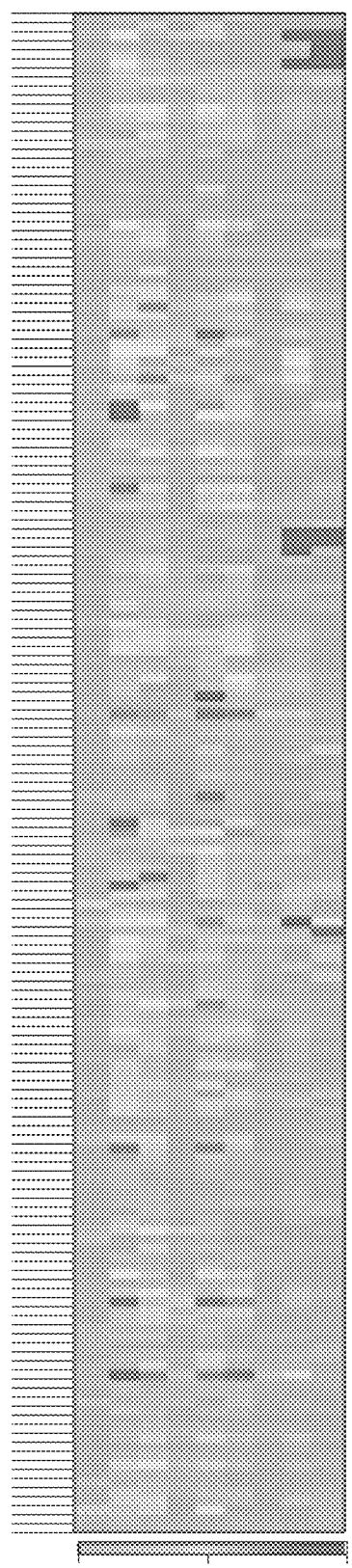
FIG. 4A: Heat Map Matrix of Biological Activity.
Figure 4C:
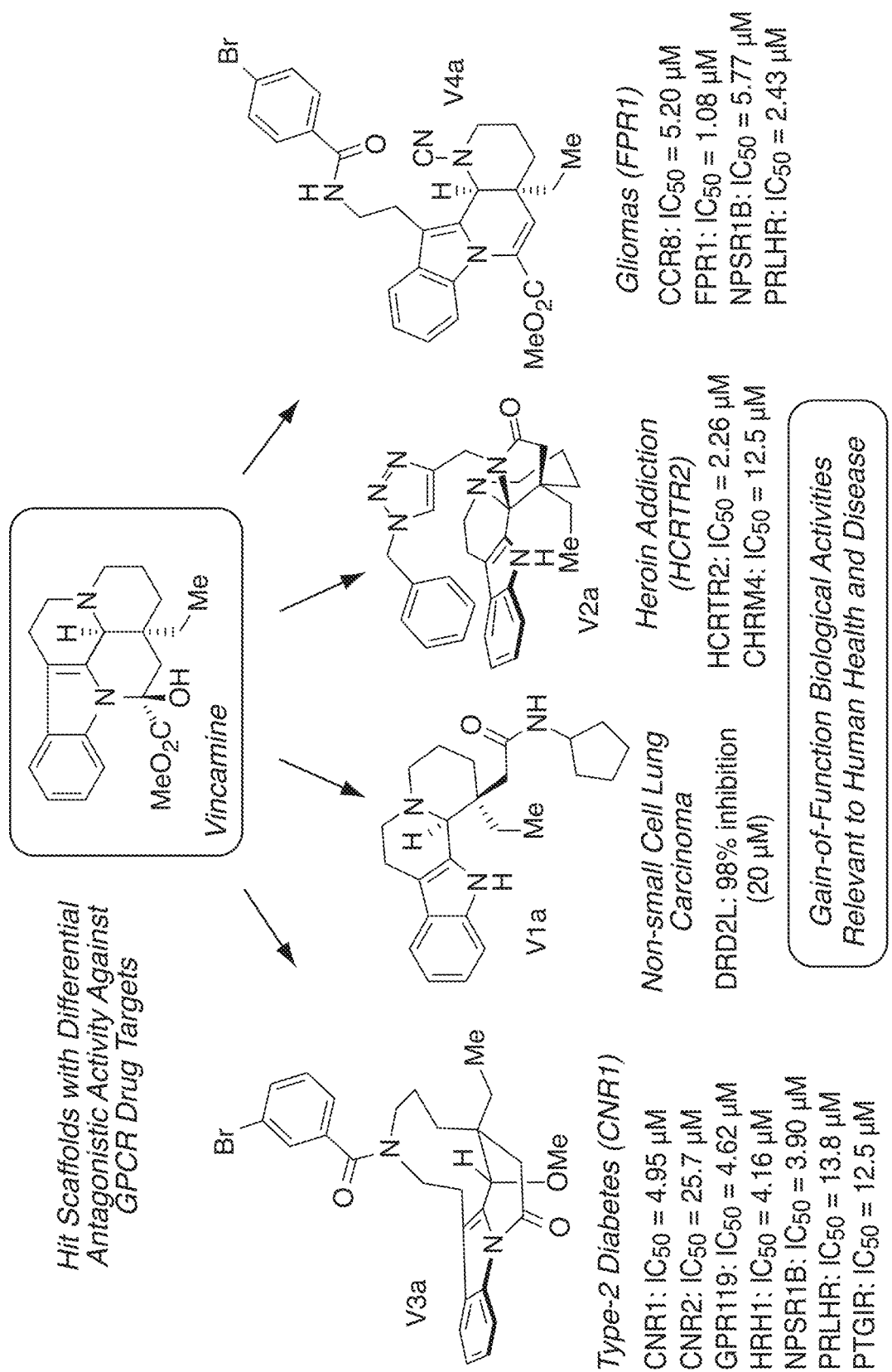
FIG. 4C. Hit Scaffolds with Differential Antagonistic Activity Against G Protein-Coupled Receptors (GPCR) Drug Targets, Relevant for Exemplary Therapeutic Effects Against Diseases. Depicted are IC$_{50}$ values against GPCR Drug Targets. Assays for IC$_{50}$ values were conducted via techniques recognized by one of ordinary skill in the art.
Figure 5:
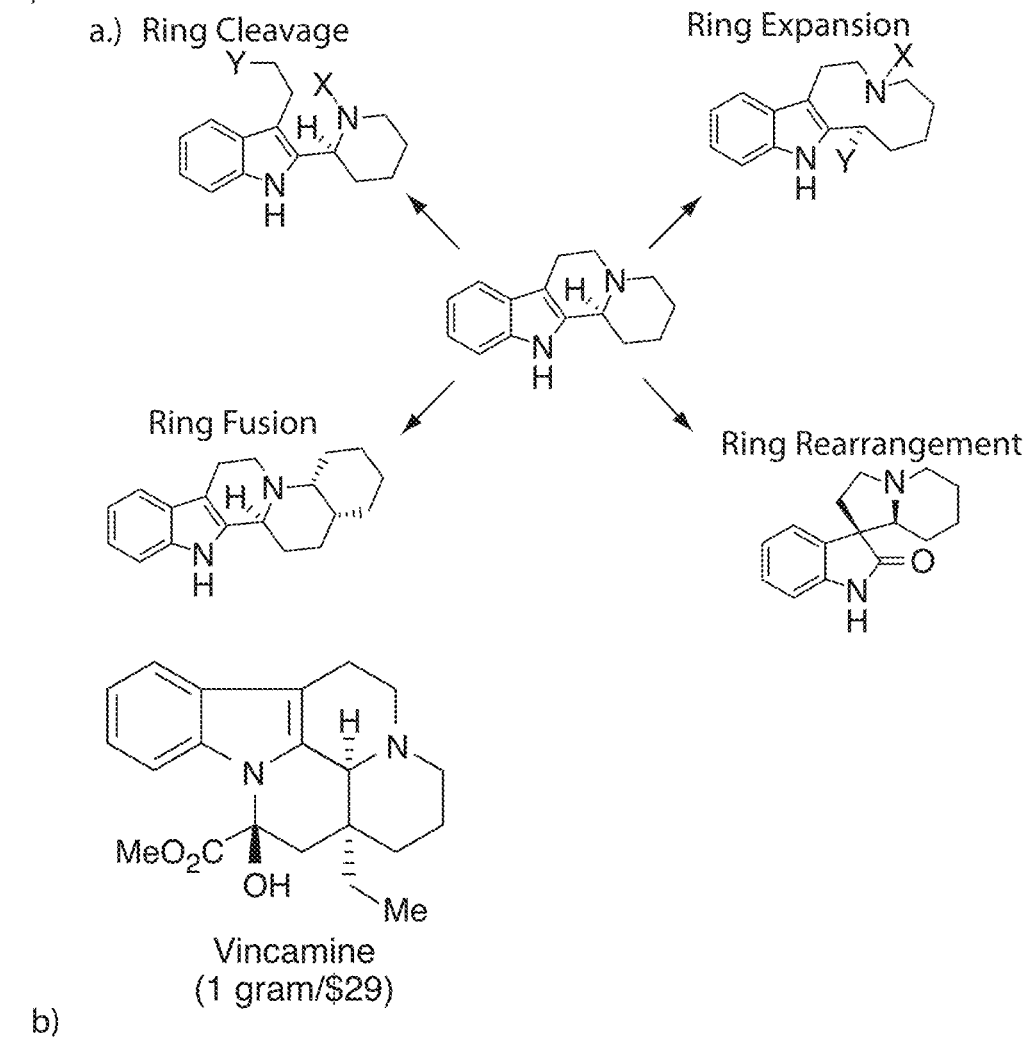
FIG. 5. Complexity-to-Diversity: Approach and Application.
Figure 5:
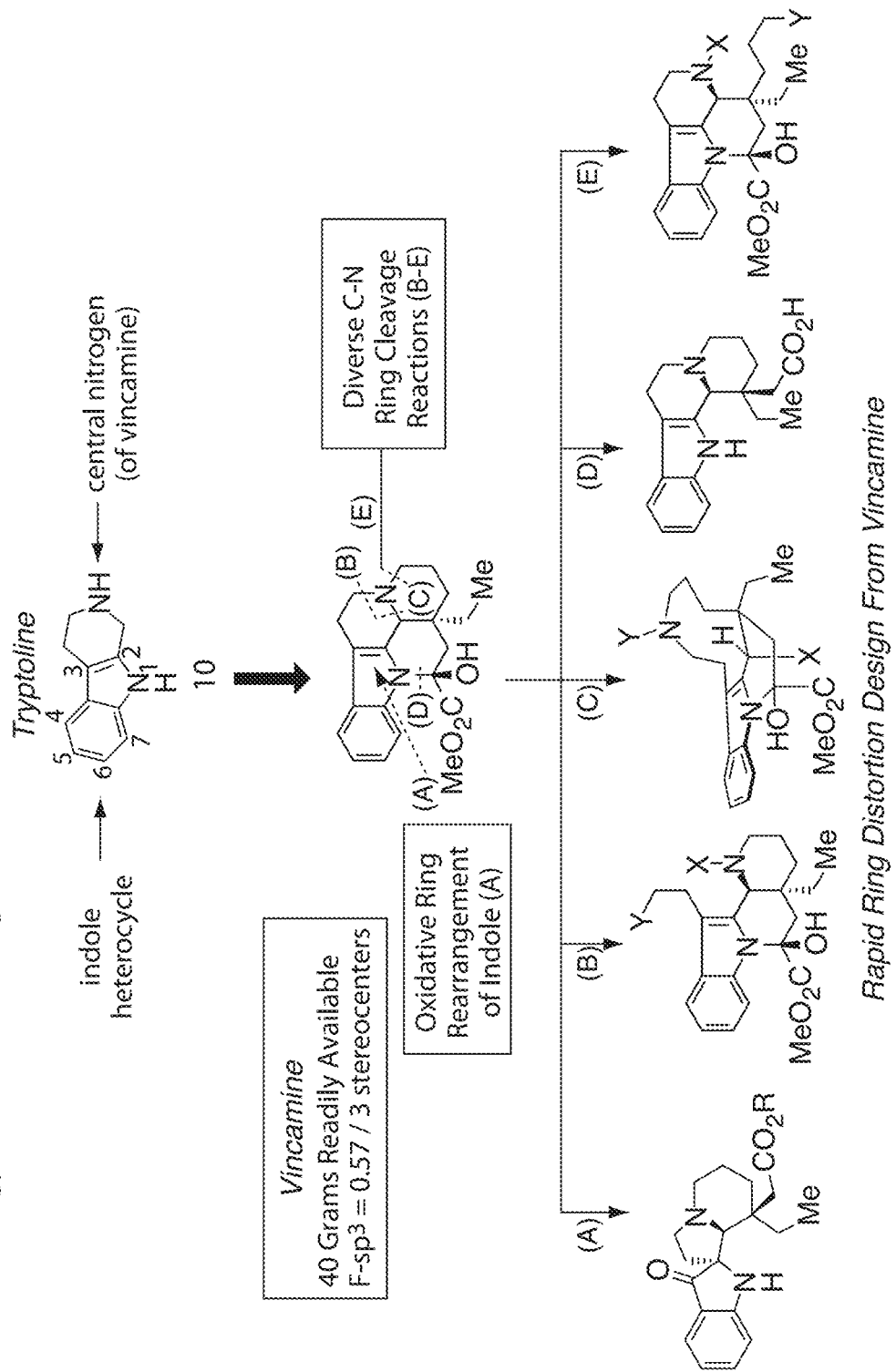
Figure 6:
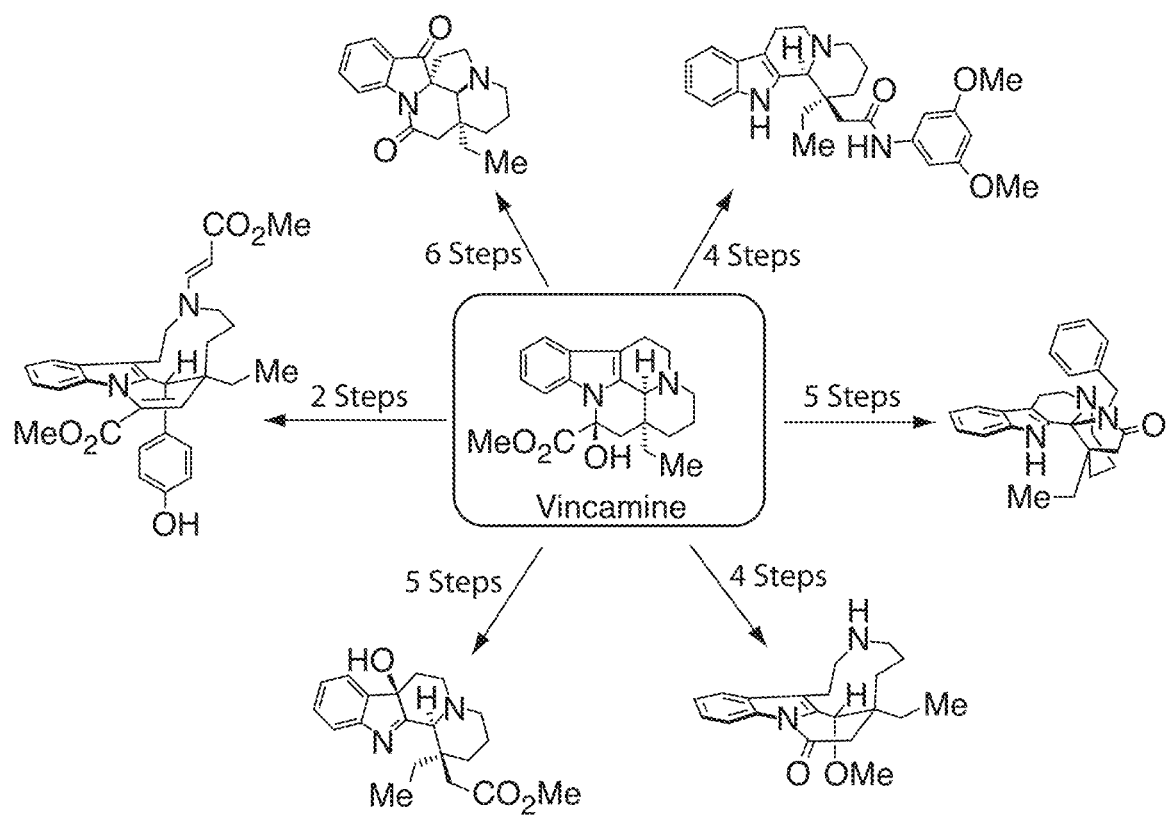
FIG. 6. Complex and Diverse Small Molecules from Vincamine.
Figure 7:
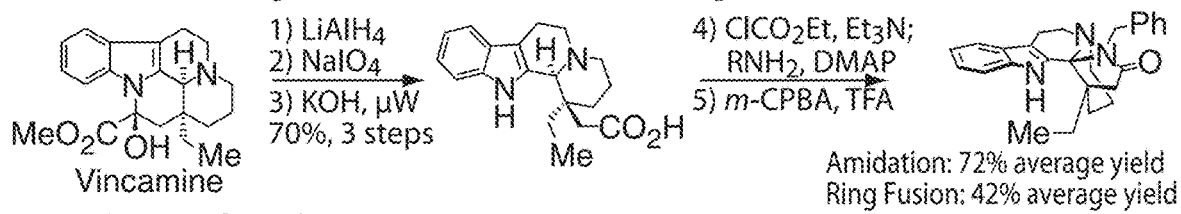
FIG. 7. Ring Cleavage and Diversification from Vincamine.
Figure 7:
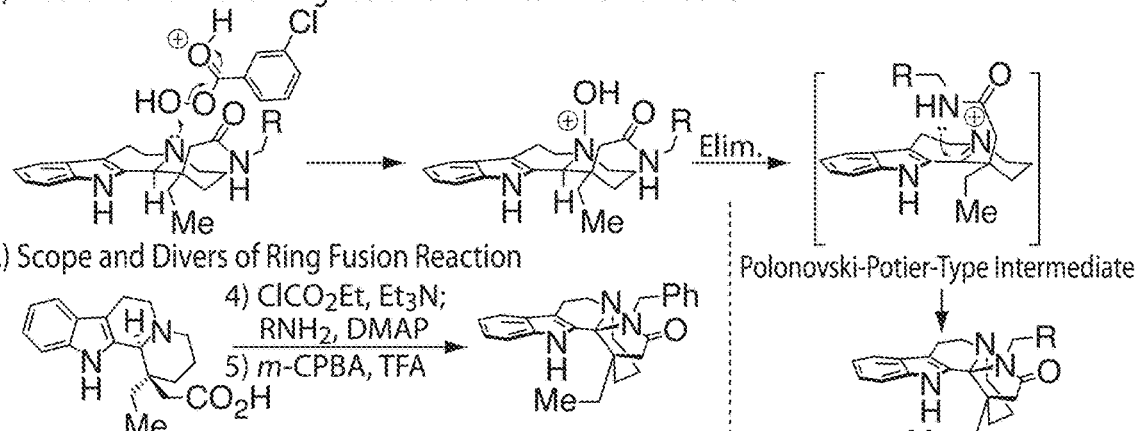
Figure 7:
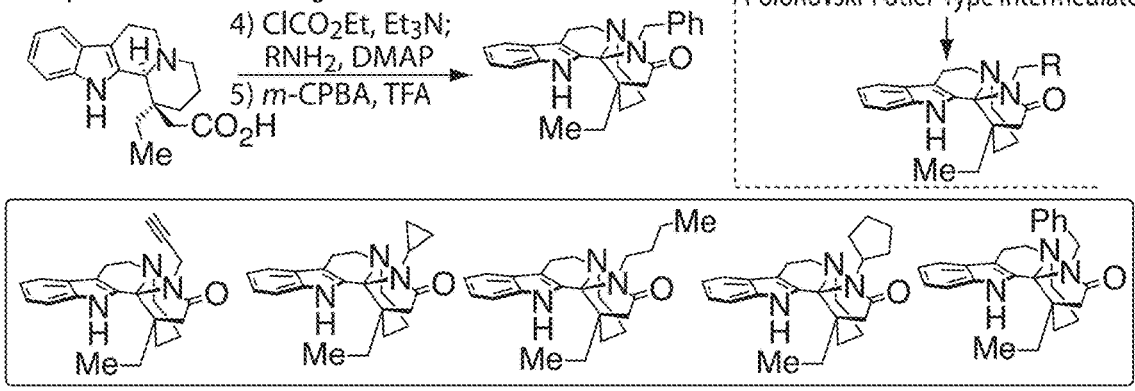
Figure 7:
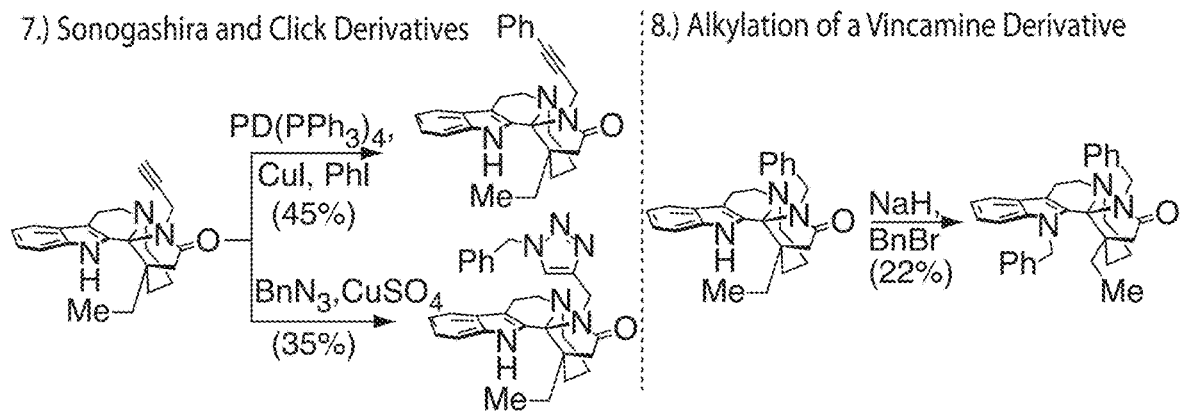
Figure 8:
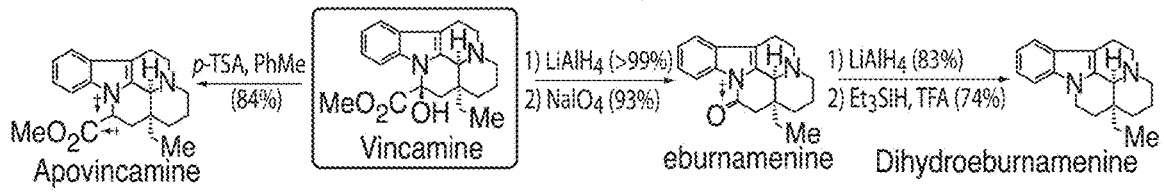
FIG. 8: Ring Distortion of Vincamine Leads to Interesting Reactivity.
Figure 8:
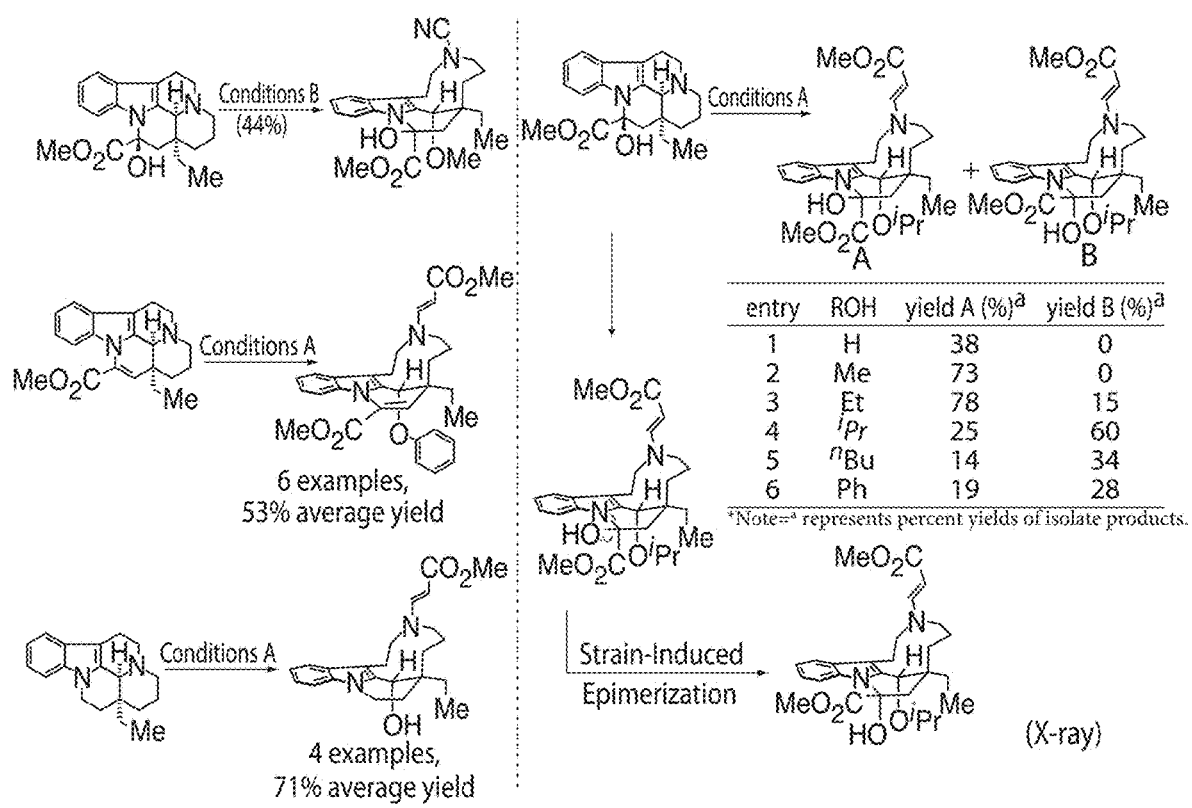
Figure 8:
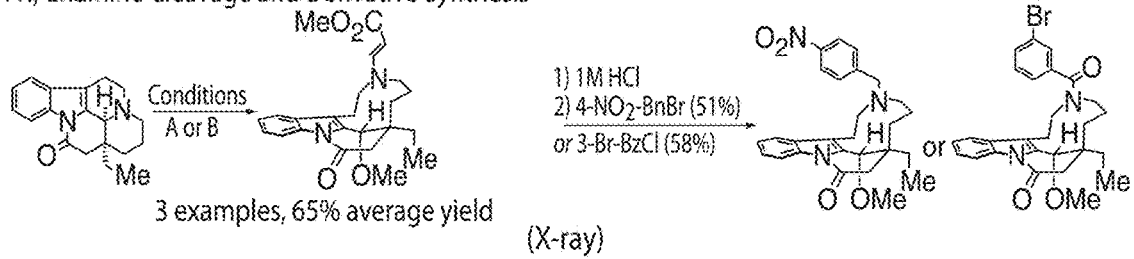
Figure 9:
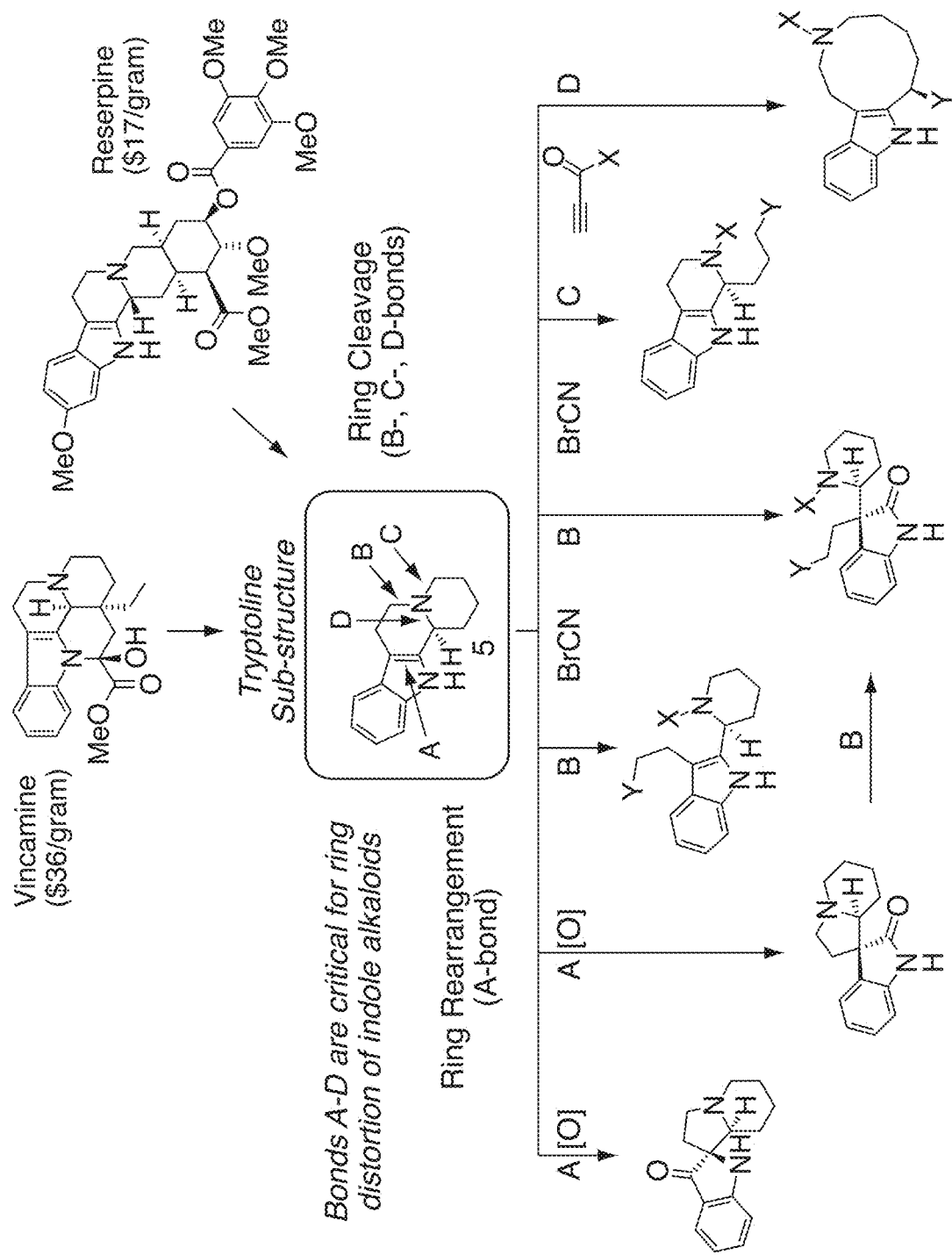
FIG. 9. Tryptoline Ring Distortion of Complex Indole Alkaloids
Figure 9A:
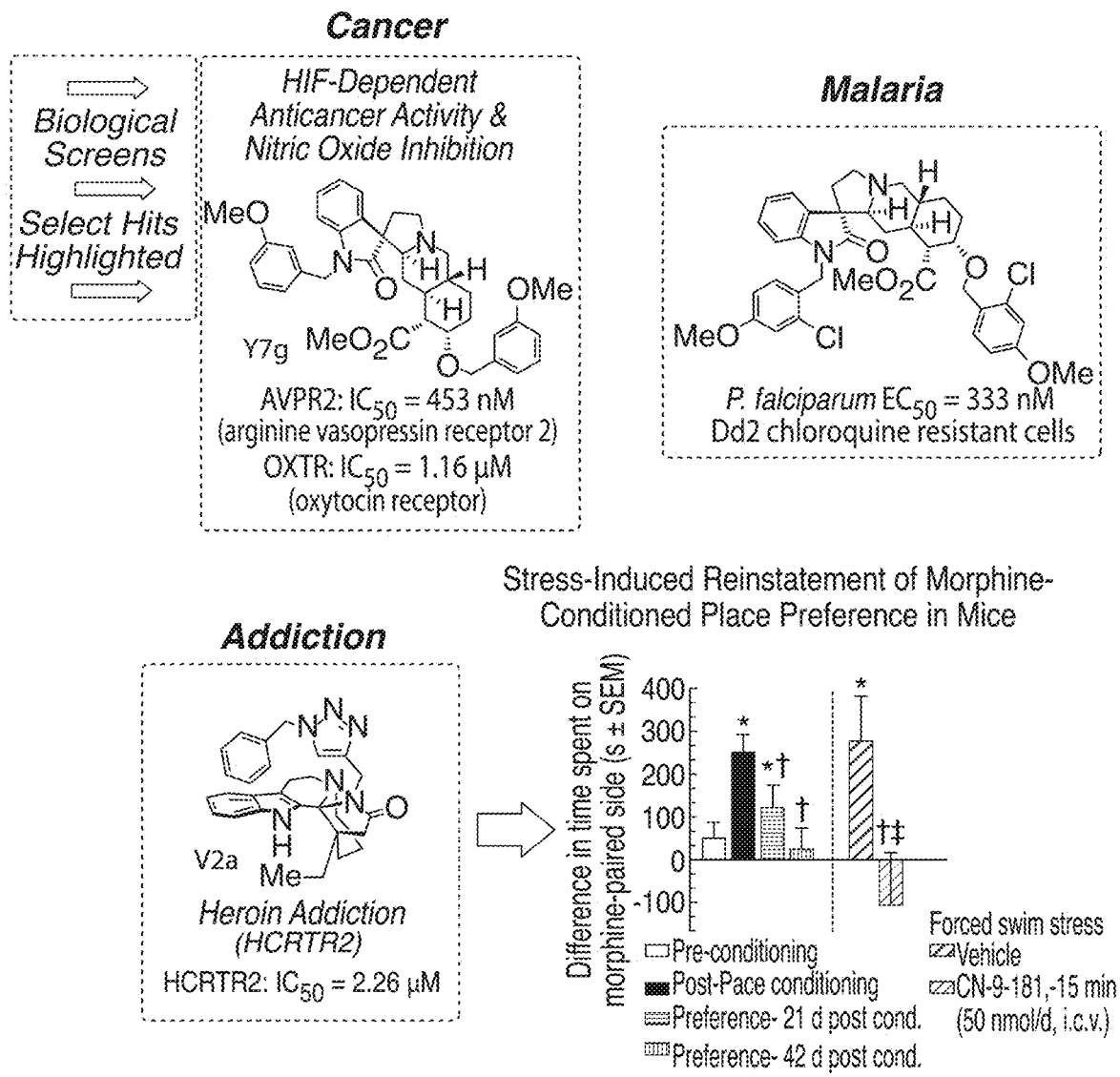
FIG. 9A. Application of Analogs Resulting from Tryptoline Ring Distortion of Complex Indole Alkaloids from FIG. 9.
Figure 10:
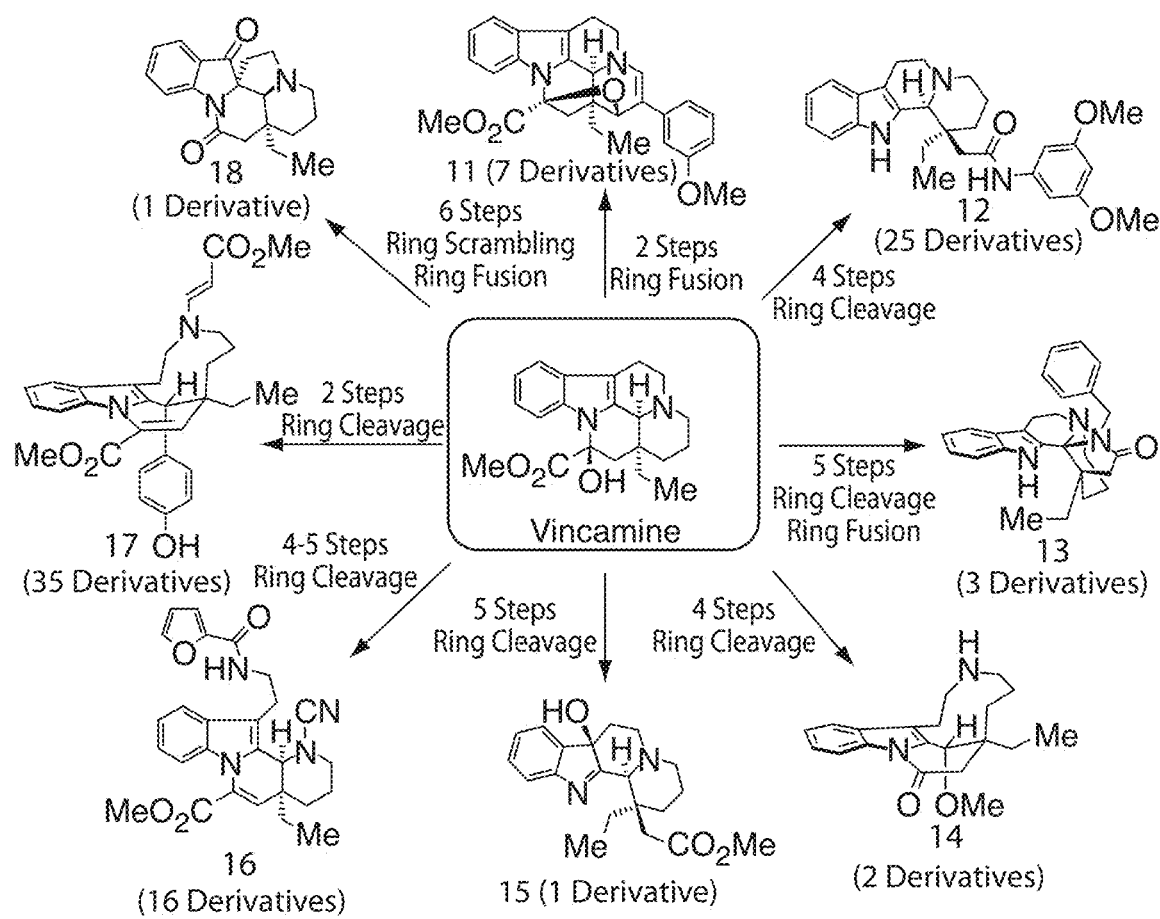
FIG. 10. Exemplary Small Molecules Derived from Vincamine.
Figure 11:
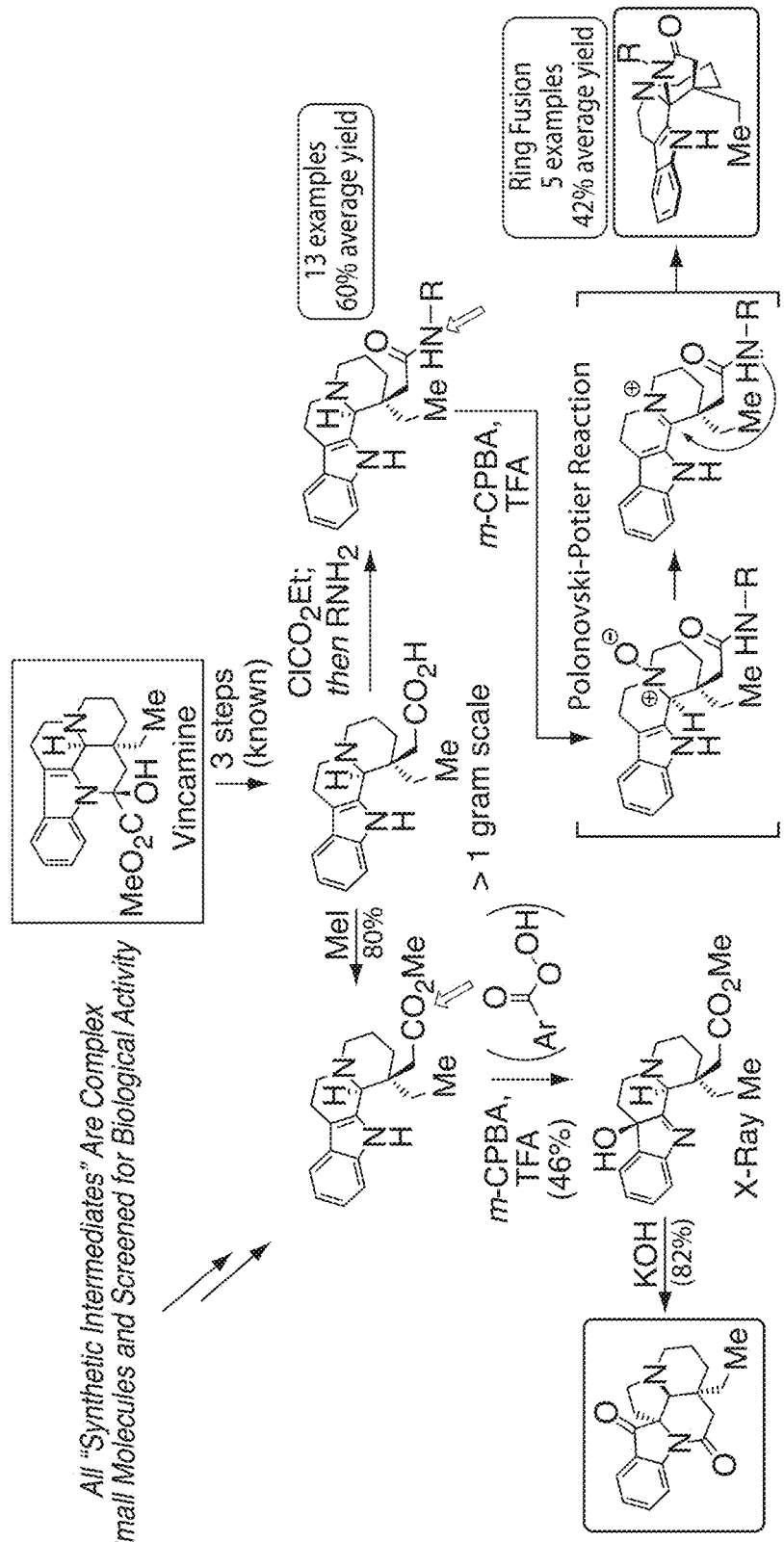
FIG. 11. Unanticipated Reactivity of Vincamine Analogs Leading to Novel Compounds.
Figure 12:
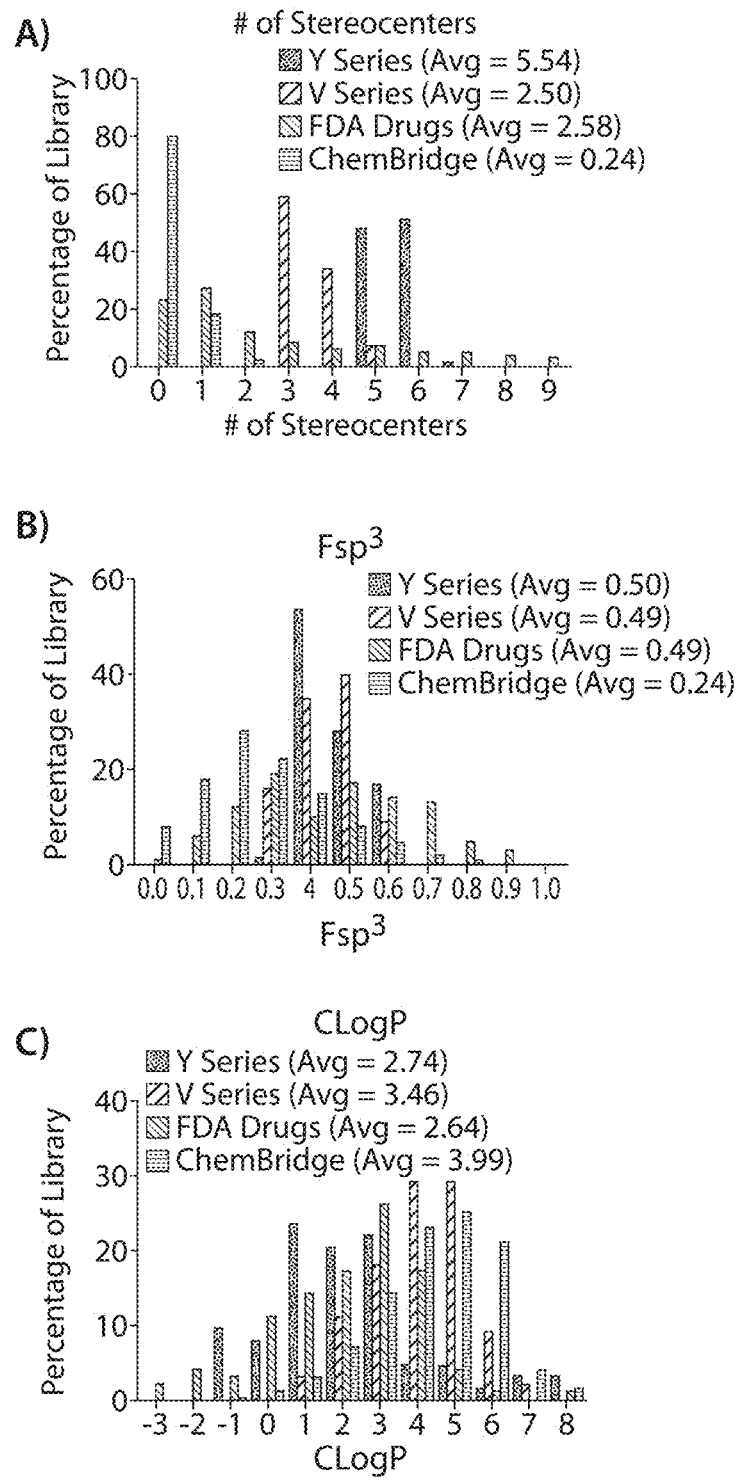
FIG. 12. Physicochemical Analysis of Ring Distortion Libraries of Alkaloids including Vincamine to ChemBridge and Top FDA Approved Drugs.
Figure 13:
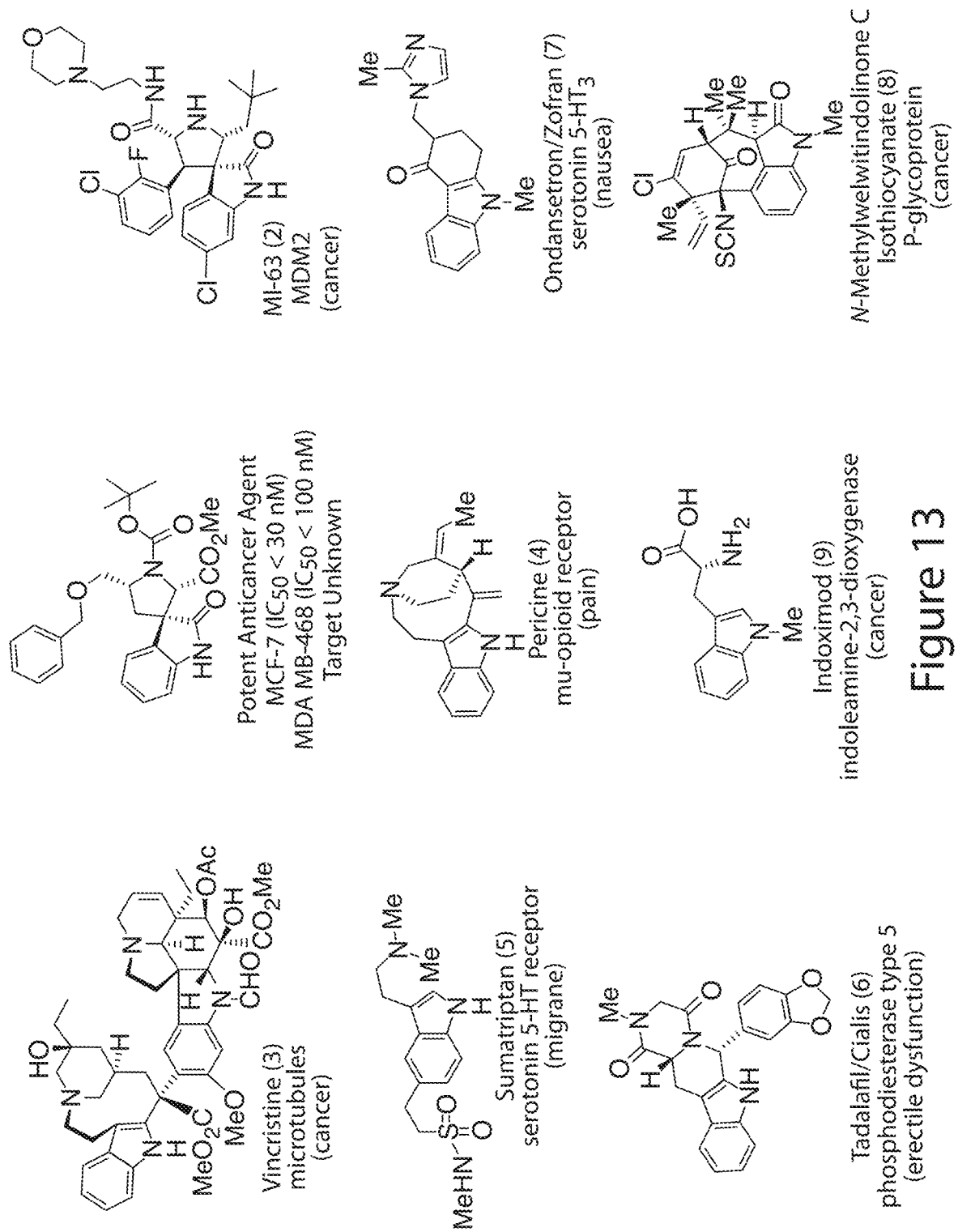
FIG. 13. Exemplary Medicinally Relevant Indole-Based Compounds with Diverse Targets and Activities.
Figure 14:
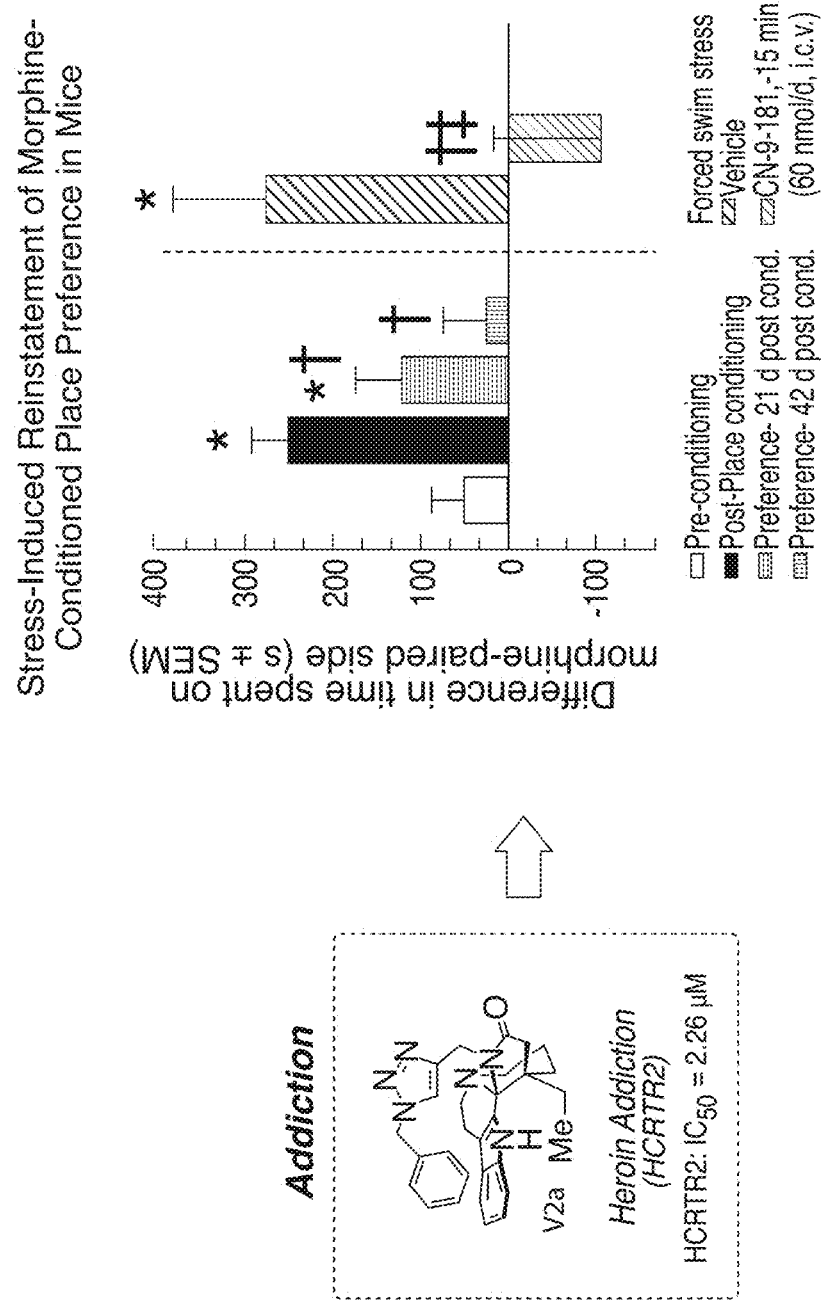
FIG. 14. Graph Showing Exemplary Compound (V2a) Inhibits Morphine Reinstatement in Mouse Model of Heroin Addiction. Stress-Induced Reinstatement of Morphine-Conditioned Place Preference in Mice. Depicted is the difference in time spent on morphine paired side in a mouse model (See protocol described in e.g., Shaham Y, Stewart J., Psychopharmacology (Berl). 1995 June; 119(3):334-41), including under the forced swim stress test. See Porsolt, Nature. 1977; 266:730-732; see also Archives internationales de pharmacodynamie et de therapie. 1977; 229:327-336.
Figure 15:
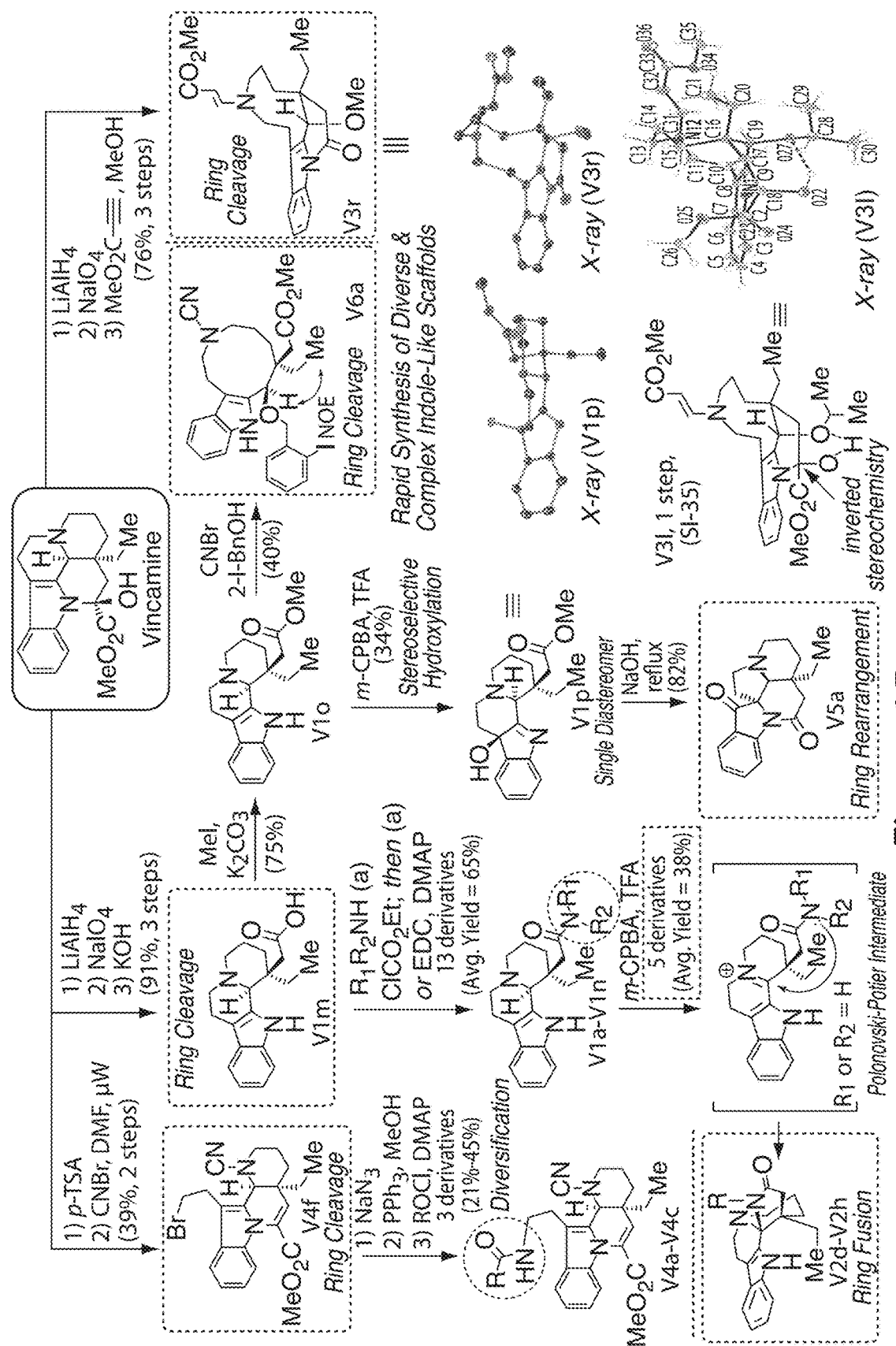
FIG. 15. Exemplary synthesis of analogs of vincamine via diverse and complex indole-like scaffolds, via ring cleavage, ring fusion, and/or ring rearrangement, starting from vincamine. Also depicted is an X-ray structure of an exemplary compound (V31).
Figure 16A:
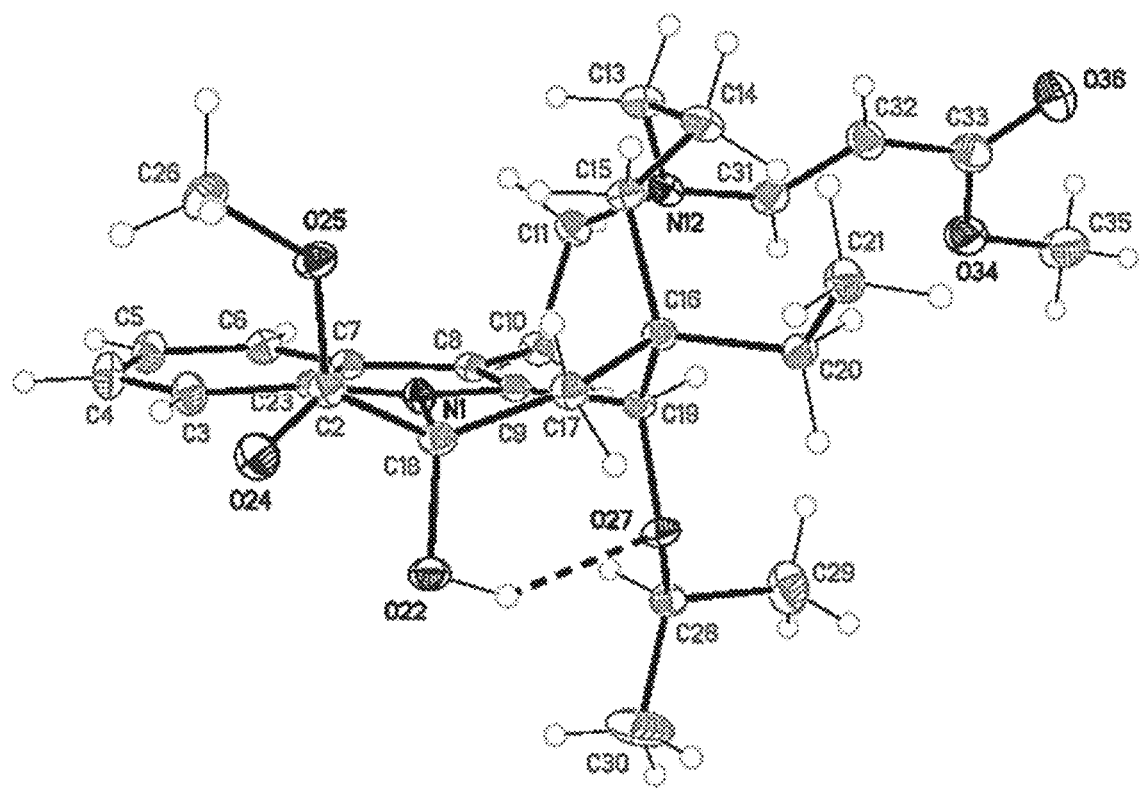
FIG. 16A. Raw crystal data and atomic numbering for V29.
Figure 16B:
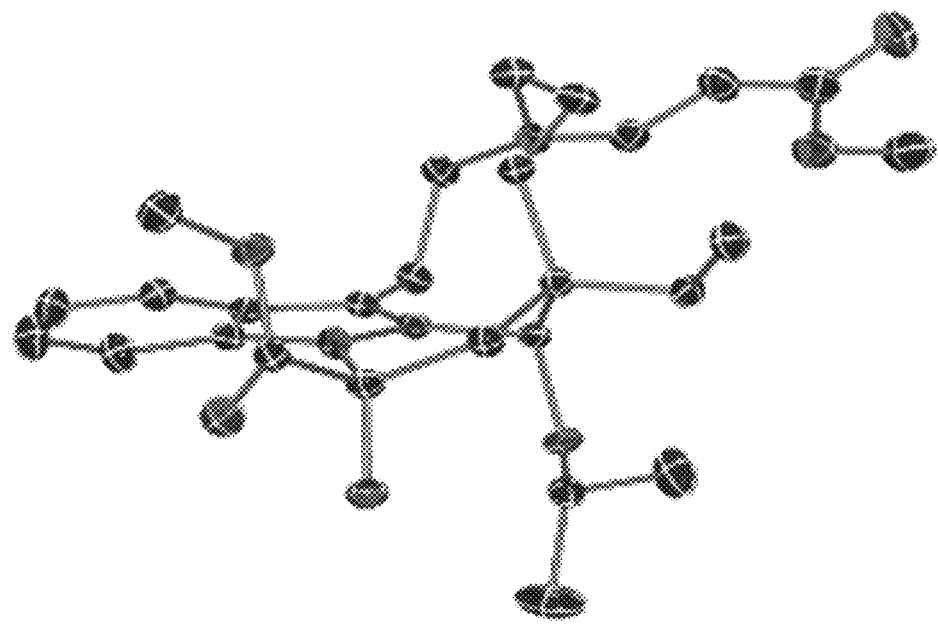
FIG. 16B. Refined crystal image of V29. Refined images were generated from Ortep3 and POV-Ray v3.7 programs from the raw X-Ray CIF file.
Figure 17A:
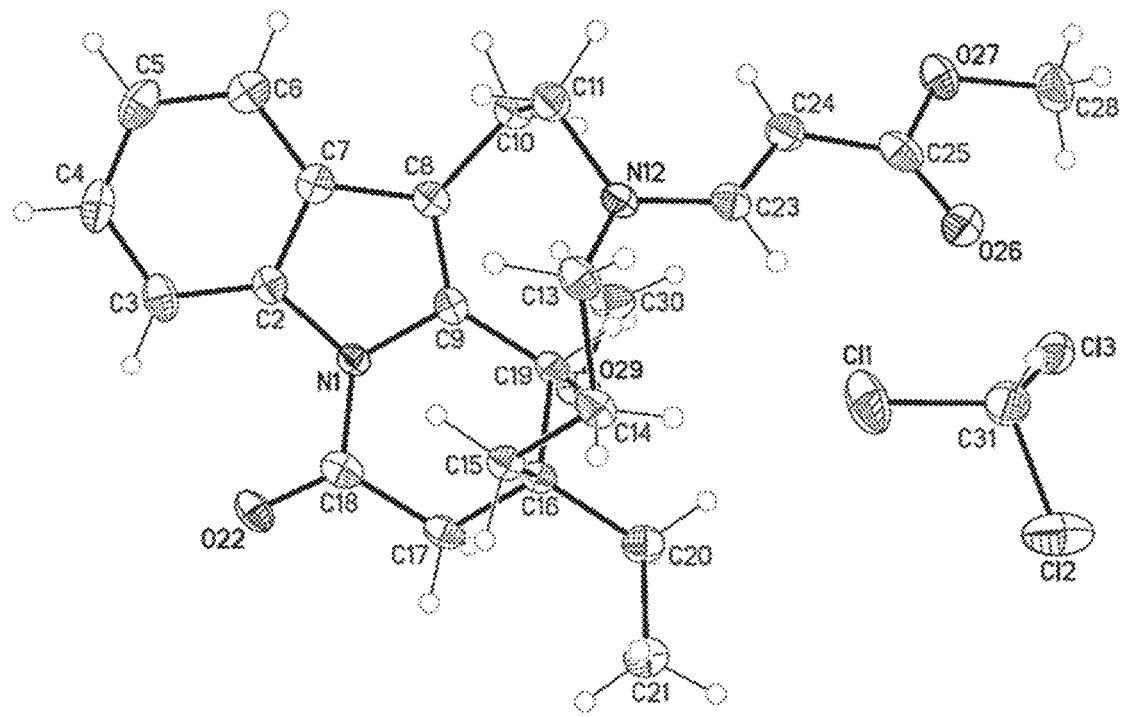
FIG. 17A. Raw crystal data and atomic numbering for V67.
Figure 17B:
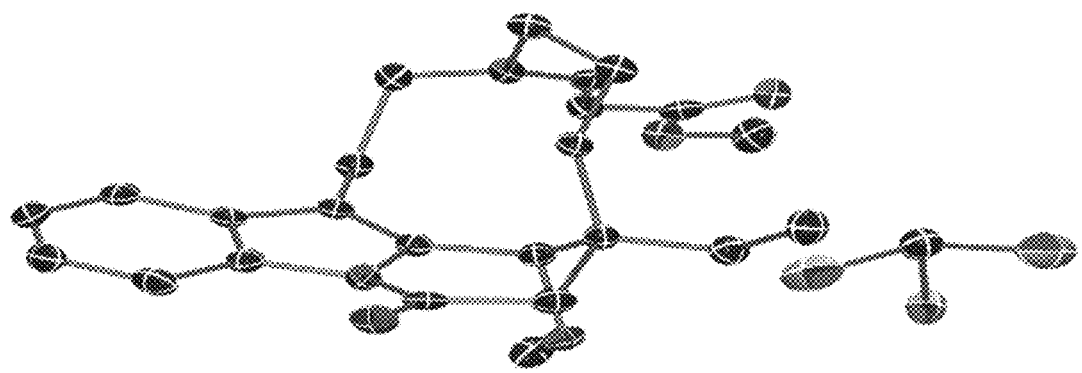
FIG. 17B. Refined crystal image of V67. Refined images were generated from Ortep3 and POV-Ray v3.7 programs from the raw X-Ray CIF file.
Figure 18A:
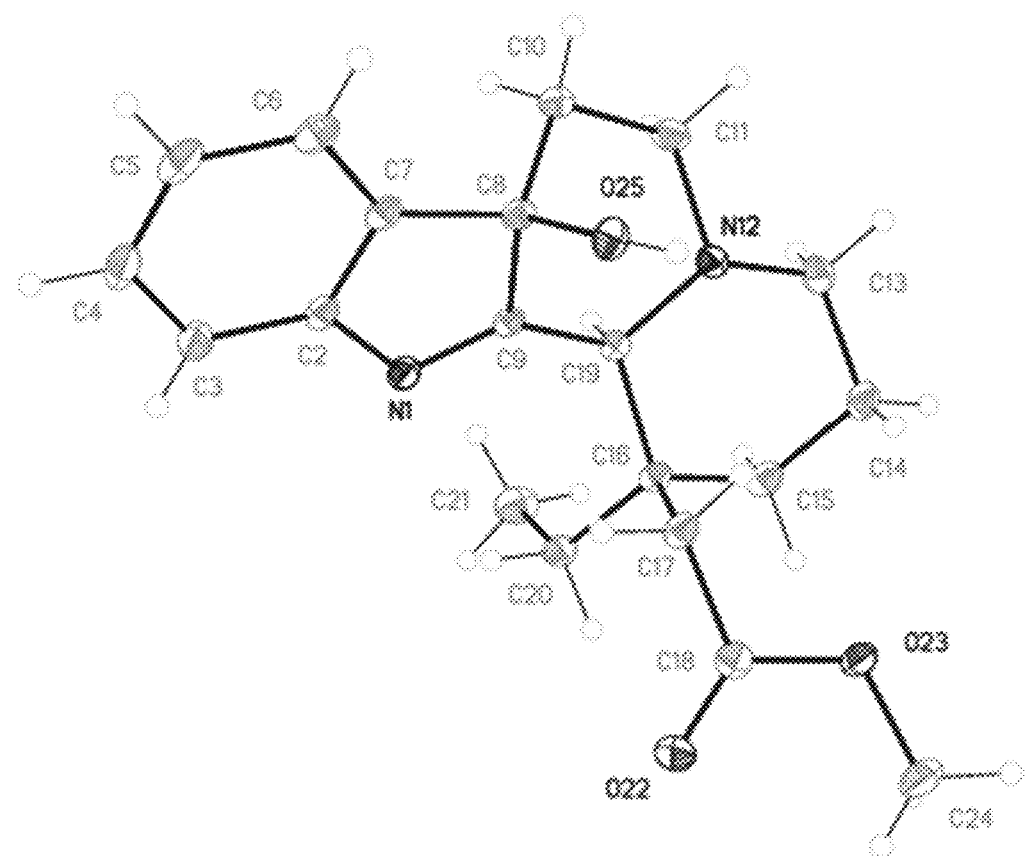
FIG. 18A. Raw crystal data and atomic numbering for V89.
Figure 18B:
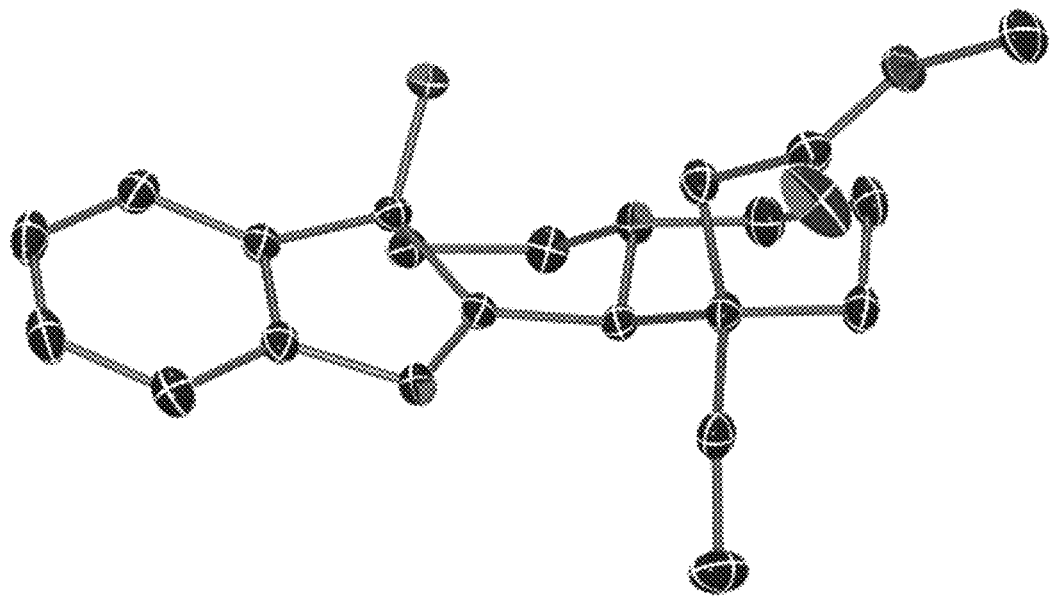
FIG. 18B. Refined crystal image of V89. Refined images were generated from Ortep3 and POV-Ray v3.7 programs from the raw X-Ray CIF file.
Figure 19:
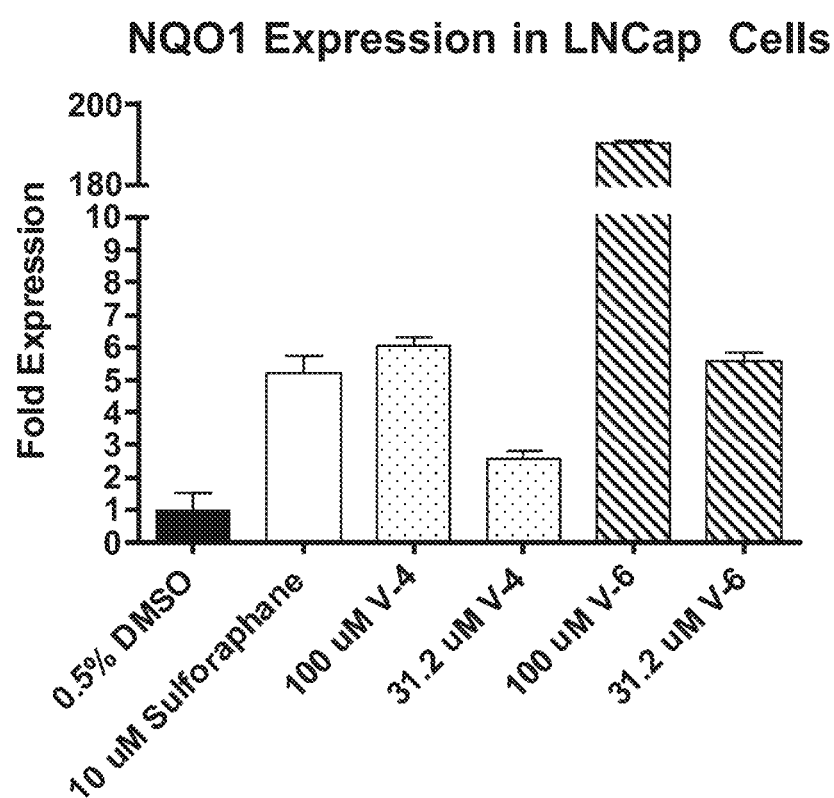
FIG. 19. Graph of NQ01 Expression in LNCaP cells via ARE luciferase assay in LNCaP cells.

The present invention provides compounds, for the prevention and/or treatment of a disease of a subject. The present invention further provides methods of using the compounds described herein, e.g., as therapeutics, e.g., in the prevention and/or treatment of diseases. The diseases include, but are not limited to, cancer (e.g., leukemia, melanoma, multiple myeloma), inflammatory diseases, CNS disorders, and infectious diseases. Also provided by the present disclosure are pharmaceutical compositions, methods of synthesis of a compound described herein, kits, methods, and uses of a compound of Formulae (I'), (I), (IA), (II'), (II), (IIA), (III"), (III'), (IIIA), (III), (IV), (V'), (V), (VI), (VII), (VIII'), (VIII), (IX'), (IX), and (X), as described herein.

Compounds

49 In certain embodiments, a compound described herein is a compound of any one of Formulae (I'), (I), (IA), (II'), (II), (IIA), (III"), (III'), (IIIA), (III), (IV), (V'), (V), (VI), (VII), (VIII'), (VIII), (IX'), (IX), and (X), or a pharmaceutically acceptable salt, solvate, hydrate, polymorph, co-crystal, tautomer, stereoisomer, isotopically labeled derivative, or prodrug thereof.

In one aspect of the present invention, provided are compounds of Formula (I'):

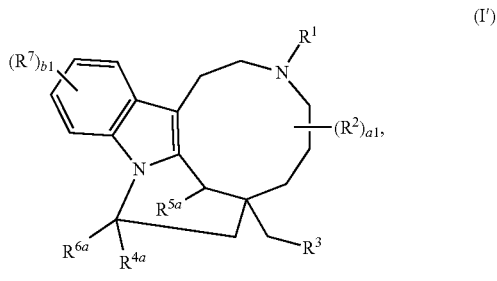

and pharmaceutically acceptable salts, solvates, hydrates, tautomers, and stereoisomers thereof, wherein:

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^2$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^3$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{4'}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{4a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —C(=O)OR$^4$, —N(R$^b$)$_2$, or —SR$^a$;

R$^5$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^{5a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^5$, —N(R$^b$)$_2$, or —SR$^a$;

R$^6$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^{6a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^6$, —N(R$^b$)$_2$, or —SR$^a$, or optionally R$^{4a}$ and R$^{6a}$ are taken together to form =O;

each instance of R$^7$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

a1 is 0, 1, 2, 3, 4, 5, 6, 7, 8, 9, or 10; and b1 is 0, 1, 2, 3, or 4.

In certain embodiments, a compound of Formula (I') is of Formula (I).

In one aspect of the present invention, provided are compounds of Formula (I):

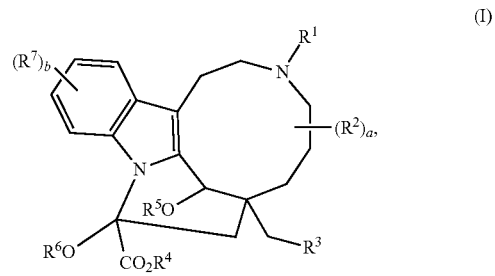

(I)

or a pharmaceutically acceptable salt, solvate, hydrate, polymorph, co-crystal, tautomer, stereoisomer, isotopically labeled derivative, or prodrug thereof, wherein:

R$^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^2$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

R$^3$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(Rb)$_2$, or —SR$^a$;

R$^4$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R$^5$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^6$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of R$^7$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

a is 1, 2, 3, 4, 5, 6, 7, 8, 9, or 10; and b is 1, 2, 3, or 4.

In certain embodiments, a compound described herein is of Formula (IA):

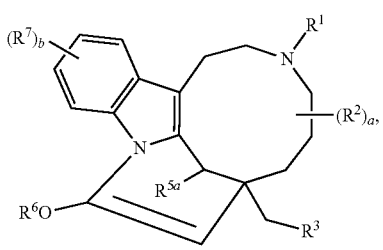

(IA)

or a pharmaceutically acceptable salt, solvate, hydrate, polymorph, co-crystal, tautomer, stereoisomer, isotopically labeled derivative, or prodrug thereof, wherein:

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^2$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^3$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^4$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^5$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{5a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^5$, —N(R$^b$)$_2$, or —SR$^a$;

$R^6$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^7$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

a is 1, 2, 3, 4, 5, 6, 7, 8, 9, or 10; and b is 1, 2, 3, or 4.

In certain embodiments, a compound described herein is of Formula (IA'):

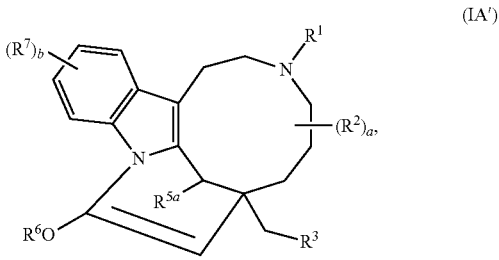

(IA')

or a pharmaceutically acceptable salt, solvate, hydrate, polymorph, co-crystal, tautomer, stereoisomer, isotopically labeled derivative, or prodrug thereof, wherein:

$R^1$, $R^2$, $R^3$, $R^5$, $R^6$, $R^7$, a, and b are as defined herein for (I') and (I);

a1 is 1, 2, 3, 4, 5, 6, 7, 8, 9, or 10; and b1 is 1, 2, 3, or 4.

Compounds of Formulae (I'), (I), (IA), and (IA') include R. In certain embodiments, $R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^1$ is hydrogen. In certain embodiments, $R^1$ is optionally substituted alkyl (e.g., substituted or unsubstituted $C_{1-6}$ alkyl). In certain embodiments, $R^1$ is optionally substituted alkenyl (e.g., substituted or unsubstituted $C_{2-6}$ alkenyl). In certain embodiments, $R^1$ is of the formula:

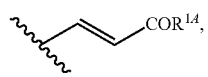

wherein: $R^{14}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^a$, or $-N(R^b)_2$, and $R^a$ and $R^b$ are as defined herein. In certain embodiments, $R^1$ is of the formula:

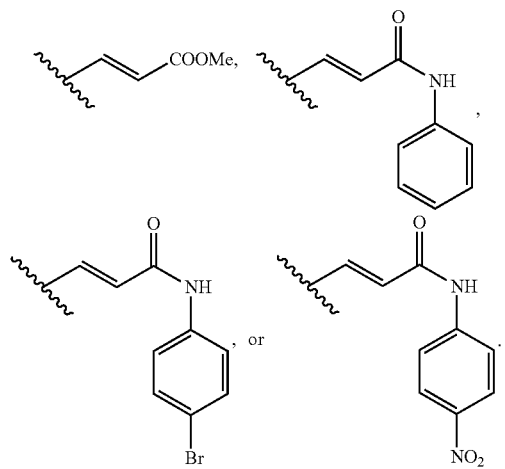

Compounds of Formulae (I'), (I), (IA), and (IA') include one or more instances of $R^2$. In certain embodiments, a is 1. In certain embodiments, a is 2. In certain embodiments, a is 3. In certain embodiments, a is 4. In certain embodiments, a is 5. In certain embodiments, a is 6. In certain embodiments, a is 7. In certain embodiments, a is 8. In certain embodiments, a is 9. In certain embodiments, a is 10. In certain embodiments, a1 is 0. In certain embodiments, a1 is 1. In certain embodiments, a1 is 2. In certain embodiments, a1 is 3. In certain embodiments, a1 is 4. In certain embodiments, a1 is 5. In certain embodiments, a1 is 6. In certain embodiments, a1 is 7. In certain embodiments, a1 is 8. In certain embodiments, a1 is 9. In certain embodiments, a1 is 10. In certain embodiments, at least one instance of $R^2$ is hydrogen, halogen, $-CN$, $-SCN$, $-NO_2$, $-N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, $-OR^a$, $-N(R^b)_2$, or $-SR^a$. In certain embodiments, at least one instance of $R^2$ is hydrogen. In certain embodiments, at least one instance of $R^2$ is halogen (e.g., F, Cl, Br, or I). In certain embodiments, at least one instance of $R^2$ is $-CN$. In certain embodiments, at least one instance of $R^2$ is substituted or unsubstituted alkyl (e.g., substituted or unsubstituted $C_{1-6}$ alkyl). In certain embodiments, at least one instance of $R^2$ is substituted or unsubstituted methyl. In certain embodiments, at least one instance of $R^2$ is substituted or unsubstituted ethyl. In certain embodiments, at least one instance of $R^2$ is substituted or unsubstituted propyl. In certain embodiments, at least one instance of $R^2$ is halogen, $-CN$, $-SCN$, $-NO_2$, $-N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, $-OR^a$, $-N(R^b)_2$, or $-SR^a$.

Compounds of Formulae (I'), (I), (IA), and (IA') include $R^3$. In certain embodiments, $R^3$ is hydrogen, halogen, $-CN$, $-SCN$, $-NO_2$, $-N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, $-OR^a$, $-N(R^b)_2$, or $-SR^a$. In certain embodiments, $R^3$ is hydrogen. In certain embodiments, $R^3$ is halogen (e.g., F, Cl, Br, or I). In certain embodiments, $R^3$ is $-CN$. In certain embodiments, $R^3$ is $-SCN$. In certain embodiments, $R^3$ is $-NO_2$. In certain embodiments, $R^3$ is $-N_3$. In certain embodiments, $R^3$ is optionally substituted alkyl (e.g., substituted or unsubstituted $C_{1-6}$ alkyl). In certain embodiments, $R^3$ is substituted methyl. In certain embodiments, $R^3$ is unsubstituted methyl. In certain embodiments, $R^3$ is substituted or unsubstituted ethyl. In certain embodiments, $R^3$ is optionally substituted acyl (e.g., $-C(=O)Me$). In certain embodiments, $R^3$ is optionally substituted alkenyl (e.g., substituted or unsubstituted $C_{2-6}$ alkenyl). In certain embodiments, $R^3$ is optionally substituted alkynyl (e.g., substituted or unsubstituted $C_{2-6}$ alkynyl). In certain embodiments, $R^3$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^3$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^3$ is optionally substituted aryl (e.g., substituted or unsubstituted, 6- to 10-membered aryl). In certain embodiments, $R^3$ is optionally substituted benzyl. In certain embodiments, $R^3$ is optionally substituted phenyl. In certain embodiments, $R^3$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^3$ is $-OR^a$ (e.g., $-OH$ or $-OMe$). In certain embodiments, $R^3$ is $-OH$. In certain embodiments, $R^3$ is $-OMe$. In certain embodiments, $R^3$ is $-N(R^b)_2$ (e.g., $-NMe_2$). In certain embodiments, $R^3$ is $-NMe_2$. In certain embodiments, $R^3$ is $-SR^a$ (e.g., $-SH$, $-SMe$). In certain embodiments, $R^3$ is optionally substituted sulfonyl. In certain embodiments, $R^3$ is halogen, $-CN$, $-SCN$, $-NO_2$, $-N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$.

Compounds of Formula (I) include R$^4$. In certain embodiments, R$^4$ is hydrogen. In certain embodiments, R$^4$ is optionally substituted alkyl (e.g., substituted or unsubstituted C$_{1-6}$ alkyl). In certain embodiments, R$^4$ is substituted methyl. In certain embodiments, R$^4$ is unsubstituted methyl. In certain embodiments, R$^4$ is substituted or unsubstituted ethyl. In certain embodiments, R$^4$ is optionally substituted acyl (e.g., —C(=O)Me). In certain embodiments, R$^4$ is optionally substituted alkenyl (e.g., substituted or unsubstituted C$_{2-6}$ alkenyl). In certain embodiments, R$^4$ is optionally substituted alkynyl (e.g., substituted or unsubstituted C$_{2-6}$ alkynyl). In certain embodiments, R$^4$ is optionally substituted carbocyclyl (e.g., substituted or unsubstituted, 3- to 7-membered, monocyclic carbocyclyl comprising zero, one, or two double bonds in the carbocyclic ring system). In certain embodiments, R$^4$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^4$ is optionally substituted aryl (e.g., substituted or unsubstituted, 6- to 10-membered aryl). In certain embodiments, R$^4$ is optionally substituted benzyl. In certain embodiments, R$^4$ is optionally substituted phenyl. In certain embodiments, R$^4$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^4$ is optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl.

Compounds of Formula (I') include R$^{4a}$. In certain embodiments, R$^{4a}$ is hydrogen. In certain embodiments, R$^{4a}$ is optionally substituted alkyl (e.g., substituted or unsubstituted C$_{1-6}$ alkyl). In certain embodiments, R$^{4a}$ is substituted methyl. In certain embodiments, R$^{4a}$ is unsubstituted methyl. In certain embodiments, R$^{4a}$ is substituted or unsubstituted ethyl. In certain embodiments, R$^{4a}$ is optionally substituted acyl (e.g., —C(=O)Me). In certain embodiments, R$^{4a}$ is optionally substituted alkenyl (e.g., substituted or unsubstituted C$_{2-6}$ alkenyl). In certain embodiments, R$^{4a}$ is optionally substituted alkynyl (e.g., substituted or unsubstituted C$_{2-6}$ alkynyl). In certain embodiments, R$^{4a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, R$^{4a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{4a}$ is optionally substituted aryl (e.g., substituted or unsubstituted, 6- to 10-membered aryl). In certain embodiments, R$^{4a}$ is optionally substituted benzyl. In certain embodiments, R$^{4a}$ is optionally substituted phenyl. In certain embodiments, R$^{4a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^{4a}$ is —OR$^a$ (e.g., —OH or —OMe). In certain embodiments, R$^{4a}$ is —C(=O)OR$^a$ (e.g., —C(=O)OH or —C(=O)OMe). In certain embodiments, R$^{4a}$ is —OH. In certain embodiments, R$^{4a}$ is —OMe. In certain embodiments, R$^{4a}$ is —N(R$^b$)$_2$ (e.g., —NMe$_2$). In certain embodiments, R$^{4a}$ is —NMe$_2$. In certain embodiments, R$^{4a}$ is —SR$^a$ (e.g., —SMe). In certain embodiments, R$^{4a}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —C(=O)OR$^4$, —N(R$^b$)$_2$, or —SR$^a$.

Compounds of Formulae (I'), (IA), and (IA') include R$^{5a}$. In certain embodiments, R$^{5a}$ is hydrogen. In certain embodiments, R$^{5a}$ is optionally substituted alkyl (e.g., substituted or unsubstituted C$_{1-6}$ alkyl). In certain embodiments, R$^{5a}$ is substituted methyl. In certain embodiments, R$^{5a}$ is unsubstituted methyl. In certain embodiments, R$^{5a}$ is substituted or unsubstituted ethyl. In certain embodiments, R$^{5a}$ is optionally substituted acyl (e.g., —C(=O)Me). In certain embodiments, R$^{5a}$ is optionally substituted alkenyl (e.g., substituted or unsubstituted C$_{2-6}$ alkenyl). In certain embodiments, R$^{5a}$ is optionally substituted alkynyl (e.g., substituted or unsubstituted C$_{2-6}$ alkynyl). In certain embodiments, R$^{5a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, R$^{5a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{5a}$ is optionally substituted aryl (e.g., substituted or unsubstituted, 6- to 10-membered aryl). In certain embodiments, R$^{5a}$ is optionally substituted benzyl. In certain embodiments, R$^{5a}$ is optionally substituted phenyl. In certain embodiments, R$^{5a}$ is of the formula:

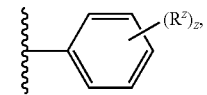

wherein R$^z$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$; and z is 0, 1, 2, 3, 4, or 5. In certain embodiments, R$^{5a}$ is of the formula

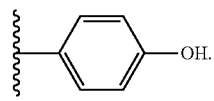

In certain embodiments, R$^{5a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{5a}$ is optionally substituted sulfonyl. In certain embodiments, $R^{5a}$ is —$OR^a$ (e.g., —OH or —OMe). In certain embodiments, $R^{5a}$ is —OH. In certain embodiments, $R^{5a}$ is —$O(R^5)$, wherein $R^5$ is optionally substituted alkyl or optionally substituted aryl. In certain embodiments, $R^{5a}$ is —O(substituted or unsubstituted $C_{1-6}$ alkyl). In certain embodiments, $R^{5a}$ is —OMe. In certain embodiments, $R^{5a}$ is —OEt. In certain embodiments, $R^{5a}$ is —O(iPr). In certain embodiments, $R^{5a}$ is —O(n-Bu). In certain embodiments, $R^{5a}$ is —O(optionally substituted phenyl). In certain embodiments, $R^{5a}$ is —OPh. In certain embodiments, $R^{5a}$ is —$N(R^b)_2$ (e.g., —$NH_2$, —$NMe_2$). In certain embodiments, $R^{5a}$ is —$NMe_2$. In certain embodiments, $R^{5a}$ is —$SR^a$ (e.g., —SMe). In certain embodiments, $R^{5a}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —$OR^5$, —$N(R^b)_2$, or —$SR^a$.

Compounds of Formulae (I'), (I), (IA), and (IA') include $R^5$. In certain embodiments, $R^5$ is hydrogen. In certain embodiments, $R^5$ is optionally substituted alkyl (e.g., substituted or unsubstituted $C_{1-6}$ alkyl). In certain embodiments, $R^5$ is substituted methyl. In certain embodiments, $R^5$ is unsubstituted methyl. In certain embodiments, $R^5$ is substituted or unsubstituted ethyl. In certain embodiments, $R^5$ is unsubstituted ethyl. In certain embodiments, $R^5$ is optionally substituted acyl (e.g., —C(=O)Me). In certain embodiments, $R^5$ is optionally substituted alkenyl (e.g., substituted or unsubstituted $C_{2-6}$ alkenyl). In certain embodiments, $R^5$ is optionally substituted alkynyl (e.g., substituted or unsubstituted $C_{2-6}$ alkynyl). In certain embodiments, $R^5$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^5$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^5$ is optionally substituted aryl (e.g., substituted or unsubstituted, 6- to 10-membered aryl). In certain embodiments, $R^5$ is optionally substituted benzyl. In certain embodiments, $R^5$ is optionally substituted phenyl. In certain embodiments, $R^5$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; substituted or unsubstituted, 9- to 10-membered, bicyclic heteroaryl, wherein one, two, three, or four atoms in the heteroaryl ring system are independently nitrogen, oxygen, or sulfur). In certain embodiments, $R^5$ is an oxygen protecting group. In certain embodiments, $R^5$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

Compounds of Formula (I') include $R^{6a}$. In certain embodiments, $R^{6a}$ is hydrogen. In certain embodiments, $R^{6a}$ is optionally substituted alkyl (e.g., substituted or unsubstituted $C_{1-6}$ alkyl). In certain embodiments, $R^{6a}$ is substituted methyl. In certain embodiments, $R^{6a}$ is unsubstituted methyl. In certain embodiments, $R^{6a}$ is substituted or unsubstituted ethyl. In certain embodiments, $R^{6a}$ is optionally substituted acyl (e.g., —C(=O)Me). In certain embodiments, $R^{6a}$ is optionally substituted alkenyl (e.g., substituted or unsubstituted $C_{2-6}$ alkenyl). In certain embodiments, $R^{6a}$ is optionally substituted alkynyl (e.g., substituted or unsubstituted $C_{2-6}$ alkynyl). In certain embodiments, $R^{6a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{6a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{6a}$ is optionally substituted aryl (e.g., substituted or unsubstituted, 6- to 10-membered aryl). In certain embodiments, $R^{6a}$ is optionally substituted benzyl. In certain embodiments, $R^{6a}$ is optionally substituted phenyl. In certain embodiments, $R^{6a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{6a}$ is —$OR^6$ (e.g., —OH, —OMe, or —OPh). In certain embodiments, $R^{6a}$ is —OH. In certain embodiments, $R^{6a}$ is —OMe. In certain embodiments, $R^{6a}$ is —$N(R^b)_2$ (e.g., —$NMe_2$). In certain embodiments, $R^{6a}$ is —$NMe_2$. In certain embodiments, $R^{6a}$ is —$SR^a$ (e.g., —SMe). In certain embodiments, $R^{4a}$ and $R^{6a}$ are taken together to form =O. In certain embodiments, $R^{4a}$ and $R^{6a}$ are both hydrogen. In certain embodiments, $R^{6a}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^6$, —$N(R^b)_2$, or —$SR^a$, or optionally $R^{4a}$ and $R^{6a}$ are taken together to form =O.

Compounds of Formulae (I'), (I), (IA), and (IA') include $R^6$. In certain embodiments, $R^6$ is hydrogen. In certain embodiments, $R^6$ is optionally substituted alkyl (e.g., substituted or unsubstituted $C_{1-6}$ alkyl). In certain embodiments, $R^6$ is substituted methyl. In certain embodiments, $R^6$ is unsubstituted methyl. In certain embodiments, $R^6$ is substituted or unsubstituted ethyl. In certain embodiments, $R^6$ is unsubstituted ethyl. In certain embodiments, $R^6$ is optionally substituted acyl (e.g., —C(=O)Me). In certain embodiments, $R^6$ is optionally substituted alkenyl (e.g., substituted or unsubstituted $C_{2-6}$ alkenyl). In certain embodiments, $R^6$ is optionally substituted alkynyl (e.g., substituted or unsubstituted $C_{2-6}$ alkynyl). In certain embodiments, $R^6$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^6$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^6$ is optionally substituted aryl (e.g., substituted or unsubstituted, 6- to 10-membered aryl). In certain embodiments, $R^6$ is optionally substituted benzyl. In certain embodiments, $R^6$ is optionally substituted phenyl. In certain embodiments, $R^6$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^6$ is an oxygen protecting group. In certain embodiments, $R^6$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

Compounds of Formulae (I'), (I), (IA), and (IA') include one or more instances of $R^7$. In certain embodiments, b is 1. In certain embodiments, b is 2. In certain embodiments, b is 3. In certain embodiments, b is 4. In certain embodiments, b1 is 0. In certain embodiments, b1 is 1. In certain embodiments, b1 is 2. In certain embodiments, b1 is 3. In certain embodiments, b1 is 4. In certain embodiments, b is b1.

In certain embodiments, at least one instance of $R^7$ is hydrogen. In certain embodiments, at least one instance of $R^7$ is halogen (e.g., F, Cl, Br, or I). In certain embodiments, at least one instance of $R^7$ is —CN. In certain embodiments, at least one instance of $R^7$ is —SCN. In certain embodiments, at least one instance of $R^7$ is —NO$_2$. In certain embodiments, at least one instance of $R^7$ is —N$_3$. In certain embodiments, at least one instance of $R^7$ is optionally substituted alkyl (e.g., substituted or unsubstituted $C_{1-6}$ alkyl). In certain embodiments, at least one instance of $R^7$ is substituted methyl. In certain embodiments, at least one instance of $R^7$ is unsubstituted methyl. In certain embodiments, at least one instance of $R^7$ is substituted or unsubstituted ethyl. In certain embodiments, at least one instance of $R^7$ is optionally substituted acyl (e.g., —C(=O)Me). In certain embodiments, at least one instance of $R^7$ is optionally substituted alkenyl (e.g., substituted or unsubstituted $C_{2-6}$ alkenyl). In certain embodiments, at least one instance of $R^7$ is optionally substituted alkynyl (e.g., substituted or unsubstituted $C_{2-6}$ alkynyl). In certain embodiments, at least one instance of $R^7$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^7$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^7$ is optionally substituted aryl (e.g., substituted or unsubstituted, 6- to 10-membered aryl). In certain embodiments, at least one instance of $R^7$ is optionally substituted benzyl. In certain embodiments, at least one instance of $R^7$ is optionally substituted phenyl. In certain embodiments, at least one instance of $R^7$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^7$ is —OR$^a$ (e.g., —OH or —OMe). In certain embodiments, at least one instance of $R^7$ is —OH. In certain embodiments, $R^7$ is —OMe. In certain embodiments, at least one instance of $R^7$ is —N(R$^b$)$_2$ (e.g., —NMe$_2$). In certain embodiments, at least one instance of $R^7$ is —NMe$_2$. In certain embodiments, at least one instance of $R^7$ is —SR$^a$ (e.g., —SMe). In certain embodiments, at least one instance of $R^7$ is optionally substituted sulfonyl. In certain embodiments, at least one instance of $R^7$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$.

In certain embodiments, each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom. In certain embodiments, each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl. In certain embodiments, at least one instance of $R^a$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom.

In certain embodiments, at least one instance of $R^b$ is hydrogen. In certain embodiments, at least one instance of $R^b$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl.

In certain embodiments, a compound of Formula (I'), (I), (IA), or (IA') is of the formula:

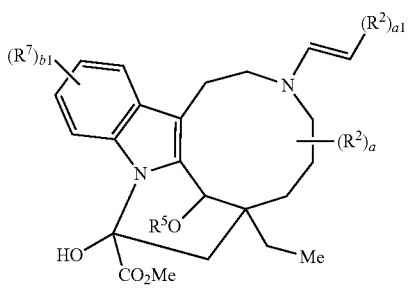

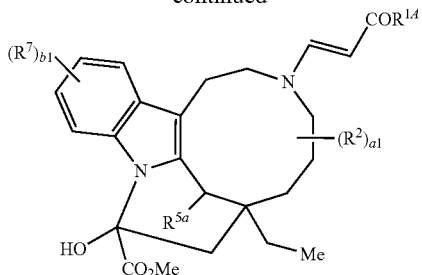

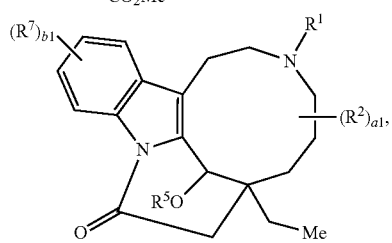

or a pharmaceutically acceptable salt, solvate, hydrate, polymorph, co-crystal, tautomer, stereoisomer, isotopically labeled derivative, or prodrug thereof.

In certain embodiments, a compound of Formula (I'), (I), (IA), or (IA') is of the formula:

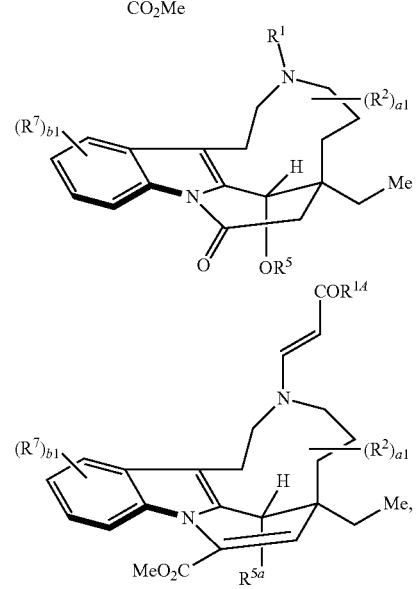

or a pharmaceutically acceptable salt, solvate, hydrate, polymorph, co-crystal, tautomer, stereoisomer, isotopically labeled derivative, or prodrug thereof.

Exemplary compounds of Formula (I'), (I), (IA), and (IA') include, but are not limited to:

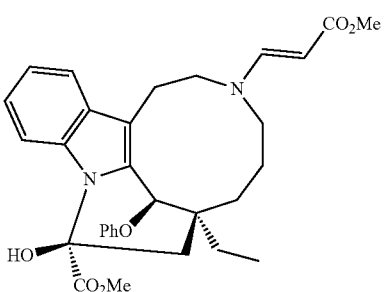

(V-3)

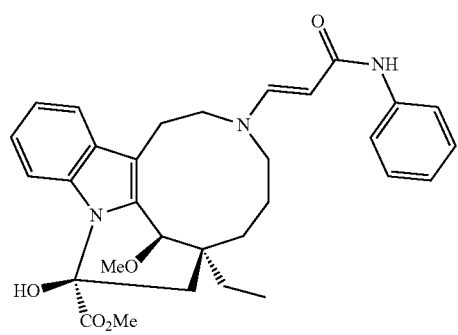

(V-4)

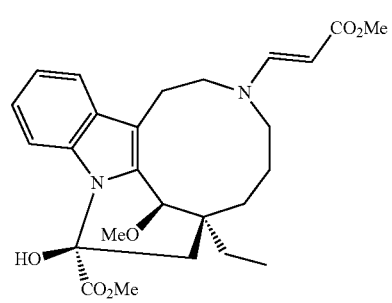

(V-18)

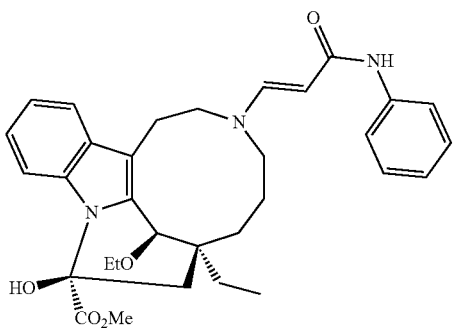

(V-20)

(V-21)

(V-22)
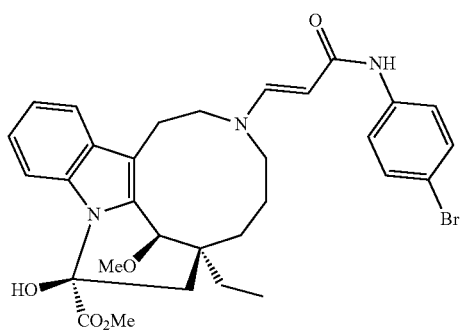
(V-27)
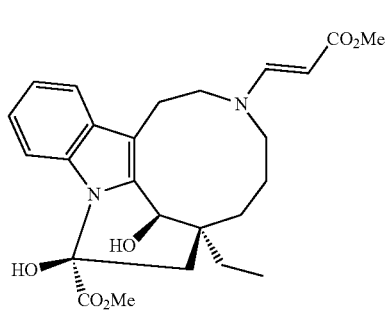
(V-28)
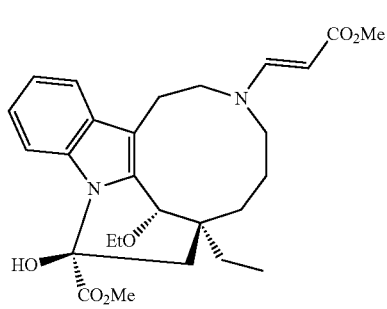
(V-29)
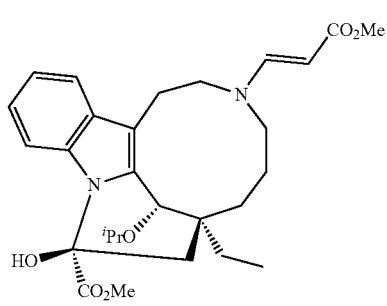
(V-30)
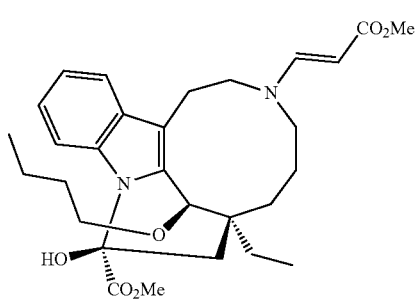
(V-31)
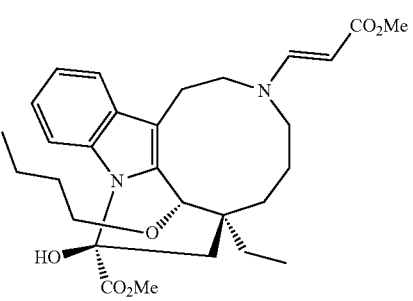
(V-46)
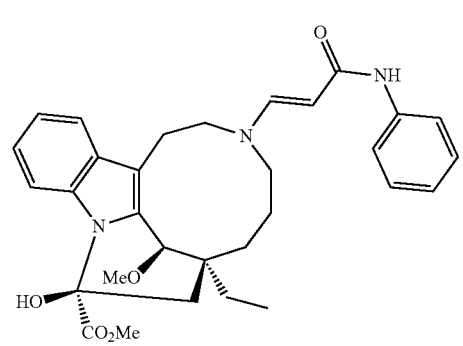
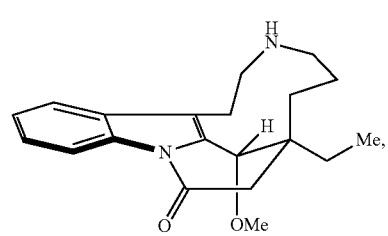
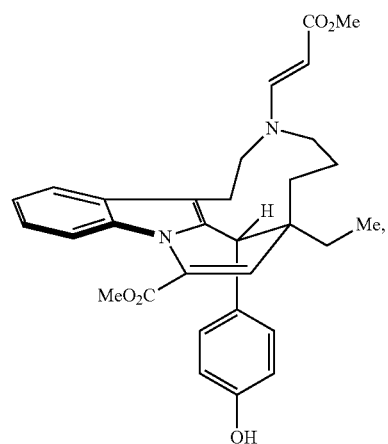
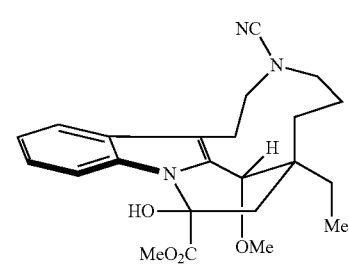

-continued

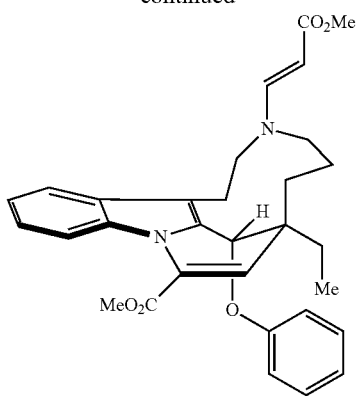

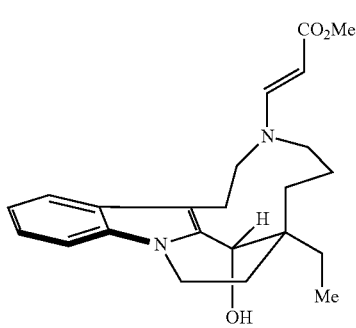

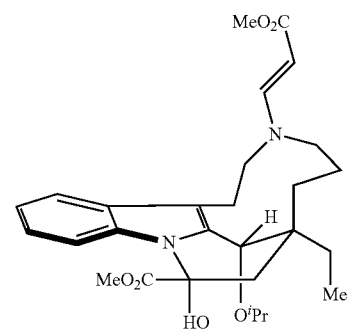

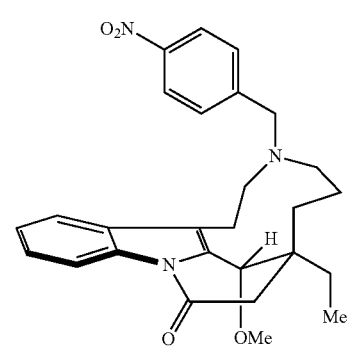

-continued

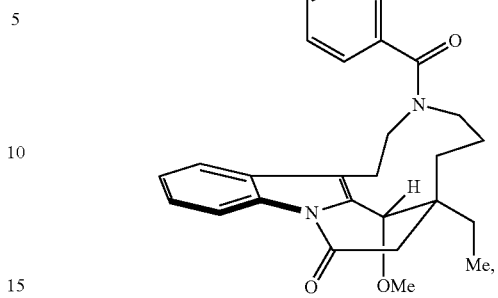

or a pharmaceutically acceptable salt, solvate, hydrate, polymorph, co-crystal, tautomer, stereoisomer, isotopically labeled derivative, or prodrug thereof.

In one aspect of the present invention, provided are compounds of Formula (II'):

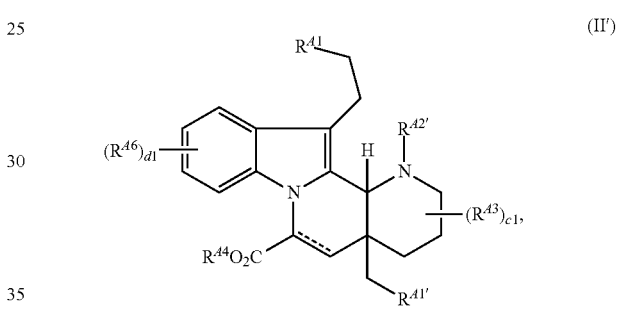

(II')

and pharmaceutically acceptable salts, solvates, hydrates, tautomers, and stereoisomers thereof, wherein:

$R^{A1'}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{A1}$ is hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(Rb)$_2$, or —SR$^a$;

$R^{A2'}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or —CN;

each instance of $R^{A3}$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{A4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c1 is 0, 1, 2, 3, 4, 5, or 6; and
d1 is 0, 1, 2, 3, or 4.

In one aspect of the present invention, provided are compounds of Formula (II):

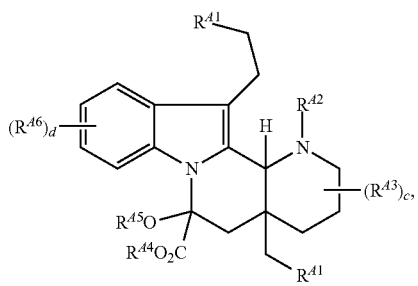

(II)

or a pharmaceutically acceptable salt, solvate, hydrate, polymorph, co-crystal, tautomer, stereoisomer, isotopically labeled derivative, or prodrug thereof, wherein:

$R^{A1}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{A2}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^{A3}$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{A4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{A5}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c is 1, 2, 3, 4, 5, or 6; and
d is 1, 2, 3, or 4.

In certain embodiments, a compound of Formula (II') is of Formula (I-i).

In one aspect of the present invention, provided are compounds of Formula (II-i):

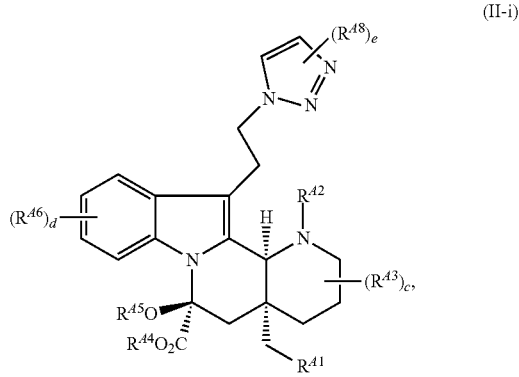

(II-i)

or a pharmaceutically acceptable salt, solvate, hydrate, polymorph, co-crystal, tautomer, stereoisomer, isotopically labeled derivative, or prodrug thereof, wherein:

$R^{A8}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$; and e is 1 or 2.

In certain embodiments, a compound of Formula (II') is of Formula (II-ii).

In one aspect of the present invention, provided are compounds of Formula (II-ii):

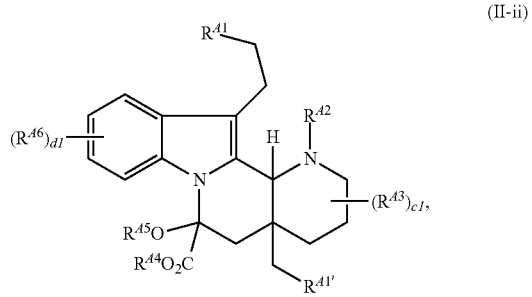

(II-ii)

or a pharmaceutically acceptable salt thereof, wherein:

R$^{A1}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

R$^{A1'}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

R$^{A2}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

R$^{A4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R$^{A5}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R$^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

c1 is 0, 1, 2, 3, 4, 5, or 6; and d1 is 0, 1, 2, 3, or 4.

In one aspect of the resent invention, provided are compounds of Formula (IIA):

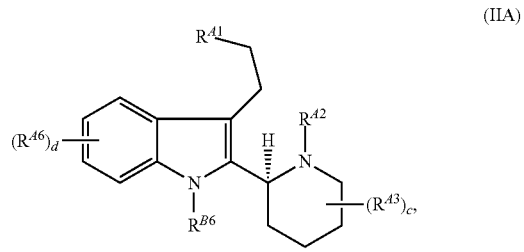

(IIA)

or a pharmaceutically acceptable salt, solvate, hydrate, polymorph, co-crystal, tautomer, stereoisomer, isotopically labeled derivative, or prodrug thereof, wherein:

R$^{A1}$ is hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(Rb)$_2$, or —SR$^a$;

R$^{A2}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^{A3}$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

R$^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c is 1, 2, 3, 4, 5, or 6; and d is 1, 2, 3, or 4.

In certain embodiments, the compound of Formula (II'), (II), (II-i), (II-ii), or (IIA) is of the formula:

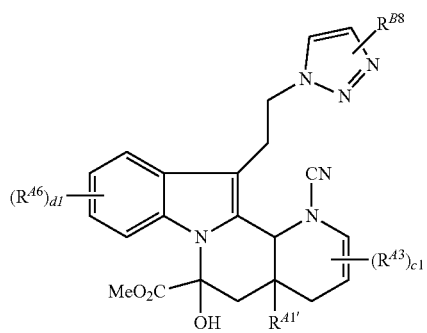

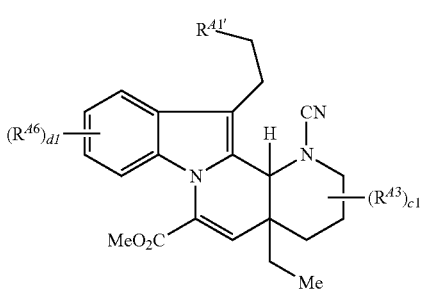

or a pharmaceutically acceptable salt, solvate, hydrate, polymorph, co-crystal, tautomer, stereoisomer, isotopically labeled derivative, or prodrug thereof.

In certain embodiments, the compound of Formula (II'), (II), (II-i), and (IA) is of the formula:

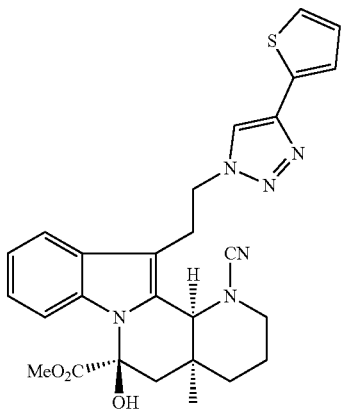

(V-35)

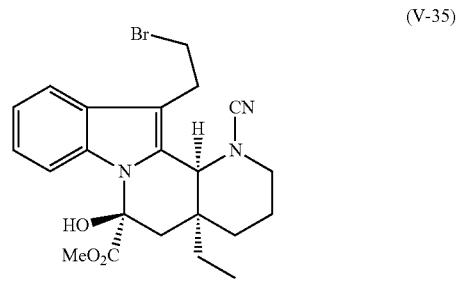

(V-36)

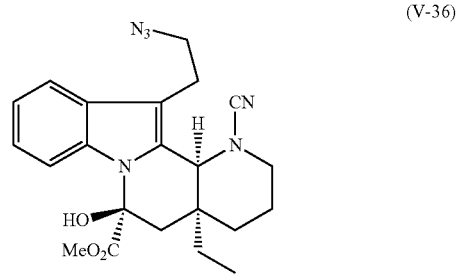

(V-38)

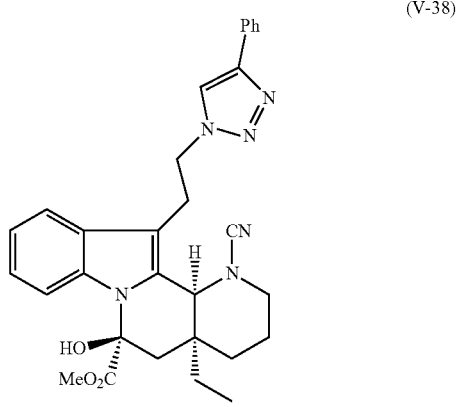

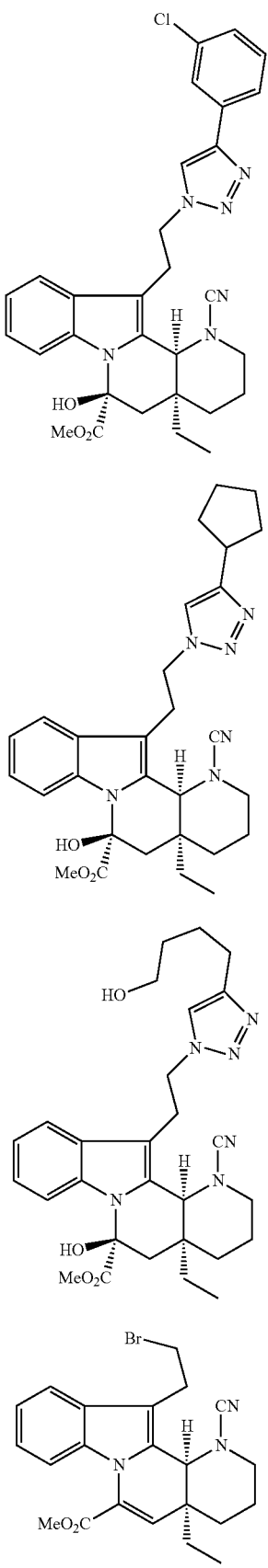

(V-39)
(V-40)
(V-41)
(V-42)

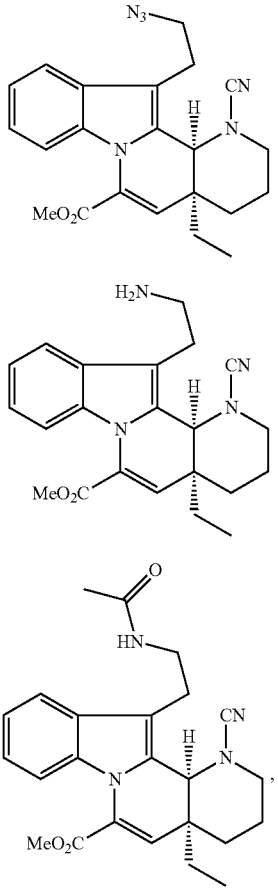

(V-43)
(V-44)
(V-45)

or a pharmaceutically acceptable salt, solvate, hydrate, polymorph, co-crystal, tautomer, stereoisomer, isotopically labeled derivative, or prodrug thereof.

In certain embodiments, the compound of Formula (II'), (II), (II-i), and (IA) is of the formula:

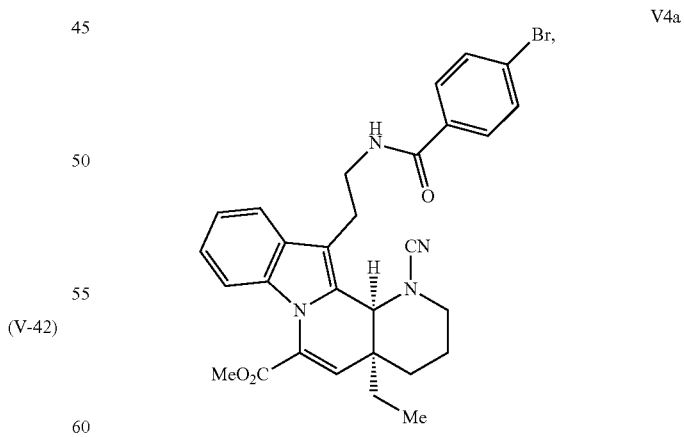

V4a or a pharmaceutically acceptable salt, solvate, hydrate, polymorph, co-crystal, tautomer, stereoisomer, isotopically labeled derivative, or prodrug thereof.

Compounds of Formulae (II') include $R^{41'}$. In certain embodiments, $R^{41'}$ is hydrogen. In certain embodiments, $R^{41'}$ is halogen (e.g., F, Cl, Br, or I). In certain embodiments, $R^{A1'}$ is —Br. In certain embodiments, $R^{A1'}$ is —CN. In certain embodiments, $R^{A1'}$ is —SCN. In certain embodiments, $R^{A1'}$ is —NO$_2$. In certain embodiments, $R^{A1'}$ is —N$_3$. In certain embodiments, $R^{A1'}$ is optionally substituted alkyl (e.g., substituted or unsubstituted C$_{1-6}$ alkyl). In certain embodiments, $R^{A1'}$ is substituted methyl. In certain embodiments, $R^{A1'}$ is unsubstituted methyl. In certain embodiments, $R^{A1'}$ is substituted or unsubstituted ethyl. In certain embodiments, $R^{A1'}$ is unsubstituted ethyl. In certain embodiments, $R^{A1'}$ is optionally substituted acyl (e.g., —C(=O)Me). In certain embodiments, $R^{A1'}$ is optionally substituted alkenyl (e.g., substituted or unsubstituted C$_{2-6}$ alkenyl). In certain embodiments, $R^{A1'}$ is optionally substituted alkynyl (e.g., substituted or unsubstituted C$_{2-6}$ alkynyl). In certain embodiments, $R^{A1'}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{A1'}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{A1'}$ is an optionally substituted 5-membered heterocyclyl groups containing 3 heteroatoms. In certain embodiments, $R^{A1'}$ is optionally substituted triazolinyl, oxadiazolinyl, or thiadiazolinyl. In certain embodiments, $R^{A1'}$ is of the formula:

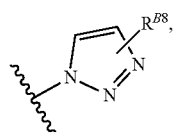

wherein $R^{B8}$ is optionally substituted alkyl, optionally substituted carbocyclyl, optionally substituted aryl, or optionally substituted heteroaryl. In certain embodiments, $R^{B8}$ is optionally substituted alkyl (e.g., substituted or unsubstituted C$_{1-6}$ alkyl). In certain embodiments, $R^{B8}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{B8}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B8}$ is optionally substituted aryl. In certain embodiments, $R^{B5}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{A1'}$ is of the formula:

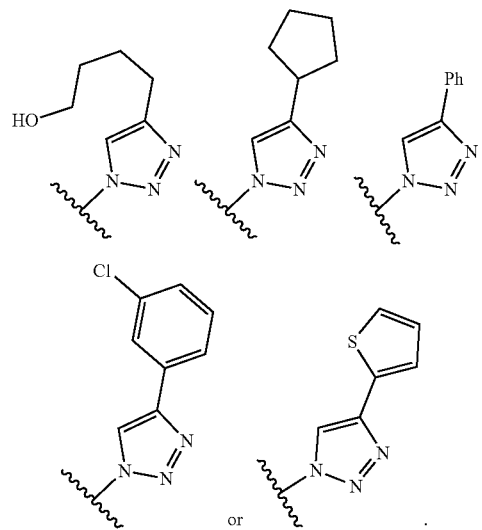 [SMILES: *n1cc(CCCCO)nn1 ; *n1cc(C2CCCC2)nn1 ; *n1cc(-c2ccccc2)nn1 ; *n1cc(-c2cccc(Cl)c2)nn1 ; *n1cc(-c2cccs2)nn1]

In certain embodiments, $R^{A1'}$ is an optionally substituted 6-membered heterocyclyl. In certain embodiments, $R^{A1'}$ is optionally substituted aryl (e.g., substituted or unsubstituted, 6- to 10-membered aryl). In certain embodiments, $R^{A1'}$ is optionally substituted benzyl. In certain embodiments, $R^{A1'}$ is optionally substituted phenyl. In certain embodiments, $R^{A1'}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{A1'}$ is —OR$^a$ (e.g., —OH or —OMe). In certain embodiments, $R^{A1'}$ is —OH. In certain embodiments, $R^{A1'}$ is —OMe. In certain embodiments, $R^{A1'}$ is —N(R$^b$)$_2$ (e.g., —NMe$_2$). In certain embodiments, $R^{A1}$ is —NH$_2$. In certain embodiments, $R^{A1'}$ is —NHC(=O)(optionally substituted C$_{1-6}$ alkyl). In certain embodiments, $R^{A1'}$ is —NHC(=O)Me.

In certain embodiments, $R^{A1'}$ is of the of formula:

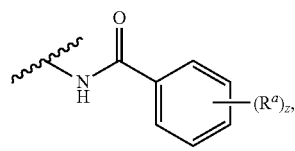

wherein $R^z$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$; and z is 0, 1, 2, 3, 4, or 5. In certain embodiments, $R^{A1'}$ is of the of formula:

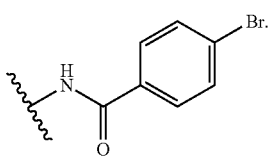 [SMILES: *NC(=O)c1ccc(Br)cc1]

In certain embodiments, $R^{41'}$ is —NMe$_2$. In certain embodiments, $R^{41'}$ is —SR$^a$ (e.g., —SMe). In certain embodiments, $R^{41'}$ is optionally substituted sulfonyl. In certain embodiments, $R^{41'}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$.

Compounds of Formulae (II'), (II), (I-i), and (IIA) include $R^{41}$. In certain embodiments, $R^{41}$ is $R^{41'}$. In certain embodiments, each instance of $R^{41}$ is different. In certain embodiments, $R^{41}$ is hydrogen. In certain embodiments, RAI is halogen (e.g., F, Cl, Br, or I). In certain embodiments, $R^{41}$ is —Br. In certain embodiments, $R^{41}$ is —CN. In certain embodiments, $R^{41}$ is —SCN. In certain embodiments, $R^{41}$ is —NO$_2$. In certain embodiments, $R^{41}$ is —N$_3$. In certain embodiments, $R^{41}$ is optionally substituted alkyl (e.g., substituted or unsubstituted C$_{1-6}$ alkyl). In certain embodiments, $R^{41}$ is substituted methyl. In certain embodiments, $R^{41}$ is unsubstituted methyl. In certain embodiments, $R^{41}$ is substituted or unsubstituted ethyl. In certain embodiments, $R^{41}$ is unsubstituted ethyl. In certain embodiments, $R^{41}$ is optionally substituted acyl (e.g., —C(=O)Me). In certain embodiments, $R^{41}$ is optionally substituted alkenyl (e.g., substituted or unsubstituted C$_{2-6}$ alkenyl). In certain embodiments, $R^{41}$ is optionally substituted alkynyl (e.g., substituted or unsubstituted C$_{2-6}$ alkynyl). In certain embodiments, $R^{41}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{41}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{41}$ is optionally substituted aryl (e.g., substituted or unsubstituted, 6- to 10-membered aryl). In certain embodiments, $R^{41}$ is optionally substituted benzyl. In certain embodiments, $R^{41}$ is optionally substituted phenyl. In certain embodiments, $R^{41}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{41}$ is —OR$^a$ (e.g., —OH or —OMe). In certain embodiments, $R^{41}$ is —OH. In certain embodiments, $R^{41}$ is —OMe. In certain embodiments, $R^{41}$ is —N(R$^b$)$_2$ (e.g., —NMe$_2$). In certain embodiments, $R^{41}$ is —NH$_2$. In certain embodiments, $R^{41}$ is —NHC(=O)(optionally substituted C$_{1-6}$ alkyl). In certain embodiments, $R^{41}$ is —NHC(=O)Me. In certain embodiments, RAI is —NMe$_2$. In certain embodiments, $R^{41}$ is —SR$^a$ (e.g., —SMe). In certain embodiments, $R^{41}$ is optionally substituted sulfonyl. In certain embodiments, $R^{41}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(Rb)$_2$, or —SR$^a$.

Compounds of Formula (II') include $R^{42'}$. In certain embodiments, $R^{42'}$ is hydrogen. In certain embodiments, $R^{42'}$ is optionally substituted alkyl (e.g., substituted or unsubstituted C$_{1-6}$ alkyl). In certain embodiments, $R^{42'}$ is substituted methyl. In certain embodiments, $R^{42'}$ is unsubstituted methyl. In certain embodiments, $R^{42'}$ is substituted or unsubstituted ethyl. In certain embodiments, $R^{42'}$ is optionally substituted acyl (e.g., —C(=O)Me). In certain embodiments, $R^{42'}$ is optionally substituted alkenyl (e.g., substituted or unsubstituted C$_{2-6}$ alkenyl). In certain embodiments, $R^{42'}$ is optionally substituted alkynyl (e.g., substituted or unsubstituted C$_{2-6}$ alkynyl). In certain embodiments, $R^{42'}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{42'}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{42'}$ is optionally substituted aryl (e.g., substituted or unsubstituted, 6- to 10-membered aryl). In certain embodiments, $R^{42'}$ is optionally substituted benzyl. In certain embodiments, $R^{42'}$ is optionally substituted phenyl. In certain embodiments, $R^{42'}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{42'}$ is a nitrogen protecting group. In certain embodiments, $R^{42'}$ is —CN. In certain embodiments, $R^{42}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or —CN.

Compounds of Formulae (II), (IIA), (VII), and (X) include $R^{42}$. In certain embodiments, $R^{42}$ is hydrogen. In certain embodiments, $R^{42}$ is optionally substituted alkyl (e.g., substituted or unsubstituted C$_{1-6}$alkyl). In certain embodiments, $R^{42}$ is optionally substituted C$_{1-6}$ alkyl. In certain embodiments, $R^{42}$ is of the formula: —(CH$_2$)$_x$R$^{A2b}$, wherein: x is 1, 2, 3, or 4; and $R^{A2b}$ is optionally substituted alkynyl, optionally substituted carbocyclyl, or optionally substituted aryl, or optionally substituted heteroaryl. In certain embodiments, $R^{41'}$ is of the formula:

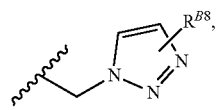

wherein $R^{B8}$ is optionally substituted alkyl, optionally substituted carbocyclyl, optionally substituted aryl, or optionally substituted heteroaryl. In certain embodiments, $R^{42}$ is

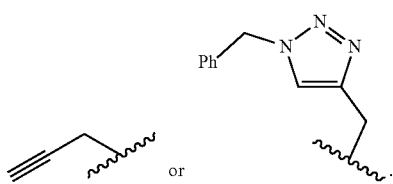

In certain embodiments, $R^{A2}$ is substituted methyl. In certain embodiments, $R^{A2}$ is unsubstituted methyl. In certain embodiments, $R^{A2}$ is substituted or unsubstituted ethyl. In certain embodiments, $R^{A2}$ is n-butyl (n-Bu). In certain embodiments, $R^{A2}$ is substituted or unsubstituted branched alkyl. In certain embodiments, $R^{A2}$ is optionally substituted acyl (e.g., —C(=O)Me). In certain embodiments, $R^{A2}$ is optionally substituted alkenyl (e.g., substituted or unsubstituted $C_{2-6}$ alkenyl). In certain embodiments, $R^{A2}$ is optionally substituted alkynyl (e.g., substituted or unsubstituted $C_{2-6}$ alkynyl). In certain embodiments, $R^{A2}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{A2}$ is optionally substituted 3- to 7-membered, monocyclic carbocyclyl comprising zero double bonds in the carbocyclic ring system. In certain embodiments, $R^{A2}$ is cyclopropyl. In certain embodiments, $R^{A2}$ is cyclopropenyl. In certain embodiments, $R^{A2}$ is cyclobutyl. In certain embodiments, $R^{A2}$ is cyclopentyl. In certain embodiments, $R^{A2}$ is cyclohexyl. In certain embodiments, $R^{A2}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{A2}$ is optionally substituted aryl (e.g., substituted or unsubstituted, 6- to 10-membered aryl). In certain embodiments, $R^{A2}$ is optionally substituted benzyl. In certain embodiments, $R^{A2}$ is unsubstituted benzyl. In certain embodiments, $R^{A2}$ is substituted benzyl. In certain embodiments, $R^{A2}$ is optionally substituted phenyl. In certain embodiments, $R^{A2}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{A2}$ is a nitrogen protecting group. In certain embodiments, $R^{A2}$ is optionally substituted $C_{1-6}$ alkyl, optionally substituted alkynyl, optionally substituted carbocycle or optionally substituted aryl. In certain embodiments, $R^{A2}$ is of the formula:

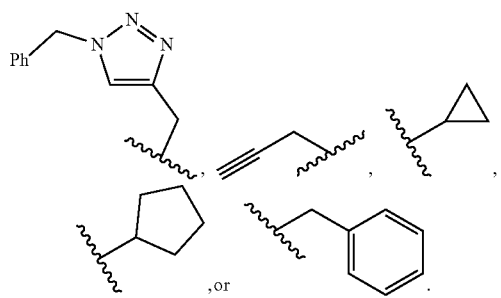

In certain embodiments, $R^{A2}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

Compounds of Formulae (II'), (II), (IIA), (IIA), (III"), (IIIA), (VIII'), (VIII), (IX'), (IX), and (X) include one or more instances of $R^3$. In certain embodiments, c is 1. In certain embodiments, c is 2. In certain embodiments, c is 3. In certain embodiments, c is 4. In certain embodiments, c is 5. In certain embodiments, c is 6. In certain embodiments, c is c. In certain embodiments, c1 is 0. In certain embodiments, c1 is 2. In certain embodiments, c1 is 3. In certain embodiments, c1 is 4. In certain embodiments, c1 is 5. In certain embodiments, c1 is 6. In certain embodiments, at least one instance of $R^{43}$ is hydrogen. In certain embodiments, there is one instance of each of $R^{43}$, $R^{46}$, and $R^{D6}$. In certain embodiments, at least one instance of $R^{43}$ is hydrogen, at least one instance of $R^{46}$ is hydrogen, and at least one instance of $R^{D6}$ is hydrogen. In certain embodiments, there is one instance of each of $R^{43}$ and $R^{46}$. In certain embodiments, at least one instance of $R^{43}$ is hydrogen and at least one instance of $R^{46}$ is hydrogen. In certain embodiments, at least one instance of $R^{43}$ is halogen (e.g., F, Cl, Br, or I). In certain embodiments, at least one instance of $R^{43}$ is —CN. In certain embodiments, at least one instance of $R^{43}$ is —SCN. In certain embodiments, at least one instance of $R^{43}$ is —NO$_2$. In certain embodiments, at least one instance of $R^{43}$ is —N$_3$. In certain embodiments, at least one instance of $R^{43}$ is optionally substituted alkyl (e.g., substituted or unsubstituted $C_{1-6}$ alkyl). In certain embodiments, at least one instance of R' is substituted methyl. In certain embodiments, at least one instance of $R^{43}$ is unsubstituted methyl. In certain embodiments, at least one instance of $R^{43}$ is substituted or unsubstituted ethyl. In certain embodiments, at least one instance of $R^{43}$ is optionally substituted acyl (e.g., —C(=O)Me). In certain embodiments, at least one instance of $R^{43}$ is optionally substituted alkenyl (e.g., substituted or unsubstituted $C_{2-6}$ alkenyl). In certain embodiments, at least one instance of $R^{43}$ is optionally substituted alkynyl (e.g., substituted or unsubstituted $C_{2-6}$ alkynyl). In certain embodiments, at least one instance of $R^{43}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{43}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{43}$ is optionally substituted aryl (e.g., substituted or unsubstituted, 6- to 10-membered aryl). In certain embodiments, at least one instance of $R^{43}$ is optionally substituted benzyl. In certain embodiments, at least one instance of $R^{43}$ is optionally substituted phenyl. In certain embodiments, at least one instance of $R^{43}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{43}$ is —OR$^a$ (e.g., —OH or —OMe). In certain embodiments, at least one instance of $R^{43}$ is —OH. In certain embodiments, at least one instance of $R^{43}$ is —OMe. In certain embodiments, at least one instance of $R^{43}$ is —N($R^b$)$_2$ (e.g., —NMe$_2$). In certain embodiments, at least one instance of $R^{43}$ is —NMe$_2$. In certain embodiments, at least one instance of $R^{43}$ is —S$R^a$ (e.g., —SMe). In certain embodiments, at least one instance of R' is optionally substituted sulfonyl. In certain embodiments, at least one instance of $R^{43}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —O$R^a$, —N($R^b$)$_2$, or —S$R^a$.

Compounds of Formulae (II'), (II), (II-i), and (X) include $R^{44}$. In certain embodiments, $R^{44}$ is hydrogen. In certain embodiments, $R^{44}$ is optionally substituted alkyl (e.g., substituted or unsubstituted C$_{1-6}$alkyl). In certain embodiments, $R^{44}$ is substituted methyl. In certain embodiments, $R^{44}$ is unsubstituted methyl. In certain embodiments, $R^{44}$ is substituted or unsubstituted ethyl. In certain embodiments, $R^{44}$ is unsubstituted ethyl. In certain embodiments, $R^{44}$ is optionally substituted acyl (e.g., —C(=O)Me). In certain embodiments, $R^{44}$ is optionally substituted alkenyl (e.g., substituted or unsubstituted C$_{2-6}$ alkenyl). In certain embodiments, $R^{44}$ is optionally substituted alkynyl (e.g., substituted or unsubstituted C$_{2-6}$ alkynyl). In certain embodiments, $R^{44}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{44}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{44}$ is optionally substituted aryl (e.g., substituted or unsubstituted, 6- to 10-membered aryl). In certain embodiments, $R^{44}$ is optionally substituted benzyl. In certain embodiments, $R^{44}$ is optionally substituted phenyl. In certain embodiments, $R^{44}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{44}$ is optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl.

Compounds of Formulae (II), (II-i), and (X) include $R^{45}$. In certain embodiments, $R^{45}$ is hydrogen. In certain embodiments, $R^{45}$ is optionally substituted alkyl (e.g., substituted or unsubstituted C$_{1-6}$ alkyl). In certain embodiments, RM is substituted methyl. In certain embodiments, $R^{45}$ is unsubstituted methyl. In certain embodiments, $R^{45}$ is substituted or unsubstituted ethyl. In certain embodiments, $R^{45}$ is unsubstituted ethyl. In certain embodiments, $R^{45}$ is optionally substituted acyl (e.g., —C(=O)Me). In certain embodiments, $R^{45}$ is optionally substituted alkenyl (e.g., substituted or unsubstituted C$_{2-6}$ alkenyl). In certain embodiments, $R^{45}$ is optionally substituted alkynyl (e.g., substituted or unsubstituted C$_{2-6}$ alkynyl). In certain embodiments, $R^{45}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{45}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{45}$ is optionally substituted aryl (e.g., substituted or unsubstituted, 6- to 10-membered aryl). In certain embodiments, $R^{45}$ is optionally substituted benzyl. In certain embodiments, RM is optionally substituted phenyl. In certain embodiments, $R^{45}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{45}$ is optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl.

Compounds of Formulae (II'), (II), (IIA), (III''), (IIIA), (VIII'), (VIII), (IX'), (IX), and (X) include one or more instances of $R^{46}$. In certain embodiments, d is 1. In certain embodiments, d is 2. In certain embodiments, d is 3. In certain embodiments, d is 4. In certain embodiments, d is d1. In certain embodiments, d1 is 0. In certain embodiments, d1 is 1. In certain embodiments, d1 is 2. In certain embodiments, d1 is 3. In certain embodiments, d1 is 4.

In certain embodiments, at least one instance of $R^{46}$ is hydrogen. In certain embodiments, at least one instance of $R^{46}$ is optionally substituted alkyl (e.g., substituted or unsubstituted C$_{1-6}$ alkyl). In certain embodiments, at least one instance of $R^{46}$ is substituted methyl. In certain embodiments, at least one instance of $R^{46}$ is unsubstituted methyl. In certain embodiments, at least one instance of $R^{46}$ is substituted or unsubstituted ethyl. In certain embodiments, at least one instance of $R^{46}$ is optionally substituted acyl (e.g., —C(=O)Me). In certain embodiments, at least one instance of $R^{46}$ is optionally substituted alkenyl (e.g., substituted or unsubstituted C$_{2-6}$ alkenyl). In certain embodiments, at least one instance of $R^{46}$ is optionally substituted alkynyl (e.g., substituted or unsubstituted C$_{2-6}$ alkynyl). In certain embodiments, at least one instance of $R^{46}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{46}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{46}$ is optionally substituted aryl (e.g., substituted or unsubstituted, 6- to 10-membered aryl). In certain embodiments, at least one instance of $R^{46}$ is optionally substituted benzyl. In certain embodiments, at least one instance of $R^{46}$ is optionally substituted phenyl. In certain embodiments, at least one instance of $R^{46}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A6}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

Formula (II-i) includes one or more instances of $R^{A8}$. In certain embodiments, e is 1. In certain embodiments, e is 2. In certain embodiments, e is e1. In certain embodiments, e1 is 0. In certain embodiments, e1 is 1. In certain embodiments, e1 is 2. In certain embodiments, $R^{A8}$ is $R^{B8}$. In certain embodiments, $R^{B8}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, $R^{B8}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$.

Compounds of Formulae (IIA), (III'), (III''), (IIIA), (VII), (IX'), and (IX) include $R^{B6}$. In certain embodiments, $R^{B6}$ is hydrogen. In certain embodiments, $R^{B6}$ is optionally substituted alkyl (e.g., substituted or unsubstituted C$_{1-6}$ alkyl). In certain embodiments, $R^{B6}$ is substituted methyl. In certain embodiments, $R^{B6}$ is unsubstituted methyl. In certain embodiments, $R^{B6}$ is substituted or unsubstituted ethyl. In certain embodiments, $R^{B6}$ is unsubstituted ethyl. In certain embodiments, $R^{B6}$ is optionally substituted acyl (e.g., —C(=O)Me). In certain embodiments, $R^{B6}$ is optionally substituted alkenyl (e.g., substituted or unsubstituted C$_{2-6}$ alkenyl). In certain embodiments, $R^{B6}$ is optionally substituted alkynyl (e.g., substituted or unsubstituted C$_{2-6}$ alkynyl). In certain embodiments, $R^{B6}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{B6}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B6}$ is optionally substituted aryl (e.g., substituted or unsubstituted, 6- to 10-membered aryl). In certain embodiments, $R^{B6}$ is optionally substituted benzyl. In certain embodiments, $R^{B6}$ is optionally substituted phenyl. In certain embodiments, $R^{B6}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B6}$ is a nitrogen protecting group. In certain embodiments, $R^{B6}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^{B6}$ is $R^{B6'}$. In certain embodiments, $R^{B6'}$ is —CN.

In one aspect of the present invention, provided are compounds of Formula (III''):

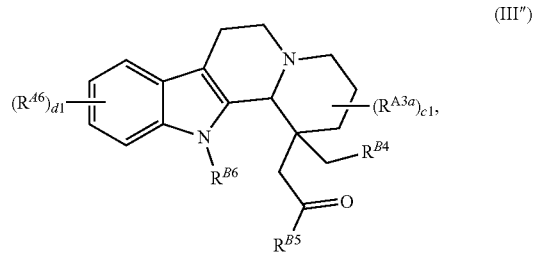

or a pharmaceutically acceptable salt, solvate, hydrate, polymorph, co-crystal, tautomer, stereoisomer, isotopically labeled derivative, or prodrug thereof, wherein:

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{A3}a$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, —SR$^a$, or optionally two instances of $R^{A3}a$ are taken together with their intervening atoms to form an optionally substituted carbocyclic ring or optionally substituted heterocyclic ring;

$R^{B4}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{B5}$ is —OR$^a$ or —N(R$^b$)$_2$;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

c1 is 0, 1, 2, 3, 4, 5, or 6; and d1 is 0, 1, 2, 3, or 4.

In one aspect of the present invention, provided are compounds of Formula (III'):

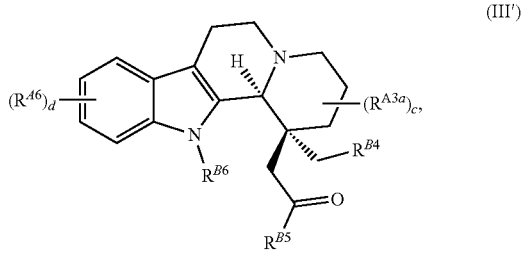

(III')

or a pharmaceutically acceptable salt, solvate, hydrate, polymorph, co-crystal, tautomer, stereoisomer, isotopically labeled derivative, or prodrug thereof, wherein:

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{A3}a$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, —SR$^a$, or optionally two instances of $R^{A3}a$ are taken together with their intervening atoms to form an optionally substituted carbocyclic ring or optionally substituted heterocyclic ring;

$R^{B4}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{B5}$ is —OR$^a$ or —N(R$^b$)$_2$;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

c is 1, 2, 3, 4, 5, or 6; and d is 1, 2, 3, or 4.

In certain embodiments, a compound of Formula (III'') is of Formula (III).

In one aspect of the present invention, provided are compounds of Formula (III):

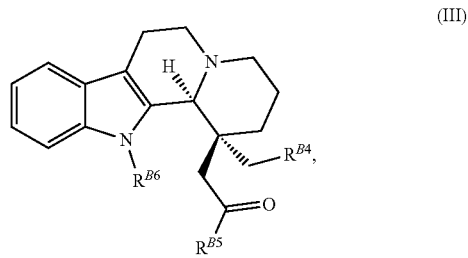

(III)

or a pharmaceutically acceptable salt, solvate, hydrate, polymorph, co-crystal, tautomer, stereoisomer, isotopically labeled derivative, or prodrug thereof, wherein:

$R^{B4}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{B5}$ is —OR$^a$ or —N(R$^b$)$_2$;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl.

In one aspect of the present invention, provided are compounds of Formula (IIIA):

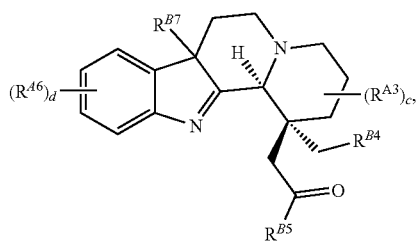

(IIIA)

or a pharmaceutically acceptable salt, solvate, hydrate, polymorph, co-crystal, tautomer, stereoisomer, isotopically labeled derivative, or prodrug thereof, wherein:

each instance of $R^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{B4}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{B5}$ is —OR$^a$ or —N(R$^b$)$_2$;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^{B7}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c is 1, 2, 3, 4, 5, or 6; and d is 1, 2, 3, or 4.

In certain embodiments, the compound of Formula (III"), (III'), (III), and (IIIA) is of the formula:

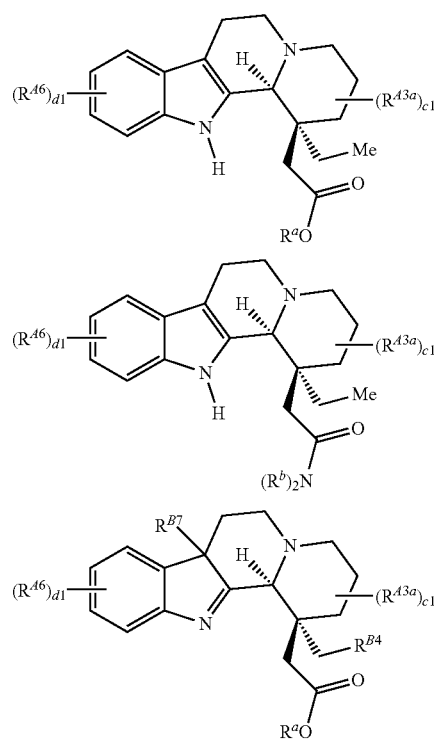

or a pharmaceutically acceptable salt, solvate, hydrate, polymorph, co-crystal, tautomer, stereoisomer, isotopically labeled derivative, or prodrug thereof.

In certain embodiments, the compound of Formula (III"), (III'), (III), and (IIIA) is of the formula:

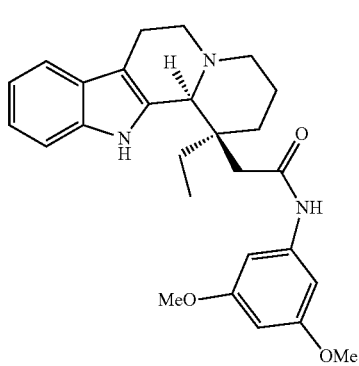

(V-5)

(V-8)
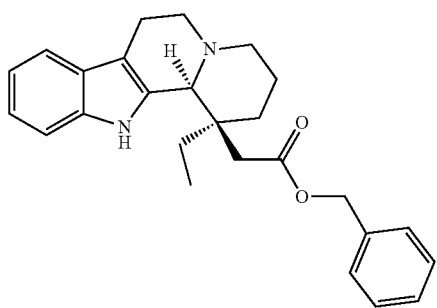
(V-9)
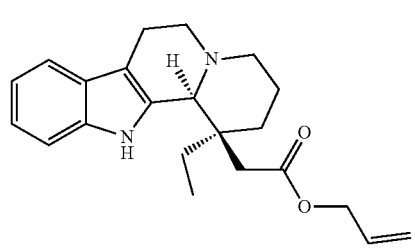
(V-10)
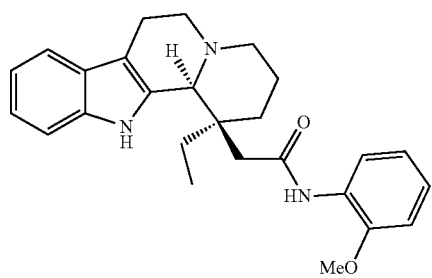
(V-11)
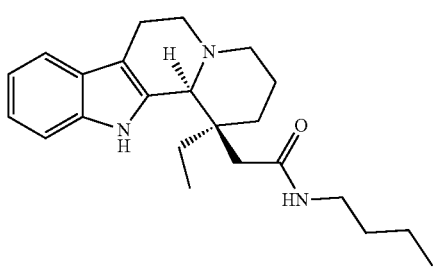
(V-19)
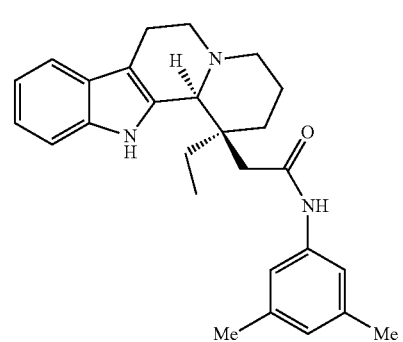
(V-23)
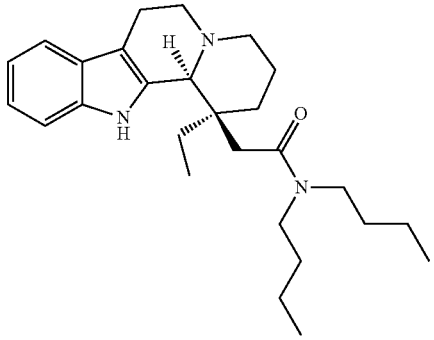
(V-24)
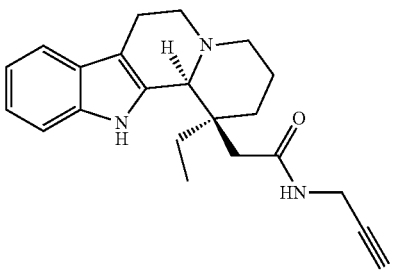
(V-25)
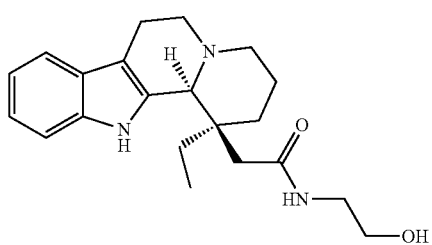
(V-26)
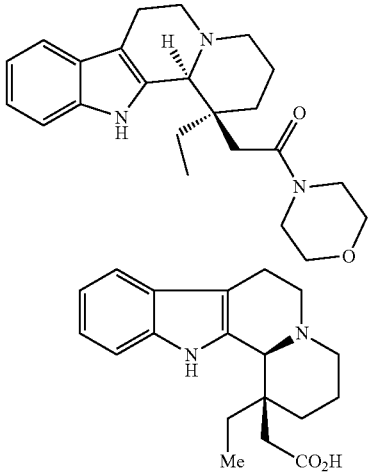
V1p
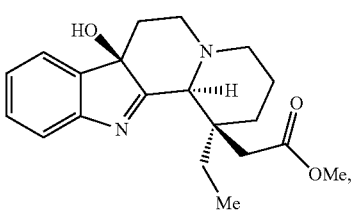
or a pharmaceutically acceptable salt, solvate, hydrate, polymorph, co-crystal, tautomer, stereoisomer, isotopically labeled derivative, or prodrug thereof.

In certain embodiments, the compound of Formula (III"), (III'), (III), and (IIIA) is of the formula:

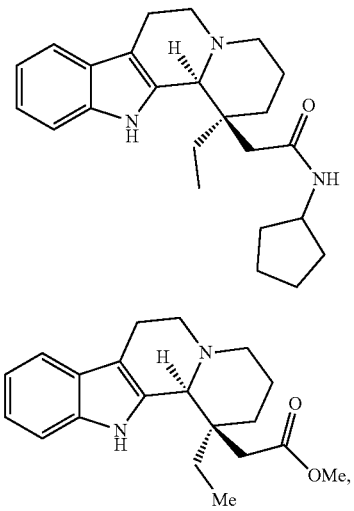

V1o or a pharmaceutically acceptable salt, solvate, hydrate, polymorph, co-crystal, tautomer, stereoisomer, isotopically labeled derivative, or prodrug thereof.

Compounds of Formula (III") and (III') include one or more instances of RA. In certain embodiments, c is 1. In certain embodiments, c is 2. In certain embodiments, c is 3. In certain embodiments, c is 4. In certain embodiments, c is 5. In certain embodiments, c is 6. In certain embodiments, at least one instance of $R^{A3a}$ is halogen (e.g., F, Cl, Br, or I). In certain embodiments, at least one instance of $R^{A3a}$ is —CN. In certain embodiments, at least one instance of $R^{A3a}$ is —SCN. In certain embodiments, at least one instance of $R^{A3a}$ is —NO$_2$. In certain embodiments, at least one instance of $R^{A3a}$ is —N$_3$. In certain embodiments, at least one instance of $R^{A3a}$ is optionally substituted alkyl (e.g., substituted or unsubstituted C$_{1-6}$ alkyl). In certain embodiments, at least one instance of $R^{A3a}$ is substituted methyl. In certain embodiments, at least one instance of $R^{A3a}$ is unsubstituted methyl. In certain embodiments, at least one instance of $R^{A3a}$ is substituted or unsubstituted ethyl. In certain embodiments, at least one instance of $R^{A3a}$ is optionally substituted acyl (e.g., —C(=O)Me). In certain embodiments, at least one instance of $R^{A3a}$ is optionally substituted alkenyl (e.g., substituted or unsubstituted C$_{2-6}$ alkenyl). In certain embodiments, at least one instance of $R^{A3a}$ is optionally substituted alkynyl (e.g., substituted or unsubstituted C$_{2-6}$ alkynyl). In certain embodiments, at least one instance of $R^{A3a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{A3a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{A3a}$ is optionally substituted aryl (e.g., substituted or unsubstituted, 6- to 10-membered aryl). In certain embodiments, at least one instance of $R^{A3a}$ is optionally substituted benzyl. In certain embodiments, at least one instance of $R^{A3a}$ is optionally substituted phenyl. In certain embodiments, at least one instance of $R^{A3a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{A3a}$ is —OR$^a$ (e.g., —OH or —OMe). In certain embodiments, at least one instance of $R^{A3a}$ is —OH. In certain embodiments, at least one instance of $R^{A3a}$ is —OMe. In certain embodiments, at least one instance of $R^{A3a}$ is —N(R$^b$)$_2$ (e.g., —NMe$_2$). In certain embodiments, at least one instance of $R^{A3a}$ is —NMe$_2$. In certain embodiments, at least one instance of $R^{A3a}$ is —SR$^a$ (e.g., —SMe). In certain embodiments, at least one instance of $R^{A3a}$ is sulfonyl. In certain embodiments, two instances of $R^{A3a}$ are taken together with their intervening atoms to form an optionally substituted carbocyclic ring (e.g., substituted or unsubstituted, 3- to 7-membered, monocyclic carbocyclyl comprising zero, one, or two double bonds in the carbocyclic ring system). In certain embodiments, two instances of $R^{A3a}$ are taken together with their intervening atoms to form an optionally substituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{A3a}$ is optionally halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, sulfonyl, —OR$^a$, —N(R$^b$)$_2$, —SR$^a$, or optionally two instances of $R^{A3a}$ are taken together with their intervening atoms to form an optionally substituted carbocyclic ring or optionally substituted heterocyclic ring.

Compounds of Formula (III"), (III'), (III), and (IIIA) include $R^{B4}$. In certain embodiments, $R^{B4}$ is hydrogen. In certain embodiments, $R^{B4}$ is halogen (e.g., F, Cl, Br, or I). In certain embodiments, $R^{B4}$ is —Br. In certain embodiments, $R^{B4}$ is —CN. In certain embodiments, $R^{B4}$ is —SCN. In certain embodiments, $R^{B4}$ is —NO$_2$. In certain embodiments, $R^{B4}$ is —N$_3$. In certain embodiments, $R^{B4}$ is optionally substituted alkyl (e.g., substituted or unsubstituted C$_{1-6}$ alkyl). In certain embodiments, $R^{B4}$ is substituted methyl. In certain embodiments, $R^{B4}$ is unsubstituted methyl. In certain embodiments, $R^{B4}$ is substituted or unsubstituted ethyl. In certain embodiments, $R^{B4}$ is unsubstituted ethyl. In certain embodiments, $R^{B4}$ is optionally substituted acyl (e.g., —C(=O)Me). In certain embodiments, $R^{B4}$ is optionally substituted alkenyl (e.g., substituted or unsubstituted C$_{2-6}$ alkenyl). In certain embodiments, $R^{B4}$ is optionally substituted alkynyl (e.g., substituted or unsubstituted C$_{2-6}$ alkynyl). In certain embodiments, $R^{B4}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{B4}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{B4}$ is optionally substituted aryl (e.g., substituted or unsubstituted, 6- to 10-membered aryl). In certain embodiments, $R^{B4}$ is optionally substituted benzyl. In certain embodiments, $R^{B4}$ is optionally substituted phenyl. In certain embodiments, $R^{B4}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{B4}$ is —$OR^a$ (e.g., —OH or —OMe). In certain embodiments, $R^{B4}$ is —OH. In certain embodiments, $R^{B4}$ is —OMe. In certain embodiments, $R^{B4}$ is —$N(R^b)_2$ (e.g., —$NMe_2$). In certain embodiments, $R^{B4}$ is —$NH_2$. In certain embodiments, $R^{B4}$ is —NHC(=O)(optionally substituted $C_{1-6}$ alkyl). In certain embodiments, $R^{B4}$ is —NHC(=O)Me. In certain embodiments, $R^{A1}$ is —$NMe_2$. In certain embodiments, $R^{B4}$ is —$SR^a$ (e.g., —SMe). In certain embodiments, $R^{B4}$ is optionally substituted sulfonyl. In certain embodiments, $R^{B4}$ is halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^a$, —$N(R^b)_2$, or —$SR^a$.

Compounds of Formula (III″), (III′), (III), and (IIIA) include $R^{B5}$. In certain embodiments, $R^{B5}$ is —$OR^a$ (e.g., —OH or —OMe). In certain embodiments, $R^{B5}$ is —$OR^a$, wherein: $R^a$ is hydrogen, optionally substituted alkyl, optionally substituted alkenyl, or optionally substituted phenyl. In certain embodiments, $R^{B5}$ is —OH, —OMe, —OBn, or of the formula:

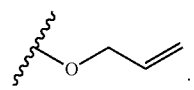 [SMILES: *OCC=C]

In certain embodiments, $R^{B5}$ is —O(optionally substituted alkyl) or —NH(optionally substituted aryl). In certain embodiments, $R^{B5}$ is —O(optionally substituted alkyl). In certain embodiments, $R^{B5}$ is —O(optionally substituted $C_{1-6}$ alkyl). In certain embodiments, $R^{B5}$ is —OMe. In certain embodiments, $R^{B5}$ is —OEt. In certain embodiments, $R^{B5}$ is —NH(optionally substituted aryl).

In certain embodiments, $R^{B5}$ is —$N(R^b)_2$. In certain embodiments, $R^{B5}$ is —$N(R^b)_2$, wherein each instance of $R^b$ is independently hydrogen, optionally substituted alkyl, optionally substituted alkynyl, optionally substituted carbocyclyl, optionally substituted phenyl, or optionally two $R^b$ are joined together with the intervening atoms to form optionally substituted heterocyclyl. In certain embodiments $R^{B5}$ is —NH(nBu). In certain embodiments, $R^{B5}$ is —$N(nBu)_2$. In certain embodiments, $R^{B5}$ is

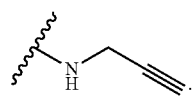 [SMILES: *NCC#C]

In certain embodiments, $R^{B5}$ is

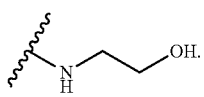 [SMILES: *NCCO]

In certain embodiments, $R^{B5}$ is

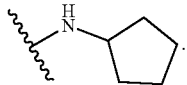

In certain embodiments, $R^{B5}$ is of the formula:

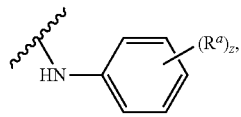

wherein $R^z$ is hydrogen, halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^a$, —$N(R^b)_2$, or —$SR^a$; and z is 0, 1, 2, 3, 4, or 5. In certain embodiments, z is 0. In certain embodiments, z is 1. In certain embodiments, z is 2. In certain embodiments, z is 3. In certain embodiments, z is 4. In certain embodiments, z is 5. In certain embodiments, $R^{B5}$ is of the formula:

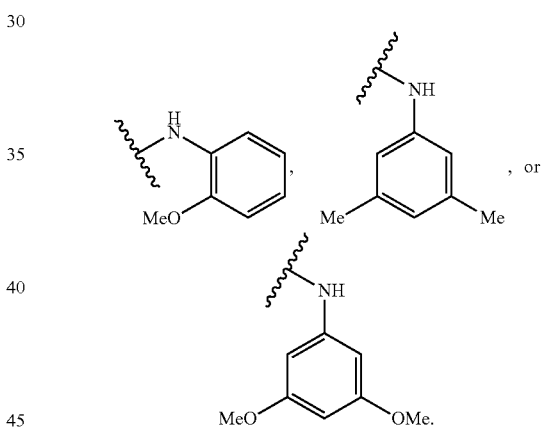

In certain embodiments, $R^{B5}$ is —$N(R^b)_2$, wherein two $R^b$ are joined together with the intervening atoms to form optionally substituted heterocyclyl. In certain embodiments, $R^{B5}$ is

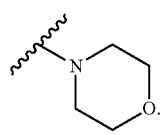

In certain embodiments, $R^{B5}$ is —$OR^a$ or —$N(R^b)_2$, wherein: $R^a$ is hydrogen, optionally substituted alkyl, optionally substituted alkenyl, or optionally substituted phenyl; and each instance of $R^b$ is independently hydrogen, optionally substituted alkyl, optionally substituted alkynyl, optionally substituted carbocyclyl, optionally substituted phenyl, or optionally two $R^b$ are joined together with the intervening atoms to form optionally substituted heterocyclyl.

In one aspect of the present invention, provided are compounds of Formula (IV):

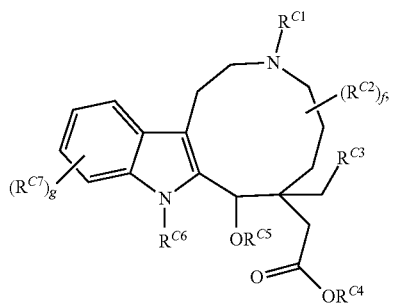

or a pharmaceutically acceptable salt, solvate, hydrate, polymorph, co-crystal, tautomer, stereoisomer, isotopically labeled derivative, or prodrug thereof, wherein:

$R^{C1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^2$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{C3}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{C4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{C5}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{C6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^{C7}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

f is 1, 2, 3, 4, 5, 6, 7, 8, 9, or 10; and g is 1, 2, 3, or 4.

In certain embodiments, the compound of Formula (IV) is of the formula:

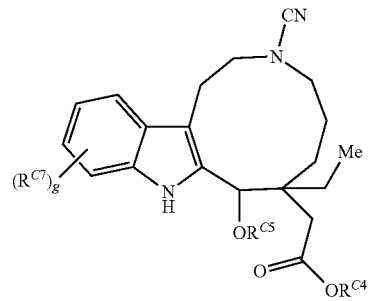

or a pharmaceutically acceptable salt, solvate, hydrate, polymorph, co-crystal, tautomer, stereoisomer, isotopically labeled derivative, or prodrug thereof.

In certain embodiments, the compound of Formula (IV) is of the formula:

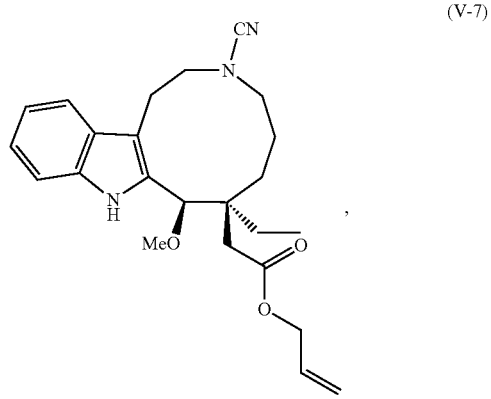

(V-7)

-continued (V6a)

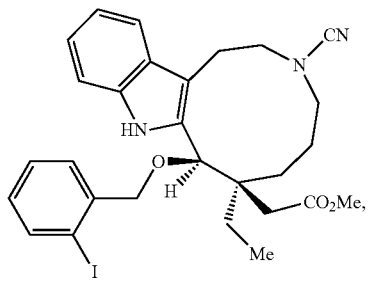

or a pharmaceutically acceptable salt, solvate, hydrate, polymorph, co-crystal, tautomer, stereoisomer, isotopically labeled derivative, or prodrug thereof.

Compounds of Formula (IV) include $R^{C1}$. In certain embodiments, $R^{C1}$ is hydrogen. In certain embodiments, $R^{C1}$ is optionally substituted alkyl (e.g., substituted or unsubstituted $C_{1-6}$ alkyl). In certain embodiments, $R^{C1}$ is substituted methyl. In certain embodiments, $R^{C1}$ is unsubstituted methyl. In certain embodiments, $R^{C1}$ is substituted or unsubstituted ethyl. In certain embodiments, $R^{C1}$ is optionally substituted acyl (e.g., —C(=O)Me). In certain embodiments, $R^{C1}$ is optionally substituted alkenyl (e.g., substituted or unsubstituted $C_{2-6}$ alkenyl). In certain embodiments, $R^{C1}$ is optionally substituted alkynyl (e.g., substituted or unsubstituted $C_{2-6}$ alkynyl). In certain embodiments, $R^{C1}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{C1}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{C1}$ is optionally substituted aryl (e.g., substituted or unsubstituted, 6- to 10-membered aryl). In certain embodiments, $R^{C1}$ is optionally substituted benzyl. In certain embodiments, $R^{C1}$ is optionally substituted phenyl. In certain embodiments, $R^{C1}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{C1}$ is a nitrogen protecting group. In certain embodiments, $R^{C1}$ is $R^{C1'}$. In certain embodiments, $R^{C1'}$ is —CN.

Compounds of Formula (IV) include one or more instances of $R^{C2}$. In certain embodiments, f is 1. In certain embodiments, f is 2. In certain embodiments, f is 3. In certain embodiments, f is 4. In certain embodiments, f is 5. In certain embodiments, f is 6. In certain embodiments, f is 7. In certain embodiments, f is 8. In certain embodiments, f is 9. In certain embodiments, f is 10.

In certain embodiments, f is f1. In certain embodiments, f1 is 0. In certain embodiments, f1 is 1. In certain embodiments, f1 is 2. In certain embodiments, f1 is 3. In certain embodiments, f1 is 4. In certain embodiments, f1 is 5. In certain embodiments, f1 is 6. In certain embodiments, f1 is 7. In certain embodiments, f1 is 8. In certain embodiments, f1 is 9. In certain embodiments, f1 is 10.

In certain embodiments, at least one instance of $R^{C2}$ is hydrogen. In certain embodiments, at least one instance of $R^{C2}$ is halogen (e.g., F, Cl, Br, or I). In certain embodiments, at least one instance of $R^{C2}$ is —CN. In certain embodiments, at least one instance of $R^{C2}$ is —SCN. In certain embodiments, at least one instance of $R^{C2}$ is —NO$_2$. In certain embodiments, at least one instance of $R^{C2}$ is —N$_3$. In certain embodiments, at least one instance of $R^{C2}$ is optionally substituted alkyl (e.g., substituted or unsubstituted $C_{1-6}$ alkyl). In certain embodiments, at least one instance of $R^{C2}$ is substituted methyl. In certain embodiments, at least one instance of $R^{C2}$ is unsubstituted methyl. In certain embodiments, at least one instance of $R^{C2}$ is substituted or unsubstituted ethyl. In certain embodiments, at least one instance of $R^{C2}$ is optionally substituted acyl (e.g., —C(=O)Me). In certain embodiments, at least one instance of $R^{C2}$ is optionally substituted alkenyl (e.g., substituted or unsubstituted $C_{2-6}$ alkenyl). In certain embodiments, at least one instance of $R^{C2}$ is optionally substituted alkynyl (e.g., substituted or unsubstituted $C_{2-6}$ alkynyl). In certain embodiments, at least one instance of $R^{C2}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{C2}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{C2}$ is optionally substituted aryl (e.g., substituted or unsubstituted, 6- to 10-membered aryl). In certain embodiments, at least one instance of $R^{C2}$ is optionally substituted benzyl. In certain embodiments, at least one instance of $R^{C2}$ is optionally substituted phenyl. In certain embodiments, at least one instance of $R^{C2}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{C2}$ is —OR$^a$ (e.g., —OH or —OMe). In certain embodiments, at least one instance of $R^{C2}$ is —OH. In certain embodiments, at least one instance of R $R^{C2\ A3}$ is —OMe. In certain embodiments, at least one instance of $R^{C2}$ is —N(R$^b$)$_2$ (e.g., —NMe$_2$). In certain embodiments, at least one instance of $R^{C2}$ is —NMe$_2$. In certain embodiments, at least one instance of $R^{C2}$ is —SR$^a$ (e.g., —SMe). In certain embodiments, at least one instance of $R^{C2}$ is optionally substituted sulfonyl. In certain embodiments, at least one instance of $R^{C2}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$.

Compounds of Formula (IV) include $R^{C3}$. In certain embodiments, $R^{C3}$ is hydrogen. In certain embodiments, $R^{C3}$ is halogen (e.g., F, Cl, Br, or I). In certain embodiments, $R^{C3}$ is —CN. In certain embodiments, R$^3$ is —SCN. In certain embodiments, $R^{C3}$ is —NO$_2$. In certain embodiments, $R^{C3}$ is —N$_3$. In certain embodiments, $R^{C3}$ is optionally substituted alkyl (e.g., substituted or unsubstituted $C_{1-6}$ alkyl). In certain embodiments, $R^{C3}$ is optionally substituted $C_{1-6}$ alkyl. In certain embodiments, R$^3$ is substituted methyl. In certain embodiments, $R^{C3}$ is unsubstituted methyl. In certain embodiments, R$^{C3}$ is substituted or unsubstituted ethyl. In certain embodiments, R$^{C3}$ is unsubstituted ethyl. In certain embodiments, R$^{C3}$ is optionally substituted acyl (e.g., —C(=O)Me). In certain embodiments, R$^{C3}$ is optionally substituted alkenyl (e.g., substituted or unsubstituted C$_{2-6}$ alkenyl). In certain embodiments, R$^{C3}$ is optionally substituted alkynyl (e.g., substituted or unsubstituted C$_{2-6}$ alkynyl). In certain embodiments, R$^{C3}$ is optionally substituted carbocyclyl (e.g., substituted or unsubstituted, 3- to 7-membered, monocyclic carbocyclyl comprising zero, one, or two double bonds in the carbocyclic ring system). In certain embodiments, R$^{C3}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{C3}$ is optionally substituted aryl (e.g., substituted or unsubstituted, 6- to 10-membered aryl). In certain embodiments, R$^{C3}$ is optionally substituted benzyl. In certain embodiments, R$^{C3}$ is optionally substituted phenyl. In certain embodiments, R$^{C3}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^{C3}$ is —OR$^a$ (e.g., —OH or —OMe). In certain embodiments, R$^{C3}$ is —OH. In certain embodiments, R$^{C3}$ is —OMe. In certain embodiments, R$^{C3}$ is —N(R$^b$)$_2$ (e.g., —NMe$_2$). In certain embodiments, R$^{C3}$ is —NMe$_2$. In certain embodiments, R$^{C3}$ is —SR$^a$ (e.g., —SMe). In certain embodiments, R$^{C3}$ is optionally substituted sulfonyl.

Compounds of Formula (IV) include R$^{C4}$. In certain embodiments, R$^{C4}$ is hydrogen. In certain embodiments, R$^{C4}$ is optionally substituted alkyl (e.g., substituted or unsubstituted C$_{1-6}$ alkyl). In certain embodiments, R$^{C4}$ is optionally substituted C$_{1-6}$ alkyl. In certain embodiments, R$^{C4}$ is substituted methyl. In certain embodiments, R$^{C4}$ is unsubstituted methyl. In certain embodiments, R$^{C4}$ is substituted or unsubstituted ethyl. In certain embodiments, R$^{C4}$ is optionally substituted acyl (e.g., —C(=O)Me). In certain embodiments, R$^{C4}$ is optionally substituted alkenyl (e.g., substituted or unsubstituted C$_{2-6}$ alkenyl). In certain embodiments, R$^{C4}$ is optionally substituted C$_{1-6}$ alkyl or optionally substituted alkenyl. In certain embodiments, R$^{C4}$ is of the formula

In certain embodiments, R$^{C4}$ is optionally substituted alkynyl (e.g., substituted or unsubstituted C$_{2-6}$ alkynyl). In certain embodiments, R$^{C4}$ is optionally substituted carbocyclyl (e.g., substituted or unsubstituted, 3- to 7-membered, monocyclic carbocyclyl comprising zero, one, or two double bonds in the carbocyclic ring system). In certain embodiments, R$^{C4}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{C4}$ is optionally substituted aryl (e.g., substituted or unsubstituted, 6- to 10-membered aryl). In certain embodiments, R$^{C4}$ is optionally substituted benzyl. In certain embodiments, R$^{C4}$ is optionally substituted phenyl. In certain embodiments, R$^{C4}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^{C4}$ is an oxygen protecting group.

Compounds of Formula (IV) include R$^{C5}$. In certain embodiments, R$^{C5}$ is hydrogen. In certain embodiments, R$^{C5}$ is optionally substituted alkyl (e.g., substituted or unsubstituted C$_{1-6}$ alkyl). In certain embodiments, R$^{C5}$ is optionally substituted C$_{1-6}$ alkyl. In certain embodiments, R$^{C5}$ is substituted methyl. In certain embodiments, R$^{C5}$ is unsubstituted methyl. In certain embodiments, R$^{C5}$ is substituted or unsubstituted ethyl. In certain embodiments, R$^{C5}$ is optionally substituted acyl (e.g., —C(=O)Me). In certain embodiments, R$^{C5}$ is optionally substituted alkenyl (e, substituted or unsubstituted C$_{2-6}$ alkenyl). In certain embodiments, R$^{C5}$ is of the formula

In certain embodiments, R$^{C5}$ is optionally substituted alkynyl (e.g., substituted or unsubstituted C$_{2-6}$ alkynyl). In certain embodiments, R$^{C5}$ is optionally substituted carbocyclyl (e.g., substituted or unsubstituted, 3- to 7-membered, monocyclic carbocyclyl comprising zero, one, or two double bonds in the carbocyclic ring system). In certain embodiments, R$^{C5}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{C5}$ is optionally substituted aryl (e.g., substituted or unsubstituted, 6- to 10-membered aryl). In certain embodiments, R$^{C5}$ is optionally substituted benzyl. In certain embodiments, R$^{C5}$ is of the formula:

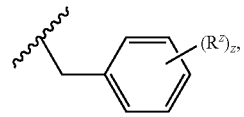

wherein R$^z$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$; and z is 0, 1, 2, 3, 4, or 5. In certain embodiments, R$^z$ is halogen (e.g., F, Cl, Br, or I). In certain embodiments, R$^z$ is optionally substituted C$_{1-6}$ alkyl. In certain embodiments, R$^{C5}$ is of the formula:

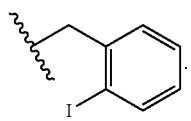 [SMILES: *Cc1ccccc1I]

In certain embodiments, $R^{C5}$ is optionally substituted phenyl. In certain embodiments, $R^{C5}$ is optionally substituted $C_{1-6}$ alkyl or optionally substituted aryl. In certain embodiments, $R^{C5}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{C5}$ is an oxygen protecting group. In certain embodiments, $R^{C5}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

Compounds of Formula (IV) include $R^{C6}$. In certain embodiments, $R^{C6}$ is hydrogen. In certain embodiments, $R^{C6}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Compounds of Formula (IV) include one or more instances of $R^7$. In certain embodiments, g is 1. In certain embodiments, g is 2. In certain embodiments, g is 3. In certain embodiments, g is 4.

In certain embodiments, g is g1. In certain embodiments, g1 is 0. In certain embodiments, g1 is 1. In certain embodiments, g1 is 2. In certain embodiments, g1 is 3. In certain embodiments, g1 is 4.

In one aspect of the present invention, provided are compounds of Formula (V'):

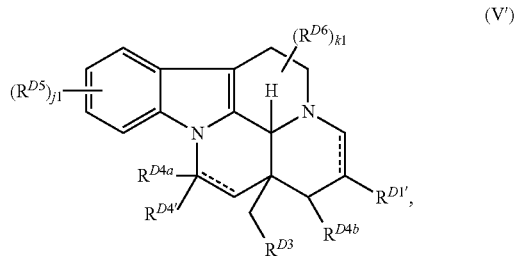

(V')

or a pharmaceutically acceptable salt, solvate, hydrate, polymorph, co-crystal, tautomer, stereoisomer, isotopically labeled derivative, or prodrug thereof, wherein:

each instance of — independently indicates a single or double bond;

$R^{D1'}$ is hydrogen, halogen, optionally substituted alkyl, optionally substituted acyl, optionally substituted alkenyl, optionally substituted alkynyl, or optionally substituted aryl;

$R^{D3}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{D4'}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —C(=O)OR$^{D4}$, —N(R$^b$)$_2$, or —SR$^a$;

$R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or optionally, $R^{D4'}$ and $R^D$ are joined together to form =O;

each instance of $R^{D4a}$ and $R^{D4b}$ is independently independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$, or optionally, $R^{D4a}$ and $R^{D4b}$ are joined together with the intervening atoms to form optionally substituted heterocyclyl;

each instance of $R^{D5}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^{D6}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

j1 is 0, 1, 2, 3, or 4; and
k1 is 0, 1, 2, 3, or 4.

In certain embodiments, a compound of Formula (V') is of Formula (V).

In one aspect of the present invention, provided are compounds of Formula (V):

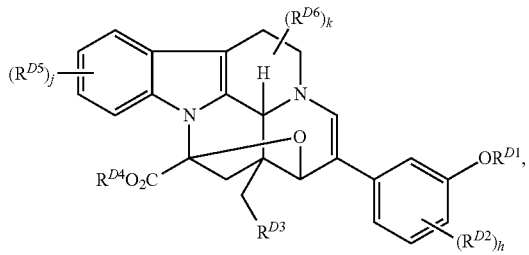

(V)

or a pharmaceutically acceptable salt, solvate, hydrate, polymorph, co-crystal, tautomer, stereoisomer, isotopically labeled derivative, or prodrug thereof, wherein:

$R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{D2}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{D3}$ is hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{D4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^{D5}$ is independently hydrogen, halogen, —CN, —SCN, —NO$_2$, —N$_3$, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^L$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

h is 1, 2, 3, or 4;
j is 1, 2, 3, or 4; and
k is 1, 2, 3, or 4.

In certain embodiments, a compound of Formula (V') is of formula:

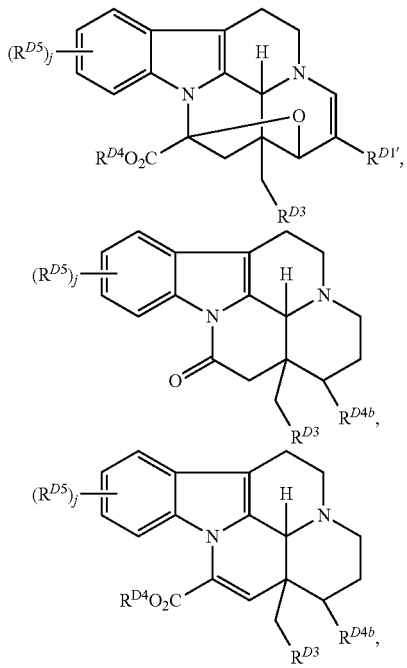

or a pharmaceutically acceptable salt, solvate, hydrate, polymorph, co-crystal, tautomer, stereoisomer, isotopically labeled derivative, or prodrug thereof.

In certain embodiments, a compound of Formula (V') is of formula:

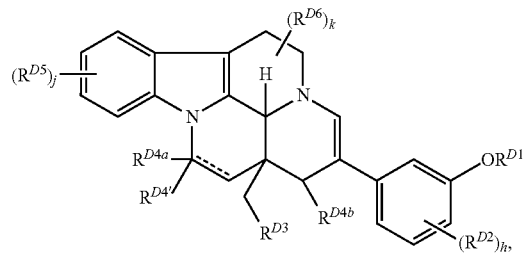

or a pharmaceutically acceptable salt, solvate, hydrate, polymorph, co-crystal, tautomer, stereoisomer, isotopically labeled derivative, or prodrug thereof, $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{D2}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$; and h is 1, 2, 3, or 4.

In certain embodiments, the compound of Formulae (V') or (V) is of the formula:

(V-6)
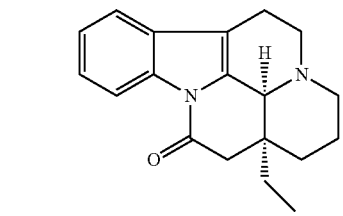

(V-12)
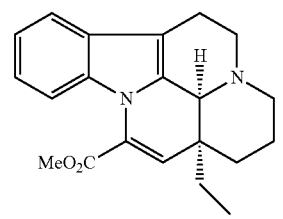

(V-13)
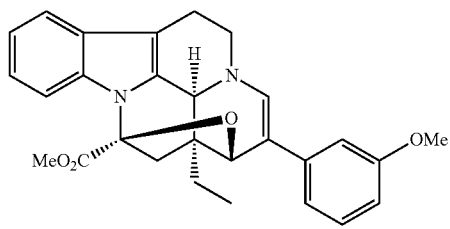

(V-15)
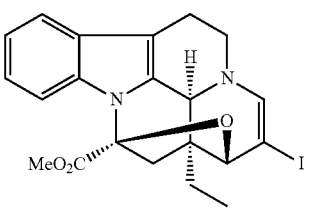

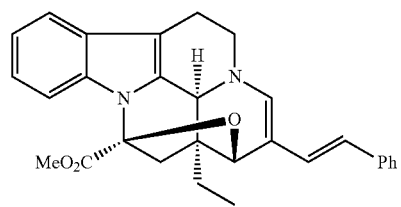

(V-16)
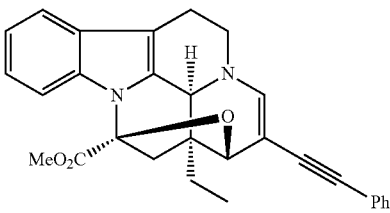

(V-17)
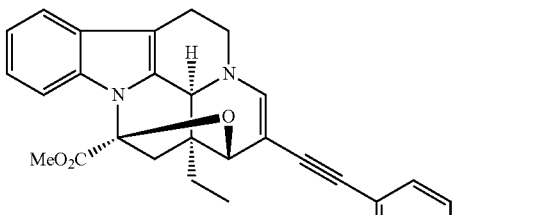

(V-47)
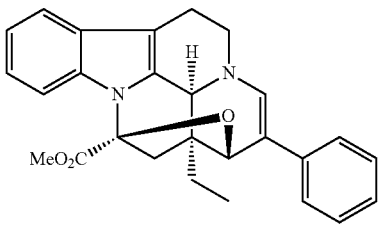

(V-48)
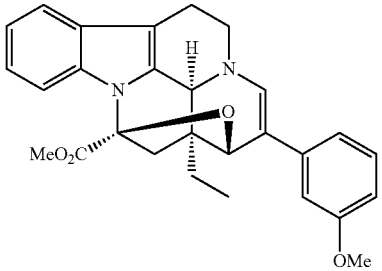

(V-49)
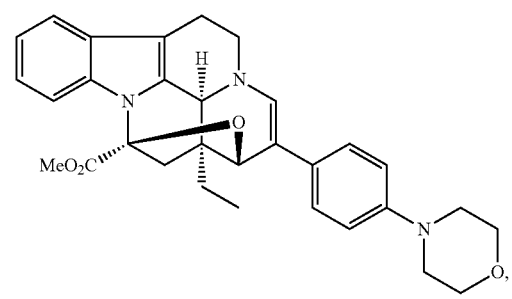

or a pharmaceutically acceptable salt, solvate, hydrate, polymorph, co-crystal, tautomer, stereoisomer, isotopically labeled derivative, or prodrug thereof.

Compounds of Formula (V') include $R^{D1'}$. In certain embodiments, $R^{D1'}$ is hydrogen. In certain embodiments, $R^{D1'}$ is halogen (e.g., F, Cl, Br, or I). In certain embodiments, $R^{D1'}$ is I. In certain embodiments, $R^{D1'}$ is optionally substituted alkyl (e.g., substituted or unsubstituted C$_{1-6}$ alkyl). In certain embodiments, $R^{D1'}$ is optionally substituted C$_{1-6}$ alkyl. In certain embodiments, $R^{D1'}$ is substituted methyl. In certain embodiments, $R^{D1'}$ is unsubstituted methyl. In certain embodiments, $R^{D1'}$ is substituted or unsubstituted ethyl.

In certain embodiments, $R^{D1'}$ is unsubstituted ethyl. In certain embodiments, $R^{D1'}$ is optionally substituted acyl (e.g., —C(=O)Me). In certain embodiments, $R^{D1'}$ is optionally substituted alkenyl (e.g., substituted or unsubstituted $C_{2-6}$ alkenyl). In certain embodiments, $R^{D1'}$ is substituted or unsubstituted $C_{2-6}$ alkenyl. In certain embodiments, $R^{D1'}$ is of formula:

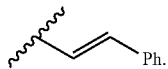 [SMILES: */C=C/c1ccccc1]

In certain embodiments, $R^{D1'}$ is optionally substituted alkynyl (e.g., substituted or unsubstituted $C_{2-6}$ alkynyl). In certain embodiments, $R^{D1'}$ is optionally substituted $C_{2-6}$ alkynyl. In certain embodiments $R^{D1'}$ is of formula:

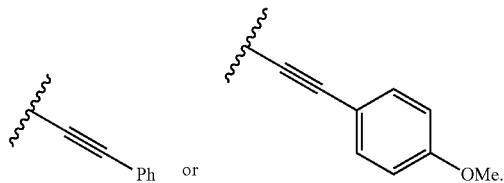 [SMILES: *C#Cc1ccccc1 ; *C#Cc1ccc(OC)cc1]

In certain embodiments, $R^{D1'}$ is optionally substituted aryl (e.g., substituted or unsubstituted, 6- to 10-membered aryl). In certain embodiments, $R^{D1'}$ is optionally substituted benzyl. In certain embodiments, $R^{D1'}$ is optionally substituted phenyl. In certain embodiments, $R^{D1'}$ is of the formula:

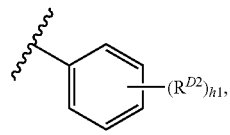

wherein: each instance of $R^{D2}$ is independently —OR$^a$ or optionally substituted heterocyclyl, and h1 is 0, 1, 2, 3, 4, or 5. In certain embodiments, h1 is h. In certain embodiments, $R^{D1'}$ is of the formula:

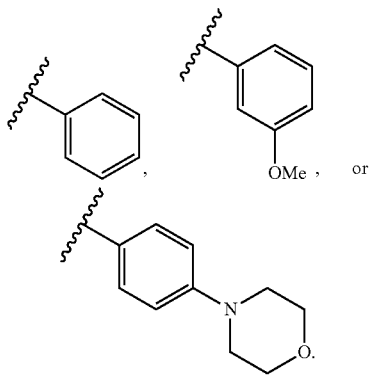

Each instance of — independently indicates a single or double bond. In certain embodiments, = is a single bond. In certain embodiments, is a double bond.

Compounds of Formula (V) include one or more instances of $R^{D2}$. In certain embodiments, h is 1, 2, 3, or 4. In certain embodiments, h is 1. In certain embodiments, h is 2. In certain embodiments h is 3. In certain embodiments, h is 4. In certain embodiments, h is h1. In certain embodiments, h1 is 0. In certain embodiments, h1 is 1. In certain embodiments, h1 is 2. In certain embodiments, hi is 3. In certain embodiments, hi is 4. In certain embodiments, at least one instance of $R^{D2}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, at least one instance of $R^{D2}$ is independently halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$.

Compounds of Formulae (V') and (V) include $R^{D3}$. In certain embodiments, $R^{D3}$ is hydrogen. In certain embodiments, $R^{D3}$ is halogen (e.g., F, Cl, Br, or I). In certain embodiments, $R^{D3}$ is —CN. In certain embodiments, $R^{D3}$ is —SCN. In certain embodiments, $R^{D3}$ is —NO$_2$. In certain embodiments, $R^{D3}$ is —N$_3$. In certain embodiments, $R^{D3}$ is optionally substituted alkyl (e.g., substituted or unsubstituted $C_{1-6}$ alkyl). In certain embodiments, $R^{D3}$ is substituted methyl. In certain embodiments, $R^{D3}$ is unsubstituted methyl. In certain embodiments, $R^{D3}$ is substituted or unsubstituted ethyl. In certain embodiments, $R^{D3}$ is optionally substituted acyl (e.g., —C(=O)Me). In certain embodiments, $R^{D3}$ is optionally substituted alkenyl (e.g., substituted or unsubstituted $C_{2-6}$ alkenyl). In certain embodiments, $R^{D3}$ is optionally substituted alkynyl (e.g., substituted or unsubstituted $C_{2-6}$ alkynyl). In certain embodiments, $R^{D3}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{D3}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D3}$ is optionally substituted aryl (e.g., substituted or unsubstituted, 6- to 10-membered aryl). In certain embodiments, $R^{D3}$ is optionally substituted benzyl. In certain embodiments, $R^{D3}$ is optionally substituted phenyl. In certain embodiments, $R^{D3}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D3}$ is —OR$^a$ (e.g., —OH or —OMe). In certain embodiments, $R^{D3}$ is —OH. In certain embodiments, $R^{D3}$ is —OMe. In certain embodiments, $R^{D3}$ is —N(R$^b$)$_2$ (e.g., —NMe$_2$). In certain embodiments, $R^{D3}$ is —NMe$_2$. In certain embodiments, $R^{D3}$ is —SR$^a$ (e.g., —SMe). In certain embodiments, $R^{D3}$ is optionally substituted sulfonyl.

Compounds of Formulae (V') include $R^{D4'}$. In certain embodiments, $R^{D4'}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —C(=O)OR$^{D4}$, —N(R$^b$)$_2$, or —SR$^a$.

Compounds of Formulae (V') and (V) include R$^{D4}$. In certain embodiments, R$^{D4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, R$^{D4'}$ and R$^{D4}$ are joined together to form =O. In certain embodiments, R$^{D4}$ is optionally substituted alkyl (e.g., substituted or unsubstituted C$_{1-6}$ alkyl). In certain embodiments, R$^{D4}$ is substituted methyl. In certain embodiments, R$^{D4}$ is unsubstituted methyl. In certain embodiments, R$^{D4}$ is substituted or unsubstituted ethyl.

In certain embodiments, each instance of R$^{D4a}$ and R$^{D4b}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, R$^{D4a}$ and R$^{D4b}$ are joined together with the intervening atoms to form optionally substituted heterocyclyl. In certain embodiments, R$^{D4a}$ and R$^{D4b}$ are joined together with the intervening atoms to form an optionally substituted, 5- to 10-membered monocyclic heterocyclic ring, wherein one or two atoms in the heterocyclic ring are independently nitrogen, oxygen, or sulfur. In certain embodiments, R$^{D4a}$ and R$^{D4b}$ are joined together with the intervening atoms to form an unsubstituted heterocyclyl with a bridging oxygen atom. In certain embodiments, R$^{D4a}$ and R$^{D4b}$ are joined together with the intervening atoms to form tetrahydrofuran.

Compounds of Formulae (V'), (V), and (VII) include one or more instances of R$^{D5}$. In certain embodiments, j is 1. In certain embodiments, j is 2. In certain embodiments, j is 3. In certain embodiments, j is 4. In certain embodiments, j is j1. In certain embodiments, j1 is 0. In certain embodiments, j1 is 1. In certain embodiments, j is 2. In certain embodiments, j1 is 3. In certain embodiments, j1 is 4. In certain embodiments, at least one instance of R$^{D5}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$.

Compounds of Formulae (V'), (V), (VII), (VIII'), (VIII), and (IX) include one or more instances of R$^{D6}$. In certain embodiments, k is 1. In certain embodiments, k is 2. In certain embodiments, k is 3. In certain embodiments, k is 4. In certain embodiments, k is k1. In certain embodiments, k1 is 0. In certain embodiments, k1 is 1. In certain embodiments, k1 is 2. In certain embodiments, k1 is 3. In certain embodiments, k1 is 4.

In certain embodiments, q is 1. In certain embodiments, q is 2. In certain embodiments, q is 3. In certain embodiments, q is 4.

In certain embodiments, q is q1. In certain embodiments, q1 is 0. In certain embodiments, q1 is 1. In certain embodiments, q1 is 2. In certain embodiments, q1 is 3. In certain embodiments, q1 is 4.

In certain embodiments, at least one instance of R$^{D6}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, j is 1 and k is 1. In certain embodiments, R$^{D5}$ and R$^{D6}$ are both hydrogen. In certain embodiments, c is 1, d is 1, and q is 1. In certain embodiments, R$^{43}$ is hydrogen, R$^{46}$ is hydrogen, and R$^{D6}$ is hydrogen.

In certain embodiments, c1 is 0, d1 is 0, and q1 is 0.

In one aspect of the present invention, provided are compounds of Formula (VI):

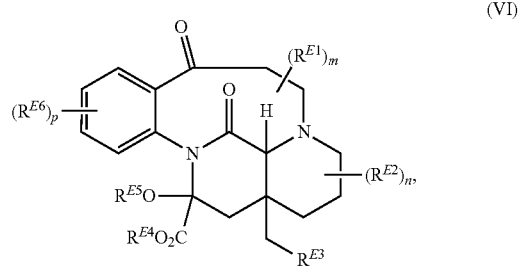

or a pharmaceutically acceptable salt, solvate, hydrate, polymorph, co-crystal, tautomer, stereoisomer, isotopically labeled derivative, or prodrug thereof, wherein:

each instance of R$^{E1}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

each instance of R$^{E2}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

R$^{E3}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

R$^{E4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R$^{E5}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{E6}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

m is 1, 2, 3, or 4;
n is 1, 2, 3, 4, 5, or 6; and
p is 1, 2, 3, or 4.

In certain embodiments, the compound of Formula (VI) is of the formula:

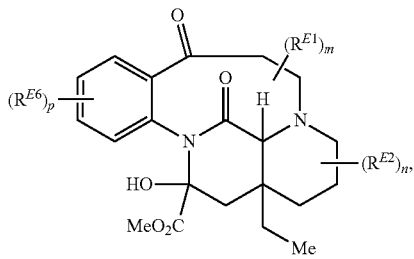

or a pharmaceutically acceptable salt, solvate, hydrate, polymorph, co-crystal, tautomer, stereoisomer, isotopically labeled derivative, or prodrug thereof.

In certain embodiments, the compound of Formula (VI) is of the formula:

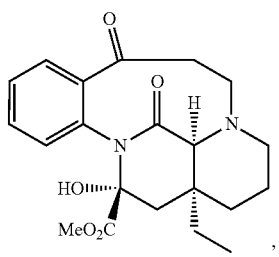 [SMILES: CC[C@@]12CCCN3CCC(=O)c4ccccc4N(C(=O)[C@@H]31)[C@](O)(C(=O)OC)C2]

or a pharmaceutically acceptable salt, solvate, hydrate, polymorph, co-crystal, tautomer, stereoisomer, isotopically labeled derivative, or prodrug thereof.

Compounds of Formula (VI) include one or more instances of $R^{E1}$. In certain embodiments, m is 1. In certain embodiments, m is 2. In certain embodiments, m is 3. In certain embodiments, m is 4.

In certain embodiments, m is m1. In certain embodiments, m1 is 0. In certain embodiments, m1 is 2. In certain embodiments, m1 is 3. In certain embodiments, m1 is 4.

In certain embodiments, at least one instance of $R^{E1}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$. In certain embodiments, at least one instance of $R^{E1}$ is hydrogen.

Compounds of Formula (VI) and (X) include one or more instances of $R^{E2}$. In certain embodiments, n is 1. In certain embodiments, n is 2. In certain embodiments, n is 3. In certain embodiments, n is 4. In certain embodiments, n is 5. In certain embodiments, n is 6.

In certain embodiments, n is n1. In certain embodiments, n1 is 0. In certain embodiments, n1 is 1. In certain embodiments, n1 is 2. In certain embodiments, n1 is 3. In certain embodiments, n1 is 4. In certain embodiments, n1 is 5. In certain embodiments, n1 is 6. In certain embodiments, p is p1. In certain embodiments, p1 is 0. In certain embodiments, p1 is 1. In certain embodiments, p1 is 2. In certain embodiments, p1 is 3. In certain embodiments, p is 4. In certain embodiments, e is 0, d1 is 0, and p1 is 0.

In certain embodiments, p is 1. In certain embodiments, p is 2. In certain embodiments, p is 3. In certain embodiments, p is 4. In certain embodiments, m is 1, n is 1, and p is 1. In certain embodiments, c is 1, d is 1, and p is 1. In certain embodiments, $R^{A3}$ is hydrogen, $R^{A6}$ is hydrogen, and $R^{E2}$ is hydrogen. In certain embodiments, at least one instance of $R^{E2}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$. In certain embodiments, at least one instance of $R^{E2}$ is hydrogen.

Compounds of Formula (VI) include $R^{E3}$. In certain embodiments, $R^{E3}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$. In certain embodiments, $R^{E3}$ is hydrogen. In certain embodiments, $R^{E3}$ is optionally substituted alkyl (e.g., substituted or unsubstituted $C_{1-6}$ alkyl). In certain embodiments, $R^{E3}$ is substituted methyl. In certain embodiments, $R^{E3}$ is unsubstituted methyl. In certain embodiments, $R^{E3}$ is substituted or unsubstituted ethyl.

Compounds of Formula (VI) include $R^{E4}$. In certain embodiments, $R^{E4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{E4}$ is hydrogen. In certain embodiments, $R^{E4}$ is optionally substituted alkyl (e.g., substituted or unsubstituted $C_{1-6}$ alkyl). In certain embodiments, $R^{E4}$ is substituted methyl. In certain embodiments, $R^{E4}$ is unsubstituted methyl. In certain embodiments, $R^{E4}$ is substituted or unsubstituted ethyl.

Compounds of Formula (VI) include $R^{E5}$. In certain embodiments, $R^{E5}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^{E5}$ is hydrogen. In certain embodiments, $R^{E5}$ is optionally substituted alkyl (e.g., substituted or unsubstituted $C_{1-6}$ alkyl). In certain embodiments, $R^{E5}$ is substituted methyl. In certain embodiments, $R^{E5}$ is unsubstituted methyl. In certain embodiments, $R^{E5}$ is substituted or unsubstituted ethyl.

Compounds of Formula (VI) include one or more instances of $R^{E6}$. In certain embodiments, p is 1. In certain embodiments, p is 2. In certain embodiments, p is 3. In certain embodiments, p is 4. In certain embodiments, at least one instance of $R^{E6}$ is hydrogen, halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —$OR^a$, —$N(R^b)_2$, or —$SR^a$. In certain embodiments, at least one instance of $R^{E6}$ is hydrogen. In certain embodiments, m is 1, n is 1, and p is 1. In certain embodiments, m1 is 0, n1 is 0, and p1 is 0.

In one aspect of the present invention, provided are compounds of Formula (VII):

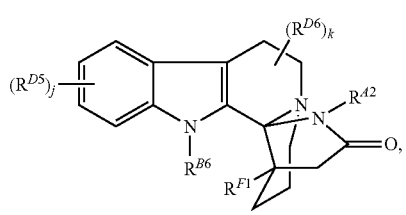

(VII)

or a pharmaceutically acceptable salt, solvate, hydrate, polymorph, co-crystal, tautomer, stereoisomer, isotopically labeled derivative, or prodrug thereof, wherein:

$R^{A2}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^{D5}$ is independently hydrogen, halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^a$, —$N(R^b)_2$, or —$SR^a$;

each instance of $R^{D6}$ is independently hydrogen, halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^a$, —$N(R^b)_2$, or —$SR^a$;

$R^{F1}$ is hydrogen, halogen, —CN, —SCN, —$NO_2$, —$N_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^a$, —$N(R^b)_2$, or —$SR^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

j is 1, 2, 3, or 4; and k is 1, 2, 3, or 4.

In certain embodiments, the compound of Formula (VII) is of the formula:

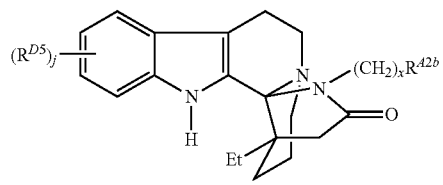

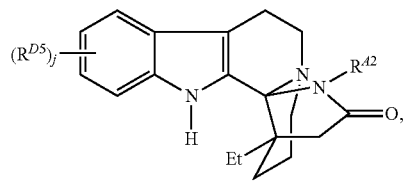

or a pharmaceutically acceptable salt, solvate, hydrate, polymorph, co-crystal, tautomer, stereoisomer, isotopically labeled derivative, or prodrug thereof.

In certain embodiments, the compound of Formula (VII) is of the formula:

123

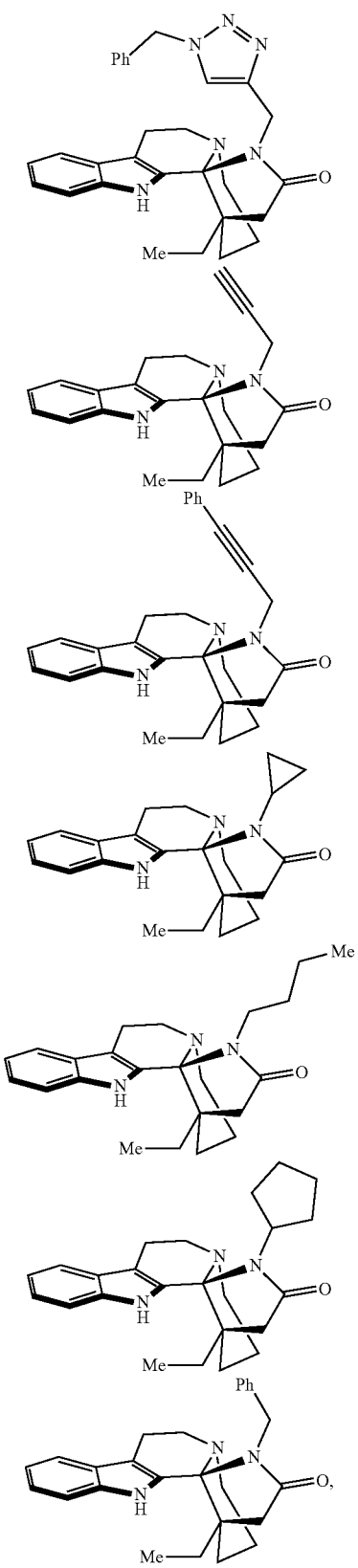

or a pharmaceutically acceptable salt, solvate, hydrate, polymorph, co-crystal, tautomer, stereoisomer, isotopically labeled derivative, or prodrug thereof.

Compounds of Formula (VII) include $R^{F1}$. In certain embodiments, $R^{F1}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, $R^{F1}$ is hydrogen. In certain embodiments, $R^{F1}$ is optionally substituted alkyl (e.g., substituted or unsubstituted C$_{1-6}$ alkyl). In certain embodiments, $R^{F1}$ is optionally substituted C$_{1-6}$ alkyl. In certain embodiments, $R^{F1}$ is substituted methyl. In certain embodiments, $R^{F1}$ is unsubstituted methyl. In certain embodiments, $R^{F1}$ is substituted or unsubstituted ethyl. In certain embodiments, $R^{F1}$ is unsubstituted ethyl. In certain embodiments, $R^{F1}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, j is 1 and k is 1.

In certain embodiments, j1 is 0 and k1 is 0.

In one aspect of the present invention, provided are compounds of Formula (VIII'):

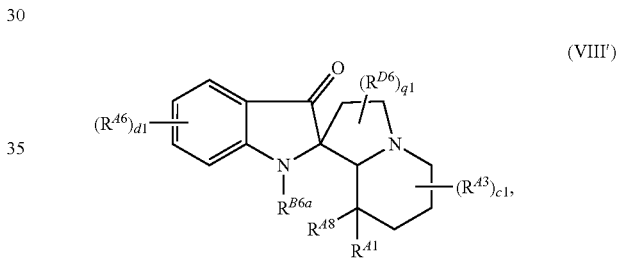

(VIII')

or a pharmaceutically acceptable salt, solvate, hydrate, polymorph, co-crystal, tautomer, stereoisomer, isotopically labeled derivative, or prodrug thereof, wherein:

$R^{A1z}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{B6}a$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R$^{A8}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^b$)$_2$, —SR$^a$;

or R$^{B6a}$ and R$^{A8}$ are taken together with their intervening atoms to form an optionally substituted heterocyclic ring;

each instance of R$^{D6}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

c1 is 1, 2, 3, 4, 5, or 6;
d1 is 1, 2, 3, or 4; and
q1 is 1, 2, 3, or 4.

In certain embodiments, a compound of Formula (VIII') is of Formula (VIII).

In one aspect of the resent invention, provided are compounds of Formula (VIII):

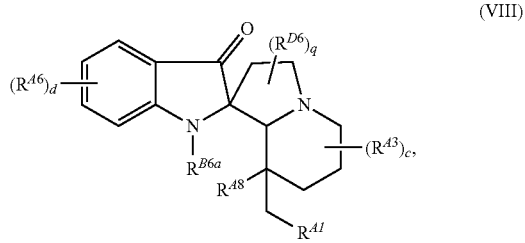

(VIII)

or a pharmaceutically acceptable salt, solvate, hydrate, polymorph, co-crystal, tautomer, stereoisomer, isotopically labeled derivative, or prodrug thereof, wherein:

R$^{A1}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

R$^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^{B6a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R$^{A8}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^b$)$_2$, —SR$^a$;

or R$^{B6a}$ and R$^{A8}$ are taken together with their intervening atoms to form an optionally substituted heterocyclic ring;

each instance of R$^{D6}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$ or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

c is 1, 2, 3, 4, 5, or 6;
d is 1, 2, 3, or 4; and
q is 1, 2, 3, or 4.

In certain embodiments, the compound of Formulae (VIII') or (VIII) is of the formula:

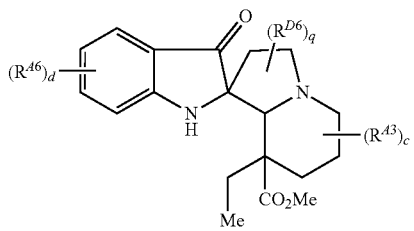

-continued

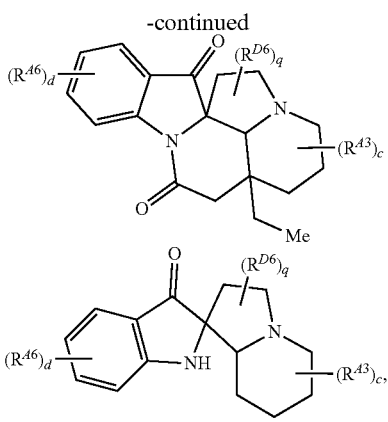

or a pharmaceutically acceptable salt, solvate, hydrate, polymorph, co-crystal, tautomer, stereoisomer, isotopically labeled derivative, or prodrug thereof.

In certain embodiments, the compound of Formulae (VIII') or (VIII) is of the formula:

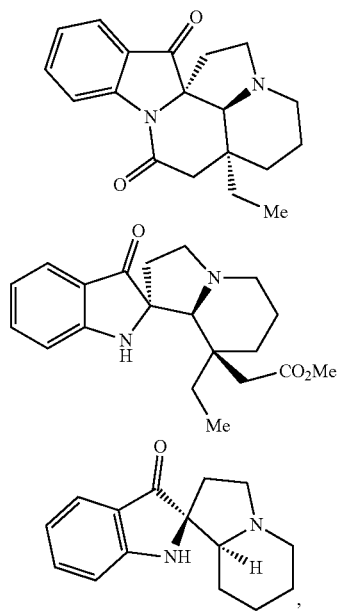

or a pharmaceutically acceptable salt, solvate, hydrate, polymorph, co-crystal, tautomer, stereoisomer, isotopically labeled derivative, or prodrug thereof.

Compounds of Formula (VIII') include $R^{A1z}$. In certain embodiments, $R^{A1z}$ is hydrogen. In certain embodiments, $R^{A1z}$ is halogen (e.g., F, Cl, Br, or I). In certain embodiments, $R^{A1z}$ is —Br. In certain embodiments, $R^{A1z}$ is —CN. In certain embodiments, $R^{A1z}$ is —SCN. In certain embodiments, $R^{A1z}$ is —NO$_2$. In certain embodiments, $R^{A1z}$ is -N$_3$. In certain embodiments, $R^{A1z}$ is optionally substituted alkyl (e.g., substituted or unsubstituted C$_{1-6}$ alkyl). In certain embodiments, $R^{A1z}$ is substituted methyl. In certain embodiments, $R^{A1z}$ is unsubstituted methyl. In certain embodiments, $R^{A1z}$ is substituted or unsubstituted ethyl. In certain embodiments, $R^{A1z}$ is unsubstituted ethyl. In certain embodiments, $R^{A1z}$ is optionally substituted acyl (e.g., —C(=O)Me). In certain embodiments, $R^{A1z}$ is optionally substituted alkenyl (e.g., substituted or unsubstituted C$_{2-6}$ alkenyl). In certain embodiments, $R^{A1z}$ is optionally substituted alkynyl (e.g., substituted or unsubstituted C$_{2-6}$ alkynyl). In certain embodiments, $R^{A1z}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{A1z}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{A1z}$ is optionally substituted aryl (e.g., substituted or unsubstituted, 6- to 10-membered aryl). In certain embodiments, $R^{A1z}$ is optionally substituted benzyl. In certain embodiments, $R^{A1z}$ is optionally substituted phenyl. In certain embodiments, $R^{A1z}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{A1z}$ is —OR$^a$ (e.g., —OH or —OMe). In certain embodiments, $R^{A1z}$ is —OH. In certain embodiments, $R^{A1}$ is —OMe. In certain embodiments, $R^{A1z}$ is —N(R$^b$)$_2$ (e.g., —NMe$_2$). In certain embodiments, $R^{A1z}$ is —NH$_2$. In certain embodiments, $R^{A1z}$ is —NHC(=O)(optionally substituted C$_{1-6}$ alkyl). In certain embodiments, $R^{A1z}$ is —NHC(=O)Me. In certain embodiments, $R^{A1z}$ is —NMe$_2$. In certain embodiments, $R^{A1z}$ is —SR$^a$ (e.g., —SMe). In certain embodiments, $R^{A1z}$ is optionally substituted sulfonyl.

Compounds of Formulae (VIII') and (VIII) include $R^{B6a}$. In certain embodiments, $R^{B6a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^{B6a}$ is hydrogen.

Compounds of Formulae (VIII') and (VIII) include $R^{A8}$. In certain embodiments, $R^{A8}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^b$)$_2$, —SR$^a$. In certain embodiments, $R^{A8}$ is hydrogen. In certain embodiments, $R^{A8}$ is optionally substituted alkyl (e.g., substituted or unsubstituted C$_{1-6}$ alkyl). In certain embodiments, $R^{A8}$ is optionally substituted C$_{1-8}$ alkyl. In certain embodiments, $R^{A8}$ is substituted methyl. In certain embodiments, $R^{A8}$ is unsubstituted methyl. In certain embodiments, $R^{A8}$ is substituted or unsubstituted ethyl. In certain embodiments, $R^{A8}$ is unsubstituted ethyl. In certain embodiments, $R^{A8}$ is —(CH$_2$)COO(optionally substituted C$_{1-6}$ alkyl). In certain embodiments, $R^{A8}$ is —(CH$_2$)COOMe. In certain embodiments, $R^{B6a}$ and $R^{A8}$ are taken together with their intervening atoms to form an optionally substituted heterocyclic ring. In certain embodiments, $R^{A8}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^b$)$_2$, —SR$^a$.

In one aspect of the present invention, provided are compounds of Formula (IX'):

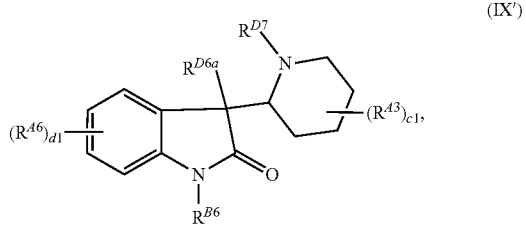

(IX')

or a pharmaceutically acceptable salt, solvate, hydrate, polymorph, co-crystal, tautomer, stereoisomer, isotopically labeled derivative, or prodrug thereof, wherein:

each instance of $R^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^{D7}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{D6a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^b$)$_2$, —SR$^a$, or optionally $R^{D7}$ and $R^{D6a}$ are joined together with the intervening atoms to form optionally substituted heterocyclyl;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c is 1, 2, 3, 4, 5, or 6;

d is 1, 2, 3, or 4.

In certain embodiments, the compound of Formula (IX') is of Formula (IX).

In certain embodiments, a compound described herein is of Formula (IX):

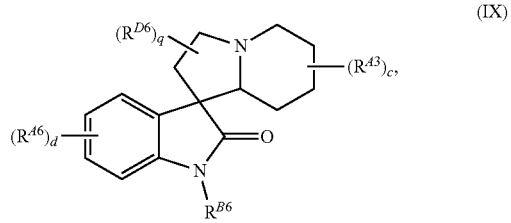

(IX)

or a pharmaceutically acceptable salt, solvate, hydrate, polymorph, co-crystal, tautomer, stereoisomer, isotopically labeled derivative, or prodrug thereof, wherein:

each instance of $R^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c is 1, 2, 3, 4, 5, or 6;

d is 1, 2, 3, or 4; and q is 1, 2, 3, or 4.

In certain embodiments, the compound of Formula (IX') or (IX) is of the formula:

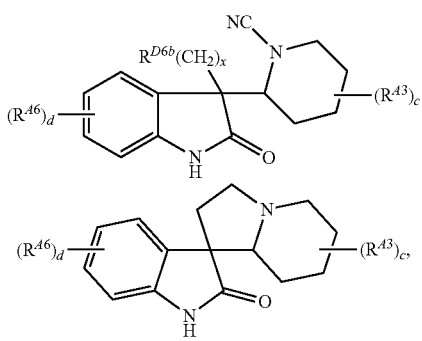

or a pharmaceutically acceptable solvate, hydrate, polymorph, co-crystal, tautomer, stereoisomer, isotopically labeled derivative, or prodrug thereof.

In certain embodiments, the compound of Formula (IX') or (IX) is of the formula:

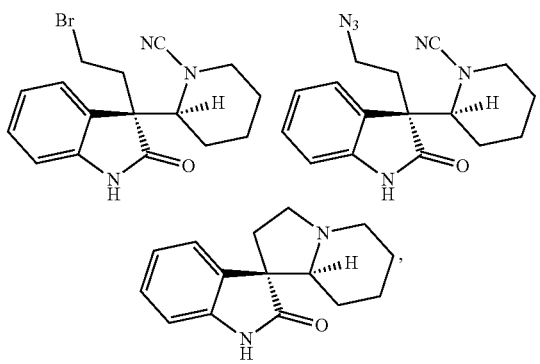

or a pharmaceutically acceptable solvate, hydrate, polymorph, co-crystal, tautomer, stereoisomer, isotopically labeled derivative, or prodrug thereof.

Compounds of Formula (IX') include $R^{D7}$. In certain embodiments, $R^{D7}$ is hydrogen. In certain embodiments, $R^{D7}$ is halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$. In certain embodiments, $R^{D7}$ is —CN.

Compounds of Formula (IX') include $R^{D a}$. In certain embodiments, $R^{D6a}$ is hydrogen. In certain embodiments, $R^{D6a}$ is optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^a$, —N(R$^b$)$_2$, —SR$^a$, or $R^{D7}$ and $R^{D6a}$ are joined together with the intervening atoms to form optionally substituted heterocyclyl. In certain embodiments, $R^{D7}$ and $R^{D6a}$ are joined together with the intervening atoms to form optionally substituted heterocyclyl. In certain embodiments, $R^{D6a}$ is optionally substituted alkyl (e.g., substituted or unsubstituted C$_{1-6}$ alkyl). In certain embodiments, $R^{D6a}$ is optionally substituted C$_{1-6}$ alkyl. In certain embodiments, $R^{D6a}$ is of the formula: —(CH$_2$)$_x$R$^{D6b}$, wherein: x is 1, 2, 3, or 4; and $R^{D6b}$ is halogen, optionally substituted carbocyclyl, —OR$^a$, or —N$_3$. In certain embodiments, x is 1. In certain embodiments, x is 2. In certain embodiments, x is 3. In certain embodiments, x is 4. In certain embodiments, $R^{D6b}$ is halogen (e.g., F, Cl, Br, or I). In certain embodiments, RD is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{D6b}$ is —OR$^a$ (e.g., —OH or —OMe). In certain embodiments, $R^{D6b}$ is —OR$^a$, wherein R$^a$ is optionally substituted C$_{1-6}$ alkyl. In certain embodiments, $R^{D6}$ is —N$_3$. In certain embodiments, $R^{6a}$ is of the formula: —(CH$_2$)$_2$Br or —(CH$_2$)$_2$N$_3$. In certain embodiments, $R^{D6a}$ is substituted methyl. In certain embodiments, $R^{D6a}$ is unsubstituted methyl. In certain embodiments, $R^{6a}$ is substituted or unsubstituted ethyl. In certain embodiments, $R^{D6a}$ is unsubstituted ethyl. In certain embodiments, c is 1, d is 1, and q is 1. In certain embodiments, c is 1 and d is 1. In certain embodiments, $R^{A3}$ is hydrogen, $R^{A6}$ is hydrogen, and $R^{D6}$ is hydrogen. In certain embodiments, $R^{A3}$ is hydrogen and $R^{A6}$ is hydrogen.

In certain embodiments, c1 is 0, 1, d1 is 0, and q1 is 0. In certain embodiments, c1 is 0 and d1 is 0.

In one aspect of the present invention, provided are compounds of Formula (X):

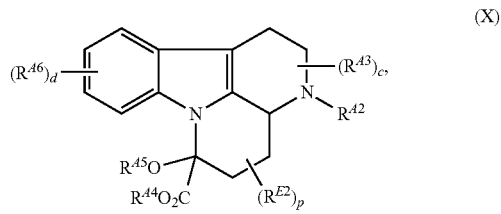

or a pharmaceutically acceptable salt, solvate, hydrate, polymorph, co-crystal, tautomer, stereoisomer, isotopically labeled derivative, or prodrug thereof, wherein:

$R^{A2}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^{A3}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{A4}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{A5}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{A6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

each instance of $R^{E2}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted sulfonyl, —OR$^a$, —N(R$^b$)$_2$, or —SR$^a$;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;

c is 1, 2, 3, 4, 5, or 6;

d is 1, 2, 3, or 4; and p is 1, 2, 3, or 4.

In certain embodiments, the compound of Formula (X) is of the formula:

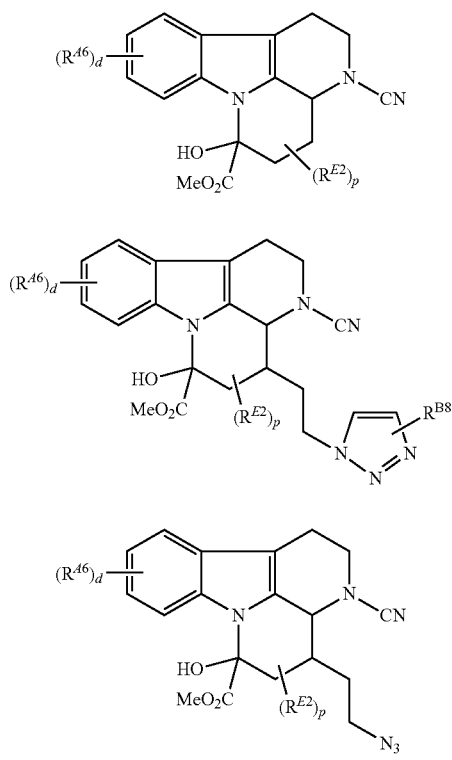

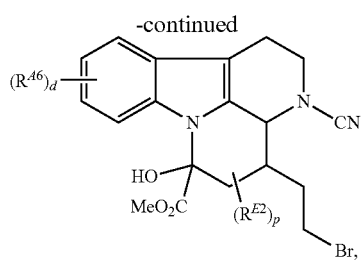

wherein $R^{B8}$ is optionally substituted alkyl, optionally substituted carbocyclyl, optionally substituted aryl, or optionally substituted heteroaryl, or a pharmaceutically acceptable solvate, hydrate, polymorph, co-crystal, tautomer, stereoisomer, isotopically labeled derivative, or prodrug thereof.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formulae (I'), (I), (IA), (II'), (II), (IIA), (III'''), (III'), (IIIA), (III), (IV), (V'), (V), (VI), (VII), (VIII'), (VIII), (IX'), (IX), or (X), or a pharmaceutically acceptable salt thereof, and a pharmaceutically acceptable excipient. In certain embodiments, a compound described herein is a compound of Formulae (I'), (I), (IA), (II'), (II), (IIA), (III'''), (III'), (IIIA), (III), (IV), (V'), (V), (VI), (VII), (VIII'), (VIII), (IX'), (IX), or (X), or a pharmaceutically acceptable salt thereof. In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for treating a disease (e.g., a proliferative disease (e.g., cancers (e.g., non-small cell lung cancer, or glioma), inflammatory diseases, autoimmune diseases), CNS disorder (e.g., drug addiction), metabolic disorder (e.g., diabetes), or infectious disease (e.g., bacterial infection or parasitic infection (e.g., malaria)). The pharmaceutical compositions described herein may be useful in treating parasitic infections. The pharmaceutical compositions described herein may be pharmaceutical compositions with anti-parasitic compounds, particularly pharmaceutical compositions with anti-plasmodial pharmaceutical compounds. The pharmaceutical compositions described herein may be useful in treating and/or preventing protozoan infections. The pharmaceutical compositions described herein may be useful in treating plasmodial infections in a subject in need thereof and/or preventing plasmodial infections in a subject at risk of developing a plasmodial infection. The compounds described herein may be anti-plasmodial compounds. The pharmaceutical compositions may be useful in treating protozoan infections in a subject in need thereof and/or preventing protozoan infections (e.g., plasmodial infections) in a subject at risk of developing a protozoan infection, treating plasmodial infections in a subject at risk of developing a plasmodial infection, treating infectious disease in a subject in need thereof and/or preventing an infectious disease in a subject at risk of developing an infectious disease (e.g., malaria), particularly treating parasitic diseases in a subject in need thereof, and as research tools (e.g., for studying plasmodial infections in a subject, biological sample, tissue, or cell). The pharmaceutical compositions may be useful as pharmaceutical compositions with anti-plasmodial compounds.

In certain embodiments, the effective amount is an amount effective for inhibiting bacterial growth. In certain embodiments, the effective amount is an amount effective for killing microorganisms. In certain embodiments, the effective amount is an amount effective for killing bacteria. In certain embodiments, the effective amount is an amount effective for killing parasites.

In certain embodiments, the bacterium which is the causative agent of the infection is a Gram-negative bacterium. In certain embodiments, the Gram-negative bacterium is selected from the group consisting of *Escherichia, Citrobacter, Enterobacter, Klebsiella, Proteus, Serratia, Shigella, Salmonella, Morganella, Providencia, Edwardsiella, Erwinia, Hafnia, Yersinia, Acinetobacter, Vibrio, Aeromonas, Pseudomonas, Haemophilus, Pasteurella, Campylobacter, Helicobacter, Branhamella, Moraxella, Neisseria, Veillonella, Fusobacterium, Bacteroides, Actinobacillus, Aggregatibacter, Agrobacterium, Porphyromonas, Prevotella, Ruminobacter, Roseburia, Caulobacter, Francisella, Borrelia, Treponema, Brucella*, and *Rickettsia*. In certain embodiments, the Gram-negative bacterium is selected from the group consisting of *Escherichia coli, Morganella morganii, Branhamella catarrhalis, Veillonella parvula, Actinobacillus actinomycetemcomitans, Aggregatibacter actinomycetemcomitans, Caulobacter crescentus*, and *Treponema pallidum*. In certain embodiments, the Gram-negative bacterium is selected from the group consisting of *Escherichia coli, Citrobacter* spp, *Enterobacter* spp, *Klebsiella* spp, *Proteus* spp, *Serratia* spp, *Shigella* spp, *Salmonella* spp, *Morganella morganii, Providencia* spp, Edwardsiella spp, *Erwinia* spp, Hafnia spp, *Yersinia* spp, *Acinetobacter* spp, *Vibrio* spp, *Aeromonas* spp, *Pseudomonas* spp, *Haemophilus* spp, *Pasteurella* spp, *Campylobacter* spp, *Helicobacter* spp, *Branhamella catarrhalis, Moraxella* spp, *Neisseria* spp, *Veillonella parvula, Fusobacterium* spp, *Bacteroides* spp, *Actinobacillus actinomycetemcomitans, Aggregatibacter actinomycetemcomitans, Agrobacterium* spp, *Porphyromonas* spp, *Prevotella* spp, Ruminobacter spp, *Roseburia* spp, *Caulobacter crescentus, Francisella* spp, *Borrelia* spp, *Treponema pallidum, Brucella* spp, and *Rickettsia*.

In certain embodiments, the bacterium is a Gram-positive bacterium. In certain embodiments, the bacterium is at least one selected from the group consisting of *Staphylococcus* sp., *Enterococcus* sp., *Escherichia coli, Bacillus* sp., *Salmonella* sp., and *Mycobacterium* sp. In certain embodiments, the Gram-positive bacterium is selected from the group consisting of *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, Corynebacterium, Capnocytophaga, Bifidobacterium*, and *Gardnerella*. In certain embodiments, the Gram-positive bacterium is selected from the group consisting of *Staphylococcus* spp, *Streptococcus* spp, *Micrococcus* spp, *Peptococcus* spp, *Peptostreptococcus* spp, *Enterococcus* spp, *Bacillus* spp, *Clostridium* spp, *Lactobacillus* spp, *Listeria* spp, *Erysipelothrix* spp, *Propionibacterium* spp, *Eubacterium* spp, *Corynebacterium* spp, *Capnocytophaga* spp, *Bifidobacterium* spp, and *Gardnerella* spp.

In certain embodiments, the effective amount is an amount effective for treating a disease described herein. In certain embodiments, the effective amount is an amount effective for preventing a disease described herein. In certain embodiments, the effective amount is a therapeutically effective amount. In certain embodiments, the effective amount is an amount effective for inhibiting bacterial growth. In certain embodiments, the effective amount is an amount effective for killing microorganisms. In certain embodiments, the effective amount is an amount effective for killing protozoa. In certain embodiments, the effective amount is an amount effective for killing parasites. In certain embodiments, the effective amount is an amount effective for killing bacteria.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell being contacted with a compound or composition described herein is in vitro. In certain embodiments, the cell being contacted with a compound or composition described herein is in vivo.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj© 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, to improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, inflammatory disease, autoimmune disease, genetic disease, hematological disease, CNS disorder, neurological disease, painful condition, psychiatric disorder, metabolic disorder, or infectious disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK$^7$M), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, CNS disorder, infectious disease, or metabolic disorder) in a subject in need thereof. In certain embodiments, the kits are useful for preventing a disease (e.g., proliferative disease, inflammatory disease, autoimmune disease, CNS disorder, infectious disease, or metabolic disorder) in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, CNS disorder, infectious disease, or metabolic disorder) in a subject in need thereof. In certain embodiments, the kits and instructions provide for preventing a disease (e.g., proliferative disease, inflammatory disease, autoimmune disease, CNS disorder, infectious disease, or metabolic disorder) in a subject in need thereof. A kit described herein may include one or more additional pharmaceutical agents described herein as a separate composition.

Methods of Treatment and Uses

The present disclosure provides compounds and pharmaceutical compositions useful for inhibiting microorganism growth (e.g., bacterial or parasites). The present invention provides compounds and pharmaceutical compositions useful for killing microorganisms (e.g., bacteria or parasites). The present disclosure also provides methods for the treatment of a wide range of diseases, such as proliferative disease, inflammatory disease, autoimmune disease, CNS disorder, infectious disease, genetic disease, hematological disease, neurological disease, painful condition, psychiatric disorder, and metabolic disorder in a subject in need thereof. The present invention provides methods for the treatment or prevention of a proliferative disease (e.g., cancers (e.g., non-small cell lung cancer, or glioma), benign neoplasms, diseases associated with angiogenesis, inflammatory diseases, autoinflammatory diseases, CNS disorder (e.g., drug addiction), metabolic disorder (e.g., diabetes), and infectious disease (e.g., bacterial infection or parasitic infection (e.g., malaria)) in a subject. In one aspect, the present invention provides methods for inhibiting bacterial growth or killing bacteria comprising administering an effective amount of a compound described herein, or a pharmaceutically acceptable salt, solvate, hydrate, polymorph, co-crystal, tautomer, stereoisomer, isotopically labeled derivative, or prodrug thereof), to a subject in need of treatment. In another aspect, the present invention provides methods for treating or preventing an infection (e.g., an infection by a microorganism, a bacterial infection, comprising administering an effective amount of a compound described herein, or a pharmaceutically acceptable salt, solvate, hydrate, polymorph, co-crystal, tautomer, stereoisomer, isotopically labeled derivative, or prodrug thereof), to a subject in need of treatment.

In certain embodiments, the effective amount is a therapeutically effective amount. In certain embodiments, the effective amount is a prophylactically effective amount. In certain embodiments, the subject is suffering from an infection (e.g., an infection by a microorganism). In certain embodiments, the subject is suffering from malaria. In certain embodiments, the subject is suffering from a bacterial or parasitic infection. In certain embodiments, the subject is susceptible to having a bacterial or parasitic infection. In certain embodiments, the subject has been exposed or is at risk of being exposed to a pathogenic microorganism. The infection may be prevented or at least the chances of infection may be reduced by the administration of a prophylactic amount of a compound described herein.

In another aspect, the present invention provides a method of killing microorganisms (e.g., bacteria, parasites). In certain embodiments, provided is a method of killing protozoa. In certain embodiments, provided is a method of killing parasites. In another aspect, the present invention provides a method of killing bacteria in a subject comprising administering an effective amount of a compound described herein, or a pharmaceutically acceptable salt, solvate, hydrate, polymorph, co-crystal, tautomer, stereoisomer, isotopically labeled derivative, or prodrug thereof. In another aspect, the present invention provides a method of killing parasites in a subject comprising administering an effective amount of a compound described herein, or a pharmaceutically acceptable salt, solvate, hydrate, polymorph, co-crystal, tautomer, stereoisomer, isotopically labeled derivative, or prodrug thereof.

In another aspect, the present invention provides a method of treating and/or preventing a proliferative disease (e.g., cancers (e.g., non-small cell lung cancer, or glioma), inflammatory diseases, autoimmune diseases), CNS disorder (e.g., drug addiction), metabolic disorder (e.g., diabetes), or infectious disease (e.g., bacterial infection or parasitic infection (e.g., malaria)).

In another aspect, provided herein is a method of treating and/or preventing a proliferative disease. In certain embodiments, provided herein is a method of treating and/or preventing cancer. In certain embodiments, provided herein is a method of treating and/or preventing non-small cell lung cancer. In certain embodiments, provided herein is a method of preventing and/or treating brain cancer. In certain embodiments, provided herein is a method of treating and/or preventing glioma. In certain embodiments, provided herein is a method of treating and/or preventing inflammatory disease. In certain embodiments, provided herein is a method of treating and/or preventing autoimmune disease. In certain embodiments, provided herein is a method of treating and/or preventing a CNS disorder. In certain embodiments, provided herein is a method of treating and/or preventing drug addiction. In certain embodiments, provided herein is a method of treating and/or preventing opioid addiction. In certain embodiments, provided herein is a method of treating and/or preventing heroin addiction. In certain embodiments, provided herein is a method of treating and/or preventing addiction to prescription pain relievers (e.g. oxycodone, codeine, morphine). In certain embodiments, provided herein is a method of treating and/or preventing a metabolic disorder. In certain embodiments, provided herein is a method of treating and/or preventing diabetes. In certain embodiments, provided herein is a method of treating and/or preventing an infectious disease. In certain embodiments, provided herein is a method of treating and/or preventing bacterial infection. In certain embodiments, provided herein is a method of treating and/or preventing parasitic infection. In certain embodiments, provided herein is a method of treating and/or preventing malaria.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the biological sample being contacted with the compound or composition is breast tissue, bone marrow, lymph node, lymph tissue, spleen, or blood.

In certain embodiments, the cell being contacted with the compound or composition is present in vitro. In certain embodiments, the cell being contacted with the compound or composition is present in vivo. In certain embodiments, the cell being contacted with the compound or composition is present ex vivo. In certain embodiments, the cell being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant red blood cell, malignant white blood cell, or malignant platelet. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a carcinoma breast cell. In certain embodiments, the cell being contacted with the compound or composition is a sarcoma cell. In certain embodiments, the cell being contacted with the compound or composition is a sarcoma cell from breast tissue.

In certain embodiments, the proliferative disease to be treated or prevented using the compounds described herein is cancer. All types of cancers disclosed herein or known in the art are contemplated as being within the scope of the invention. In certain embodiments, the proliferative disease is a cancer associated with BCL-2 anti-apoptotic proteins (e.g., MCL-1 and/or XIAP) (e.g., cancer associated with dependence on BCL-2 anti-apoptotic proteins). In certain embodiments, the proliferative disease is a cancer associated with overexpression of MYC (a gene that codes for a transcription factor). In certain embodiments, the cancer is a MYC-dependent cancer. In certain embodiments, the proliferative disease is a cancer associated with the amplification of BRCA1. In certain embodiments, the proliferative disease is a cancer associated with the amplification of HER2. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is a leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2-breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. In some embodiments, the proliferative disease is brain cancer. In some embodiments, the proliferative disease is glioma. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis.

In certain embodiments, the proliferative disease is an acute inflammatory disease. In certain embodiments, the acute inflammatory disease is rheumatoid arthritis, Crohn's disease, or fibrosis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the CNS disorder is drug addiction. In certain embodiments, the drug addiction is opioid addiction. In certain embodiments, the drug addiction is heroin addiction. In certain embodiments, the drug addiction is fentanyl addiction. In certain embodiments, the drug addiction is addiction to prescription pain relievers (e.g. oxycodone, codeine, morphine).

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In some embodiments, the additional pharmaceutical agent is etoposide, obatoclax, or navitoclax, and the disease to be treated is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and the disease to be treated is Ewing's sarcoma. In some embodiments, the additional pharmaceutical agent is JQ1 or NVP2, and the disease to be treated is leukemia, e.g., acute myelogenous leukemia, myeloblastic leukemia, promyelocytic leukemia, myelomonocytic leukemia, monocytic leukemia, monoblastic leukemia, or megakaryoblastic leukemia. In certain embodiments, a pharmaceutical composition described herein further comprises a combination of the additional pharmaceutical agents described herein.

In certain embodiments, a kit described herein includes a first container comprising a compound or pharmaceutical composition described herein. In certain embodiments, a kit described herein is useful in treating and/or preventing a proliferative disease (e.g., cancers (e.g., non-small cell lung cancer, or glioma), inflammatory diseases, autoimmune diseases), CNS disorder (e.g., drug addiction), metabolic disorder (e.g., diabetes), or infectious disease (e.g., bacterial infection or parasitic infection (e.g., malaria)), in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for in treating and/or preventing a proliferative disease (e.g., cancers (e.g., non-small cell lung cancer, or glioma), inflammatory diseases, autoimmune diseases), CNS disorder (e.g., drug addiction), metabolic disorder (e.g., diabetes), or infectious disease (e.g., bacterial infection or parasitic infection (e.g., malaria)) in need thereof. A kit described herein may include one or more additional pharmaceutical agents described herein as a separate composition.

Methods of Synthesis

The present disclosure provides methods of synthesizing compounds described herein. In view of the Examples and disclosure provided herein, one of ordinary skill in the art would understand synthetic techniques to synthesize the compounds, including analogs of vincamine, described herein. One of ordinary skill in the art would recognize the synthetic techniques (e.g., standard organic synthetic reactions) to synthesize analogs of vincamine based on the Examples and disclosure provided herein.

EXAMPLES

In order that the disclosure may be more fully understood, the following examples are set forth. The examples described in this application are offered to illustrate the compounds, pharmaceutical compositions, uses, and methods provided herein and are not to be construed in any way as limiting their scope.

All reactions were carried out under an atmosphere of argon unless otherwise specified. Anhydrous solvents were transferred via syringe to flame-dried glassware, which was cooled under a stream of dry argon. Anhydrous tetrahydrofuran, and all chemical reagents for synthesis were used without further purification. Analytical thin layer chromatography (TLC) was performed using 250 μm Silica Gel 60 F254 pre-coated plates (EMD Chemicals Inc.). Flash column chromatography was performed using 230-400 Mesh 60 Å Silica Gel (Sorbent Technologies).

$^1$H NMR experiments were recorded on a Varian Unity spectrometer (at 400 MHz), Agilent/Varian VNMRS-600 spectrometer (at 600 MHz), or Avance II spectrometer (at 600 MHz). $^{13}$C NMR experiments were recorded on a Varian Unity spectrometer (at 400 MHz), Agilent/Varian VNMRS-600 spectrometer (at 150 MHz), or Avance II spectrometer (at 150 MHz). Spectra were obtained in the following solvents (reference peaks also included for $^1$H and $^{13}$C NMRs): CDCl$_3$ ($^1$H NMR: 7.26 ppm; $^{13}$C NMR: 77.23 ppm), d$_6$-DMSO ($^1$H NMR: 2.50 ppm; $^{13}$C NMR: 39.52 ppm), CD$_3$CN ($^1$H NMR: 1.94 ppm; $^{13}$C: 1.32 ppm). NMR samples where the respective solvent peaks were buried in the sample signals referenced TMS at 0.00 ppm for $^1$H NMR experiments. NMR experiments were performed at room temperature unless otherwise indicated. Chemical shift values (δ) are reported in parts per million (ppm) for all $^1$H NMR and $^{13}$C NMR spectra. H NMR multiplicities are reported as: s=singlet, d=doublet, t=triplet, q=quartet, m=multiplet.

EXPERIMENTAL PROCEDURES

Example 1. Chemical Synthesis and Characterization of Selected Compounds

Chemical Synthesis and Characterization

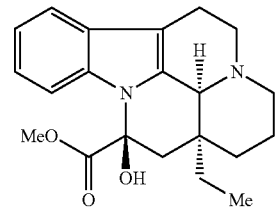

V $^1$H NMR: (400 MHz, CDCl$_3$) δ 7.48 (m, 1H), 7.16-7.07 (m, 3H), 4.59 (s, 1H), 3.91 (s, 1H), 3.82 (s, 3H), 3.41-3.22 (m, 2H), 2.99 (m, 1H), 2.67-2.45 (m, 3H), 2.32-2.18 (m, 2H), 2.12 (d, 1H), 1.82-1.58 (m, 3H), 1.53-1.31 (m, 3H), 0.91 (t, 3H). $^{13}$C NMR: (100 MHz, CDCl$_3$) δ 174.7, 134.3, 131.6, 129.2, 121.8, 120.4, 118.7, 110.5, 106.1, 82.1, 59.4, 54.5, 51.2, 44.8, 44.6, 35.3, 29.1, 25.3, 21.0, 17.1, 7.8.

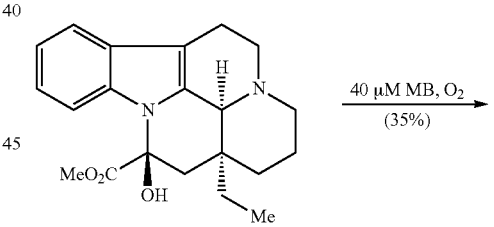

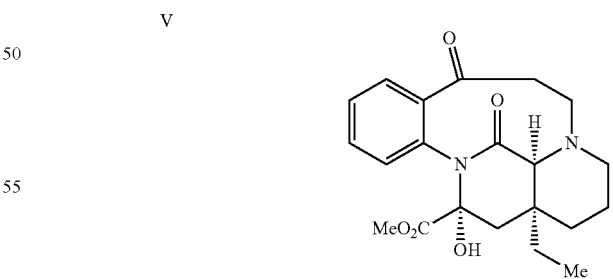

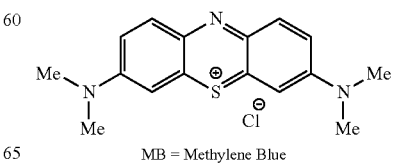

MB = Methylene Blue

Procedure for the synthesis of V14: V (51.6 mg, 0.146 mmol) was added to a round-bottom flask and dissolved in a 40 μM methylene blue solution (12.1 mL). The round-bottom flask was placed in a dewar and irradiated with a 627 nm 3 W LED. The reaction proceeded for 24 hours, concentrated in vacuo, and crude product was purified via column chromatography using a gradient of dichloromethane 100% to dichloromethane:methanol 99:1 to yield V14 (19.9 mg, 35%) as a white solid. Note: V14 is a known compound (CAS No. 59373-44-3), the spectral data below were consistent with literature.[1] $^1$H NMR: (600 MHz, CDCl$_3$) δ 7.70 (d, J=8.1 Hz, 1H), 7.46 (dd, J=7.4, 1.2 Hz, 1H), 7.46 (td, J=7.7, 1.6 Hz, 1H), 7.23 (td, J=7.7, 0.9 Hz, 1H), 4.33 (s, 1H), 3.60 (s, 3H), 3.39 (dd, J=13.3, 5.9 Hz, 1H), 3.33 (d, J=13.3 Hz, 1H), 3.09 (ddd, J=14.0, 6.1 Hz, 1H), 2.97-2.90 (m, 2H), 2.71 (s, 1H), 2.62 (td, J=12.9, 1.3 Hz, 1H), 2.47 (td, J=11.8, 2.7 Hz, 1H), 2.02 (sextet, J=7.3 Hz, 1H), 1.82 (qt, J=13.2, 4.6 Hz, 1H), 1.70 (dd, J=13.8, 2.5 Hz, 1H), 1.65 (d, J=13.3 Hz, 1H), 1.54 (dq, J=13.9, 2.2 Hz, 1H), 1.30 (sextet, J=7.3 Hz, 1H), 1.14 (td, J=13.9, 5.5 Hz, 1H), 0.96 (t, J=7.3 Hz, 3H). $^{13}$C NMR: (150 MHz, CDCl$_3$) δ 204.4, 173.2, 173.0, 138.9, 137.7, 131.9, 129.1, 126.5, 122.3, 89.4, 74.5, 56.8, 54.2, 53.5, 43.7, 37.7, 37.1, 33.0, 30.9, 22.5, 7.8. HRMS (ESI): calc. for $C_{21}H_{27}N_2O_5$ [M+H]$^+$: 387.1914, found: 387.1928.

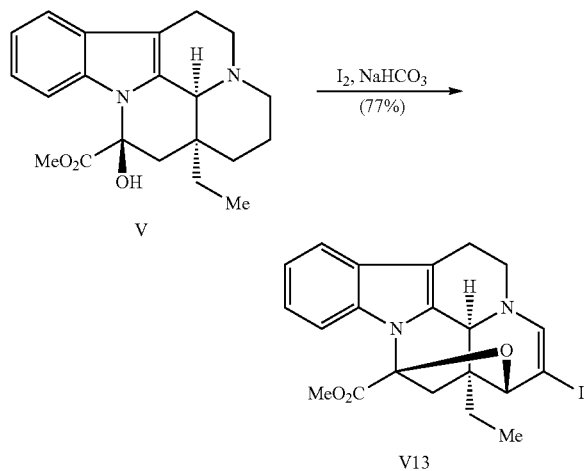

Procedure for the synthesis of V13: V (317.1 mg, 0.895 mmol) was added to a round-bottom flask and dissolved in a 2:1 solution of saturated aqueous sodium bicarbonate:chloroform (19.0 mL). Iodine (965.1 mg, 3.80 mmol) was added to the reaction, which proceeded for 6 hours. At this time, the reaction was quenched with saturated sodium thiosulfate, extracted with ethyl acetate, extract dried with sodium sulfate, and the organic layer was concentrated in vacuo. The crude product was purified via column chromatography using a gradient of 100% hexanes to 3:1 hexanes:ethyl acetate with 1% triethylamine throughout to afford V13 (331.4 mg, 77%) as a white-yellow solid. Note: V14 is a known compound (CAS No. 74947-45-8). $^1$H NMR: (400 MHz, CDCl$_3$) δ 7.38 (m, 1H), 7.12 (td, J=7.0, 6.2, 3.6 Hz, 2H), 6.98 (m, 1H), 6.29 (s, 1H), 4.29 (s, 2H), 4.04 (s, 3H), 3.58 (dd, J=14.1, 7.2 Hz, 1H), 3.26 (ddd, J=14.1, 11.0, 6.4 Hz, 1H), 2.84 (d, J=12.0 Hz, 1H), 2.75 (dddd, J=18.4, 11.0, 7.6, 1.5 Hz, 1H), 2.61 (d, J=16.4, 6.2 Hz, 1H), 2.42 (d, J=12.0 Hz, 1H), 1.73 (sextet, J=7.5 Hz, 1H), 1.49 (sextet, J=7.5 Hz, 1H), 1.01 (t, J=7.5 Hz, 3H). $^{13}$C NMR: (100 MHz, CDCl$_3$) δ 168.8, 143.2, 137.7, 135.1, 131.1, 122.9, 121.3, 118.6, 112.0, 111.6, 91.1, 85.4, 63.0, 53.5, 53.3, 49.9, 45.8, 45.7, 25.0, 21.5, 9.3. HRMS (ESI): calc. for $C_{21}H_{22}IN_2O_3$ [M+H]+: 477.0670, found: 477.0661. MP: 173-175° C., decomposed, lit. 173-175° C., decomposed.[2]

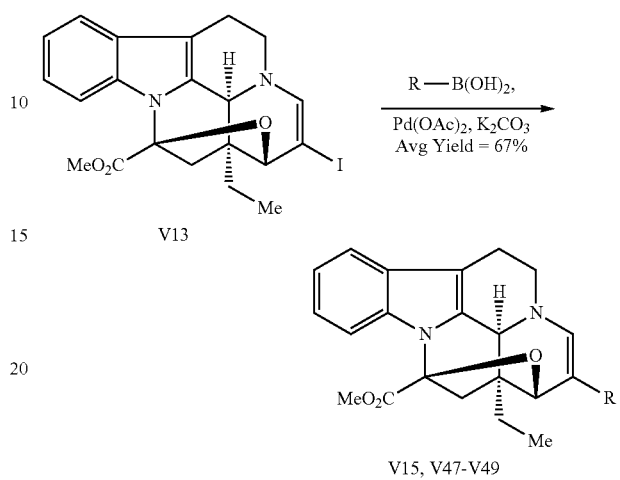

General Procedure for the synthesis of V15, V47-V49: To a flame-dried round-bottom flask was added V13 (32.0 mg, 0.067 mmol), trans-phenylboronic acid (10.4 mg, 0.071 mmol), and potassium carbonate (27.9 mg, 0.202 mmol). Methanol (2.0 mL) was added, then a 0.04 M solution of Pd(OAc)$_2$ (4.5 mg, 0.020 mmol) in methanol was added dropwise at room temperature. The resulting reaction mixture was heated to reflux for 3 hours, cooled to room temperature, quenched with 1 M HCl, extracted with ethyl acetate, organics were washed with brine. The organics were dried with sodium sulfate, filtered, and concentrated in vacuo. Then crude product purified via column chromatography using a gradient of 100% hexanes to 3:1 hexanes:ethyl acetate with 1% triethylamine throughout to afford V15 (26.8 mg, 88%) as a colorless solid.

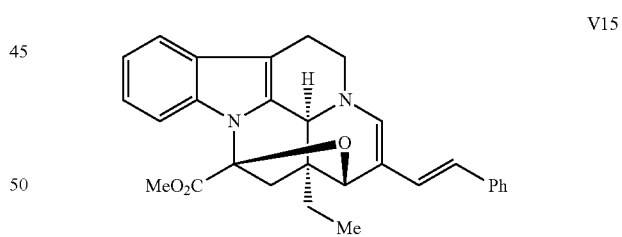

Yield: 88%; 26.8 mg of V15 isolated as a colorless solid. $^1$H NMR: (400 MHz, CDCl$_3$) δ 7.35 (m, 1H), 7.27-7.22 (m, 2H), 7.17 (dd, J=7.4 Hz, 2H), 7.11-7.01 (m, 3H), 6.96 (m, 1H), 6.49 (d, J=16.1 Hz, 1H), 6.28 (d, J=16.1 Hz, 1H), 6.07 (s, 1H), 4.53 (d, J=1.8 Hz, 1H), 4.39 (s, 1H), 4.06 (s, 3H), 3.70 (dd, J=14.1, 7.4 Hz, 1H), 3.50 (ddd, J=14.1, 10.9, 6.5 Hz, 1H), 2.92-2.77 (m, 2H), 2.70 (ddd, J=16.3, 6.5, 1.6 Hz, 1H), 2.49 (d, J=12.0 Hz, 1H), 1.70 (sextet, J=7.5 Hz, 1H), 1.50 (sextet, J=7.5 Hz, 1H), 1.05 (t, J=7.5 Hz, 3H). Note: $^1$H spectrum referenced TMS at 0.00 ppm. $^{13}$C NMR: (100 MHz, CDCl$_3$) δ 169.3, 138.6, 138.3, 137.9, 136.0, 131.3, 129.4, 128.5, 126.0, 125.7, 122.8, 121.7, 121.3, 118.6, 112.7, 112.1, 111.7, 91.7, 77.4, 54.9, 53.5, 50.4, 45.5, 43.8, 25.1, 21.8, 9.5. Note: The presence of a carbon at 77.4 was

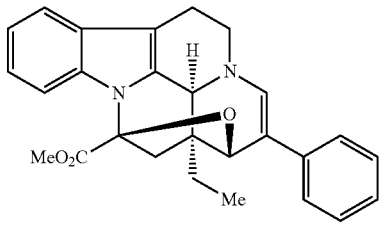

V47

Yield: 40%; 15.7 mg of V47 isolated as a yellow residue. $^1$H NMR: (400 MHz, CDCl$_3$) 7.33 (dd, J=6.6, Hz, 1H), 7.26 (d, J=8.3, 2H), 7.15 (dd, J=7.8 Hz, 2H), 7.11-6.93 (m, 4H), 6.41 (s, 1H), 4.47 (d, J=1.8 Hz, 1H), 4.42 (s, 1H), 4.07 (s, 3H), 3.76 (dd, J=14.1, 7.3 Hz, 1H), 3.55 (ddd, J=14.1, 11.0, 6.5 Hz, 1H), 2.90-2.77 (m, 2H), 2.70 (ddd, J=16.4, 6.5, 1.9 Hz, 1H), 2.48 (d, J=12.0 Hz, 1H), 1.74 (sextet, J=7.5 Hz, 1H), 1.49 (sextet, J=7.5 Hz, 1H), 1.05 (t, J=7.5 Hz, 3H). Note: $^1$H spectrum referenced TMS at 0.00 ppm. $^{13}$C NMR: (100 MHz, CDCl$_3$) δ 169.4, 140.2, 138.1, 136.2, 134.6, 131.5, 128.5, 125.2, 124.4, 122.8, 121.3, 118.6, 112.1, 111.9, 111.8, 91.6, 80.1, 54.5, 53.5, 50.6, 45.4, 43.9, 25.1, 21.7, 9.5. HRMS (ESI): calc. for C$_{27}$H$_{27}$N$_2$O$_3$ [M+H]$^+$: 427.2016, found: 427.2002.

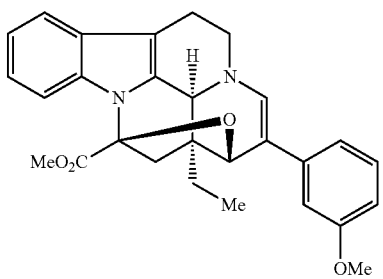

V48

Yield: 72%; 27.0 mg of V48 isolated as a colorless residue. $^1$H NMR: (400 MHz, CDCl$_3$) δ 7.34 (dd, J=6.4, 2.0 Hz, 1H), 7.13-7.03 (m, 3H), 6.98 (dd, J=6.4, 2.0 Hz, 1H), 6.88 (d, J=8.1 Hz, 1H), 6.82 (dd, J=2.1 Hz, 1H), 6.59 (dd, J=8.1, 2.5 Hz, 1H), 6.43 (s, 1H), 4.47 (d, J=1.8 Hz, 1H), 4.42 (s, 1H), 4.07 (s, 3H), 3.80-3.71 (m, 4H), 3.54 (ddd, J=14.1, 11.0, 6.5 Hz, 1H), 2.91-2.78 (m, 2H), 2.71 (ddd, J=16.3, 6.3, 1.9 Hz, 1H), 2.49 (d, J=12.0 Hz, 1H), 1.74 (sextet, J=7.5 Hz, 1H), 1.50 (sextet, J=7.5 Hz, 1H), 1.06 (t, J=7.5 Hz, 3H). $^{13}$C NMR: (100 MHz, CDCl$_3$) δ 169.3, 159.8, 141.7, 138.1, 136.2, 134.8, 131.5, 129.4, 122.7, 121.2, 118.6, 117.1, 112.0 (2C), 111.6, 110.4, 110.2, 91.6, 80.0, 55.3, 54.4, 53.4, 50.5, 45.4, 43.9, 25.1, 21.8, 9.4. HRMS (ESI): calc. for C$_{28}$H$_{29}$N$_2$O$_4$ [M+H]$^+$: 457.2122, found: 457.2102.

proven by HSQC. HRMS (ESI): calc. for C$_{29}$H$_{28}$N$_2$O$_3$ [M+H]$^+$: 453.2173, found: 453.2162. MP: 225-227° C., decomposed.

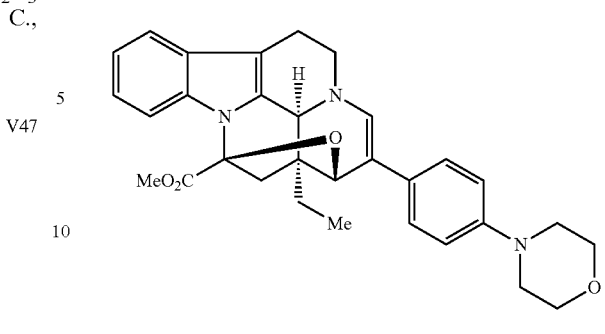

V49

Yield: 66%; 22.5 mg of V49 isolated as a colorless residue. $^1$H NMR: (400 MHz, CDCl$_3$) δ 7.33 (dd, J=6.4, 2.1 Hz, 1H), 7.19 (d, J=8.4 Hz, 2H), 7.11-7.02 (m, 2H), 6.96 (dd, J=6.4, 2.1 Hz, 1H), 6.74 (d, J=8.4 Hz, 2H), 6.31 (s, 1H), 4.45 (d, J=1.8 Hz, 1H), 4.42 (s, 1H), 4.07 (s, 3H), 3.84-3.77 (m, 4H), 3.74 (dd, J=14.1, 7.2 Hz, 1H), 3.53 (ddd, J=14.4, 11.1, 6.6 Hz, 1H), 3.07-2.95 (m, 4H), 2.90-2.77 (m, 2H), 2.70 (ddd, J=16.3, 6.3, 1.6 Hz, 1H), 2.48 (d, J=12.0 Hz, 1H), 1.75 (sextet, J=7.5 Hz, 1H), 1.49 (sextet, J=7.5 Hz, 1H), 1.05 (t, J=7.5 Hz, 3H). $^{13}$C NMR: (100 MHz, CDCl$_3$) δ 169.4, 149.2, 138.0, 136.2, 133.1, 132.4, 131.5, 125.2, 122.7, 121.2, 118.6, 116.1, 112.0, 111.9, 111.7, 91.5, 80.2, 67.1, 54.5, 53.4, 50.5, 49.9, 45.5, 43.9, 25.1, 21.6, 9.5. HRMS (ESI): calc. for C$_{31}$H$_{34}$N$_3$O$_4$ [M+H]$^+$: 512.2544, found: 512.2550.

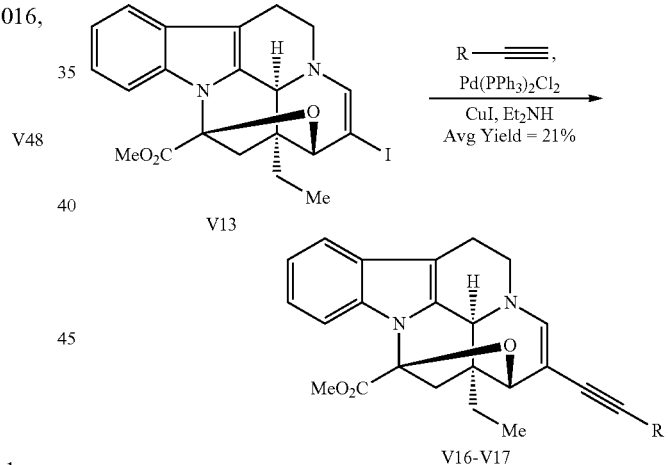

General Procedure for the synthesis of V16-V17: To a flame-dried round-bottom flask was added V13 (58.5 mg, 0.123 mmol), Bis(triphenylphosphine)palladium(II) dichloride (17.2 mg, 0.025 mmol), and copper(I) iodide (9.4 mg, 0.049 mmol). Phenylacetylene (20.0 µL, 0.184 mmol) was added dropwise, and the resulting dry materials were dissolved in a 2:1 diethylamine:anhydrous N,N-dimethylformamide solution (1.2 mL). The reaction was heated to 60° C. and proceeded for thirty-minutes. At this time, the reaction was quenched with deionized water, washed with 1 M HCl, and extracted with ethyl acetate. Crude extract was filtered through a plug of celite, dried with sodium sulfate, filtered, and concentrated in vacuo. Crude product purified via column chromatography using a gradient of 100% hexanes to 5:1 hexanes:ethyl acetate with 1% triethylamine to afford V16 (16.6 mg, 30%) as a brown resin.

V16

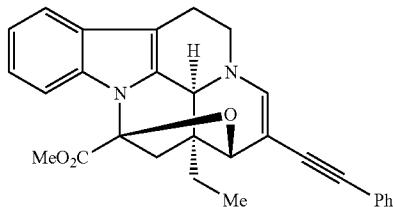

Yield: 30%; 16.6 mg of V16 isolated as a brown residue. ¹H NMR: (400 MHz, CDCl$_3$) δ 7.39 (m, 1H), 7.30-7.25 (m, 2H), 7.23-7.05 (m, 5H), 6.98 (m, 1H), 6.43 (s, 1H), 4.43 (s, 1H), 4.35 (d, J=1.8 Hz, 1H), 4.07 (s, 3H), 3.74 (dd, J=14.4, 7.4 Hz, 1H), 3.54 (ddd, J=14.1, 11.2, 6.7 Hz, 1H), 2.91 (m, 1H), 2.82 (d, J=12.0 Hz, 1H), 2.74 (ddd, J=16.3, 6.5, 1.7 Hz, 1H), 2.49 (d, J=12.0 Hz, 1H), 1.73 (sextet, J=7.5 Hz, 1H), 1.54 (sextet, J=7.5 Hz, 1H), 1.06 (t, J=7.5 Hz, 3H). ¹³C NMR: (100 MHz, CDCl$_3$) δ 169.1, 143.4, 137.9, 135.5, 131.3, 131.1, 128.2, 127.1, 124.4, 123.0, 121.4, 118.7, 112.1, 112.0, 94.4, 91.5, 90.6, 87.0, 80.2, 54.1, 53.6, 50.5, 45.4, 43.8, 24.9, 22.0, 9.4. HRMS (ESI): calc. for C$_{29}$H$_{27}$N$_2$O$_3$ [M+H]⁺: 451.2016, found: 451.2035.

V17

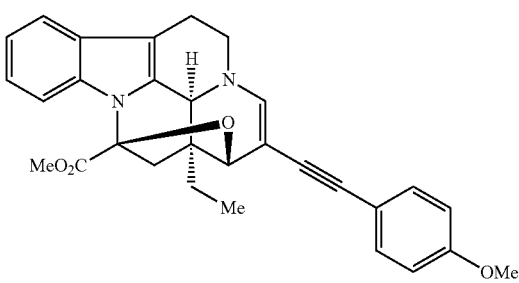

Yield: 12%; 7.2 mg of V17 isolated as a pinkish-red residue. ¹H NMR: (400 MHz, CDCl$_3$) δ 7.38 (m, 1H), 7.22 (d, J=8.5 Hz, 2H), 7.15-7.07 (m, 2H), 6.98 (m, 1H), 6.73 (d, J=8.5 Hz, 2H), 6.39 (s, 1H), 4.42 (s, 1H), 4.33 (d, J=1.9 Hz, 1H), 4.06 (s, 3H), 3.77-3.69 (m, 4H), 3.54 (ddd, J=14.1, 11.3, 6.4 Hz, 1H), 2.91 (m, 1H), 2.81 (d, J=12.0 Hz, 1H), 2.74 (ddd, J=16.2, 6.0, 1.5 Hz, 1H), 2.49 (d, J=12.0 Hz, 1H), 1.73 (sextet, J=7.5 Hz, 1H), 1.51 (m, 1H), 1.06 (t, J=7.5 Hz, 3H). ¹³C NMR: (100 MHz, CDCl$_3$) δ 169.1, 158.8, 142.8, 137.9, 135.6, 132.6, 131.4, 123.0, 121.4, 118.7, 116.6, 113.9, 112.1, 112.0, 94.8, 91.5, 88.9, 86.6, 80.3, 55.4, 54.1, 53.6, 50.5, 45.5, 43.8, 24.9, 22.0, 9.4. HRMS (ESI): calc. for C$_{30}$H$_{29}$N$_2$O$_4$ [M+H]⁺: 481.2122, found: 481.2142.

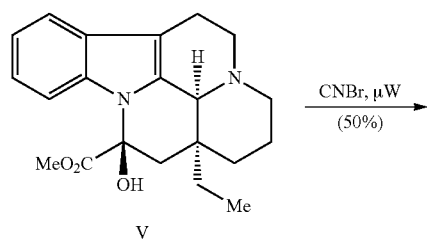

V → CNBr, μW (50%) →

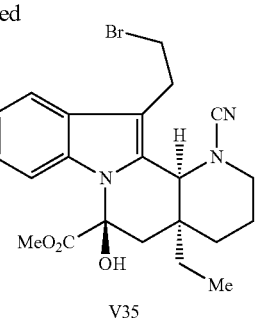

V35

Procedure for the synthesis of V35: V (802.1 mg, 2.26 mmol) was added to a flame-dried microwave flask and dissolved in N,N-dimethylformamide (17.5 mL). A 3.0 M solution of cyanogen bromide in dichloromethane (2.30 mL, 6.79 mmol) was added dropwise to the resulting solution. The reaction was subjected to microwave irradiation at 100° C. for three minutes. The reaction was cooled to room temperature, diluted with ethyl acetate, and quenched with brine (3×100 mL). The organic layer was dried with sodium sulfate, filtered, and concentrated in vacuo. The crude material was purified via column chromatography using a gradient of 100% chloroform to 24:1 chloroform:acetone to yield V35 (520.0 mg, 50%) as a white solid. ¹H NMR: (400 MHz, CDCl$_3$) δ 7.56 (m, 1H), 7.26 (m, 1H), 7.22-7.12 (m, 2H), 4.77 (s, 1H), 4.31 (s, 1H), 3.72-3.59 (m, 5H), 3.51-3.34 (m, 2H), 3.28-3.13 (m, 2H), 2.45 (d, J=15.0 Hz, 1H), 2.25 (d, J=15.0 Hz, 1H), 1.92 (m, 1H), 1.73-1.50 (m, 4H), 1.46 (ddd, J=14.1, 8.4, 4.3 Hz, 1H), 0.80 (t, J=7.4 Hz, 3H). ¹³C NMR: (100 MHz, CDCl$_3$) δ 173.0, 135.5, 128.5, 128.2, 123.6, 121.1, 119.0, 118.2, 114.2, 111.8, 82.4, 59.8, 54.2, 48.0, 40.9, 36.3, 32.3, 29.9, 29.1, 28.5, 19.9, 7.4. HRMS (ESI): calc. for C$_{22}$H$_{26}$BrN$_3$O$_3$ [M+Na]⁺: 482.1050, found: 482.1071. MP: 155-157° C.

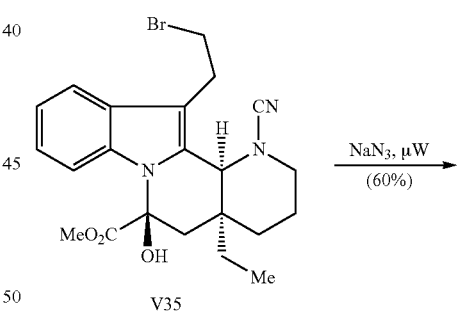

V35 → NaN$_3$, μW (60%) →

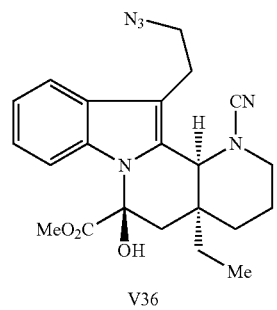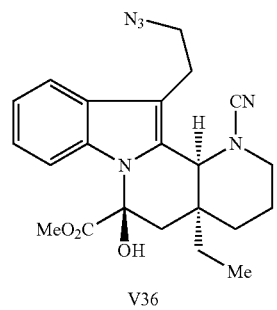

V36

Procedure for the synthesis of V36: V35 (203.0 mg, 0.441 mmol) was added to a flame-dried microwave flask and dissolved in N,N-dimethylformamide (4.41 mL). Sodium azide (229.5 mg, 3.53 mmol) was added to the resulting solution. The reaction was subjected to microwave irradiation at 100° C. for four minutes. The reaction was cooled to room temperature, diluted with ethyl acetate, and quenched with brine (3×50 mL). The organic layer was dried with sodium sulfate, filtered, and concentrated in vacuo. The crude material was purified via column chromatography using a gradient of 100% chloroform to 49:1 chloroform:acetone to yield V36 (111.4 mg, 60%) as a white solid. $^1$H NMR: (400 MHz, CDCl$_3$) δ 7.57 (m, 1H), 7.24-7.11 (m, 3H), 4.73 (s, 1H), 4.19 (d, J=1.4 Hz, 1H), 3.82 (s, 3H), 3.72 (ddd, J=12.2, 7.0, 5.8 Hz, 1H), 3.64-3.52 (m, 2H), 3.25 (td, J=12.6, 3.0 Hz, 1H), 3.10 (ddd, J=8.5, 6.7, 1.8 Hz, 2H), 2.98 (m, 1H), 1.97-1.82 (m, 3H), 1.75-1.63 (m, 2H), 1.43 (td, J=14.2, 6.5 Hz, 1H), 1.18 (sextet, J=7.4 Hz, 1H), 0.91 (t, J=7.4 Hz, 3H). $^{13}$C NMR: (100 MHz, CDCl$_3$) δ 174.6, 135.0, 128.4, 128.0, 123.8, 120.9, 119.6, 116.5, 114.3, 111.4, 82.2, 57.8, 54.8, 51.6, 51.0, 35.4, 35.1, 32.9, 30.1, 24.5, 20.4, 7.3. HRMS (ESI): calc. for C$_{22}$H$_{26}$N$_6$O$_3$ [M+Na]$^+$: 445.1959, found: 445.1979. MP: 127-129° C.

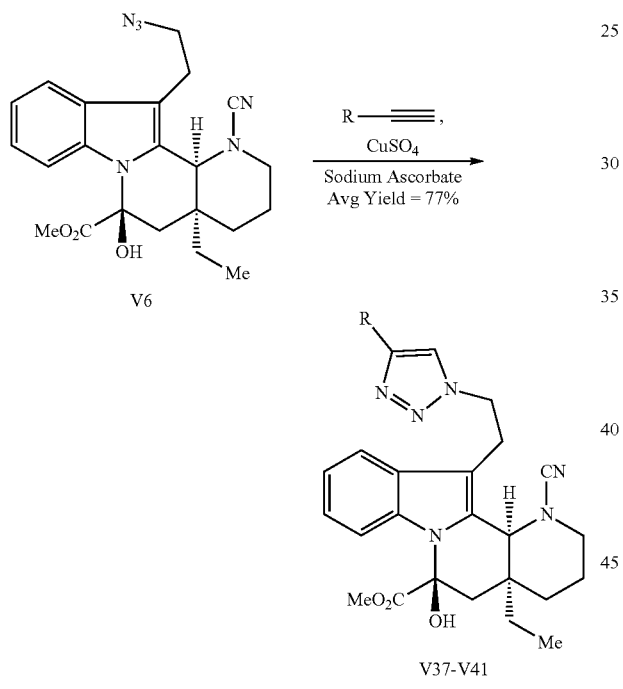

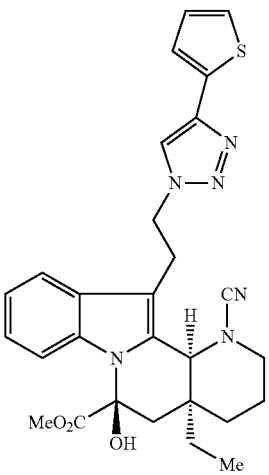

V37

Yield: 79%; 22.7 mg of V37 isolated as a purple residue. $^1$H NMR: (400 MHz, CDCl$_3$) δ 7.54 (m, 1H), 7.25-7.14 (m, 6H), 6.98 (dd, J=5.1, 3.6 Hz, 1H), 4.91 (ddd, J=13.6, 6.2, 4.2 Hz, 1H), 4.71-4.60 (m, 2H), 3.80 (s, 3H), 3.77 (d, J=1.1 Hz, 1H), 3.64-3.49 (m, 2H), 3.44 (ddd, J=15.3, 6.3, 4.1 Hz, 1H), 3.19 (td, J=12.6, 3.1 Hz, 1H), 2.85 (d, J=14.4 Hz, 1H), 1.86-1.71 (m, 3H), 1.67-1.54 (m, 2H), 1.38-1.21 (m, 2H), 0.74-0.55 (m, 3H). $^{13}$C NMR: (100 MHz, CDCl$_3$) δ 174.4, 142.6, 135.1, 133.0, 128.7, 127.9, 127.6, 125.0, 124.2, 124.0, 121.2, 120.7, 119.3, 116.6, 113.3, 111.5, 82.2, 57.7, 54.8, 50.8, 50.4, 34.8 (2C), 32.8, 30.2, 26.1, 20.3, 7.1. HRMS (ESI): calc. for C$_{28}$H$_{31}$N$_6$O$_3$S [M+H]$^+$: 531.2173, found: 531.2155.

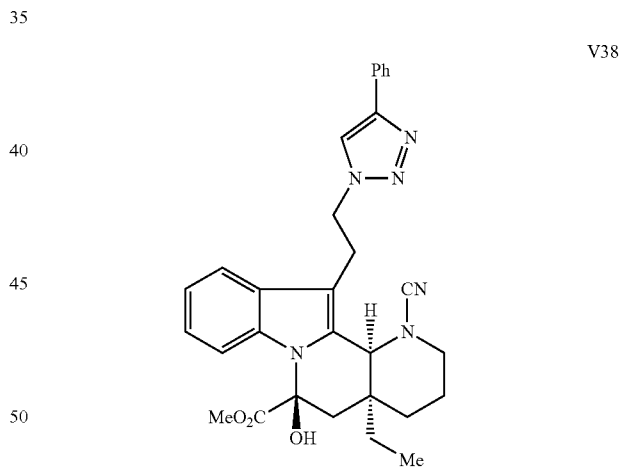

General Procedure for the synthesis of V37-V41: Anhydrous copper sulfate (4.6 mg, 0.03 mmol) and sodium ascorbate (16.6 mg, 0.08 mmol) were added to a vial and dissolved in a solution of tert-butanol:H$_2$O (1:2). The resultant solution was added to a round-bottom flask containing V36 (24.1 mg, 0.06 mmol). Phenylacetylene (18.8 μL, 0.17 mmol) was added dropwise to the reaction as a 0.3 M solution in dichloromethane. The reaction was vigorously stirred at room temperature for 1.5 hours, upon completion, the biphasic mixture was quenched with brine. The crude reaction mixture was extracted with dichloromethane, the organic layer was dried with sodium sulfate, filtered, and concentrated in vacuo. Crude product was purified via column chromatography using a gradient of 100% dichloromethane to 99:1 dichloromethane:methanol to afford V38 (27.0 mg, 90%) as a yellow residue.

Yield: 90%; 27.0 mg of V38 isolated as a white-yellow solid. $^1$H NMR: (400 MHz, CDCl$_3$) δ 7.68-7.62 (m, 2H), 7.54 (m, 1H), 7.38-7.30 (m, 3H), 7.27 (m, 1H), 7.25-7.11 (m, 3H), 4.93 (ddd, J=13.6, 6.2, 4.0 Hz, 1H), 4.72 (s, 1H), 4.66 (ddd, J=13.6, 6.2, 4.0 Hz, 1H), 3.79 (s, 3H), 3.76 (s, 1H), 3.63-3.49 (m, 2H), 3.46 (ddd, J=14.9, 5.8, 4.3 Hz, 1H), 3.19 (td, J=12.6, 3.0 Hz, 1H), 2.83 (d, J=14.3 Hz, 1H), 1.86-1.69 (m, 3H), 1.59 (m, 1H), 1.36-1.18 (m, 3H), 0.70-0.52 (m, 3H). $^{13}$C NMR: (100 MHz, CDCl$_3$) δ 174.5, 147.5, 135.0, 130.6, 128.9, 128.6, 128.1, 127.9, 125.8, 124.0, 121.2, 121.2, 119.3, 116.6, 113.4, 111.5, 82.1, 57.7, 54.8, 50.8, 50.3, 34.8, 34.7, 32.8, 30.2, 26.2, 20.3, 7.0. HRMS (ESI): calc. for C$_{30}$H$_{33}$N$_6$O$_3$ [M+H]$^+$: 525.2609, found: 525.2585. MP: 118-120° C.

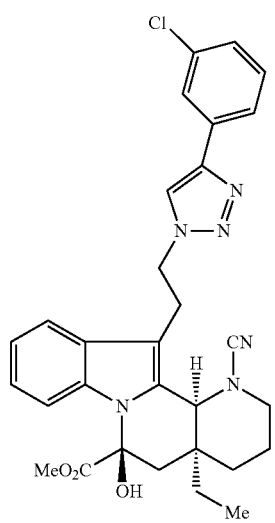

V39

Yield: 91%; 18.2 mg of V39 isolated as a white solid. $^1$H NMR: (400 MHz, CDCl$_3$) δ 7.64 (m, 1H), 7.54-7.46 (m, 2H), 7.34 (s, 1H), 7.29-7.12 (m, 5H), 4.94 (ddd, J=13.5, 6.1, 4.1 Hz, 1H), 4.73-4.61 (m, 2H), 3.81 (s, 3H), 3.78 (d, J=1.1 Hz, 1H), 3.62-3.50 (m, 2H), 3.44 (m, 1H), 3.20 (td, J=12.7, 3.3 Hz, 1H), 2.85 (d, J=14.3 Hz, 1H), 1.86-1.73 (m, 3H), 1.69-1.57 (m, 2H), 1.36-1.19 (m, 2H), 0.68-0.57 (m, 3H). $^{13}$C NMR: (100 MHz, CDCl$_3$) δ 174.4, 146.4, 135.2, 135.0, 132.7, 130.2, 128.6, 128.2, 128.1, 126.1, 124.1, 124.0, 121.6, 121.3, 119.3, 116.6, 113.5, 111.6, 82.4, 57.9, 54.7, 51.0, 50.5, 35.2, 35.0, 33.0, 30.3, 26.2, 20.4, 7.1. HRMS (ESI): calc. for C$_{30}$H$_{31}$ClN$_6$O$_3$ [M+Na]$^+$: 581.2038, found: 581.2030. MP: 101-103° C.

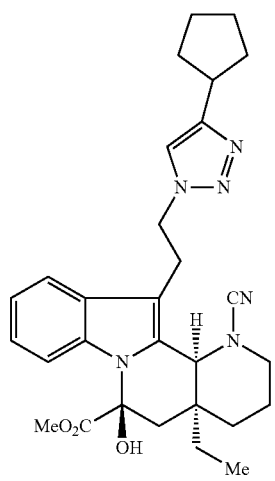

V40

Yield: 54%; 17.4 mg of V40 isolated as a clear residue. $^1$H NMR: (400 MHz, CDCl$_3$) δ 7.40 (d, J=7.8 Hz, 1H), 7.22-7.09 (m, 3H), 6.97 (s, 1H), 4.79 (ddd, J=13.6, 6.9, 4.3 Hz, 1H), 4.71 (s, 1H), 4.57 (ddd, J=13.6, 9.6, 6.5 Hz, 1H), 3.94 (d, J=1.7 Hz, 1H), 3.81 (s, 3H), 3.64-3.51 (m, 2H), 3.36 (ddd, J=15.2, 6.2, 4.0 Hz, 1H), 3.23 (td, J=12.9, 2.3 Hz, 1H), 3.04 (pentet, J=7.7 Hz, 1H), 2.90 (d, J=14.3 Hz, 1H), 2.05-1.74 (m, 5H), 1.67-1.26 (m, 9H), 0.93-0.79 (m, 4H). $^{13}$C NMR: (100 MHz, CDCl$_3$) δ 174.4, 152.5, 135.1, 128.4, 128.3, 123.9, 121.2, 121.1, 119.4, 116.6, 113.9, 111.5, 82.4, 57.9, 54.6, 51.0, 50.2, 36.9, 35.4, 35.0, 33.4, 33.3, 33.0, 30.1 (2C), 25.9, 25.3, 20.5, 7.3. HRMS (ESI): calc. for C$_{29}$H$_{36}$N$_6$O$_3$Na [M+Na]$^+$: 539.2741, found: 539.2766.

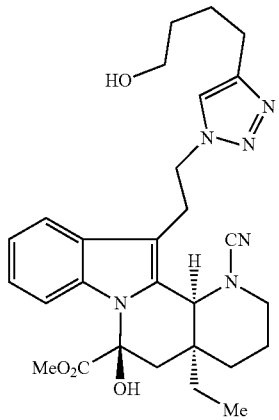

V41

Yield: 70%; 21.6 mg of V41 isolated as a yellow residue. $^1$H NMR: (400 MHz, CDCl$_3$) δ 7.39 (d, J=7.7 Hz, 1H), 7.23-7.07 (m, 3H), 7.05 (s, 1H), 4.86-4.74 (m, 2H), 4.63 (m, 1H), 3.95 (s, 1H), 3.80 (s, 3H), 3.62-3.45 (m, 4H), 3.37 (m, 1H), 3.23 (td, J=12.6, 2.9 Hz, 1H), 2.91 (d, J=14.3 Hz, 1H), 2.66-2.54 (m, 2H), 1.94-1.76 (m, 3H), 1.73-1.54 (m, 5H), 1.51-1.29 (m, 4H), 0.98-0.82 (m, 3H). $^{13}$C NMR: (100 MHz, CDCl$_3$) δ 174.4, 147.5, 134.9, 128.4, 128.2, 123.9, 122.6, 121.1, 119.3, 116.7, 113.6, 111.4, 82.2, 62.5, 57.7, 54.8, 50.8, 50.2, 35.0, 34.9, 32.9, 32.1, 30.0, 26.0, 25.3, 25.2, 20.3, 7.4. HRMS (ESI): calc. for C$_{28}$H$_{36}$N$_6$O$_4$Na [M+Na]$^+$: 534.2690, found: 543.2726.

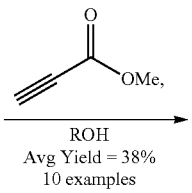

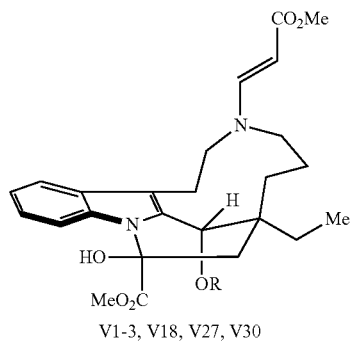

V1-3, V18, V27, V30

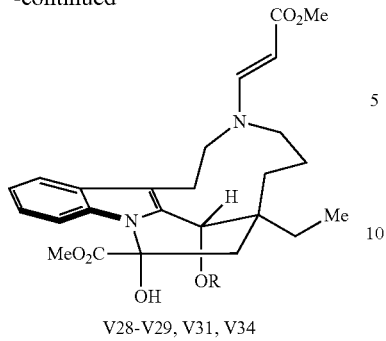

V28-V29, V31, V34

General Procedure for the synthesis of V1-V3, V18, V27-V31, & V34: V (106.0 mg, 0.300 mmol) was added to a flame-dried round-bottom flask and dissolved in a 2.5:1.0 (THF:H$_2$) solution (30 mL). Methyl propiolate (40 µL, 0.449 mmol) was added dropwise and the reaction was stirred at room temperature. The reaction was heated to 66° C. for 3.5 hours, after this time, the reaction was cooled to room temperature and quenched with brine (2×50 mL). The reaction mixture was diluted with ethyl acetate, extracted, dried with sodium sulfate, filtered, and concentrated in vacuo. The crude product was purified via column chromatography using a gradient of 100% hexanes to 1:1 hexanes:ethyl acetate to afford V18 (51.7 mg, 38%) as a white solid. Note: The presence of two carbon signals at ~22.0 ppm for V1-V3, V18, V27-V31 &V34 was proven by HSQC with V27 & V29.

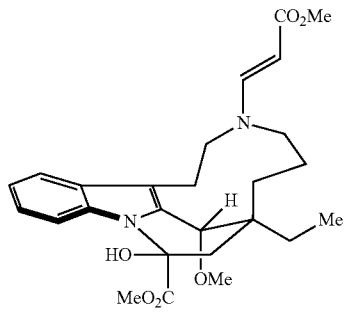

V18

Yield: 73%; 101.3 mg of V18 isolated as a white solid. $^1$H NMR: (400 MHz, CDCl$_3$ at 50° C.) δ 7.60 (d, J=13.3 Hz, 1H), 7.53 (m, 1H), 7.25-7.13 (m, 3H), 4.83 (d, J=13.3 Hz, 1H), 4.69 (s, 1H), 4.22 (s, 1H), 3.81 (s, 3H), 3.72 (m, 4H), 3.52 (dd, J=13.9, 6.9 Hz, 1H), 3.24-3.20 (m, 4H), 2.95 (dd, J=16.0, 1.8 Hz, 1H), 2.88 (t, J=14.0, 12.2 Hz, 1H), 2.76 (d, J=13.8 Hz, 1H), 2.29 (ddd, J=14.1, 9.4, 1.7 Hz, 1H), 1.92-1.67 (m, 4H), 1.65-1.48 (m, 2H), 1.36-1.23 (m, 2H), 0.87 (t, J=7.6 Hz, 3H). $^{13}$C NMR: (100 MHz, CDCl$_3$ at 50° C.) δ 174.7, 169.7, 150.8, 135.5, 133.4, 128.1, 123.0, 120.5, 118.4, 113.4, 112.2, 87.0, 83.1, 75.3, 59.3, 56.7, 56.2, 54.1, 50.7, 41.0, 40.6, 33.2, 27.2, 22.0 (2C), 8.0. MP: 205-207° C., lit. 205° c.$^3$

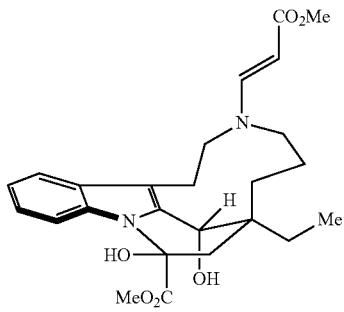

V27

Yield: 38%; 51.7 mg of V27 isolated as a white solid. $^1$H NMR: (400 MHz, CDCl$_3$ at 50° C.) δ 7.56 (d, J=13.3 Hz, 1H), 7.51 (dd, J=7.3, 1.2 Hz 1H), 7.23-7.18 (m, 2H), 7.15 (m, 1H), 4.84-4.73 (m, 2H), 4.66 (s, 1H), 3.83 (s, 3H), 3.74-3.63 (m, 4H), 3.50 (dd, J=14.1, 7.2 Hz, 1H), 3.16 (td, J=14.9, 12.0, 2.1 Hz, 1H), 2.88 (m, 2H), 2.78 (d, J=14.2 Hz, 1H), 2.27 (dd, J=14.2, 8.8 HZ, 1H), 1.98-1.84 (m, 3H), 1.83-1.66 (m, 2H), 1.63 (m, 1H), 1.53 (m, 1H), 1.29 (dd, J=15.8, 7.8 Hz, 1H), 0.89 (td, J=7.6, 1.2 Hz, 3H). $^{13}$C NMR: (100 MHz, CDCl$_3$ at 50° C.) δ 174.6, 169.8, 151.0, 136.0, 135.3, 128.3, 123.2, 120.7, 118.8, 112.1, 111.8, 87.3, 83.0, 66.5, 58.9, 56.8, 54.4, 50.7, 40.8, 40.0, 33.1, 27.0, 21.8 (2C), 8.0. HRMS (ESI): calc. for C$_{25}$H$_{32}$N$_2$O$_6$Na [M+Na]$^+$: 479.2153, found: 479.2140. MP: 178-180° C.

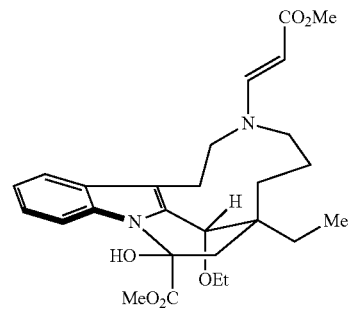

V1

Yield: 78%; 110.0 mg of V1 as a yellow residue. $^1$H NMR: (400 MHz, CDCl$_3$ at 50° C.) δ 7.60 (d, J=13.3 Hz, 1H), 7.52 (dd, J=8.3, 1.6 Hz 1H), 7.24-7.11 (m, 3H), 4.82 (d, J=13.3 Hz, 1H), 4.65 (s, 1H), 4.30 (s, 1H), 3.81 (s, 3H), 3.74-3.66 (m, 4H), 3.52 (dd, J=13.9, 6.9 Hz, 1H), 3.45-3.31 (m, 2H), 3.19 (dd, J=13.6 Hz, 1H), 2.95-2.81 (m, 3H), 2.28 (dd, J=14.8, 8.4 Hz, 1H), 1.92-1.80 (m, 3H), 1.74 (m, 1H), 1.64-1.49 (m, 2H), 1.28 (m, 1H), 1.12-1.03 (t, J=6.9 Hz, 3H), 0.87 (t, J=7.6 Hz, 3H). $^{13}$C NMR: (100 MHz, CDCl$_3$ at 50° C.) δ 174.8, 169.7, 150.8, 135.5, 134.2, 128.1, 122.9, 120.4, 118.4, 112.9, 112.2, 87.0, 83.2, 73.2, 63.3, 59.2, 56.7, 54.1, 50.7, 40.9, 40.8, 33.2, 27.2, 22.0 (2C), 15.3, 8.0. HRMS (ESI): calc. for C$_{27}$H$_{37}$N$_2$O$_6$ [M+H]$^+$: 485.2646, found: 485.2655.

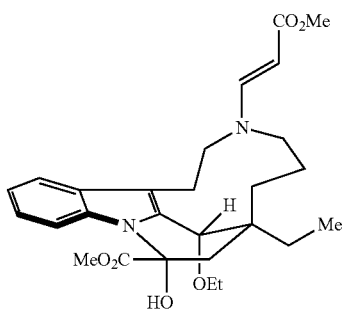

V28

Yield: 15%; 20.9 mg of V28 as a yellow residue. $^1$H NMR: (400 MHz, CDCl$_3$ at 50° C.) δ 7.60-7.46 (m, 2H), 7.23-7.12 (m, 2H), 7.10 (dd, J=7.3, 1.0 Hz, 1H), 4.76 (m, 2H), 4.30 (s, 1H), 3.83 (s, 1H), 3.76-3.65 (m, 4H), 3.49-3.27 (m, 3H), 3.12 (m, 1H), 3.03-2.96 (m, 2H), 2.53 (m, 1H), 2.45 (d, J=14.6 Hz, 1H), 2.28 (d, J=14.6 Hz, 1H), 1.89 (sextet, J=14.6, 7.3 Hz, 1H), 1.73-1.57 (m, 4H), 1.36 (m, 1H), 1.09 (t, J=7.0 Hz, 1H), 0.88 (t, J=7.5 Hz, 1H). $^{13}$C NMR: (100 MHz, CDCl$_3$ at 50° C.) δ 172.3, 169.8, 151.5, 135.6, 134.0, 127.7, 123.1, 120.4, 118.6, 112.5, 111.1, 86.8, 82.4, 74.5, 64.0, 58.2, 56.3, 53.6, 50.7, 46.1, 41.9, 34.0, 29.4, 22.4 (2C), 15.2, 8.1. HRMS (ESI): calc. for C$_{27}$H$_{36}$N$_2$O$_6$Na [M+Na]$^+$: 507.2466, found: 507.2486.

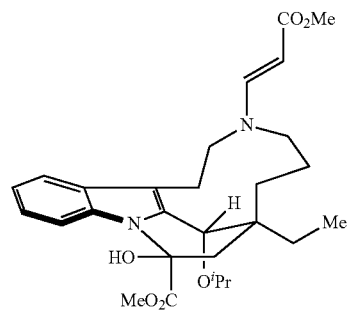

V2

Yield: 25%; 35.7 mg of V2 as a clear-brown residue. $^1$H NMR: (400 MHz, CDCl$_3$ at 50° C.) δ 7.61 (d, J=13.3 Hz, 1H), 7.51 (dd, J=7.2, 1.0 Hz, 1H), 7.22-7.12 (m, 3H), 4.82 (d, J=13.3 Hz, 1H), 4.55 (s, 1H), 4.40 (s, 1H), 3.80 (s, 3H), 3.75-3.67 (m, 4H), 3.59-3.47 (m, 2H), 3.16 (dd, J=13.8 Hz, 1H), 3.00-2.81 (m, 3H), 2.30 (dd, J=13.8, 9.2 Hz, 1H), 1.93-1.70 (m, 4H), 1.60-1.49 (m, 2H), 1.22 (dd, J=15.9, 7.9 Hz, 1H), 1.14 (d, J=6.0 Hz, 3H), 0.90 (d, J=6.1 Hz, 3H), 0.86 (t, J=7.6 Hz, 3H). $^{13}$C NMR: (100 MHz, CDCl$_3$ at 50° C.) δ 175.0, 169.7, 150.6, 135.6, 135.2, 128.3, 122.9, 120.5, 118.4, 112.6, 112.3, 87.3, 83.2, 70.3, 67.5, 59.4, 56.7, 54.0, 50.7, 41.0, 40.9, 33.2, 27.3, 23.7, 22.0 (2C), 21.3, 8.1. HRMS (ESI): calc. for C$_{27}$H$_{36}$N$_2$O$_6$Na [M+Na]$^+$: 521.2622, found: 521.2630.

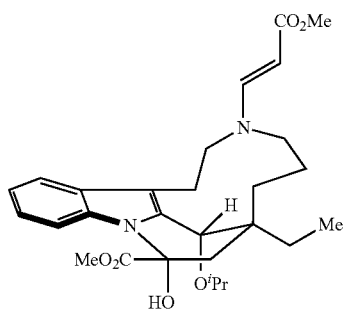

V29

Yield: 60%; 84.4 mg of V29 as a clear solid. $^1$H NMR: (400 MHz, CDCl$_3$ at 50° C.) δ 7.56-7.50 (m, 2H), 7.20-7.11 (m, 2H), 7.08 (m, 1H), 4.95 (s, 1H), 4.75 (d, J=13.3 Hz, 1H), 4.41 (s, 1H), 3.83 (s, 3H), 3.73 (m, 1H), 3.67 (s, 3H), 3.51 (septet, J=5.9 Hz, 1H), 3.41 (dd, J=14.0, 8.1 Hz, 1H), 3.11 (m, 1H), 3.04-2.94 (m, 2H), 2.50 (ddd, J=14.1, 8.1, 2.0 Hz, 1H), 2.44 (d, J=14.7 Hz, 1H), 2.27 (d, J=14.6 Hz, 1H), 1.87 (sextet, J=7.5 Hz, 1H), 1.70-1.53 (m, 3H), 1.39 (m, 1H), 1.27 (m, 1H), 1.15 (d, J=5.9 Hz, 3H), 0.92 (d, J=5.9 Hz, 3H), 0.86 (t, J=7.5 Hz, 3H) $^{13}$C NMR: (100 MHz, CDCl$_3$ at 50° C.) δ 172.0, 169.6, 151.3, 135.4, 134.6, 127.6, 123.0, 120.3, 118.5, 111.9, 111.0, 86.7, 82.3, 71.8, 68.9, 58.0, 56.1, 53.4, 50.6, 46.5, 41.8, 34.1, 29.4, 23.4, 22.3 (2C), 21.2, 8.1. HRMS (ESI): calc. for C$_{28}$H$_{38}$N$_2$O$_6$Na [M+Na]$^+$: 521.2622, found: 521.2628. MP: 158-160° C.

TABLE 1

Crystal data and structure refinement for chip2.

| | |
|---|---|
| Identification code | chip2 |
| Empirical formula | C28H38N2O6 |
| Formula weight | 498.60 |
| Temperature | 100(2) K |
| Wavelength | 1.54178 Å |
| Crystal system | Monoclinic |
| Space group | P2$_1$ |
| Unit cell dimensions | a = 8.4703(3) Å   α = 90°. |
| | b = 17.3342(5) Å   β = 113.5528(11)°. |
| | c = 9.7261(3) Å   γ = 90°. |
| Volume | 1309.08(7) Å$^3$ |
| Z | 2 |
| Density (calculated) | 1.265 Mg/m$^3$ |
| Absorption coefficient | 0.720 mm$^{-1}$ |
| F(000) | 536 |
| Crystal size | 0.211 × 0.101 × 0.083 mm$^3$ |
| Theta range for data collection | 4.960 to 67.953°. |
| Index ranges | −9 ≤ h ≤ 10, −18 ≤ k ≤ 19, −11 ≤ l ≤ 11 |
| Reflections collected | 11256 |
| Independent reflections | 4338 [R(int) = 0.0388] |
| Completeness to theta = 67.679° | 96.0% |
| Absorption correction | Analytical |
| Max. and min. transmission | 0.9654 and 0.9123 |
| Refinement method | Full-matrix least-squares on F$^2$ |
| Data/restraints/parameters | 4338/1/345 |
| Goodness-of-fit on F$^2$ | 1.095 |
| Final R indices [I > 2sigma(I)] | R1 = 0.0328, wR2 = 0.0870 [4175] |
| R indices (all data) | R1 = 0.0352, wR2 = 0.0936 |
| Absolute structure parameter | 0.05(9) |
| Largest diff. peak and hole | 0.282 and −0.287 e · Å$^{-3}$ |

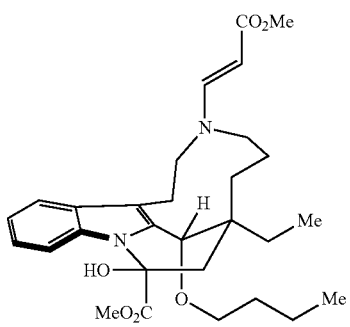

V30

Yield: 14%; 21.7 mg of V30 as a white solid. $^1$H NMR: (400 MHz, CDCl$_3$ at 50° C.) δ 7.59 (d, J=13.3 Hz, 1H), 7.52 (d, J=7.1 Hz, 1H), 7.21-7.10 (m, 3H), 4.81 (d, J=13.3 Hz, 1H), 4.56 (s, 1H), 4.28 (s, 1H), 3.81 (s, 3H), 3.74-3.66 (m, 4H), 3.54 (dd, J=14.0, 7.0 Hz, 1H), 3.40-3.26 (m, 2H), 3.19 (dd, J=13.6 Hz, 1H), 2.99-2.77 (m, 3H), 2.30 (dd, J=14.1, 9.5 Hz, 1H), 1.91-1.80 (m, 3H), 1.74 (m, 1H), 1.65-1.50 (m, 2H), 1.49-1.40 (m, 2H), 1.37-1.18 (m, 3H), 0.89-0.81 (m, 6H). $^{13}$C NMR: (100 MHz, CDCl$_3$ at 50° C.) δ 175.1, 169.8, 151.0, 135.6, 134.3, 128.3, 123.0, 120.5, 118.5, 113.1, 112.3, 87.1, 83.2, 73.4, 67.8, 59.6, 56.7, 54.1, 50.8, 41.1, 40.8, 33.3, 32.2, 27.4, 22.1 (2C), 19.7, 14.0, 8.1. HRMS (ESI): for C$_{29}$H$_{41}$N$_2$O$_6$ [M+H]$^+$: 513.2959, found: 513.2968. MP: 128-130° C.

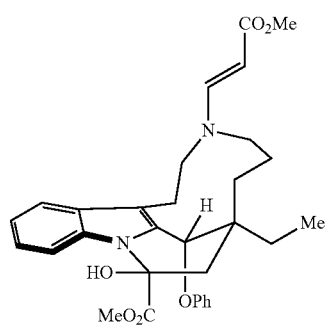

V3

Yield: 19%; 31.5 mg of V3 as a white solid. $^1$H NMR: (400 MHz, CDCl$_3$ at 50° C.) δ 7.63 (d, J=13.4 Hz, 1H), 7.41 (d, J=7.7 Hz, 1H), 7.24-7.09 (m, 5H), 6.99 (dd, J=7.8 Hz, 1H), 6.81 (d, J=7.8 Hz, 2H), 5.15 (s, 1H), 4.75 (d, J=13.4 Hz, 1H), 4.66 (s, 1H), 3.91 (s, 3H), 3.80 (s, 3H), 3.65-3.48 (m, 2H), 3.01 (d, J=13.9 Hz, 1H), 2.73 (dd, J=12.7 Hz, 1H), 2.54-2.35 (m, 2H), 2.30 (dd, J=13.6, 10.2 Hz, 1H), 2.07-1.73 (m, 4H), 1.63-1.56 (m, 2H), 1.37 (dd, J=16.0, 8.3 Hz, 1H), 0.95 (t, J=7.6 Hz, 3H). $^{13}$C NMR: (100 MHz, CD$_3$Cl at 50° C.) δ 175.0, 169.7, 158.4, 150.3, 135.5, 133.1, 129.4, 128.2, 123.2 (2C), 121.0, 120.5, 118.8, 113.6, 112.1, 88.1, 83.1, 77.7, 59.5, 56.7, 54.4, 50.8, 41.0, 40.8, 33.3, 27.6, 22.0 (2C), 8.1. HRMS (ESI): calc. for C$_{31}$H$_{36}$N$_2$O$_6$Na [M+Na]$^+$: 555.2466, found: 555.2464. MP: 98-100° C.

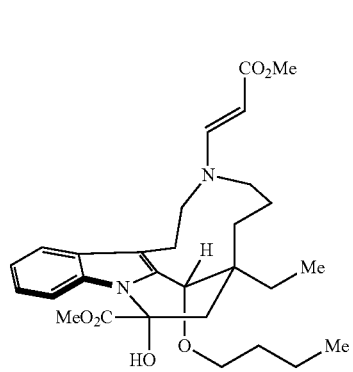

V31

Yield: 34%; 50.2 mg of V31 as a clear residue. $^1$H NMR: (400 MHz, CDCl$_3$ at 50° C.) δ 7.53 (m, 2H), 7.22-7.12 (m, 2H), 7.10 (dd, J=6.8, 1.4 Hz, 1H), 4.82-4.71 (m, 2H), 4.28 (s, 1H), 3.82 (s, 3H), 3.76-3.66 (m, 4H), 3.42 (ddd, J=14.4, 7.7 Hz, 1H), 3.36-3.22 (m, 2H), 3.13 (m, 1H), 3.05-2.92 (m, 2H), 2.50 (dd, J=14.4, 7.7 Hz, 1H), 2.46 (d, J=14.6 Hz, 1H), 2.28 (d, J=14.6 Hz, 1H), 1.88 (sextet, J=7.5 Hz, 1H), 1.75-1.54 (m, 4H), 1.50-1.35 (m, 2H), 1.33-1.23 (m, 3H), 0.87 (t, J=7.6 Hz, 3H), 0.82 (t, J=7.5 Hz, 3H). 13C NMR: (100 MHz, CDCl$_3$ at 50° C.) δ 172.2, 169.7, 151.5, 135.5, 133.9, 127.6, 123.0, 120.4, 118.5, 112.5, 111.1, 86.7, 82.4, 74.6, 68.4, 57.9, 56.1, 53.5, 50.7, 46.1, 42.0, 33.9, 31.9, 29.4, 22.4 (2C), 19.6, 14.0, 8.1. HRMS (ESI): C$_{29}$H$_{40}$N$_2$O$_6$Na [M+Na]$^+$: 535.2779, found: 535.2762.

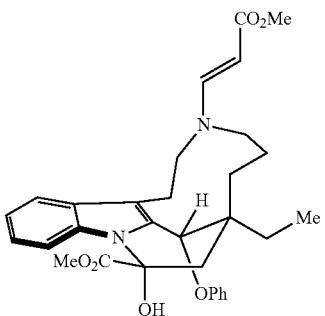

V34

Yield: 28%; 45.7 mg of V34 as a pinkish-white solid. $^1$H NMR: (400 MHz, CDCl$_3$ at 50° C.) δ 7.56 (d, J=13.3 Hz, 1H), 7.44 (d, J=7.7 Hz, 1H), 7.23-7.09 (m, 5H), 6.96 (dd, J=7.4, 7.2 Hz, 1H), 6.82 (d, J=8.4 Hz, 2H), 5.15 (s, 1H), 4.71 (d, J=13.3 Hz, 1H), 4.42 (s, 1H), 3.80 (s, 3H), 3.76 (s, 3H), 3.63-3.46 (m, 2H), 2.87 (td, J=14.0, 2.0 Hz, 1H), 2.75 (d, J=14.8 Hz, 1H), 2.65-2.47 (m, 2H), 2.47-2.32 (m, 2H), 2.05 (sextet, J=7.6 Hz, 1H), 1.90-1.74 (m, 2H), 1.73-1.57 (m, 3H), 1.37 (m, 1H), 0.92 (t, J=7.6 Hz, 3H). $^{13}$C NMR: (100 MHz, CD$_3$Cl at 50° C.) δ 173.4, 169.7, 158.3, 150.7, 135.8, 133.3, 129.5, 127.8, 123.3, 123.2, 120.5, 120.3, 118.8, 115.6, 112.8, 111.1, 87.9, 82.3, 77.9, 58.4, 56.4, 53.8, 50.8, 45.1, 42.3, 28.6, 22.2, 8.1. HRMS (ESI): calc. for C$_{31}$H$_{37}$N$_2$O$_6$ [M+H]$^+$: 532.2646, found: 533.2649. MP: 78-80° C.

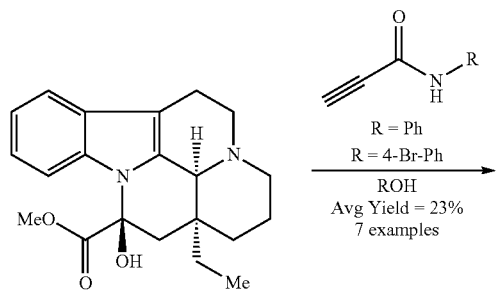

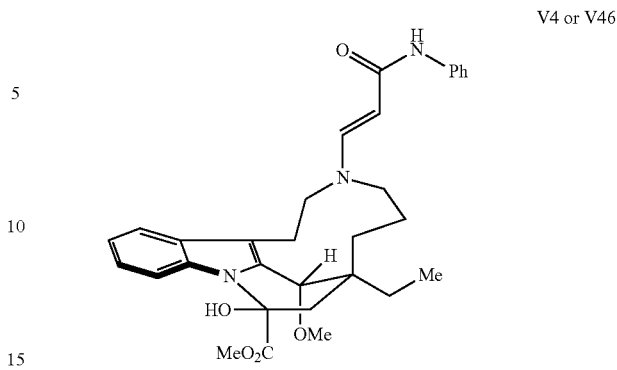

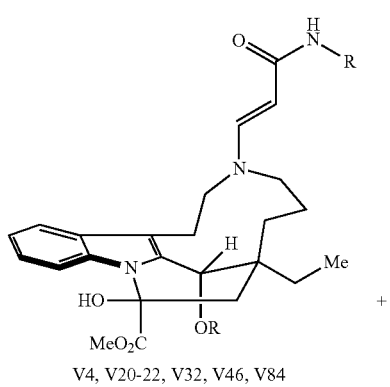

Yield: 36%; 59.3 mg of V4 or V46 as a yellow solid. H NMR: (400 MHz, CDCl$_3$ at 50° C.) δ 7.69 (d, J=13.0 Hz, 1H), 7.58 (d, J=8.6, 2H), 7.53 (m, 1H), 7.29 (dd, J=8.3 Hz, 2H), 7.24-7.14 (m, 4H), 7.04 (dd, J=7.4 Hz, 1H), 4.90 (d, J=13.0 Hz, 1H), 4.64 (s, 1H), 4.25 (s, 1H), 3.82 (s, 3H), 3.67 (d, J=13.7 Hz, 1H), 3.51 (dd, J=13.9, 6.6 Hz, 1H), 3.27-3.15 (m, 4H), 2.96-2.83 (m, 2H), 2.76 (d, J=13.5 Hz, 1H), 2.29 (dd, J=14.2, 8.6 Hz, 1H), 1.92-1.69 (m, 4H), 1.62 (m, 1H), 1.51 (m, 1H), 1.28 (m, 1H), 0.86 (t, J=7.6 Hz, 3H). $^{13}$C NMR: (100 MHz, CDCl$_3$ at 50° C.) δ 174.9, 167.1, 149.4, 139.7, 135.6, 133.6, 129.1, 128.2, 123.3, 123.1, 120.5, 120.0, 118.5, 113.5, 112.3, 90.1, 83.2, 75.5, 59.3, 56.9, 56.3, 54.3, 41.0, 40.6, 33.2, 27.2, 22.4, 22.0, 8.1. HRMS (ESI): calc. for C$_{31}$H$_{38}$N$_3$O$_5$ [M+H]$^+$: 532.2086, found: 532.2781. MP: 207-209° C.

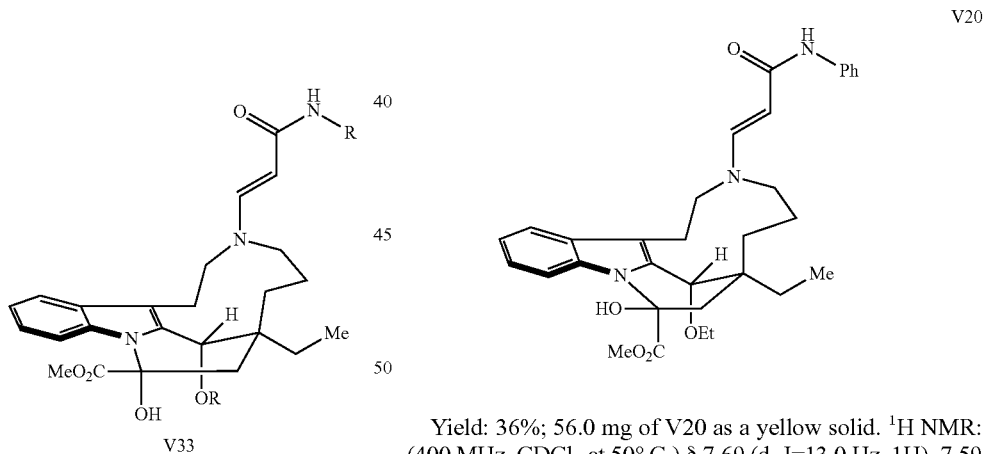

General Procedure for the synthesis of V4 or V46, V20-V22, V32-V33 & V84: V (108.4 mg, 0.306 mmol) was added to a flame-dried round bottom flask and dissolved in methanol (30.6 mL). N-phenylpropiolamide (67.0 mg, 0.458 mmol) was added as one portion, the reaction was heated to 64° C. and proceeded for 19 hours. Upon completion, the reaction was concentrated in vacuo, and the crude product was purified via column chromatography using a gradient of 100% hexanes to 1:1 hexanes:ethyl acetate to afford V4 or V46 (59.3 mg, 36%) as a yellow solid.

Yield: 36%; 56.0 mg of V20 as a yellow solid. $^1$H NMR: (400 MHz, CDCl$_3$ at 50° C.) δ 7.69 (d, J=13.0 Hz, 1H), 7.59 (d, J=8.1 Hz, 2H), 7.52 (m, 1H), 7.30 (dd, J=2H), 7.25-7.10 (m, 4H), 7.04 (td, J=7.3, 1.1 Hz, 1H), 4.89 (d, J=13.0 Hz, 1H), 4.65 (s, 1H), 4.34 (s, 1H), 3.81 (s, 3H), 3.67 (d, J=13.6 Hz, 1H), 3.51 (dd, J=14.2, 6.4 Hz, 1H), 3.39 (sextet, J=7.5 Hz, 2H), 3.17 (dd, J=15.2, 13.7 Hz, 1H), 2.95-2.79 (m, 3H), 2.28 (dd, J=13.2, 9.0 Hz, 1H), 1.93-1.79 (m, 3H), 1.74 (m, 1H), 1.67-1.42 (m, 2H), 1.26 (m, 1H), 1.07 (t, J=7.1 Hz, 3H), 0.86 (t, J=7.5 Hz, 3H). $^{13}$C NMR: (100 MHz, CDCl$_3$ at 50° C.) δ 174.9, 167.1, 149.4, 139.7, 135.5, 134.3, 129.1, 128.2, 123.3, 122.9, 120.4, 120.0, 118.5, 112.9, 112.3, 90.1, 83.2, 73.4, 63.4, 59.2, 56.9, 54.1, 41.0, 40.8, 33.3, 27.2, 22.5, 21.9, 15.4, 8.1. HRMS (ESI): calc. for C$_{32}$H$_{39}$N$_3$O$_5$Na [M+Na]$^+$: 568.2782, found: 568.2789. MP: 220-222° C.

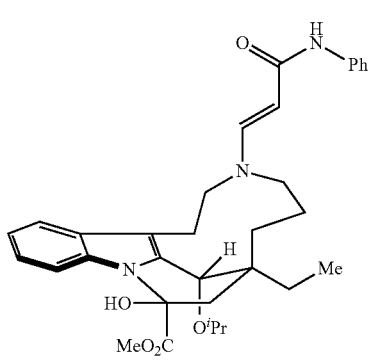

V32

Yield: 5%; 8.5 mg of V32 as a yellow solid. $^1$H NMR: (600 MHz, CDCl$_3$ at 50° C.) δ 7.71 (d, J=13.0 Hz, 1H), 7.53 (d, J=7.6 Hz, 3H), 7.30 (dd, J=7.8 Hz, 2H), 7.23-7.11 (m, 3H), 7.05 (dd, J=7.4 Hz, 1H), 6.82 (s, 1H), 4.85 (d, J=13.0 Hz, 1H), 4.54 (s, 1H), 4.43 (s, 1H), 3.80 (s, 3H), 3.70 (d, J=14.7 Hz, 1H), 3.58-3.48 (m, 2H), 3.15 (dd, J=13.7 Hz, 1H), 2.99-2.78 (m, 3H), 2.31 (dd, J=14.1, 9.7 Hz, 1H), 1.92-1.72 (m, 4H), 1.66-1.56 (m, 3H), 1.15 (d, J=5.9 Hz, 3H), 0.90 (d, J=5.9 Hz, 3H), 0.85 (t, J=7.8 Hz, 4H). $^{13}$C NMR: (150 MHz, CDCl$_3$ at 50° C.) δ 175.1, 166.9, 149.3, 139.6, 135.6, 135.3, 129.1, 128.4, 123.5, 122.9, 120.5, 120.2, 118.5, 112.6, 112.4, 90.1, 83.3, 70.4, 67.6, 59.4, 56.8, 54.0, 41.0, 40.9, 33.1, 27.3, 23.7, 22.0, 21.5 (2C), 8.1. HRMS (ESI): calc. for C$_{33}$H$_{41}$N$_3$O$_5$Na [M+Na]$^+$: 582.2938, found: 582.2953. MP: 226-228° C.

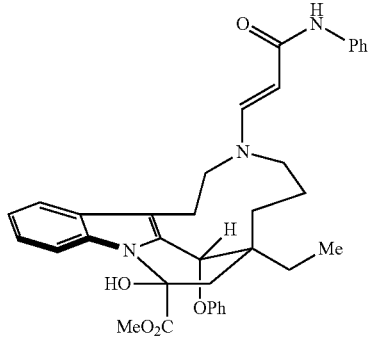

V21

Yield: 23%; 45.5 mg of V21 as a yellow solid. $^1$H NMR: (400 MHz, CDCl$_3$ at 50° C.) δ 7.72 (d, J=13.1 Hz, 1H), 7.61 (d, J=8.2 Hz, 2H), 7.40 (dd, J=8.4, 7.6 Hz, 1H), 7.31 (dd, J=8.5, 7.4 Hz, 2H), 7.22-7.16 (m, 2H), 7.15-7.08 (m, 3H), 7.07-7.02 (m, 2H), 6.92 (td, J=7.3, 1.1 Hz, 1H), 6.84-6.80 (m, 2H), 5.14 (s, 1H), 4.76 (d, J=13.1 Hz, 1H), 4.70 (s, 1H), 3.88 (s, 3H), 3.58-3.42 (m, 2H), 2.97 (d, J=14.1 Hz, 1H), 2.72 (dt, J=14.0, 6.9 Hz, 1H), 2.48-2.38 (m, 2H), 2.24 (dd, J=14.0, 9.7 Hz, 1H), 2.04-1.76 (m, 5H), 1.55 (ddd, J=16.7, 9.0, 6.1 Hz, 1H), 1.35 (dd, J=15.7, 8.3 Hz, 1H), 0.91 (t, J=7.6 Hz, 3H). Note: $^1$H spectrum referenced TMS at 0.00 ppm. $^{13}$C NMR: (100 MHz, CDCl$_3$ at 50° C.): δ 175.0, 166.9, 158.4, 148.1, 139.6, 135.2, 133.1, 129.3, 129.2, 128.0, 123.3, 123.0, 121.2, 120.4, 119.7, 118.7, 113.3, 112.1, 90.7, 82.9, 78.0, 60.1, 55.7, 54.5, 40.7, 40.5, 33.1, 27.4, 22.0, 20.6 (2C), 8.1. HRMS (ESI): calc. for C$_{36}$H$_{40}$N$_3$O$_5$ [M+H]$^+$: 594.2962, found: 594.2986. MP: 200-202° C.

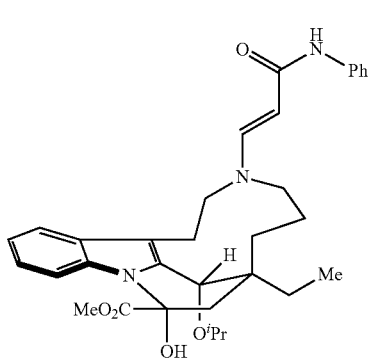

V33

Yield: 5%; 8.5 mg of V33 as a yellow solid. $^1$H NMR: (400 MHz, CDCl$_3$ at 50° C.) δ 7.70 (d, J=12.8 Hz, 1H), 7.55-7.48 (m, 3H), 7.28 (dd, J=8.6 Hz, 2H), 7.21-7.11 (m, 3H), 7.04 (dd, J=7.4 Hz, 1H), 6.66 (s, 1H), 4.86 (s, 1H), 4.73 (d, J=12.8 Hz, 1H), 4.45 (s, 1H), 3.79 (s, 3H), 3.70 (d, J=13.9 Hz, 1H), 3.54 (m, 1H), 3.15 (dd, J=13.5 Hz, 1H), 2.97-2.79 (m, 3H), 2.31 (dd, J=13.8, 8.5 Hz, 1H), 1.91-1.72 (m, 4H), 1.66-1.44 (m, 3H), 1.28 (m, 1H), 1.16 (d, J=6.1 Hz, 3H), 0.92 (d, J=6.2 Hz, 3H), 0.86 (t, J=7.5 Hz, 3H). $^{13}$C NMR: (100 MHz, CDCl$_3$ at 50° C.) δ 172.3, 166.9, 149.8, 139.6, 135.6, 134.9, 129.1, 127.9, 123.4, 123.0, 120.3, 120.0, 118.6, 111.7, 111.2, 89.8, 82.3, 72.0, 69.1, 57.7, 55.7, 53.6, 46.6, 42.0, 33.7, 29.3, 23.5, 22.5, 21.4, 8.2. HRMS (ESI): calc. for C$_{33}$H$_{41}$N$_3$O$_5$Na [M+Na]$^+$: 582.2938, found: 582.2943. MP: 160-162° C.

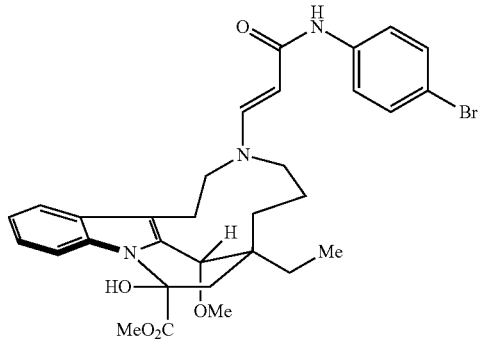

V22

Yield: 45%; 95.2 mg of V22 as a yellow solid. $^1$H NMR: (400 MHz, CDCl$_3$ at 50° C.) δ 7.65 (d, J=12.8 Hz, 1H), 7.55-7.47 (m, 3H), 7.41 (s, 1H), 7.37 (d, J=9.0 Hz, 2H), 7.24-7.15 (m, 3H), 4.88 (d, J=12.8 Hz, 1H), 4.70 (s, 1H), 4.21 (s, 1H), 3.81 (s, 3H), 3.62 (d, J=14.2 Hz, 1H), 3.47 (dd, J=14.2, 7.2 Hz, 1H), 3.25-3.11 (m, 4H), 2.94-2.82 (m, 2H), 2.75 (d, J=14.0 Hz, 1H), 2.27 (dd, J=14.5, 8.7 Hz, 1H), 1.92-1.63 (m, 4H), 1.64-1.41 (m, 2H), 1.26 (dd, J=16.0, 7.6 Hz, 1H), 0.85 (t, J=7.5 Hz, 3H). $^{13}$C NMR: (100 MHz, CDCl$_3$ at 50° C.) δ 174.7, 167.1, 149.6, 138.9, 135.6, 133.4, 131.9, 128.2, 123.1, 121.3, 120.5, 118.5, 115.5, 113.4, 112.3, 89.8, 83.2, 75.4, 59.1, 56.7, 56.3, 54.2, 41.0, 40.6, 33.1, 27.2, 22.3, 22.0, 8.1. HRMS (ESI): calc. for C$_{31}$H$_{36}$BrN$_3$O$_5$ [M+Na]$^+$: 632.1731, found: 632.1759. MP: 201-203° C.

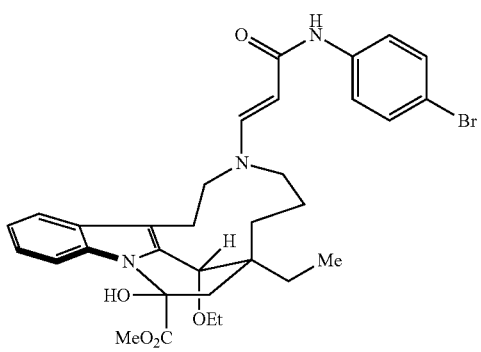

V84

Yield: 11%; 8.8 mg of V84 as a yellow solid. ¹H NMR: (400 MHz, CDCl₃ at 50° C.) δ 7.68 (d, J=13.2 Hz, 1H), 7.53 (m, 1H), 7.46 (d, J=9.0 Hz, 2H), 7.41 (d, J=9.0 Hz, 2H), 7.24-7.12 (m, 3H), 6.78 (s, 1H), 4.80 (d, J=13.2 Hz, 1H), 4.54 (s, 1H), 4.32 (s, 1H), 3.81 (s, 3H), 3.70 (d, J=14.4 Hz, 1H), 3.55 (dd, J=14.6, 7.0 Hz, 1H), 3.38 (dd, J=15.0, 13.8 Hz, 2H), 3.19 (dd, J=13.5 Hz, 1H), 3.00-2.87 (m, 2H), 2.83 (d, J=14.0 Hz, 1H), 2.34 (dd, J=14.1, 8.7 Hz, 1H), 1.95-1.69 (m, 4H), 1.65-1.53 (m, 2H), 1.24 (m, 1H), 1.06 (t, J=6.9 Hz, 3H), 0.86 (t, J=7.3 Hz, 3H). ¹³C NMR: (100 MHz, CDCl₃ at 50° C.) δ 175.0, 166.8, 149.8, 138.8, 135.6, 134.4, 132.1, 128.3, 123.1, 121.4, 120.6, 118.5, 115.7, 112.9, 112.4, 89.7, 83.2, 73.4, 63.5, 59.3, 57.0, 54.2, 41.1, 40.8, 33.2, 27.2, 22.0 (2C), 15.5, 8.1. HRMS (ESI): calc. for C₃₂H₃₈BrN₃O₅ [M+Na]⁺: 646.1887, found: 646.1898. MP: 215-217° C.

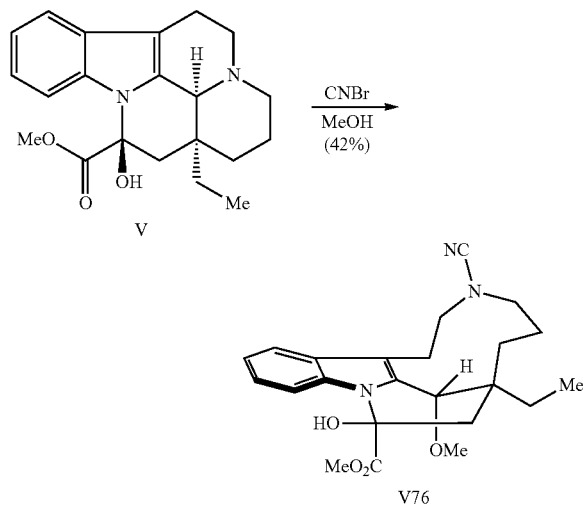

Procedure for the synthesis of V76: V (139.9 mg, 0.395 mmol) was added to a flame-dried round-bottom flask and subsequently dissolved in a (2:1) chloroform:methanol solution (7.3 mL). A 3.0 M solution of cyanogen bromide in dichloromethane (0.39 mL, 1.18 mmol) was added dropwise and the reaction was stirred at room temperature for 4 hours. The reaction mixture was diluted with brine and extracted with dichloromethane. The organic layer was dried with sodium sulfate, filtered, and concentrated in vacuo. The crude product was purified via column chromatography using a gradient of 100% chloroform to 24:1 chloroform: acetone to afford V76 (68.0 mg, 42%) as a white solid. ¹H NMR: (400 MHz, CDCl₃) δ 7.52 (d, J=7.3z Hz, 1H), 7.23-7.13 (m, 3H), 4.70 (s, 1H), 4.55 (s, 1H), 3.84 (s, 3H), 3.79 (dt, J=13.7, 2.9 Hz, 1H), 3.53 (dd, J=13.1, 6.4 Hz, 1H), 3.35 (s, 3H), 3.16 (ddd, J=15.3, 12.3, 3.1 Hz, 1H), 3.06 (dt, J=13.7, 2.9 Hz, 1H), 2.80 (d, J=13.8 Hz, 1H), 2.68 (ddd, J=15.3, 12.3, 3.1 Hz, 1H), 2.08 (dd, J=13.1, 6.4 Hz, 1H), 1.98-1.85 (m, 3H), 1.82-1.67 (m, 2H), 1.59 (m, 1H), 1.30 (dd, J=15.9, 8.2 Hz, 1H), 0.89 (t, J=7.6 Hz, 3H). ¹³C NMR: (100 MHz, CDCl₃) δ 174.8, 135.3, 133.7, 127.9, 123.1, 120.6, 118.3, 118.0, 112.1, 112.0, 83.0, 75.5, 56.8, 56.4, 55.4, 54.5, 41.0, 40.6, 32.6, 26.8, 23.5, 21.4, 8.1. HRMS (ESI): calc. for C₂₃H₂₉N₃O₄Na [M+Na]⁺: 434.2050, found: 434.2068. MP: 241-243° C.

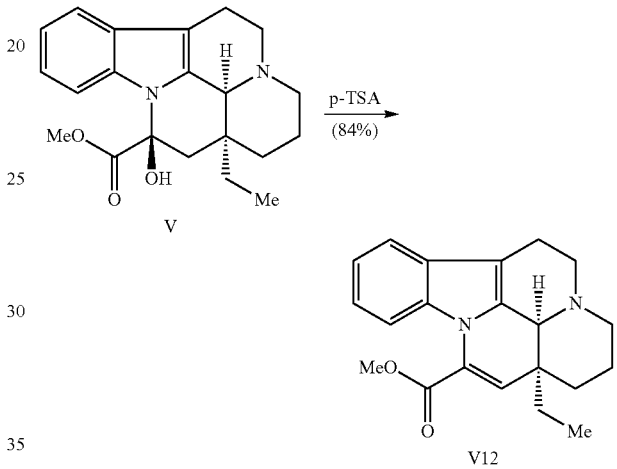

Procedure for the synthesis of V12: V (2.01 g, 5.66 mmol) was added to a flame-dried round-bottom flask and dissolved in toluene (19.0 mL). p-Toluenesulfonic acid monohydrate (2.15 g, 11.32 mmol) was added to the solution and the round-bottom flask was equipped with a dean-stark trap. The reaction was heated to reflux for 2 hours, upon completion, the reaction was basified to pH ~6-7 with 1 M NaOH and extracted with ethyl acetate. The crude extract was dried with sodium sulfate, filtered, concentrated in vacuo, and purified via column chromatography using a gradient of 100% hexanes to 1:1 hexanes:ethyl acetate with 1% triethylamine throughout to afford V12 (1.61 g, 84%) as a light yellow solid. Note: V12 is a known compound (CAS No. 4880-92-6). The spectral data below are consistent with literature.[4] ¹H NMR: (600 MHz, CDCl₃) δ 7.47 (d, J=7.7 1H), 7.23 (d, J=8.3 Hz, 1H), 7.17 (td, J=7.1, 1.1 Hz, 1H), 7.13 (td, J=7.2, 0.9 Hz, 1H), 6.14 (s, 1H), 4.17 (s, 1H), 3.95 (s, 3H), 3.38 (dd, J=13.9, 6.2 Hz, 1H), 3.27 (td, J=11.7, 5.5 Hz, 1H), 3.03 (m 1H), 2.70-2.60 (m, 2H), 2.54 (dd, J=16.4, 3.4 Hz, 1H), 2.00-1.86 (m, 2H), 1.75 (m, 1H), 1.52 (d, J=13.7 Hz, 1H), 1.42 (dt, J=13.2, 2.9 Hz, 1H), 1.06-0.98 (m, 4H). ¹³C NMR: (150 MHz, CDCl₃) δ 164.0, 134.3, 130.9, 129.2, 128.4, 128.3, 122.2, 120.5, 118.5, 112.6, 108.9, 55.9, 52.7, 51.7, 45.1, 37.9, 28.7, 27.5, 20.4, 16.5, 8.9. MP: 159-161° C.

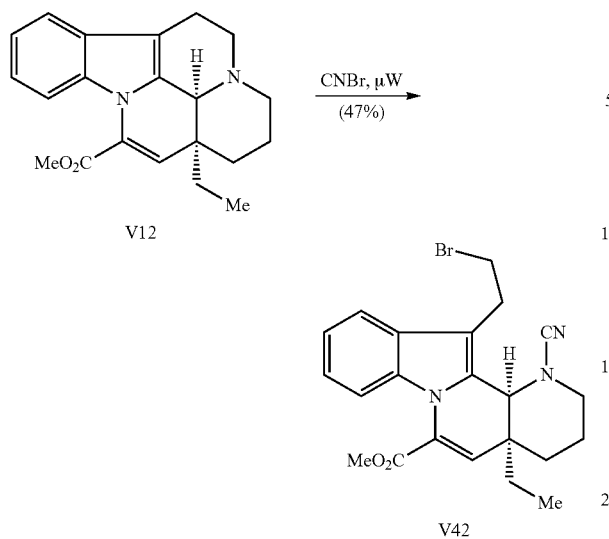

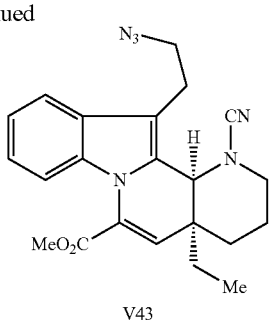

Procedure for the synthesis of V43: V42 (256.1 mg, 0.579 mmol) was added to a flame-dried microwave flask and dissolved in N,N-dimethylformamide (6.00 mL). Sodium azide (301.1 mg, 4.63 mmol) was added to the resulting solution and the reaction was subjected to microwave irradiation at 100° C. for six minutes. The reaction was cooled to room temperature, diluted with ethyl acetate, and quenched with brine (3×50 mL). The organic layer was dried with sodium sulfated, filtered, and concentrated in vacuo. The crude material was purified via column chromatography using a gradient of 100% chloroform to 99:1 chloroform:acetone to yield V43 (174.0 mg, 73%) as a white foam. $^1$H NMR: (400 MHz, CDCl$_3$) δ 7.58 (m, 1H), 7.26 (m, 1H), 7.23-7.15 (m, 2H), 6.15 (d, J=1.7 Hz, 1H), 4.11 (d, J=1.7 Hz, 1H), 3.96 (s, 3H), 3.72 (ddd, J=12.2, 8.2, 5.7 Hz, 1H), 3.61 (dt, J=12.2, 7.9 Hz, 1H), 3.48 (dp, J=10.3, 2.1 Hz, 1H), 3.21-3.03 (m, 3H), 2.13 (dt, J=13.8, 3.5 Hz, 1H), 1.89-1.70 (m, 2H), 1.42 (td, J=13.2, 4.2 Hz, 1H), 1.17-1.01 (m, 2H), 0.75 (t, J=7.5 Hz, 3H). Note: $^1$H spectrum referenced TMS at 0.00 ppm. $^{13}$C NMR: (100 MHz, CDCl$_3$) δ 163.4, 134.7, 130.1, 128.2, 128.1, 127.4, 124.0, 121.2, 119.3, 116.7, 116.6, 112.7, 56.8, 52.8, 51.5, 50.1, 39.4, 32.3, 31.4, 24.4, 21.8, 8.1. HRMS (ESI): calc. for C$_{22}$H$_{24}$N$_6$O$_2$Na [M+Na]$^+$: 427.1853, found: 427.1860. MP: 41-43° C.

Procedure for the synthesis of V42: V12 (503.2 mg, 1.50 mmol) was added to a flame-dried microwave flask and dissolved in N,N-dimethylformamide (15.0 mL). A 3M solution of cyanogen bromide in dichloromethane (1.5 mL, 4.50 mmol) was added dropwise to the resulting solution. The reaction was subjected to microwave irradiation at 100° C. for six minutes. The reaction was cooled to room temperature, diluted with ethyl acetate, and quenched with brine (3×100 mL). The organic layer was dried with sodium sulfate, filtered, and concentrated in vacuo. The crude material was purified via column chromatography using a gradient of 100% chloroform to 99:1 chloroform:acetone to yield V42 (310.2 mg, 47%) as an orange-white solid. $^1$H NMR: (400 MHz, CDCl$_3$) δ 7.59 (d, J=7.6, 1H), 7.28-7.14 (m, 3H), 6.15 (d, J=1.5 Hz, 1H), 4.11 (d, J=1.5 Hz, 1H), 3.93 (s, 3H), 3.76 (td, J=9.5, 7.1 Hz, 1H), 3.63 (td, J=9.5, 7.1 Hz, 1H), 3.48-3.29 (m, 3H), 3.07 (td, J=12.1, 3.0 Hz, 1H), 2.01 (d, J=13.4 Hz, 1H), 1.79-1.56 (m, 2H), 1.30 (td, J=13.1, 3.9 Hz, 1H), 1.11-0.96 (m, 2H), 0.69 (t, J=7.5 Hz, 3H). Note: H spectrum referenced TMS at 0.00 ppm. $^{13}$C NMR: (100 MHz, CDCl$_3$) δ 163.2, 134.6, 129.9, 128.0, 127.9, 127.6, 123.9, 121.2, 119.2, 117.5, 116.6, 112.7, 56.6, 52.8, 49.9, 39.4, 32.2, 31.5, 31.4, 28.6, 21.7, 8.1. HRMS (ESI): calc. for C$_{22}$H$_{24}$BrN$_3$O$_2$Na [M+Na]$^+$: 464.0944, found: 464.0959. MP: 115-117° C.

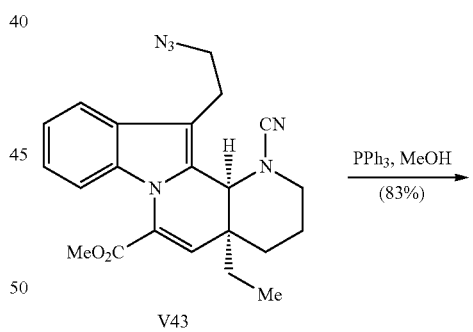

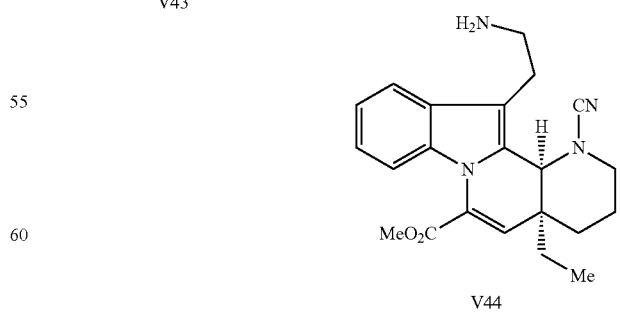

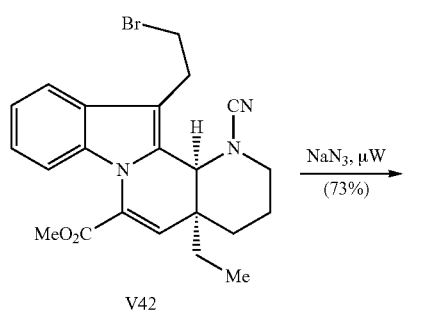

Procedure for the synthesis of V44: V43 (157.0 mg, 0.388 mmol) was added to a flame-dried round-bottom flask and dissolved in methanol (6.50 mL). Triphenylphosphine (152.7 mg, 0.582 mmol) was added to the resulting solution, and the reaction was heated to reflux. The reaction proceeded for 1 hour, then cooled to room temperature and concentrated in vacuo. The crude material was purified via column chromatography using a gradient of 100% ethyl acetate to 90:10 ethyl acetate:methanol with 1% triethylamine throughout to yield V44 (121.7 mg, 83%) as a clear residue. $^1$H NMR: (400 MHz, CDCl$_3$) δ 7.59 (d, J=7.8 Hz, 1H), 7.23-7.09 (m, 3H), 6.12 (d, J=1.7 Hz, 1H), 4.13 (d, J=1.7 Hz, 1H), 3.92 (s, 3H), 3.38 (d, J=12.2 Hz, 1H), 3.17-2.86 (m, 5H), 2.18 (s, 2H), 2.03 (d, J=13.2 Hz, 1H), 1.81-1.61 (m, 2H), 1.35 (td, J=14.0, 4.2 Hz, 1H), 0.99 (q, J=7.5 Hz, 2H), 0.71-0.63 (t, J=7.5 Hz, 3H). $^{13}$C NMR: (100 MHz, CDCl$_3$) δ 163.5, 134.8, 130.2, 128.7, 127.8, 127.2, 123.8, 121.0, 119.7, 118.2, 116.7, 112.5, 56.6, 52.7, 49.9, 42.4, 39.5, 32.3, 31.4, 28.1, 21.8, 8.0. HRMS (ESI): calc. for C$_{22}$H$_{26}$N$_4$O$_2$Na [M+Na]$^+$: 401.1948, found: 401.1962.

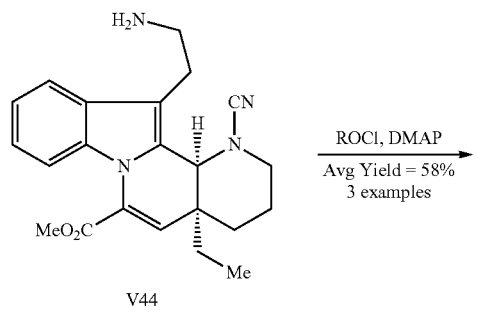

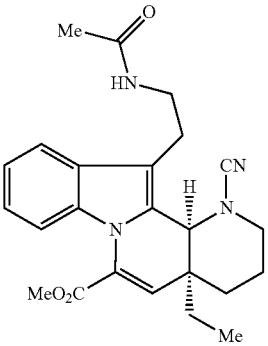

V45

Yield: 65%; 22.7 mg of V45 as a clear residue. $^1$H NMR: (400 MHz, CDCl$_3$) δ 7.64-7.57 (d, J=7.8 Hz, 1H), 7.30-7.14 (m, 3H), 6.21-6.10 (m, 2H), 4.08 (d, J=1.7 Hz, 1H), 3.98 (s, 3H), 3.72 (ddd, J=13.7, 6.7, 5.3 Hz, 1H), 3.60 (ddd, J=13.7, 6.4, 5.3 Hz, 1H), 3.49 (dt, J=12.3, 1.8 Hz, 1H), 3.26-3.14 (m, 2H), 2.86 (ddd, J=14.4, 7.5, 5.3 Hz, 1H), 2.12 (d, J=11.4 Hz, 1H), 1.92 (s, 3H), 1.89-1.70 (m, 3H), 1.46 (td, J=13.5, 4.3 Hz, 1H), 1.03 (sextet, J=7.5 Hz, 2H), 0.73 (t, J=7.5 Hz, 3H). Note: 1H spectrum referenced TMS at 0.00 ppm. $^{13}$C NMR: (100 MHz, CDCl$_3$) δ 170.9, 163.5, 134.9, 130.3, 128.8, 127.7, 127.4, 124.1, 121.3, 119.6, 118.0, 117.1, 112.7, 56.4, 52.9, 49.7, 40.1, 39.7, 32.3, 31.4, 24.4, 23.5, 21.9, 8.0. HRMS (ESI): calc. for C$_{24}$H$_{28}$N$_4$O$_3$Na [M+Na]$^+$: 443.2054, found: 443.2090.

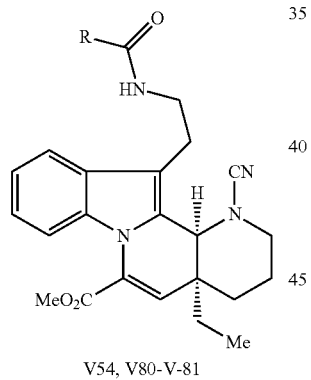

V54, V80-V-81

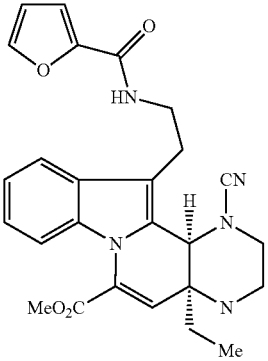

V80

General Procedure for the synthesis of V45, V80-V81: V44 (31.5 mg, 0.083 mmol) was added to a flame-dried round-bottom flask and dissolved in dichloromethane (1.2 mL). The reaction was cooled to 0° C. in an ice-water bath, then triethylamine (23.0 μL, 0.166 mmol) was added dropwise. Acetyl chloride (5.0 μL, 0.091 mmol) and catalytic dimethylaminopyridine in dichloromethane were added dropwise to the reaction. The reaction slowly warmed to room temperature and proceeded for 5 hours, then was quenched with saturated aqueous sodium bicarbonate, extracted with dichloromethane, washed with brine, and crude extract was dried with sodium sulfate. The organic layer was filtered, concentrated in vacuo, and purified via column chromatography using a gradient of 100% hexanes to 49:1 ethyl acetate:methanol to yield V45 (22.7 mg, 65%) as a clear residue.

Yield: 34%; 13.4 mg of V80 as a clear residue. $^1$H NMR: (400 MHz, CDCl$_3$) δ 7.65 (d, J=7.8, 1H), 7.39 (m, 1H), 7.26-7.13 (m, 3H), 7.10 (dt, J=3.4, 0.8 Hz, 1H), 6.78 (t, J=6.3 Hz, 1H), 6.46 (ddd, J=3.5, 1.8, 0.7 Hz, 1H), 6.14 (d, J=1.7 Hz, 1H), 4.06 (d, J=1.7 Hz, 1H), 3.97 (s, 3H), 3.84 (dq, J=13.4, 6.7 Hz, 1H), 3.73 (dq, J=13.0, 6.7 Hz, 1H), 3.36-3.23 (m, 2H), 3.12-2.98 (m, 2H), 2.11 (dt, J=13.9, 3.1 Hz, 1H), 1.86-1.70 (m, 2H), 1.40 (td, J=13.4, 3.9 Hz, 1H), 1.12-0.91 (m, 2H), 0.70 (t, J=7.5 Hz, 3H). Note: $^1$H spectrum referenced TMS at 0.00 ppm. $^{13}$C NMR: (100 MHz, CDCl$_3$) δ 163.5, 159.0, 148.2, 144.2, 134.9, 130.4, 128.6, 127.9, 127.2, 124.0, 121.2, 119.6, 117.7, 116.7, 114.1, 112.7, 112.1, 56.6, 52.8, 49.7, 40.2, 39.5, 32.4, 31.5, 24.7, 21.9, 8.1. HRMS (ESI): calc. for C$_{27}$H$_{28}$N$_4$O$_4$Na [M+Na]$^+$: 495.2003, found: 495.2021.

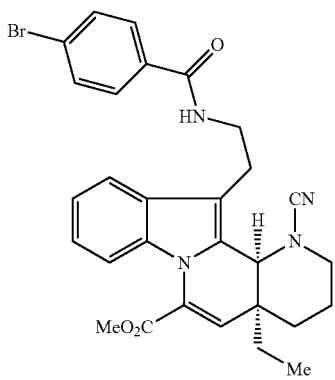

V81

Yield: 75%; 33.8 mg of V81 as a white foam. ¹H NMR: (400 MHz, CDCl₃) δ 7.63-7.57 (m, 3H), 7.49 (d, J=8.6 Hz, 2H), 7.24-7.17 (m, 2H), 7.13 (td, J=7.3, 1.4 Hz, 1H), 6.84 (t, J=6.2 Hz, 1H), 6.13 (d, J=1.7 Hz, 1H), 4.04 (d, J=1.7 Hz, 1H), 3.97 (s, 3H), 3.90-3.75 (m, 2H), 3.35 (ddd, J=14.6, 7.5, 5.7 Hz, 1H), 3.18 (dt, J=12.7, 2.1 Hz, 1H), 3.03-2.88 (m, 2H), 2.09 (d, J=14.1 Hz, 1H), 1.87-1.62 (m, 2H), 1.40 (td, J=14.1, 4.0 Hz, 1H), 1.11-0.93 (m, 2H), 0.71 (t, J=7.5 Hz, 3H). ¹³C NMR: (100 MHz, CDCl₃) δ 167.0, 163.4, 134.8, 133.2, 131.7, 130.3, 129.1, 128.9, 127.6, 127.2, 126.2, 124.1, 121.3, 119.6, 118.0, 117.0, 112.7, 56.5, 52.9, 49.4, 41.1, 39.6, 32.3, 31.4, 24.2, 21.9, 8.0. HRMS (ESI): calc. for $C_{29}H_{29}BrN_4O_3Na$ [M+Na]⁺: 583.1315, found: 583.1299. MP: 83-85° C.

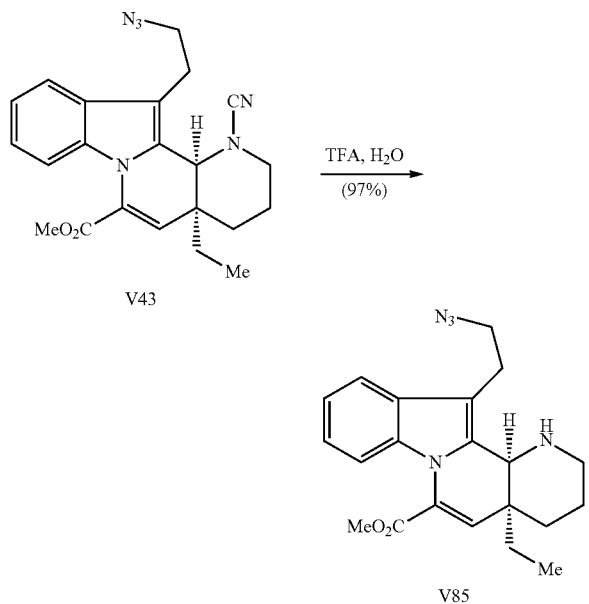

V43

TFA, H₂O
(97%)

V85

Procedure for the synthesis of V85: V43 (19.7 mg, 0.049 mmol) was added to a flame-dried round-bottom flask and dissolved in toluene (0.250 mL). Water (4.0 μL, 0.245 mmol) and trifluoroacetic acid (11.0 μL, 0.097 mmol) were added sequentially to the resultant solution. The reaction was heated to 80° C. and proceeded for 8 hours. The reaction was quenched with 1 M aqueous sodium carbonate, extracted with ethyl acetate, washed with brine, and dried with sodium sulfate. The crude extract was filtered, concentrated in vacuo, and purified via column chromatography using a gradient of 100% hexanes, 3:1 hexanes:ethyl acetate, and 100% ethyl acetate with 1% triethylamine throughout to yield V85 (17.9 mg, 97%) as a clear residue. ¹H NMR: (400 MHz, CDCl₃) δ 7.52 (dt, J=7.5, 1.2 Hz, 1H), 7.23-7.12 (m, 3H), 6.26 (d, J=1.8 Hz, 1H), 3.95 (s, 3H), 3.70 (d, J=1.8 Hz, 1H), 3.61-3.55 (m, 2H), 3.15-2.91 (m, 3H), 2.70 (td, J=12.2, 3.1 Hz, 1H), 2.09 (dt, J=13.6, 3.7 Hz, 1H), 2.01 (s, 1H), 1.73-1.54 (m, 2H), 1.43 (td, J=13.8, 4.1 Hz, 1H), 1.25 (m, 1H), 1.11-0.99 (m, 2H), 0.74 (t, J=7.5 Hz, 3H). ¹³C NMR: (100 MHz, CDCl₃) 164.0, 135.0, 134.3, 130.8, 129.0, 128.5, 122.8, 120.7, 118.4, 112.5, 111.7, 55.8, 52.7, 52.0, 45.9, 39.4, 33.7, 31.8, 24.1, 23.9, 8.1. HRMS (ESI): calc. for $C_{21}H_{26}N_5O_2$ [M+H]⁺: 380.2081, found: 380.2095.

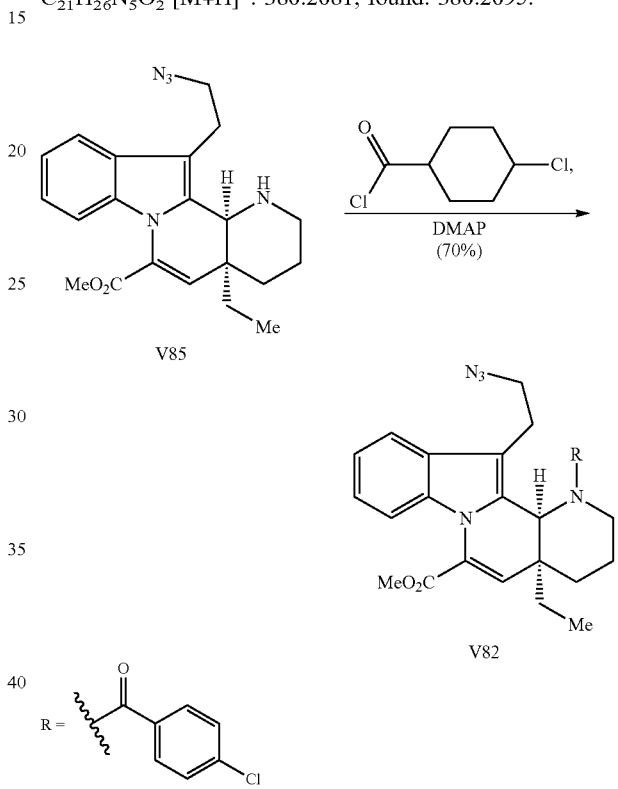

Procedure for the synthesis of V82: AV # (31.7 mg, 0.084 mmol) was added to a flame-dried round-bottom flask and dissolved in dichloromethane (1.7 mL). The reaction was cooled to 0° C. in an ice-water bath, then triethylamine (23.4 μL, 0.168 mmol) was added dropwise. 4-chlorobenzoyl chloride (11.0 μL, 0.088 mmol) and catalytic dimethylaminopyridine in dichloromethane was added dropwise to the reaction. The reaction slowly warmed to room temperature and proceeded for 3 hours, then quenched with saturated aqueous sodium bicarbonate, extracted with dichloromethane, washed with brine, and crude extract was dried with sodium sulfate. The organic layer was filtered, concentrated in vacuo, and purified via column chromatography using a gradient of 100% hexanes to 5:1 hexanes:ethyl acetate to yield V82 (30.6 mg, 70%) as a white-yellow residue. ¹H NMR: (400 MHz, CDCl₃) δ 7.56 (dd, J=6.5, 1.7 Hz, 1H), 7.50 (d, J=8.7 Hz, 2H), 7.46 (d, J=8.7 Hz, 2H), 7.24-7.14 (m, 2H), 7.04 (dd, J=6.5, 1.7 Hz, 1H), 6.20 (s, 1H), 6.02 (s, 1H), 3.94 (s, 3H), 3.81 (m, 1H), 3.66-3.48 (m, 2H), 3.19-3.06 (m, 2H), 2.87 (m, 1H), 1.84-1.57 (m, 4H), 1.50 (td, J=13.2, 4.0 Hz, 1H), 1.39 (d, J=13.7 Hz, 1H), 1.03 (t, J=7.4 Hz, 3H). ¹³C NMR: (100 MHz, CDCl₃) δ 170.9, 163.9, 136.4, 134.3, 133.9, 129.5, 129.3, 129.2, 128.7, 128.4, 126.5, 123.0, 121.1, 118.4, 112.2, 112.0, 53.4, 52.8, 51.6, 43.0, 39.5, 28.7, 27.1, 24.3, 20.9, 8.8. HRMS (ESI): calc. for $C_{28}H_{28}ClN_5O_3Na$ [M+Na]$^+$: 540.1773, found: 540.1765.

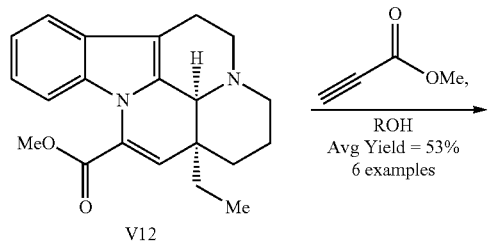

V12

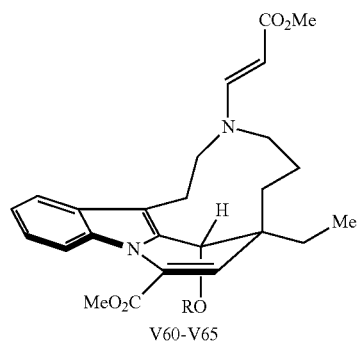

V60-V65

General Procedure for the synthesis of V60-V65: V12 (157.7 mg, 0.469 mmol) was added to a flame-dried round-bottom flask and dissolved in a 2:1 tetrahydrofuran:water solution (30.0 mL). Methyl propiolate (62.5 µL, 0.703 mmol) was added dropwise and the reaction was stirred at room temperature. The reaction was heated to 66° C. for 4 hours, then the reaction was cooled to room temperature, washed with saturated aqueous brine, and extracted with ethyl acetate. The organic layer was dried with sodium sulfate, filtered, concentrated in vacuo, and the crude product was purified via column chromatography using a gradient of 100% hexanes to 3:2 hexanes:ethyl acetate to afford V60 (154.0 mg, 75%) as a white foam.

V60

Yield: 75%; 154.0 mg of V60 as a white foam. $^1$H NMR: (400 MHz, CDCl$_3$ at 50° C.) δ 7.48-7.41 (m, 2H), 7.24 (d, J=7.6 Hz, 1H), 7.20 (td, J=7.0, 1.2 Hz, 1H), 7.15 (td, J=7.0, 1.2 Hz, 1H), 6.16 (s, 1H), 4.69 (d, J=13.3 Hz, 1H), 4.53 (s, 1H), 3.92 (s, 3H), 3.72-3.60 (m, 4H), 3.25-3.08 (m, 2H), 2.93-2.77 (m, 2H), 2.41 (ddd, J=14.9, 6.4, 3.3 Hz, 1H), 2.32 (s, 1H), 1.83-1.65 (m, 2H), 1.58 (ddd, J=15.5, 7.2, 3.2, Hz 1H), 1.32 (m, 1H), 0.97 (t, J=7.2 Hz, 3H), 0.86 (m, 1H), 0.59 (m, 1H). $^{13}$C NMR: (100 MHz, CDCl$_3$ at 50° C.) δ 169.7, 164.2, 152.1, 136.1, 135.8, 129.7, 129.0, 128.2, 123.7, 121.1, 118.7, 114.4, 112.9, 86.6, 65.7, 58.6, 55.8, 52.6, 50.7, 44.1, 31.3, 26.7, 21.7 (2C), 8.0. Note: Presence of two overlapping carbon signals confirmed by HSQC, see NMR spectra. HRMS (ESI): calc. for $C_{25}H_{31}N_2O_5$ [M+H]$^+$: 439.2227, found: 439.2230. MP: 93-95° C.

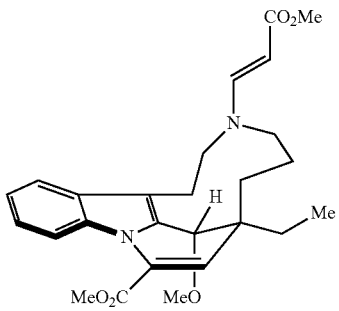

V61

Yield: 91%; 70.3 mg of V61 as a white solid. $^1$H NMR: (400 MHz, CDCl$_3$ at 50° C.) δ 7.57-7.48 (m, 2H), 7.29 (d, J=8.1 Hz, 1H), 7.23 (dd, J=7.0, 1.1 Hz, 1H), 7.18 (dd, J=7.0, 1.1 Hz, 1H), 6.22 (s, 1H), 4.78 (d, J=13.3 Hz, 1H), 4.09 (s, 1H), 3.93 (s, 3H), 3.76 (dt, J=13.7, 3.1 Hz, 1H), 3.70 (s, 3H), 3.31 (dd, J=14.5, 9.6 Hz, 1H), 3.26-3.18 (m, 4H), 3.01-2.91 (m, 2H), 2.47 (ddd, J=14.4, 6.9, 2.7 Hz, 1H), 1.88-1.59 (m, 3H), 1.40 (m, 1H), 0.97 (t, J=7.4 Hz, 3H), 0.93-0.61 (m, 2H). $^{13}$C NMR: (100 MHz, CDCl$_3$ at 50° C.) δ 169.6, 164.1, 151.8, 135.9, 133.3, 129.8, 129.5, 128.0, 123.7, 121.0, 118.4, 116.5, 113.0, 86.7, 74.9, 59.1, 56.1 (2C), 52.5, 50.7, 43.7, 31.7, 26.8, 21.9 (2C), 8.0. HRMS (ESI): calc. for $C_{26}H_{33}N_2O_5$ [M+H]$^+$: 453.2384, found: 453.2381. MP: 76-78° C.

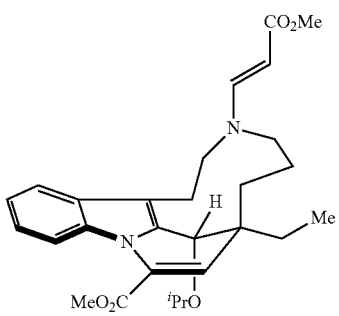

V62

Yield: 87%; 130.0 mg of V62 as a white solid. $^1$H NMR: (400 MHz, CDCl$_3$ at 50° C.) δ 7.55 (d, J=13.3 Hz, 1H), 7.48 (d, J=7.6 Hz, 1H), 7.27 (m, 1H), 7.21 (td, J=6.9, 1.2 Hz, 1H), 7.16 (td, J=6.9, 1.2 Hz, 1H), 6.23 (d, J=1.5 Hz, 1H), 4.78 (d, J=13.3 Hz, 1H), 4.30 (d, J=1.5 Hz, 1H), 3.93 (s, 3H), 3.75 (dt, J=13.6, 3.3 Hz, 1H), 3.69 (s, 3H), 3.58 (septet, J=7.0 Hz, 1H), 3.31 (dd, J=14.3, 8.5 Hz, 1H), 3.189 (m, 1H), 3.01-2.91 (m, 2H), 2.45 (ddd, J=14.3, 8.5, 2.3 Hz, 1H), 1.82 (sextet, J=7.4 Hz, 1H), 1.74-1.57 (m, 2H), 1.45 (m, 1H), 1.13 (d, J=7.0 Hz, 3H), 0.97 (t, J=7.4 Hz, 3H), 0.90 (d, J=7.0 Hz, 3H), 0.87-0.80 (m, 2H). $^{13}$C NMR: (100 MHz, CDCl$_3$ at 50° C.) δ 169.5, 164.2, 151.8, 135.8, 135.0, 130.3, 129.4, 128.0, 123.5, 120.9, 118.3, 115.3, 112.8, 86.7, 70.5, 68.4, 59.1, 56.0, 52.4, 50.6, 44.0, 31.4, 26.5, 23.6, 21.7 (2C), 21.3, 8.0.

HRMS (ESI): calc. for $C_{28}H_{37}N_2O_5$ [M+H]$^+$: 481.2697, found: 481.2685. MP: 72-74° C.

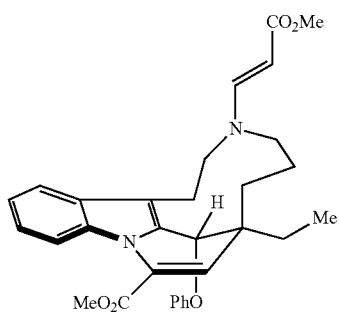

V63

Yield: 15%; 19.9 mg of V63 as a white solid. $^1$H NMR: (400 MHz, CDCl$_3$ at 50° C.) δ 7.59 (d, J=13.4 Hz, 1H), 7.41 (dd, J=7.8, 1.3 Hz, 1H), 7.29 (m, 1H), 7.23 (td, J=6.9, 1.2 Hz, 1H), 7.20-7.12 (m, 3H), 6.96 (m, 1H), 6.88-6.83 (m, 2H), 6.35 (d, J=1.5 Hz, 1H), 5.04 (d, J=1.5 Hz, 1H), 4.78 (d, J=13.4 Hz, 1H), 4.00 (s, 3H), 3.77 (s, 3H), 3.67 (dt, J=13.6, 3.0 Hz, 1H), 3.39 (dd, J=14.4, 8.3 Hz, 1H), 2.87 (t, J=12.6 Hz, 1H), 2.77 (t, J=13.1 Hz, 1H), 2.65 (d, J=14.4 Hz, 1H), 2.48 (ddd, J=14.1, 7.8, 2.4 Hz, 1H), 2.00 (sextet, J=7.5 Hz, 1H), 1.88 (sextet, J=7.5 Hz, 1H), 1.78 (ddd, J=14.1, 7.8, 2.4 Hz, 1H), 1.56 (m, 1H), 1.06 (t, J=7.5 Hz, 3H), 0.99-0.89 (m, 2H). $^{13}$C NMR: (100 MHz, CDCl$_3$ at 50° C.) δ 169.6, 164.2, 158.1, 151.3, 135.8, 133.3, 129.8, 129.5, 129.3, 128.0, 123.8, 123.0, 121.0, 119.9, 118.7, 116.0, 112.9, 87.5, 76.0, 59.2, 56.1, 52.6, 50.8, 43.9, 31.8, 26.7, 21.8 (2C), 8.2. HRMS (ESI): calc. for $C_{31}H_{34}N_2O_5Na$ [M+Na]$^+$: 537.2360, found: 537.2365. MP: 108-111° C.

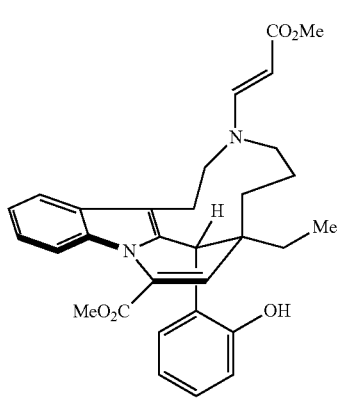

V64

Yield: 15%; 19.9 mg of V64 as a white solid. $^1$H NMR: (400 MHz, CDCl$_3$ at 50° C.) δ 7.67 (d, J=13.4 Hz, 1H), 7.38 (d, J=7.3 Hz, 1H), 7.25-7.16 (m, 2H), 7.13 (dd, J=7.2 Hz, 1H), 7.02-6.96 (m, 2H), 6.75 (dd, J=7.9, 0.7 Hz, 1H), 6.72 (dd, J=7.7 Hz, 1H), 6.29 (s, 1H), 6.25 (s, 1H), 5.11 (s, 1H), 4.76 (d, J=13.4 Hz, 1H), 4.02 (s, 3H), 3.84-3.65 (m, 4H), 3.61 (dd, J=14.0, 7.5 Hz, 1H), 3.19 (dd, J=14.9, 13.3 Hz, 1H), 2.98 (dd, J=14.1, 13.3 Hz, 1H), 2.67 (d, J=14.7 Hz, 1H), 2.58 (dd, J=14.3, 8.4 Hz, 1H), 1.93-1.66 (m, 3H), 1.40 (m, 1H), 1.10 (sextet, J=7.7 Hz, 1H), 0.94 (m, 1H), 0.82 (t, J=7.7 Hz, 3H). $^{13}$C NMR: (100 MHz, CDCl$_3$ at 50° C.) δ 170.7, 164.7, 154.0, 152.2, 138.2, 135.3, 130.6, 130.0, 129.9, 128.8, 127.7, 126.3, 122.6, 121.0 (2C), 118.1, 115.6, 113.4, 112.2, 87.2, 59.3, 57.3, 52.7, 51.0, 44.1, 36.7, 34.7, 24.6, 21.7 (2C), 8.2. HRMS (ESI): calc. for $C_{31}H_{35}N_2O_5$ [M+H]$^+$: 515.2540, found: 515.2549. MP: 240-242° C., decomposed.

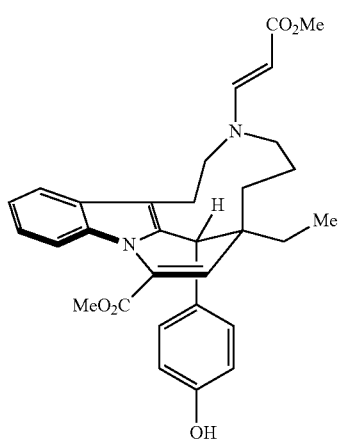

V65

Yield: 35%; 46.5 mg of V65 as a brown-white solid. $^1$H NMR: (400 MHz, CDCl$_3$ at 50° C.) δ 7.66 (d, J=13.3 Hz, 1H), 7.36 (d, J=7.6 Hz, 1H), 7.25-7.16 (m, 2H), 7.13 (m, 1H), 6.92 (d, J=8.2 Hz, 2H), 6.68 (d, J=8.2 Hz, 2H), 6.41 (s, 1H), 6.16 (s, 1H), 4.83 (d, J=13.3 Hz, 1H), 4.09 (s, 1H), 4.00 (s, 3H), 3.77 (s, 3H), 3.72 (m, 1H), 3.50 (dd, J=14.3, 7.5 Hz, 1H), 3.05-2.95 (m, 2H), 2.63 (dd, J=14.0, 4.0 Hz, 1H), 2.51 (dd, J=14.3, 8.2 Hz, 1H), 1.77-1.72 (m, 2H), 1.64 (m, 1H), 1.29 (m, 1H), 1.03-0.90 (m, 2H), 0.78 (t, J=7.3 Hz, 3H). $^{13}$C NMR: (100 MHz, CDCl$_3$ at 50° C.): δ 170.6, 164.6, 155.5, 151.8, 138.0, 135.1, 130.5, 130.3, 130.2, 129.6, 128.7, 122.6, 121.1, 118.0, 115.5, 112.8, 112.2, 86.8, 52.8, 59.1, 56.4, 51.1, 45.6, 43.2, 34.4, 27.2, 21.8 (2C), 8.2. HRMS (ESI): calc. for $C_{31}H_{35}N_2O_5$ [M+H]$^+$: 515.2540, found: 515.2547. MP: 157-159° C.

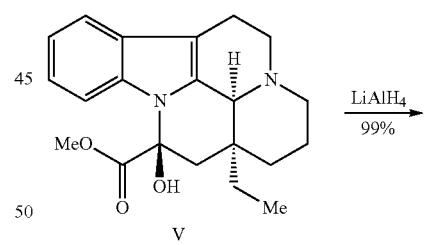

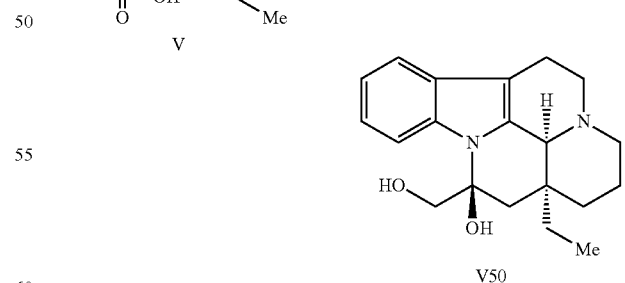

V50

Procedure for the synthesis of V50: Lithium aluminum hydride (2.69 g, 70.8 mmol) was added to a round-bottom flask containing tetrahydrofuran (142 mL) at 0° C. V (5.02 g, 14.2 mmol) was added portion-wise at 0° C. then warmed to room temperature. The reaction was heated to 66° C. and allowed to react for ~1.5 hours, upon completion, the reaction was quenched with 1 M NaOH (~2 mL) and distilled water (~10 mL). This crude mixture was filtered through a frit funnel containing celite, and the filtrate was rinsed with warm ethyl acetate. Crude product was dried with sodium sulfate and concentrated in vacuo to afford V50 (4.17 g, 99%) as a yellow-white foam. Note: V50 is a known compound (CAS No. 3382-95-4). $^1$H NMR: (400 MHz, CDCl$_3$) δ 7.63 (m, 1H), 7.48 (m, 1H), 7.17-7.09 (m, 2H), 4.10 (d, J=11.4 Hz, 1H), 3.87 (d, J=11.4 Hz, 1H), 3.71 (s, 1H), 3.19 (m, 2H), 2.94 (m, 1H), 2.55-2.47 (m, 2H), 2.33 (td, J=12.3, 3.0 Hz, 1H), 2.26-2.13 (m, 2H), 2.04 (d, J=15.1 Hz, 1H), 1.69 (qt, J=13.7, 4.7 Hz, 1H), 1.49 (m, 1H), 1.43-1.22 (m, 5H), 0.91 (t, J=7.5 Hz, 3H). $^{13}$C NMR: (100 MHz, CDCl$_3$) δ 134.0, 132.4, 129.3, 121.3, 120.1, 118.5, 112.7, 105.7, 84.8, 67.6, 59.5, 50.8, 44.3, 44.2, 34.5, 28.9, 25.9, 20.8, 16.9, 7.8. MP: 180-182° C., lit. 180-182° C.$^5$

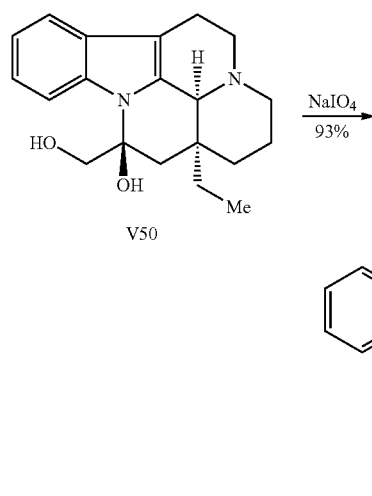

Procedure for the synthesis of V6: V50 (4.17 g, 12.8 mmol) was added to a round-bottom flask and dissolved in 3:1 solution of tetrahydrofuran:water (128 mL). Sodium periodate (13.7 g, 64.0 mmol) was added portion-wise and the reaction stirred at room temperature for 4 hours. The reaction was quenched with saturated aqueous sodium thiosulfate, extracted with ethyl acetate, and extract was dried with sodium sulfate. The crude extract was concentrated in vacuo to yield V6 (3.69 g, 93%) as a brownish-white solid. Note: V6 is a known compound (CAS No. 4880-88-0). $^1$H NMR: (400 MHz, CDCl$_3$) δ 8.30 (dd, J=7.1, 1.8 Hz, 1H), 7.30 (dd, J=7.6, 1.8 Hz, 1H), 7.23-7.16 (m, 2H), 3.57 (s, 1H), 3.14 (dd, J=13.8, 6.3 Hz, 1H), 2.94 (ddd, J=13.0, 6.2 Hz, 1H), 2.72 (m, 1H), 2.50-2.37 (m, 3H), 2.28-2.13 (m, 2H), 1.89 (sextet, J=7.5 Hz, 1H), 1.60 (qt, J=12.9, 4.0 Hz, 1H), 1.48 (sextet, J=7.5 Hz, 1H), 1.32 (d, J=13.7 Hz, 1H), 1.22 (d, J=13.7 Hz, 1H), 0.83 (t, J=7.5 Hz, 4H). $^{13}$C NMR: (100 MHz, CDCl$_3$) δ 167.4, 134.0, 132.0, 130.0, 124.0, 123.7, 117.9, 116.0, 112.1, 57.1, 50.3, 44.1, 43.9, 38.0, 28.1, 26.7, 20.5, 16.3, 7.6. MP: 168-170° C., lit. 168-170° C.$^6$

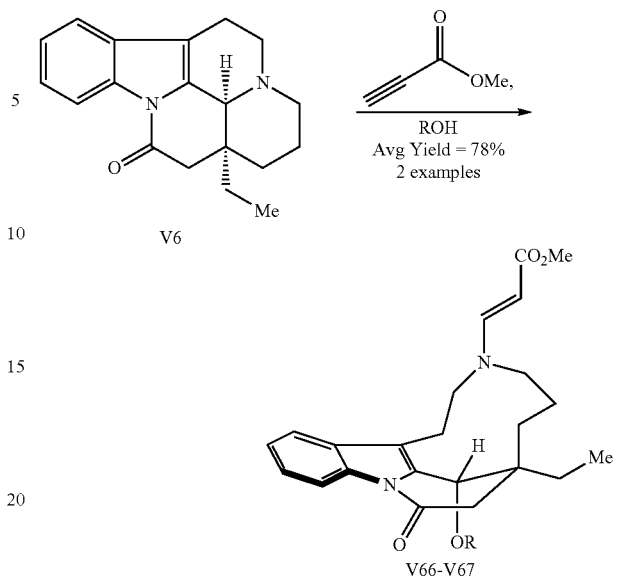

General Procedure for the synthesis of V66-V67: V6 (56.1 mg, 0.191 mmol) was added to a flame-dried round-bottom flask and dissolved in a 2:1 tetrahydrofuran:water solution (30.0 mL). Methyl propiolate (25.4 μL, 0.286 mmol) was added dropwise and the reaction was stirred at room temperature. The reaction was heated to 66° C. for 24 hours, then the reaction was washed with saturated aqueous brine, and extracted with ethyl acetate. The organic layer was dried with sodium sulfate, filtered, concentrated in vacuo, and the crude product was purified via column chromatography using a gradient of 100% hexanes to 3:2 hexanes:ethyl acetate to afford V66 (55.0 mg, 72%) as a white solid.

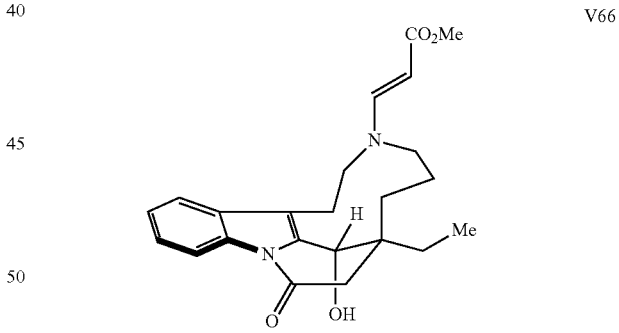

Yield: 72%; 55.0 mg of V66 as a white solid. $^1$H NMR: (400 MHz, CDCl$_3$ at 50° C.) δ 8.41 (d, J=8.1 Hz, 1H), 7.47 (d, J=13.4 Hz, 1H), 7.44 (d, J=8.1 Hz, 1H), 7.35 (td, J=7.3, 1.3 Hz, 1H), 7.29 (td, J=7.5, 1.3 Hz, 1H), 4.73-4.70 (m, 2H), 3.69-3.61 (m, 4H), 3.47 (dd, J=14.3, 7.4 Hz, 1H), 3.13-3.01 (m, 2H), 2.93-2.80 (m, 2H), 2.73 (s, 1H), 2.37 (d, J=17.4 Hz, 1H), 2.28 (dd, J=14.0, 8.7 Hz, 1H), 1.89 (sextet, J=7.5 Hz, 1H), 1.84-1.66 (m, 2H), 1.64-1.49 (m, 2H), 0.87 (t, J=7.5 Hz, 3H), 0.79 (dd, J=14.0, 8.7 Hz, 1H). $^{13}$C NMR: (100 MHz, CDCl$_3$ at 50° C.) δ 169.7, 169.3, 150.6, 136.7, 135.2, 129.1, 125.9, 124.2, 118.3, 117.1, 117.0, 87.8, 66.1, 58.6, 56.0, 50.8, 43.6, 40.0, 33.8, 26.4, 22.3, 21.7, 7.9. HRMS (ESI): calc. for C$_{23}$H$_{28}$N$_2$O$_4$Na [M+Na]$^+$: 419.1941, found: 419.1945. MP: 86-88° C. solid.

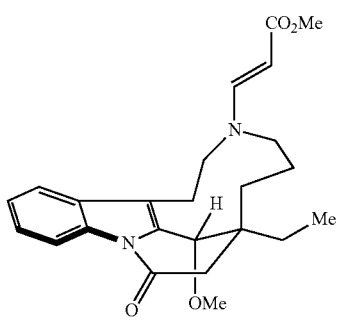

V67

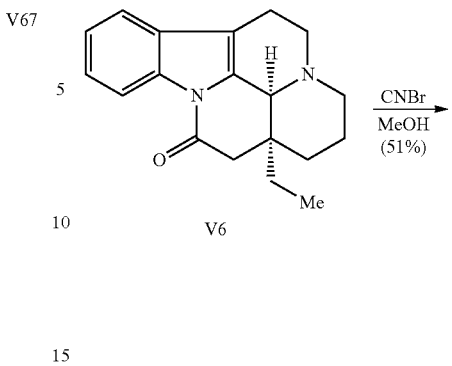

Yield: 83%; 45.0 mg of V67 as a white solid. $^1$H NMR: (400 MHz, CDCl$_3$ at 50° C.) δ 8.46 (d, J=7.4 Hz, 1H), 7.55 (d, J=13.3 Hz, 1H), 7.48 (dd, J=7.4, 0.7 Hz, 1H), 7.39 (td, J=7.4, 0.7 Hz, 1H), 7.32 (td, J=7.4, 0.7 Hz, 1H), 4.80 (d, J=13.4 Hz, 1H), 4.14 (s, 1H), 3.77-3.66 (m, 4H), 3.55 (dd, J=14.2, 6.8 Hz, 1H), 3.21 (s, 3H), 3.14 (td, J=14.1, 2.6 Hz, 1H), 3.01 (d, J=17.3 Hz, 1H), 2.93 (m, 1H), 2.40-2.30 (m, 2H), 1.94 (sextet, J=7.6 Hz, 1H), 1.88-1.69 (m, 3H), 1.62-1.52 (m, 2H), 0.92-0.79 (m, 4H). $^{13}$C NMR: (100 MHz, CDCl$_3$ at 50° C.) S 169.6, 169.4, 150.4, 135.5, 133.7, 128.9, 126.0, 124.1, 118.9, 118.2, 117.2, 87.9, 75.5, 58.9, 56.5, 55.8, 50.9, 43.6, 40.9, 34.1, 26.6, 22.4, 22.0, 7.9 HRMS (ESI): calc. for C$_{24}$H$_{31}$N$_2$O$_4$ [M+H]$^+$: 411.2278, found: 411.2269. MP: 116-118° C.

TABLE 2

Crystal data and structure refinement for chip3.

| | |
|---|---|
| Identification code | chip3 |
| Empirical formula | C25H31Cl3N2O4 |
| Formula weight | 529.87 |
| Temperature | 100(2) K |
| Wavelength | 1.54178 Å |
| Crystal system | Monoclinic |
| Space group | P2$_1$ |
| Unit cell dimensions | a = 9.1112(2) Å   α = 90°. |
| | b = 11.8304(3) Å   β = 95.6953(16)°. |
| | c = 11.7934(3) Å   γ = 90°. |
| Volume | 1264.93(5) Å$^3$ |
| Z | 2 |
| Density (calculated) | 1.391 Mg/m$^3$ |
| Absorption coefficient | 3.565 mm$^{-1}$ |
| F(000) | 556 |
| Crystal size | 0.135 × 0.042 × 0.021 mm$^3$ |
| Theta range for data collection | 3.767 to 60.433°. |
| Index ranges | −8 ≤ h ≤ 10, −13 ≤ k ≤ 13, −13 ≤ l ≤ 13 |
| Reflections collected | 17062 |
| Independent reflections | 3665 [R(int) = 0.0762] |
| Completeness to theta = 60.000° | 98.5% |
| Absorption correction | Analytical |
| Max. and min. transmission | 0.9418 and 0.7793 |
| Refinement method | Full-matrix least-squares on F$^2$ |
| Data/restraints/parameters | 3665/1/307 |
| Goodness-of-fit on F$^2$ | 0.979 |
| Final R indices [I > 2sigma(I)] | R1 = 0.0325, wR2 = 0.0721 [3241] |
| R indices (all data) | R1 = 0.0381, wR2 = 0.0738 |
| Absolute structure parameter | −0.001(11) |
| Largest diff. peak and hole | 0.234 and −0.226 e · Å$^{-3}$ |

Procedure for the synthesis of V6: V6 (89.0 mg, 0.302 mmol) was added to a flame-dried round-bottom flask and dissolved in a (2:1) chloroform:methanol solution (6.6 mL). A 3.0 M solution of cyanogen bromide in dichloromethane (0.30 mL, 0.906 mmol) was added dropwise to the reaction mixture and the reaction was stirred at room temperature for 21 hours. The reaction mixture was diluted with brine and extracted with dichloromethane. The organic layer was dried with sodium sulfate, filtered, and concentrated in vacuo. The crude product was purified via column chromatography using a gradient of 100% hexanes, 3:1 hexanes:ethyl acetate, and 100% ethyl acetate to afford V77 (54.5 mg, 51%) as a brown residue. $^1$H NMR: (400 MHz, CDCl$_3$) δ 8.46 (dt, J=8.1 Hz, 1H), 7.47 (d, J=7.5 Hz, 1H), 7.39 (td, J=8.1, 1.2 Hz, 1H), 7.32 (td, J=7.5, 1.2 Hz, 1H), 4.45 (d, J=1.3 Hz, 1H), 3.77 (dt, J=13.9, 3.0 Hz, 1H), 3.45 (ddd, J=13.1, 7.4, 1.7 Hz, 1H), 3.29 (s, 3H), 3.09-3.02 (m, 3H), 2.82 (m, 1H), 2.40 (dd, J=17.4, 1.3 Hz, 1H), 2.24 (dd, J=13.1, 8.6 Hz, 1H), 2.10 (sextet, J=7.6 Hz, 1H), 1.86-1.58 (m, 4H), 0.94-0.86 (m, 4H). $^{13}$C NMR: (100 MHz, CDCl$_3$) δ 169.4, 135.2, 133.9, 128.6, 126.0, 124.1, 118.0, 117.4, 117.2, 117.1, 75.5, 56.5, 55.2, 54.0, 43.5, 41.0, 32.8, 26.2, 23.1, 21.5, 7.9. HRMS (ESI): calc. for C$_{21}$H$_{26}$N$_3$O$_2$ [M+H]$^+$: 352.2020, found: 352.2025.

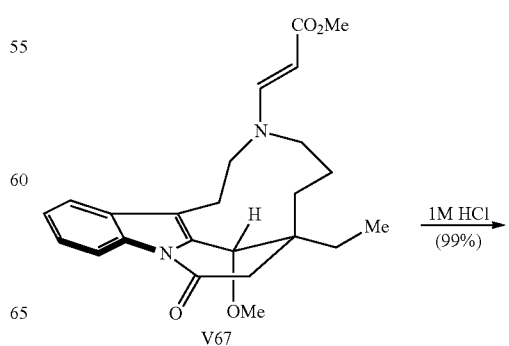

V67

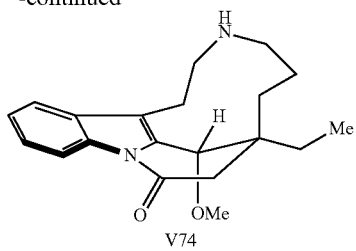

Procedure for the synthesis of V74: V67 (639.6 mg, 1.56 mmol) was added to a flame-dried round-bottom flask containing a stirring 1.0 M (HCl:MeOH) solution (15.6 mL). The reaction stirred at room temperature for 1.5 hours. Then the reaction was diluted with brine and was extracted with ethyl acetate. The organic layer was dried with sodium sulfate, filtered, and concentrated in vacuo. The crude product was purified via column chromatography using a gradient of 100% hexanes, 3:1 hexanes:ethyl acetate, and 100% ethyl acetate with 1% triethylamine throughout to afford V74 (503 mg, 99%) as a clear-yellow residue. $^1$H NMR: (400 MHz, CDCl$_3$) δ 8.42 (d, J=8.0 Hz, 1H), 7.45 (d, J=7.5 Hz, 1H), 7.34-7.19 (m, 2H), 4.69 (s, 1H), 3.15 (s, 3H), 3.05-2.89 (m, 3H), 2.82 (dd, J=13.7, 4.0 Hz, 1H), 2.78-2.66 (m, 2H), 2.03-1.94 (m, 2H), 1.98 (sextet, J=7.6 Hz, 1H), 1.62-1.50 (m, 2H), 1.39-1.33 (m, 2H), 1.08-0.98 (m, 1H), 0.84 (t, J=7.6 Hz, 3H), 0.74 (s, 1H). $^{13}$C NMR: (100 MHz, CDCl$_3$) δ 169.3, 135.1, 133.7, 129.0, 125.1, 123.5, 118.5, 117.8, 116.5, 75.3, 55.8, 45.7, 45.4, 43.5, 41.2, 28.8, 25.6, 23.8, 22.4, 7.5. HRMS (ESI): calc. for C$_{20}$H$_{27}$N$_2$O$_2$ [M+H]$^+$: 327.2067, found: 327.2082.

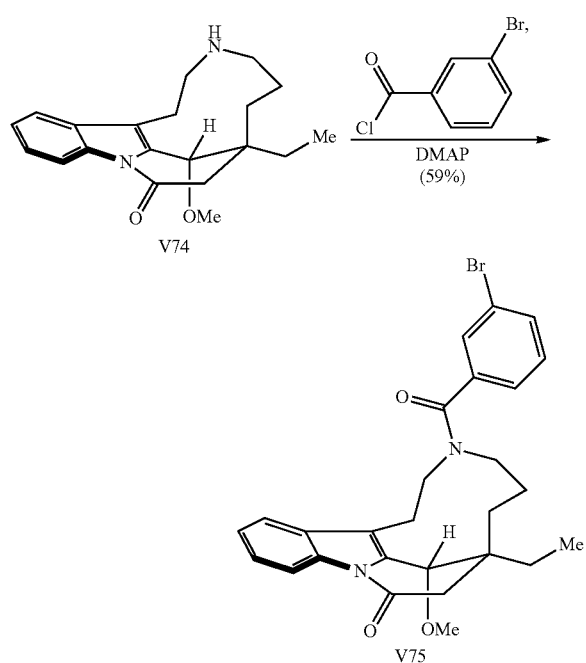

Procedure for the synthesis of V75: V74 (18.2 mg, 0.056 mmol) in a 8 mL borosilicate-vial was added dichloromethane (0.5 mL) and triethylamine (16.0 μL, 0.112 mmol). The reaction was cooled to 0° C., then 3-bromobenzoyl chloride (8.0 μL, 0.061 mmol) and 4-dimethylaminopyridine in dichloromethane was added to the reaction mixture. The reaction slowly warmed to room temperature and reacted for 3 hours. Upon completion, the reaction quenched with brine, extracted with dichloromethane, and dried with sodium sulfate. The organic layer was filtered, concentrated in vacuo, and crude product was purified via column chromatography using a gradient of 100% hexanes to 3:1 hexanes:ethyl acetate to afford V75 (17 mg, 59%) as a white-brown solid. $^1$H NMR: (400 MHz, CD$_3$CN at 65° C.) δ 8.38 (dt, J=8.2, 0.8 Hz, 1H), 7.52-7.44 (m, 3H), 7.39 (td, J=7.7, 1.1 Hz, 1H), 7.27 (td, J=7.5, 1.0 Hz, 1H), 7.13 (s, 1H), 7.10 (t, J=8.0 Hz, 1H), 6.74 (d, J=8.0 Hz, 1H), 4.54 (d, J=1.3 Hz, 1H), 3.64 (m, 1H), 3.52-3.39 (m, 2H), 3.29 (s, 3H), 3.16 (m, 1H), 2.94 (d, J=17.6 Hz, 1H), 2.71 (dt, J=14.0, 4.9 Hz, 1H), 2.36 (dd, J=17.6, 1.3 Hz, 1H), 2.05 (m, 1H), 1.90 (m, 1H), 1.68-1.57 (m, 4H), 0.89 (t, J=7.6 Hz, 3H). $^{13}$C NMR: (100 MHz, CD$_3$CN at 65° C.) δ 172.7, 170.4, 136.4, 134.9, 133.0, 131.4, 130.6, 130.4, 126.6, 126.1, 125.0, 123.0, 120.6, 119.5, 117.2, 75.8, 75.8, 56.8, 51.6, 50.2, 44.4, 41.8, 31.6, 27.3, 23.5, 22.5, 8.2. HRMS (ESI): calc. for C$_{27}$H$_{30}$BrN$_2$O$_3$ [M+H]$^+$: 509.1434, found: 509.1447. MP: 68-70° C.

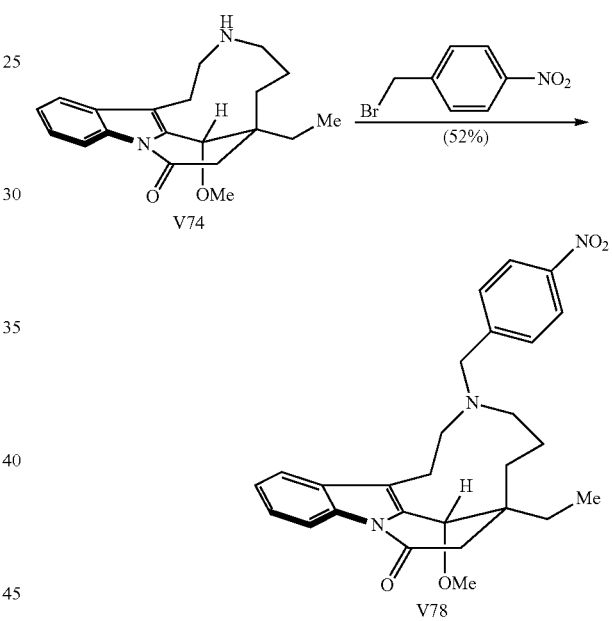

Procedure for the synthesis of V78: V74 (36.0 mg, 0.110 mmol) was added to a round-bottom flask. Anhydrous N,N-dimethylformamide (2.8 mL), potassium carbonate (61.0 mg, 0.440 mmol), and 4-nitrobenzyl bromide (48.0 mg, 0.220 mmol) were added sequentially at room temperature. The reaction stirred at this temperature for ~2 hours, upon completion, the reaction was quenched with brine and extracted with dichloromethane. The crude extract was dried with sodium sulfate, filtered, concentrated in vacuo, and purified via column chromatography using a gradient of 100% hexanes to 7:1 hexanes:ethyl acetate with 1% triethylamine throughout to afford V78 (26.3 mg, 52%) as a brown solid. $^1$H NMR: (400 MHz, CD$_3$CN at 65° C.) 8.40 (d, J=8.1 Hz, 1H), 7.54 (d, J=8.4 Hz, 2H), 7.35 (ddd, J=7.5, 1.0 Hz, 1H), 7.17 (d, J=7.9 Hz, 1H), 7.04 (dd, J=7.4 Hz, 1H), 6.73 (d, J=8.4 Hz, 2H), 4.63 (s, 1H), 3.63 (d, J=14.6 Hz, 1H), 3.23 (s, 3H), 3.18 (d, J=14.6 Hz, 1H), 3.10-2.95 (m, 2H), 2.94-2.86 (m, 2H), 2.59 (td, J=12.1, 4.6 Hz, 1H), 2.47 (dd, J=12.5, 4.6 Hz, 1H), 2.35 (d, J=17.4 Hz, 1H), 2.19 (dt, J=14.7, 3.3 Hz, 1H), 2.02 (m, 1H), 1.75 (sextet, J=7.6 Hz, 1H), 1.65 (m, 1H), 1.51 (m, 1H), 1.41-1.26 (m, 2H), 0.93 (t, J=7.6 Hz, 3H). $^{13}$C NMR: (100 MHz, CD$_3$CN at 65° C.) δ 170.7, 149.0, 147.9, 136.4, 134.9, 131.0, 130.2, 126.0, 124.6, 123.7, 120.2, 120.1, 117.2, 76.8, 58.2, 56.5, 52.1, 51.7, 45.1, 42.4, 29.0, 27.0, 22.5 (2C), 8.1. Note: The presence of overlapping signals was proven by HSQC. HRMS (ESI): calc. for C$_{27}$H$_{32}$N$_3$O$_4$ [M+H]$^+$: 462.2387, found: 462.2403. MP: 173-175° C.

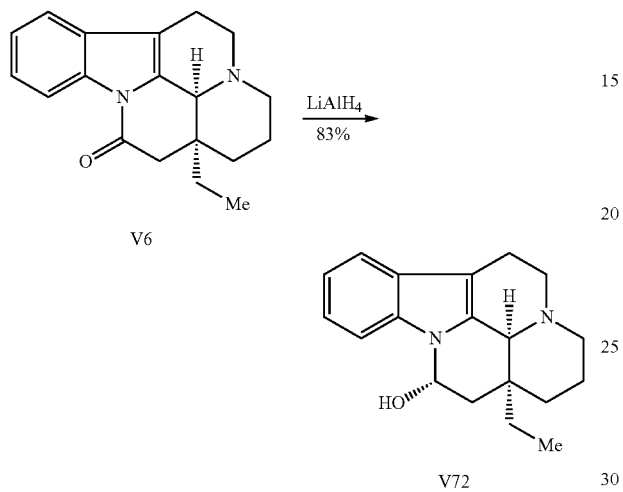

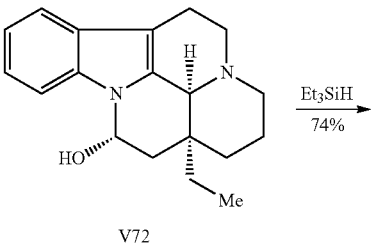

Procedure for the synthesis of V72: Lithium aluminum hydride (135.0 mg, 3.57 mmol) was added to a flame-dried round-bottom flask containing tetrahydrofuran (7.14 mL) at 0° C. V6 (210.2 mg, 0.714 mmol) was added portion-wise at 0° C., then warmed to room temperature for approximately two minutes. The reaction was heated to 66° C. and allowed to react for 1 hour, upon completion, the reaction was quenched with 1 M NaOH (~5-6 drops) and distilled water (~1.0 mL). This crude mixture was filtered through a frit funnel containing celite, and the filtrate was rinsed with warm ethyl acetate. The organic layer was dried with sodium sulfate and concentrated in vacuo. Crude product was purified via column chromatography 100% hexanes to 4:1 hexanes:ethyl acetate with 1% triethylamine throughout to afford V72 (179.0 mg, 84%) as a white powder. Note: V72 is a known compound (CAS No. 19877-90-8). Spectral data below are consistent with literature.[7,8] $^1$H NMR: (400 MHz, CDCl$_3$) δ 7.79 (d, J=7.7 Hz, 1H), 7.49 (dd, J=7.5 Hz, 1H), 7.23-7.16 (m, 2H), 5.74-5.34 (m, 2H), 3.21 (s, 1H), 3.15 (dd, J=13.1, 6.0 Hz, 1H), 3.01 (td, J=12.7, 6.2 Hz, 1H), 2.89 (m, 1H), 2.47-2.41 (m, 2H), 2.26 (td, J=12.0, 2.9 Hz, 1H), 2.12 (dd, J=14.1, 4.6 Hz, 1H), 1.96 (sextet, J=7.5 Hz, 1H), 1.62 (dd, J=14.2, 8.6 Hz, 1H), 1.41 (dd, J=13.6, 9.6 Hz, 1H), 1.34-1.21 (m, 3H), 0.84 (t, J=7.5 Hz, 3H), 0.76 (td, J=13.7, 3.8 Hz, 1H). $^{13}$C NMR: (100 MHz, CDCl$_3$) δ 136.9, 132.7, 128.7, 121.2, 120.1, 118.1, 112.4, 105.2, 76.5, 58.5, 50.7, 44.3, 43.0, 36.7, 28.5, 24.8, 20.4, 16.9, 7.7. HRMS (ESI): calc. for C$_{19}$H$_{25}$N$_2$O [M+H]$^+$: 297.1961, found: 297.1966. MP: 83-85° C.

Procedure for the synthesis of DHE: V72 (70.2 mg, 0.237 mmol) was added to a round-bottom flask. Anhydrous dichloromethane (2.4 mL), triethylsilane (2.1 mL, 13.0 mmol), and trifluoroacetic acid (0.472 mL, 6.2 mmol) were added to the flask sequentially. The reaction stirred for ~2 hours, upon completion, the reaction was quenched with saturated aqueous sodium bicarbonate and brine. This mixture was extracted with dichloromethane, dried with sodium sulfate, filtered, and the organic layer was concentrated in vacuo. The crude product was purified via column chromatography 100% hexanes to 5:1 hexanes:ethyl acetate with 1% triethylamine throughout to afford V73 (53.0 mg, 80%) as a colorless residue. Note: V73 is a known compound (CAS No. 65026-49-5). The spectral data below are consistent with literature.[8] $^1$H NMR: (400 MHz, CDCl$_3$) δ 7.55 (m, 1H), 7.32 (ddd, J=8.0, 1.2, 0.8 Hz, 1H), 7.22 (td, J=7.5, 1.2 Hz, 1H), 7.16 (td, J=7.6, 1.2 Hz, 1H), 4.12 (ddd, J=11.8, 5.9, 1.9 Hz, 1H), 3.89 (s, 1H), 3.77 (td, J=12.0, 5.2 Hz, 1H), 3.39-3.25 (m, 2H), 3.03 (dddd, J=15.8, 11.1, 6.9, 2.3 Hz, 1H), 2.65-2.55 (m, 2H), 2.48 (td, J=12.6, 3.1 Hz, 1H), 2.17 (sextet, J=7.6 Hz, 1H), 2.03-1.73 (m, 3H), 1.58 (sextet, J=7.5 Hz, 1H), 1.40 (dq, J=13.0, 3.1 Hz, 1H), 1.32 (m, 1H), 1.09 (td, J=13.3, 4.1 Hz, 1H), 0.97 (t, J=7.6 Hz, 3H). $^{13}$C NMR: (100 MHz, CDCl$_3$) δ 136.4, 132.9, 128.2, 120.6, 119.4, 118.2, 109.4, 104.5, 59.3, 51.4, 44.7, 38.6, 34.2, 32.0, 29.1, 24.0, 21.0, 17.3, 7.7. HRMS (ESI): calc. for C$_{19}$H$_{25}$N$_2$ [M+H]$^+$: 281.2012, found: 281.2008.

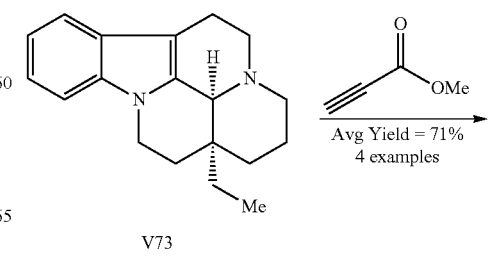

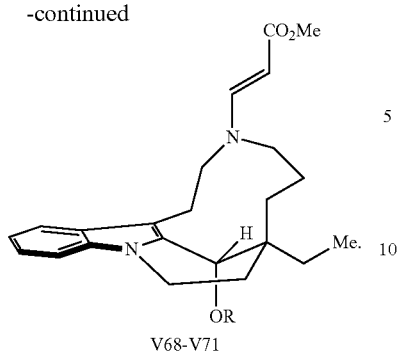

V68-V71

General Procedure for the synthesis of V68-V71: V73 (55.6 mg, 0.198 mmol) was added to a flame-dried round-bottom flask and subsequently dissolved in a 2:1 tetrahydrofuran:water solution (12.0 mL). Methyl propiolate (26.0 µL, 0.297 mmol) was added dropwise and the reaction was stirred at room temperature. The reaction was equipped with a reflux condenser and heated to 66° C. for 2.5 hours. Upon completion, the reaction was washed with saturated aqueous brine, and extracted with ethyl acetate. The organic layer was dried with sodium sulfate, filtered, and concentrated in vacuo. Crude product was purified via column chromatography using a gradient of 100% hexanes to 1:1 hexanes:ethyl acetate to afford V68 (58.0 mg, 76%) as a yellow residue.

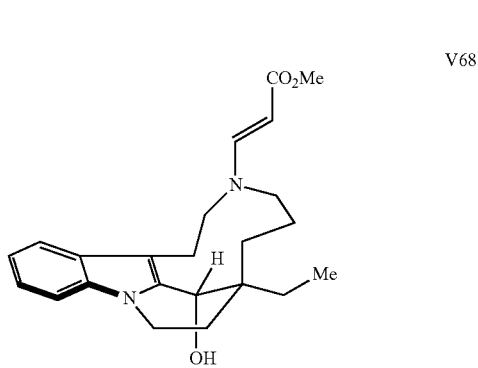

V68

Yield: 76%; 58.0 mg of V68 as a yellow residue. $^1$H NMR: (400 MHz, CDCl$_3$ at 50° C.) δ 7.55-7.50 (m, 2H), 7.30 (d, J=8.2 Hz, 1H), 7.23 (td, J=7.5, 1.1 Hz, 1H), 7.13 (td, J=7.5, 0.9 Hz, 1H), 4.74 (d, J=13.3 Hz, 1H), 4.68 (s, 1H), 4.24 (ddd, J=12.3, 7.5, 3.4 Hz, 1H), 3.88 (ddd, J=12.3, 9.6, 2.6 Hz, 1H), 3.74-3.62 (m, 4H), 3.37 (dd, J=14.2, 8.4 Hz, 1H), 3.14 (td, J=13.6, 1.6 Hz, 1H), 2.96-2.83 (m, 2H), 2.37-2.22 (m, 2H), 1.93-1.72 (m, 2H), 1.71-1.55 (m, 4H), 1.24 (m, 1H), 1.02-0.78 (m, 4H). $^{13}$C NMR: (100 MHz, CDCl$_3$ at 50° C.) δ 169.9, 151.6, 137.5, 137.4, 127.3, 122.2, 119.8, 118.6, 110.0, 109.9, 86.7, 67.2, 58.5, 56.7, 50.7, 40.1, 39.7, 32.4, 28.4, 27.2, 22.3, 21.9, 8.2. HRMS (ESI): calc. for C$_{23}$H$_{31}$N$_2$O$_3$ [M+H]$^+$: 383.2329, found: 383.2322.

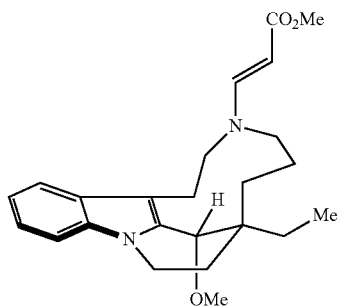

V69

Yield: 83%; 36.0 mg of V69 as a yellow residue. $^1$H NMR: (400 MHz, CDCl$_3$ at 50° C.) δ 7.60-7.51 (m, 2H), 7.31 (d, J=8.1 Hz, 1H), 7.24 (td, J=8.1, 1.1 Hz, 1H), 7.15 (td, J=7.5, 1.2 Hz, 1H), 4.79 (d, J=13.3 Hz, 1H), 4.20 (ddd, J=12.2, 7.5, 4.1 Hz, 1H), 4.11 (s, 1H), 3.91 (ddd, J=12.2, 7.5, 3.5 Hz, 1H), 3.74-3.67 (m, 4H), 3.39 (dd, J=14.0, 8.1 Hz, 1H), 3.24-3.16 (m, 4H), 3.03-2.87 (m, 2H), 2.38-2.18 (m, 2H), 1.80 (sextet, J=7.5 Hz, 1H), 1.72-1.53 (m, 4H), 1.24 (m, 1H), 0.97-0.78 (m, 4H). $^{13}$C NMR: (100 MHz, CDCl$_3$ at 50° C.) δ 169.9, 151.5, 137.5, 134.8, 127.2, 122.1, 119.6, 118.4, 111.8, 109.9, 86.4, 76.4, 58.8, 56.6, 56.2, 50.7, 40.5, 39.6, 33.1, 28.9, 28.4, 22.2 (2C), 8.3. HRMS (ESI): calc. for C$_{24}$H$_{33}$N$_2$O$_3$ [M+H]$^+$: 397.2486, found: 397.2500.

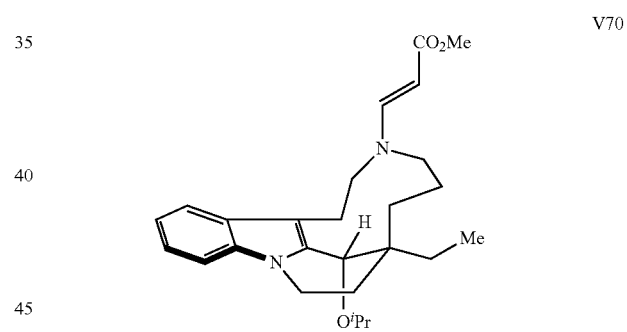

V70

Yield: 67%; 41.8 mg of V70 as a yellow residue. $^1$H NMR: (400 MHz, CDCl$_3$ at 50° C.) δ 7.58 (d, J=13.3 Hz, 1H), 7.53 (dt, J=7.8, 1.0 Hz, 1H), 7.31 (dt, J=8.0, 0.9 Hz, 1H), 7.23 (ddd, J=8.0, 7.0, 1.1 Hz, 1H), 7.13 (ddd, J=8.0, 7.0, 1.1 Hz, 1H), 4.78 (d, J=13.3 Hz, 1H), 4.33 (s, 1H), 4.21 (ddd, J=12.4, 7.5, 5.0 Hz, 1H), 3.95 (ddd, J=12.4, 7.6, 4.5 Hz, 1H), 3.74-3.68 (m, 4H), 3.51 (septet, J=6.0 Hz, 1H), 3.36 (ddd, J=14.0, 8.6, 1.3 Hz, 1H), 3.16 (t, J=13.5 Hz, 1H), 2.95 (q, J=13.0 Hz, 2H), 2.34 (ddd, J=14.1, 7.8, 2.1 Hz, 1H), 2.24 (ddd, J=13.5, 7.7, 6.1 Hz, 1H), 1.81 (sextet, J=7.6 Hz, 1H), 1.70-1.51 (m, 5H), 1.14 (d, J=6.0 Hz, 3H), 0.91-0.87 (m, 7H). $^{13}$C NMR: (100 MHz, CDCl$_3$ at 50° C.) 169.8, 151.5, 137.3, 136.6, 127.2, 121.8, 119.4, 118.4, 110.6, 109.7, 86.4, 71.7, 68.3, 58.1, 56.3, 50.7, 40.6, 39.4, 33.3, 29.1, 28.9, 23.8, 22.1 (2C), 21.4, 8.3. HRMS (ESI): calc. for C$_{26}$H$_{37}$N$_2$O$_3$ [M+H]$^+$: 425.2799, found: 425.2811.

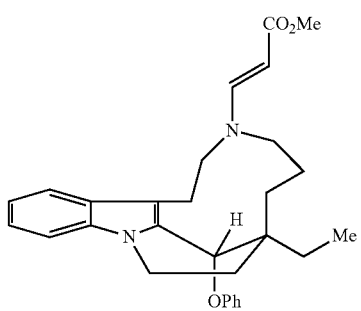

V71

Yield: 57%; 28.0 mg of V71 as a clear foam. $^1$H NMR: (400 MHz, CDCl$_3$ at 50° C.) δ 7.61 (d, J=13.4 Hz, 1H), 7.46 (dt, J=7.9, 1.0 Hz, 1H), 7.34 (dt, J=8.1, 0.9 Hz, 1H), 7.24 (m, 1H), 7.17 (dd, J=8.2, 7.5 Hz, 2H), 7.12 (ddd, J=8.0, 7.0, 1.1 Hz, 1H), 6.95 (ddd, J=7.7, 7.0, 1.1 Hz, 1H), 6.86-6.84 (m, 2H), 5.13 (s, 1H), 4.75 (d, J=13.4 Hz, 1H), 4.37 (ddd, J=12.2, 7.5, 3.8 Hz, 1H), 3.99 (ddd, J=12.2, 7.4, 3.1 Hz, 1H), 3.78 (s, 3H), 3.59 (dt, J=13.9, 2.9 Hz, 1H), 3.45 (dd, J=14.1, 7.5 Hz, 1H), 2.82 (ddd, J=14.4, 7.6, 6.4 Hz, 1H), 2.71-2.62 (m, 2H), 2.49 (ddd, J=14.1, 8.3, 5.1 Hz, 1H), 2.31 (dd, J=14.4, 8.5 Hz, 1H), 1.95 (sextet, J=7.5 Hz, 1H), 1.88-1.67 (m, 3H), 1.37-1.22 (m, 2H), 1.05-0.83 (m, 4H). $^{13}$C NMR: (100 MHz, CDCl$_3$ at 50° C.) δ 169.8, 158.7, 151.1, 137.5, 134.6, 129.5, 127.2, 122.6, 122.2, 119.6, 118.7, 111.4, 109.9, 87.3, 77.4, 58.9, 56.7, 50.8, 40.6, 39.7, 32.9, 28.9, 28.2, 22.0 (2C), 8.3. HRMS (ESI): calc. for C$_{29}$H$_{35}$N$_2$O$_3$ [M+H]$^+$: 459.2642, found: 459.2651. MP: 70-72° C.

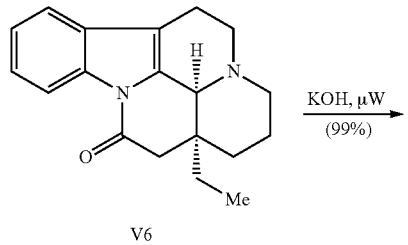

V6

Procedure for the synthesis of V54: V6 (3.53 g, 12.0 mmol) was reacted in a flame-dried microwave flask in 7 equal portions portions. Each portion was dissolved in ethanol (8.5 mL) and a 5.0 M aqueous potassium hydroxide solution was added (5.0 mL). The resultant reaction mixture was subjected to microwave irradiation at 180° C. for twenty minutes. These cycles (~7) were combined and acidified to pH ~5-6, extracted with dichloromethane, and extract was dried with sodium sulfate. Crude extract was filtered, concentrated in vacuo, and purified via column chromatography 99:1 dichloromethane:triethylamine to 94.5:4.5:1.0 dichloromethane:methanol:triethylamine to afford V54 (3.80 g, 99%) as a white foam. $^1$H NMR: (400 MHz, d$_6$-DMSO) δ 12.59 (s, 1H), 9.86 (s, 1H), 7.46 (d, J=8.1 Hz, 1H), 7.36 (d, J=7.5 Hz, 1H), 7.03 (dd, J=7.5 Hz, 1H), 6.95 (dd, J=7.4 Hz, 1H), 3.40 (s, 1H), 3.02-2.97 (m, 2H), 2.81-2.72 (m, 2H), 2.60-2.52 (m, 2H), 2.41 (td, J=11.7, 2.7 Hz, 1H), 2.04 (dq, J=15.0, 7.5 Hz, 1H), 1.95-1.70 (m, 3H), 1.68-1.48 (m, 3H), 1.06 (t, J=7.5 Hz, 3H). $^{13}$C NMR: (100 MHz, d6-DMSO) δ 174.1, 136.6, 132.1, 126.1, 120.8, 118.5, 117.2, 111.9, 110.6, 66.1, 56.0, 53.2, 39.2, 38.9, 31.4, 31.1, 21.7, 21.5, 8.4. HRMS (ESI): calc. for C$_{19}$H$_{25}$N$_2$O$_2$ [M+H]$^+$: 313.1911, found: 313.1918. MP: 204-206° C., lit. 204-206° C.$^9$

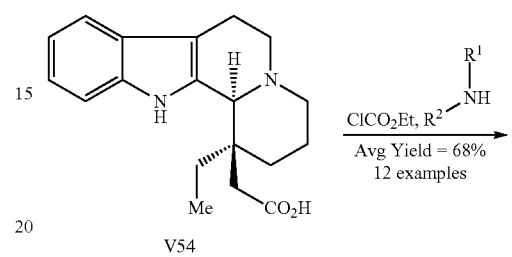

V54

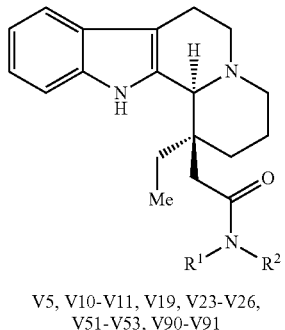

V5, V10-V11, V19, V23-V26, V51-V53, V90-V91

General Procedure for the synthesis of V5, V10-V11, V19, V23-V26, V51-V53, & V90-V91: V54 (181.2 mg, 0.580 mmol) was added to a flame-dried round-bottom flask and dissolved in anhydrous dichloromethane (4.8 mL). The reaction was cooled to 0° C. and triethylamine (0.162 mL, 1.16 mmol) was added dropwise. After stirring for ~5 minutes ethyl chloroformate (61 μL, 0.638 mmol) was added and the reaction stirred for ~30 minutes. Benzyl amine (0.633 mL, 5.8 mmol) and N,N-dimethylaminopyridine (catalytic) as a 0.3 M solution in anhydrous dichloromethane were added, and the reaction warmed to room temperature. At room temperature, the reaction stirred for 3 hours and was quenched with brine when complete by thin layer chromatography. Crude reaction mixture was extracted with dichloromethane, dried with sodium sulfate, filtered, and the organic layer was concentrated in vacuo. The crude product was purified via column chromatography using a gradient of 100% hexanes to 5:1 hexanes:ethyl acetate with 1% triethylamine throughout to afford V52 (135.0 mg, 58%) as a yellowish-brown foam.

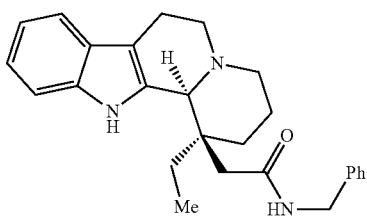

V52

Yield: 58%; 135.0 mg of V52 as a yellowish-brown foam. $^1$H NMR: (400 MHz, CDCl$_3$) 8.06 (s, 1H), 7.50 (d, J=7.5 Hz, 1H), 7.35 (dd, J=8.1, 0.9 Hz, 1H), 7.32-7.22 (m, 3H), 7.23-7.06 (m, 4H), 6.08 (s, 1H), 4.27 (dd, J=14.6, 6.5 Hz, 1H), 3.75 (dd, J=14.6, 4.4 Hz, 1H), 3.37 (s, 1H), 3.00-2.95 (m, 2H), 2.85 (m, 1H), 2.73-2.53 (m, 3H), 2.41 (td, J=12.7, 2.2 Hz, 1H), 2.17 (d, J=14.0 Hz, 1H), 2.13-1.85 (m, 4H), 1.67-1.55 (m, 2H), 1.20 (t, J=7.6 Hz, 3H). Note: H spectrum referenced TMS at 0.00 ppm. $^{13}$C NMR: (100 MHz, CDCl$_3$) δ 172.1, 138.4, 136.1, 133.1, 128.5, 127.9, 127.2, 126.7, 121.8, 119.5, 117.9, 111.7, 111.0, 66.6, 56.9, 54.0, 43.5, 40.7, 40.4, 33.3, 31.7, 22.2, 21.9, 8.2. HRMS (ESI): calc. for C$_{26}$H$_{32}$N$_2$O$_3$ [M+H]$^+$: 402.2540, found: 402.2550. MP: 151-153° C.

V51

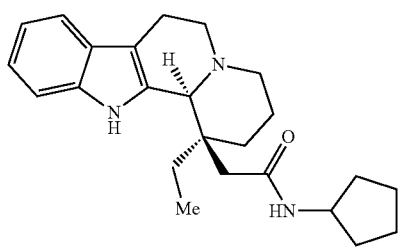

Yield: 91%; 152.0 mg of V51 as a yellow-white foam. $^1$H NMR: (400 MHz, CDCl$_3$) δ 8.08 (s, 1H), 7.46 (d, J=7.6 Hz, 1H), 7.32 (d, J=7.9 Hz, 1H), 7.13 (td, J=7.4, 0.9 Hz, 1H), 7.08 (td, J=7.7, 1.2 Hz, 1H), 5.64 (d, J=7.2 Hz, 1H), 4.95 (d, J=7.4 Hz, 1H), 3.98 (p, J=6.9 Hz, 1H), 3.86 (q, J=6.9 Hz, 1H), 3.34 (s, 1H), 3.08-2.83 (m, 3H), 2.73-2.53 (m, 3H), 2.40 (t, J=11.4 Hz, 1H), 2.13-1.85 (m, 7H), 1.79 (dt, J=12.8, 6.3 Hz, 1H), 1.72-1.24 (m, 13H), 1.16 (t, J=7.6 Hz, 4H), 1.01 (dt, J=12.7, 6.5 Hz, 1H). Note: Spectrum represents a 2:1 ratio of amide rotamers. $^{13}$C NMR: (100 MHz, CDCl$_3$) δ 172.0, 158.2, 136.2, 133.2, 126.7, 121.7, 119.4, 117.9, 111.8, 111.1, 66.8, 56.9, 54.1, 51.8, 51.0, 40.9, 40.4, 33.7, 33.6, 33.3, 32.9, 32.7, 31.6, 23.7, 23.8, 23.7, 22.3, 22.0, 8.2. Note: Spectrum represents a mixture of rotamers. HRMS (ESI): calc. for C$_{24}$H$_{34}$N$_3$O [M+H]$^+$: 380.2696, found: 380.2710. MP: 64-66° C.

V11

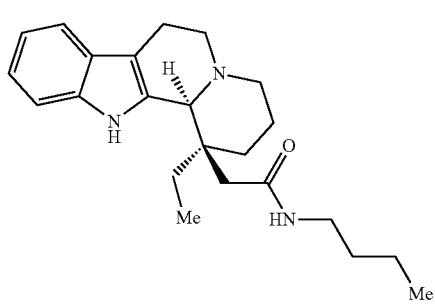

Yield: 99%; 63.6 mg of V11 as a greenish-white foam. $^1$H NMR: (400 MHz, CDCl$_3$) δ 8.04 (s, 1H), 7.45 (d, J=7.6 Hz, 1H), 7.31 (dd, J=8.1, 0.9 Hz, 1H), 7.13 (td, J=8.1, 1.3 Hz, 1H), 7.07 (td, J=7.6, 1.2 Hz, 1H), 5.55 (s, 1H), 5.16 (t, J=4.7 Hz, 1H), 3.35 (s, 1H), 3.12 (q, J=7.1 Hz, 3H), 3.07-2.82 (m, 4H), 2.72-2.54 (m, 3H), 2.39 (td, J=11.8, 2.5 Hz, 1H), 2.13 (d, J=13.9 Hz, 1H), 2.05-1.82 (m, 4H), 1.64-1.53 (m, 2H), 1.48-1.38 (m, 3H), 1.37-1.24 (m, 3H), 1.21-1.10 (m, 6H), 0.90 (t, J=7.3 Hz, 3H), 0.84-0.77 (m, 2H). Note: Spectrum represents a 2:1 ratio of amide rotamers. $^{13}$C NMR: (100 MHz, CDCl$_3$) δ 172.4, 159.1, 136.2, 133.3, 126.7, 121.8, 119.5, 117.9, 111.7, 111.1, 66.7, 57.0, 54.1, 40.8, 40.4, 40.1, 39.2, 33.6, 32.6, 31.5, 31.3, 22.3, 22.1, 20.2, 20.1, 14.0, 13.8, 8.3. Note: Spectrum represents a mixture of rotamers. HRMS (ESI): calc. for C$_{23}$H$_{34}$N$_3$O [M+H]$^+$: 368.2696, found: 368.2679. MP: 47-49° C.

V24

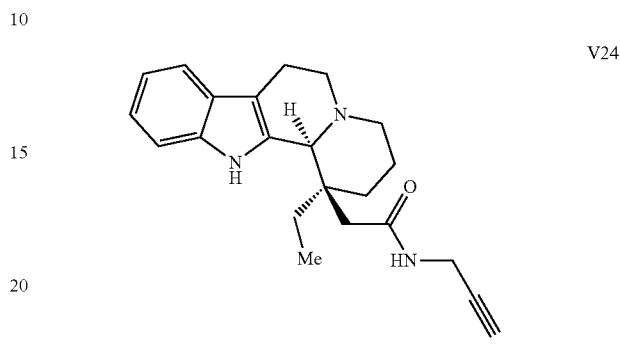

Yield: 52%; 73.0 mg of V24 as a brown residue. $^1$H NMR: (400 MHz, CDCl$_3$) δ 7.93 (s, 1H), 7.47 (d, J=7.8 Hz, 1H), 7.32 (dt, J=8.1, 0.9 Hz, 1H), 7.15 (ddd, J=8.2, 7.1, 1.2 Hz, 1H), 7.09 (ddd, J=7.8, 7.1, 1.2 Hz, 1H), 6.11 (s, 1H), 3.76 (ddd, J=17.8, 5.9, 2.5 Hz, 1H), 3.42-3.32 (m, 2H), 3.05-3.02 (m, 2H), 2.94 (dd, J=17.7, 14.4 Hz, 1H), 2.68 (d, J=15.1 Hz, 1H), 2.65-2.53 (m, 2H), 2.41 (td, J=11.9, 2.8 Hz, 1H), 2.19 (d, J=14.1 Hz, 1H), 2.11 (m, 1H), 2.05-1.91 (m, 3H), 1.85 (m, 1H), 1.67-1.56 (m, 2H), 1.17 (t, J=7.6 Hz, 3H). $^{13}$C NMR: (100 MHz, CDCl$_3$) δ 172.2, 136.1, 132.9, 126.7, 121.9, 119.5, 117.9, 111.8, 111.1, 79.9, 71.2, 66.8, 56.9, 54.1, 40.5, 40.5, 33.3, 31.8, 28.9, 22.2, 22.0, 8.2. HRMS (ESI): calc. for C$_{22}$H$_{28}$N$_3$O [M+H]$^+$: 350.2227, found: 350.2232.

V53

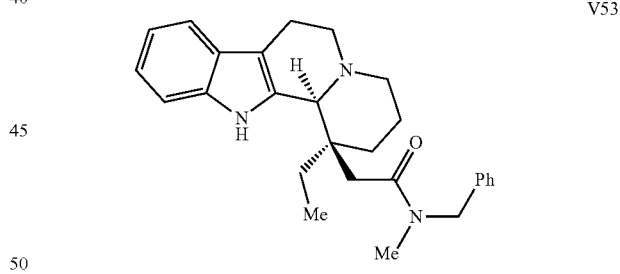

Yield: 77%; 209.0 mg of V53 as a brown residue. $^1$H NMR: (400 MHz, CDCl$_3$) δ 8.08-8.01 (m, 2H), 7.45 (d, J=Hz, 2H), 7.30 (dd, J=7.8, 4.3 Hz, 2H), 7.22-7.11 (m, 7H), 7.11-7.04 (m, 5H), 6.87 (dd, J=7.0, 3.7 Hz, 2H), 4.81 (d, J=16.8 Hz, 1H), 4.55 (d, J=14.7 Hz, 1H), 3.92 (d, J=14.7 Hz, 1H), 3.72 (d, J=16.8 Hz, 1H), 3.34 (d, J=2.2 Hz, 1H), 3.27 (s, 1H), 3.03-2.84 (m, 6H), 2.70 (s, 3H), 2.68-2.51 (m, 3H), 2.42 (s, 4H), 2.40-2.20 (m, 5H), 2.13 (m, 1H), 2.05-1.89 (m, 3H), 1.76 (m, 1H), 1.64-1.46 (m, 3H), 1.21-1.11 (m, 5H). Note: $^1$H spectrum referenced TMS at 0.00 ppm. Spectrum represents a 1:1 ratio of amide rotamers. Rotamers verified using a known method.[9] $^{13}$C NMR: (100 MHz, CDCl$_3$) δ 172.9, 172.6, 137.7, 137.6, 136.3, 133.3, 128.6, 128.4, 127.9, 127.2, 127.1, 126.8, 126.6, 126.4, 121.6, 121.6, 119.4, 119.3, 117.8, 117.6, 112.0, 111.5, 111.1, 111.0, 67.1, 66.7, 57.1, 57.0, 54.7, 54.4, 54.2, 50.5, 41.3, 41.1, 35.9,

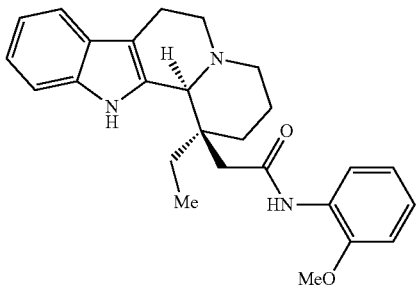

V10

34.6, 34.5, 34.4, 34.1, 32.8, 31.2, 31.1, 22.4, 22.2, 22.0, 8.3, 8.3. HRMS (ESI): calc. for $C_{27}H_{34}N_3O$ [M+H]$^+$: 416.2696, found: 416.2709.

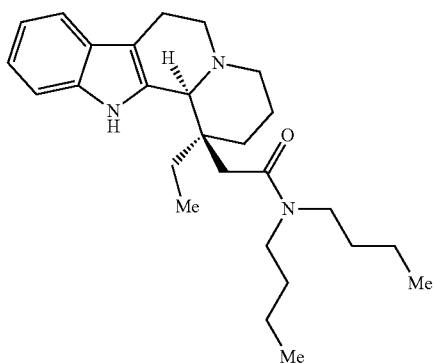

V23

Yield: 76%; 58.3 mg of V10 as a dark-red foam. $^1$H NMR: (400 MHz, CDCl$_3$) δ 8.26 (dd, J=8.0, 1.2 Hz, 1H), 7.99 (s, 1H), 7.83 (s, 1H), 7.47 (d, J=7.8 Hz, 1H), 7.35 (d, J=8.0 Hz, 1H), 7.16 (ddd, J=8.3, 7.0, 1.2 Hz, 1H), 7.10 (ddd, J=8.0, 7.5, 0.9 Hz, 1H), 6.98 (td, J=7.8, 1.5 Hz, 1H), 6.87 (td, J=7.8, 1.4 Hz, 1H), 6.80 (dd, J=8.1, 1.1 Hz, 1H), 3.82 (s, 3H), 3.43 (s, 1H), 3.12-2.93 (m, 4H), 2.75-2.59 (m, 2H), 2.45 (td, J=11.6, 2.7 Hz, 1H), 2.20-2.00 (m, 5H), 1.68 (dd, J=13.9, 3.6 Hz, 2H), 1.23 (t, J=7.6 Hz, 3H). $^{13}$C NMR: (100 MHz, CDCl$_3$) δ 170.8, 148.0, 136.2, 132.9, 127.8, 126.8, 123.5, 121.9, 121.0, 119.9, 119.6, 118.0, 112.3, 111.1, 109.9, 66.8, 57.1, 55.7, 54.3, 42.0, 40.9, 32.5, 32.0, 22.5, 22.1, 8.4. HRMS (ESI): calc. for $C_{26}H_{32}N_3O_2$ [M+H]$^+$: 418.2489, found: 418.2492. MP: 57-59° C.

Yield: 62%; 72.0 mg of V23 as an off-white powder. $^1$H NMR: (400 MHz, CDCl$_3$) δ 7.96 (s, 1H), 7.45 (d, J=7.8 Hz, 1H), 7.30 (d, J=7.8 Hz, 1H), 7.12 (dd, J=8.1, 6.4 Hz, 1H), 7.07 (dd, J=7.4, 7.1 Hz, 1H), 3.34 (s, 1H), 3.27 (ddd, J=14.8, 9.2, 6.2 Hz, 1H), 3.10 (m, 1H), 3.04-2.97 (m, 2H), 2.90 (m, 1H), 2.78 (ddd, J=14.8, 9.2, 5.7 Hz, 1H), 2.70-2.62 (m, 2H), 2.58 (td, J=11.1, 3.7 Hz, 1H), 2.37 (td, J=11.9, 2.4 Hz, 1H), 2.34-2.18 (m, 3H), 2.12 (m, 1H), 2.00-1.85 (m, 2H), 1.65-1.49 (m, 2H), 1.36-1.23 (m, 2H), 1.23-1.08 (m, 7H), 1.05-0.86 (m, 2H), 0.81 (t, J=6.7, 3H), 0.67 (t, J=7.4 Hz, 3H). $^{13}$C NMR: (100 MHz, CDCl$_3$) δ 172.2, 136.3, 133.4, 126.9, 121.7, 119.4, 117.8, 112.1, 111.0, 67.1, 57.2, 54.3, 48.7, 46.1, 41.2, 34.5, 33.3, 31.3, 30.9, 29.9, 22.5, 22.2, 20.5, 19.9, 14.0, 13.6, 8.4. HRMS (ESI): calc. for $C_{27}H_{42}N_3O$ [M+H]$^+$: 424.3322, found: 424.3301. MP: 110-112° C.

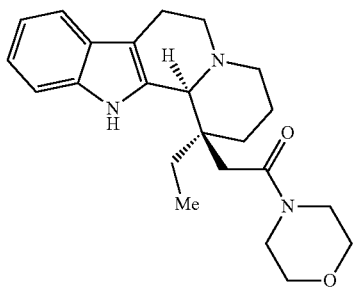

V26

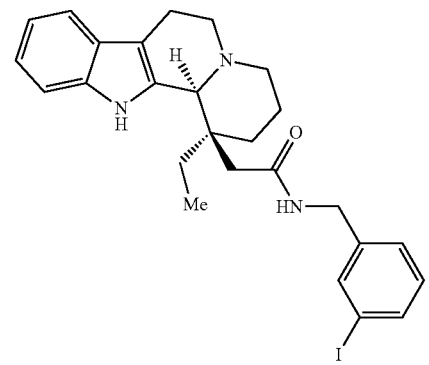

V91

Yield: 82%; 151.0 mg of V26 as a yellow foam. $^1$H NMR: (400 MHz, CDCl$_3$) δ 7.98 (s, 1H), 7.47 (d, J=7.5 Hz, 1H), 7.32 (d, J=8.0 Hz, 1H), 7.15 (ddd, J=8.0, 7.1, 1.3 Hz, 1H), 7.10 (td, J=7.7, 7.4, 1.2 Hz, 1H), 3.51-3.41 (m, 2H), 3.41-3.27 (m, 4H), 3.27-3.15 (m, 2H), 3.09 (ddd, J=11.6, 6.8, 3.4 Hz, 1H), 3.05-2.97 (m, 2H), 2.87 (m, 1H), 2.70-2.53 (m, 4H), 2.44-2.33 (m, 2H), 2.25 (sextet, J=7.6 Hz, 1H), 2.07-1.82 (m, 3H), 1.68-1.53 (m, 2H), 1.19 (t, J=7.6 Hz, 3H). $^{13}$C NMR: (100 MHz, CDCl$_3$) δ 171.4, 136.2, 133.4, 126.9, 121.9, 119.7, 118.0, 112.0, 111.1, 67.0, 66.7, 66.6, 57.2, 54.5, 46.8, 41.6, 41.2, 33.9, 33.8, 31.4, 22.4, 22.2, 8.4. HRMS (ESI): calc. for $C_{23}H_{32}N_3O_2$ [M+H]$^+$: 382.2489, found: 382.2496. MP: 65-67° C.

Yield: 28%; 49.0 mg of V91 as a yellow-white solid. $^1$H NMR: (400 MHz, CDCl$_3$) δ 7.95 (s, 1H), 7.54 (dt, J=7.1, 1.8 Hz, 1H), 7.46 (d, J=7.9 Hz, 1H), 7.39 (s, 1H), 7.32 (dd, J=7.9, 0.7 Hz, 1H), 7.16 (ddd, J=8.3, 7.4, 1.2 Hz, 1H), 7.11 (ddd, J=7.9, 7.0, 1.2 Hz, 1H), 7.03-6.92 (m, 2H), 5.92 (s, 1H), 4.15 (dd, J=14.9, 7.0 Hz, 1H), 3.50 (dd, J=14.9, 4.6 Hz, 1H), 3.36 (s, 1H), 3.02-2.91 (m, 2H), 2.80 (m, 1H), 2.68-2.51 (m, 3H), 2.39 (td, J=12.0, 2.6 Hz, 1H), 2.28 (d, J=14.0 Hz, 1H), 2.11-1.79 (m, 3H), 1.66-1.54 (m, 2H), 1.19 (t, J=7.6 Hz, 3H). $^{13}$C NMR: (100 MHz, CDCl$_3$) δ 172.3, 140.9, 136.8, 136.4, 136.2, 133.2, 130.3, 127.2, 126.7, 122.0, 119.8, 118.0, 111.8, 111.1, 94.5, 66.8, 57.1, 54.2, 42.9, 40.9, 40.7, 34.0, 31.7, 22.3, 22.1, 8.3. HRMS (ESI): calc. for $C_{26}H_{31}IN_3O$ [M+H]$^+$: 528.1506, found: 528.1515. MP: 140-142° C.

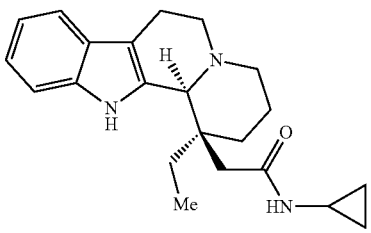

V90

Yield: 62%; 72.0 mg of V90 as a yellow-green residue. ¹H NMR: (400 MHz, CDCl₃) δ 8.02 (s, 1H), 7.45 (d, J=7.7 Hz, 1H), 7.32 (d, J=8.0 Hz, 1H), 7.13 (td, J=7.4, 0.8 Hz, 1H), 7.08 (td, J=7.3, 0.8 Hz, 1H), 5.81 (s, 1H), 3.36 (s, 1H), 3.05-2.97 (m, 2H), 2.89 (m, 1H), 2.67 (m, 1H), 2.59 (td, J=11.4, 3.1 Hz, 1H), 2.49 (d, J=14.0 Hz, 1H), 2.40 (td, J=12.0, 2.5 Hz, 1H), 2.26 (octet, J=3.8 Hz, 1H), 2.17 (d, J=14.0 Hz, 1H), 2.09-1.89 (m, 3H), 1.85 (m, 1H), 1.64-1.61 (m, 2H), 1.16 (t, J=7.6 Hz, 3H), 0.50 (m, 1H), 0.40 (m, 1H), 0.12 (m, 1H), 0.03 (m, 1H). ¹³C NMR: (100 MHz, CDCl₃) δ 173.9, 136.2, 133.1, 126.7, 121.9, 119.6, 117.9, 111.7, 111.2, 66.8, 57.0, 54.2, 40.6, 40.5, 33.8, 31.5, 22.4, 22.1, 22.0, 8.3, 6.3, 6.0. HRMS (ESI): calc. for $C_{22}H_{30}N_3O$ $[M+H]^+$: 352.2383, found: 352.2396.

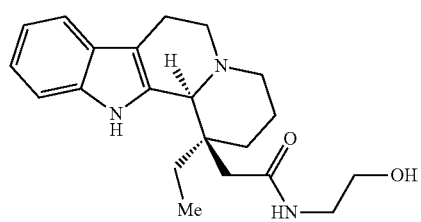

V25

Yield: 93%; 101.0 mg of V25 as a yellow-white foam. ¹H NMR: (400 MHz, CDCl₃) δ 8.16 (s, 1H), 7.44 (d, J=7.8 Hz, 1H), 7.35 (d, J=8.0 Hz, 1H), 7.13 (dd, J=8.3, 7.2 Hz, 1H), 7.07 (dd, J=8.0, 7.2 Hz, 1H), 6.47 (s, 1H), 3.43 (s, 1H), 3.34 (ddd, J=11.1, 6.4, 3.5 Hz, 1H), 3.24 (ddd, J=11.1, 6.7, 3.2 Hz, 1H), 3.13-2.91 (m, 5H), 2.82-2.59 (m, 3H), 2.48-2.38 (m, 2H), 2.33 (d, J=13.9 Hz, 1H), 2.10-1.88 (m, 3H), 1.79 (m, 1H), 1.65-1.58 (m, 2H), 1.14 (t, J=7.6 Hz, 3H). ¹³C NMR: (100 MHz, CDCl₃) 173.4, 136.5, 132.1, 126.5, 122.2, 119.8, 117.9, 111.5, 111.3, 67.2, 61.9, 56.9, 54.6, 42.4, 40.6, 40.3, 34.0, 31.8, 21.7, 21.6, 8.3. HRMS (ESI): calc. for $C_{21}H_{30}N_3O_2$ $[M+H]^+$: 356.2333, found: 356.2348. MP: 61-63° C.

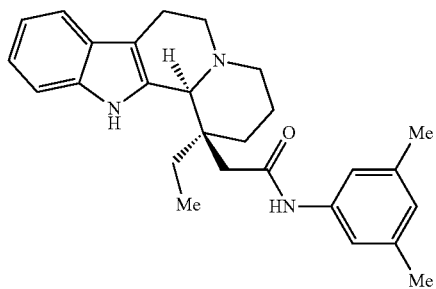

V19

Yield: 39%; 12.7 mg of V19 as a white-brown solid. ¹H NMR: (400 MHz, CDCl₃) δ 7.92 (s, 1H), 7.46 (d, J=7.4 Hz, 2H), 7.29 (d, J=8.1 Hz, 1H), 7.13 (td, J=7.9, 1.4 Hz, 1H), 7.09 (td, J=7.7, 0.9 Hz, 1H), 6.75 (s, 2H), 6.62 (s, 1H), 3.41 (s, 1H), 3.11-2.91 (m, 3H), 2.77-2.68 (m, 2H), 2.64 (td, J=11.2, 2.8 Hz, 1H), 2.45 (dd, J=13.3, 11.3 Hz, 1H), 2.36 (d, J=14.2 Hz, 1H), 2.17 (s, 6H), 2.15-1.90 (m, 4H), 1.64 (ddt, J=13.4, 9.7, 5.4 Hz, 2H), 1.20 (t, J=7.6 Hz, 3H). ¹³C NMR: (100 MHz, CDCl₃) δ 170.9, 138.5, 138.0, 136.3, 133.0, 126.9, 125.7, 122.2, 119.9, 118.1, 117.4, 112.4, 111.2, 67.2, 57.0, 54.2, 42.8, 41.1, 33.9, 32.0, 29.9, 22.4, 22.3, 21.5, 8.4. HRMS (ESI): calc. for $C_{27}H_{34}N_3O$ $[M+H]^+$: 416.2696, found: 416.2712. MP: 164-166° C.

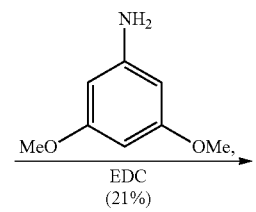

V54

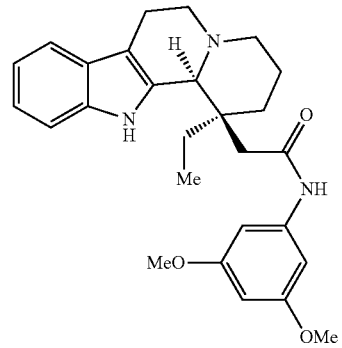

V5

Procedure for the synthesis of V5: V54 (32.8 mg, 0.105 mmol) was added to a flame-dried round-bottom flask and dissolved in anhydrous dichloromethane (2.6 mL). 1-ethyl-3-(3-dimethylaminopropyl)carbodiimide (24.0 μL, 0.136 mmol) was added dropwise and the reaction stirred for ~5 minutes. Over a period of 20 minutes, 3,5 dimethoxyaniline (21.0 mg, 0.136 mmol) as a 0.3 M solution in anhydrous dichloromethane was added and the reaction proceeded for 72 hours. Upon completion, the reaction was quenched with deionized water, extracted with ethyl acetate, and crude extract dried with sodium sulfate. The organic layer was filtered, concentrated in vacuo, and purified via column chromatography using a gradient of 100% hexanes to 3:1 hexanes:ethyl acetate with 1% triethylamine throughout to yield V5 (10.1 mg, 21%) as a white-brown residue. ¹H NMR: (400 MHz, CDCl₃) δ 8.15 (s, 1H), 7.90 (s, 1H), 7.42 (d, J=7.7 Hz, 1H), 7.30 (d, J=8.0 Hz, 1H), 7.13 (td, J=7.3, 1.2 Hz, 1H), 7.07 (td, J=7.6, 0.9 Hz, 1H), 6.52 (d, J=2.1 Hz, 2H), 6.12 (t, J=2.1 Hz, 1H), 3.69 (s, 6H), 3.43 (s, 1H), 3.11-3.02 (m, 2H), 2.95 (m, 1H), 2.78-2.58 (m, 3H), 2.46 (dd, J=11.6 Hz, 1H), 2.30-2.18 (m, 2H), 2.10-1.90 (m, 5H), 1.76-1.55 (m, 2H), 1.19 (t, J=7.6 Hz, 3H). ¹³C NMR: (100 MHz, CDCl₃) δ 171.0, 161.0, 140.1, 136.3, 132.7, 126.9, 122.1, 119.8, 118.1, 112.3, 111.1, 97.6, 96.5, 67.2, 56.9, 55.6, 55.5, 54.2, 43.1, 41.0, 33.2, 32.6, 22.3, 22.2, 8.4. HRMS (ESI): calc. for $C_{27}H_{34}N_3O_3$ $[M+H]^+$: 448.2595, found: 448.2595.

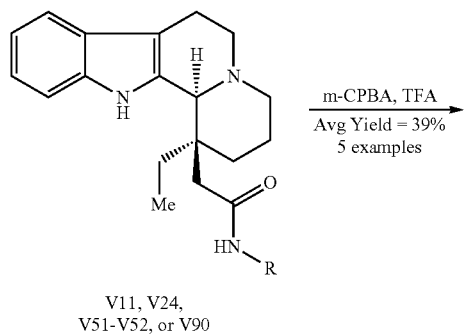

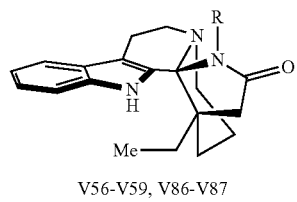

V11, V24,
V51-V52, or V90

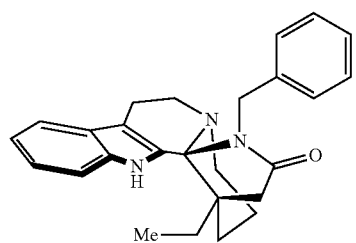

V56-V59, V86-V87

General Procedure for the synthesis of V56-V57, V59 & V86-V87: V52 (45.4 mg, 0.113 mmol) was added to a flame-dried round-bottom flask and dissolved in anhydrous dichloromethane (4.52 mL). The reaction was cooled to −41° C. in an acetonitrile dry ice bath, and trifluoroacetic acid (0.155 mL, 1.921 mmol) was added. This reaction mixture reacted for ~5-10 minutes, then meta-chloroperoxybenzoic acid (20.0 mg, 0.113 mmol) was added as a 0.3 M solution in anhydrous dichloromethane. The reaction stirred for 8 hours, then the reaction was quenched with 3 M aqueous ammonium hydroxide. Crude reaction was extracted with dichloromethane, washed with brine, and the organic layer was dried with sodium sulfate. The organic layer was concentrated in vacuo and crude product was purified via column chromatography using a gradient of 100% hexanes to 4:1 hexanes:ethyl acetate with 1% triethylamine to afford V56 (20.0 mg, 44%) as a light-green foam.

V56

Yield: 44%; 20.0 mg of V56 as a light-green foam. $^1$H NMR: (400 MHz, CDCl$_3$) δ 9.40 (s, 1H), 7.48 (dd, J=7.6, 1.4 Hz, 1H), 7.30-7.21 (m, 3H), 7.18-7.10 (m, 3H), 7.08-6.98 (m, 2H), 4.46 (d, J=14.8 Hz, 1H), 3.81 (d, J=14.8 Hz, 1H), 3.30 (ddd, J=11.7, 6.9, 4.9 Hz, 1H), 3.20-3.10 (m, 2H), 2.91-2.75 (m, 2H), 2.62 (dt, J=12.8, 4.4 Hz, 1H), 2.54 (ddd, J=13.2, 9.5, 3.7 Hz, 1H), 2.36 (d, J=16.9 Hz, 1H), 2.01 (m, 1H), 1.76 (m, 1H), 1.64-1.50 (m, 2H), 1.36-1.24 (m, 2H), 0.84 (t, J=7.5 Hz, 3H). $^{13}$C NMR: (100 MHz, CDCl$_3$) δ 175.2, 137.8, 137.4, 132.5, 128.7, 128.1, 126.8, 126.0, 122.3, 119.1, 118.2, 114.3, 112.1, 84.5, 49.9, 49.6, 44.8, 44.3, 43.6, 32.8, 27.2, 22.3, 17.7, 9.6. HRMS (ESI): calc. for C$_{26}$H$_3$N$_3$O [M+H]$^+$: 400.2383, found: 400.2393. MP: 90-92° C.

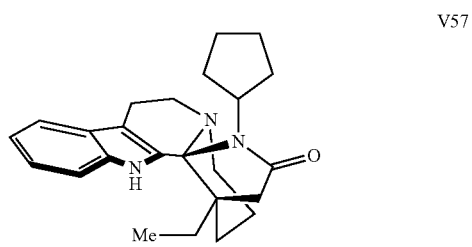

V57

Yield: 37%; 24.0 mg of V57 as an off-white foam. $^1$H NMR: (400 MHz, CDCl$_3$) δ 9.41 (s, 1H), 7.54-7.45 (m, 2H), 7.17 (ddd, J=8.0, 7.0, 1.3 Hz, 1H), 7.09 (ddd, J=8.0, 7.0, 1.1 Hz, 1H), 3.68 (p, J=9.7 Hz, 1H), 3.58 (ddd, J=11.7, 9.1, 4.5 Hz, 1H), 3.25-3.13 (m, 2H), 3.04-2.86 (m, 4H), 2.78 (dt, J=15.1, 4.5 Hz, 1H), 2.49 (ddd, J=14.5, 10.0, 9.0 Hz, 1H), 2.09 (d, J=16.5 Hz, 1H), 2.02 (m, 1H), 1.90-1.71 (m, 4H), 1.70-1.42 (m, 3H), 1.42-1.30 (m, 2H), 1.29-1.04 (m, 2H), 0.79 (t, J=7.5 Hz, 3H). $^{13}$C NMR: (100 MHz, CDCl$_3$) δ 173.4, 137.3, 133.2, 126.3, 122.2, 119.2, 118.2, 113.3, 112.0, 83.7, 52.9, 50.1, 49.9, 45.3, 43.3, 32.4, 28.6, 28.0, 26.8, 25.3, 24.8, 22.2, 17.1, 9.7. HRMS (ESI): calc. for C$_{24}$H$_{32}$N$_3$O [M+H]$^+$: 378.2540, found: 378.2546. MP: 210-212° C.

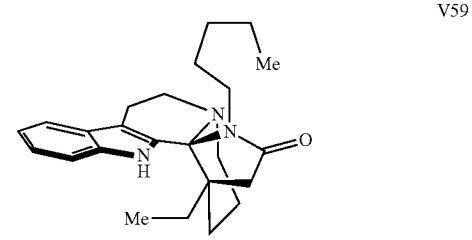

V59

Yield: 43%; 27.0 mg of V59 as a light-green foam. $^1$H NMR: (400 MHz, CDCl$_3$) δ 9.41 (s, 1H), 7.50 (d, J=8.7 Hz, 2H), 7.16 (ddd, J=8.2, 7.0, 1.1 Hz, 1H), 7.08 (ddd, J=7.9, 7.2, 0.9 Hz, 1H), 3.39 (m, 1H), 3.25-3.06 (m, 3H), 3.06-2.93 (m, 5H), 2.85-2.78 (m, 2H), 2.19 (d, J=16.8 Hz, 1H), 2.02 (m, 1H), 1.82 (m, 1H), 1.62-1.45 (m, 2H), 1.45-1.11 (m, 2H), 0.98 (sextet, J=7.3 Hz, 2H), 0.80 (t, J=7.5 Hz, 3H), 0.59 (t, J=7.3 Hz, 3H). $^{13}$C NMR: (100 MHz, CDCl$_3$) δ 174.6, 137.3, 133.1, 126.2, 122.2, 119.2, 118.2, 113.5, 112.1, 83.5, 50.3, 50.0, 46.0, 44.4, 43.7, 41.3, 32.8, 30.0, 26.6, 22.4, 20.7, 18.3, 13.7, 9.6. HRMS (ESI): calc. for C$_{23}$H$_{32}$N$_3$O [M+H]$^+$: 366.2540, found: 366.2547. MP: 170-172° C.

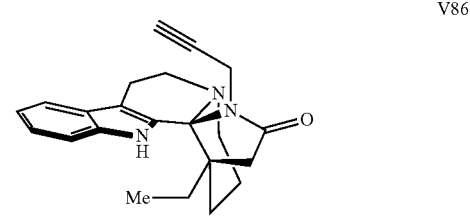

V86

Yield: 38%; 81.0 mg of V86 as an off-white residue. $^1$H NMR: (400 MHz, CDCl$_3$) δ 9.63 (s, 1H), 7.66 (dt, J=8.1, 0.8 Hz, 1H), 7.53 (d, J=7.9 Hz, 1H), 7.20 (ddd, J=7.9, 6.9, 1.2 Hz, 1H), 7.11 (ddd, J=8.1, 6.9, 0.8 Hz, 1H), 3.94 (dd, J=17.3, 2.6 Hz, 1H), 3.61 (dd, J=17.3, 2.6 Hz, 1H), 3.47-3.34 (m, 2H), 3.25 (ddd, J=11.8, 6.2, 5.9 Hz, 1H), 3.16 (d, J=17.0 Hz, 1H), 3.01 (dt, J=12.8, 4.2 Hz, 1H), 2.94-2.79 (m, 2H), 2.31 (d, J=17.0 Hz, 1H), 2.05 (dtd, J=12.9, 4.3, 2.0 Hz, 1H), 1.98 (t, J=2.6 Hz, 1H), 1.88 (m, 1H), 1.68-1.52 (m, 2H), 1.47 (m, 1H), 1.33 (sextet, J=7.6 Hz, 1H), 0.86 (t, J=7.6 Hz, 3H). $^{13}$C NMR: (100 MHz, CDCl$_3$) δ 174.4, 137.5, 131.6, 126.0, 122.4, 119.2, 118.2, 114.4, 112.4, 83.6, 78.9, 70.8, 50.1, 49.6, 43.9, 43.7, 32.8, 29.8, 27.1, 22.1, 18.0, 9.5. HRMS (ESI): calc. for C$_{22}$H$_{26}$N$_3$O [M+H]$^+$: 348.2070, found: 348.2075.

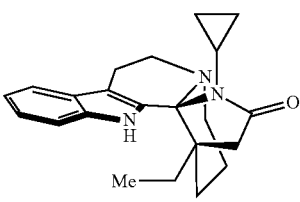

V87

Yield: 35%; 25.4 mg of V87 as a green-yellow residue. $^1$H NMR: (400 MHz, CDCl$_3$) δ 9.47 (s, 1H), 7.55 (d, J=8.2 Hz, 1H), 7.51 (d, J=7.8 Hz, 1H), 7.17 (td, J=7.4, 1.0 Hz, 1H), 7.09 (dd, J=7.5 Hz, 1H), 3.53 (ddd, J=11.6, 9.1, 4.5 Hz, 1H), 3.21-3.10 (m, 2H), 3.09-2.98 (m, 2H), 2.89-2.72 (m, 2H), 2.22-2.10 (m, 2H), 1.98-1.89 (m, 1H), 1.81 (m, 1H), 1.59-1.35 (m, 4H), 1.13 (sextet, J=7.5 Hz, 1H), 0.78 (t, J=7.5 Hz, 3H), 0.55 (m, 1H), 0.39-0.22 (m, 2H). $^{13}$C NMR: (100 MHz, CDCl$_3$) δ 175.5, 136.9, 133.3, 126.2, 122.1, 119.2, 118.3, 113.6, 112.2, 84.6, 50.4, 49.9, 44.5, 43.7, 33.2, 26.7, 24.7, 22.6, 20.0, 9.4, 6.8, 5.5. HRMS (ESI): calc. for C$_{22}$H$_{28}$N$_3$O [M+H]$^+$: 350.2227, found: 350.2213.

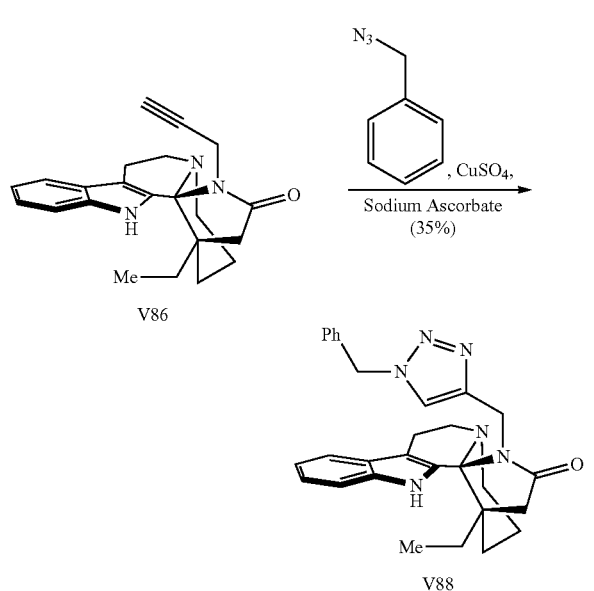

Procedure for the synthesis of V88: Anhydrous copper sulfate (6.5 mg, 0.04 mmol) and sodium ascorbate (25.0 mg, 0.126 mmol) were added to a round-bottom flask and dissolved in a solution of tert-butanol:H$_2$O (1:2) (2.25 mL). V86 (29.9 mg, 0.086 mmol) was added, then benzyl azide (11.0 µL, 0.09 mmol) as a solution in dichloromethane (0.180 mL) was added and the reaction was stirred for 2 hours. Upon completion, the reaction was quenched with brine, extracted with dichloromethane, and the organic layer was dried with sodium sulfate. Crude extract was filtered, concentrated in vacuo, and purified via column chromatography using a gradient of 100% hexanes, 1:1 hexanes:ethyl acetate, and 100% ethyl acetate with 1% triethylamine throughout to afford V88 (14.5 mg, 35%) as a yellow powder. $^1$H NMR: (400 MHz, CDCl$_3$) δ 9.03 (s, 1H), 7.40 (dd, J=8.1, 3.8 Hz, 2H), 7.21-7.14 (m, 2H), 7.12-7.04 (m, 3H), 6.80-6.71 (m, 3H), 4.67 (d, J=15.0 Hz, 1H), 4.56 (d, J=15.0 Hz, 2H), 4.09 (d, J=15.0 Hz, 1H), 3.37 (dt, J=11.8, 6.3 Hz, 1H), 3.26 (dt, J=11.8, 5.0 Hz, 1H), 3.01-2.85 (m, 3H), 2.68-2.61 (m, 2H), 2.24 (d, J=16.6 Hz, 1H), 2.04 (m, 1H), 1.82 (m, 1H), 1.56 (sextet, J=7.4 Hz, 1H), 1.43 (dd, J=13.5 Hz, 1H), 1.36-1.19 (m, 2H), 0.80 (t, J=7.4 Hz, 3H). $^{13}$C NMR: (100 MHz, CDCl$_3$) δ 173.6, 143.1, 137.2, 134.6, 133.0, 128.9, 128.7, 127.9, 126.2, 122.4, 121.5, 119.5, 118.7, 114.0, 111.8, 82.6, 52.9, 50.2, 49.8, 44.7, 43.6, 35.3, 32.3, 25.9, 21.8, 17.7, 9.7. HRMS (ESI): calc. for C$_{29}$H$_{33}$N$_6$O [M+H]$^+$: 481.2710, found: 481.2731. MP: 83-85° C.

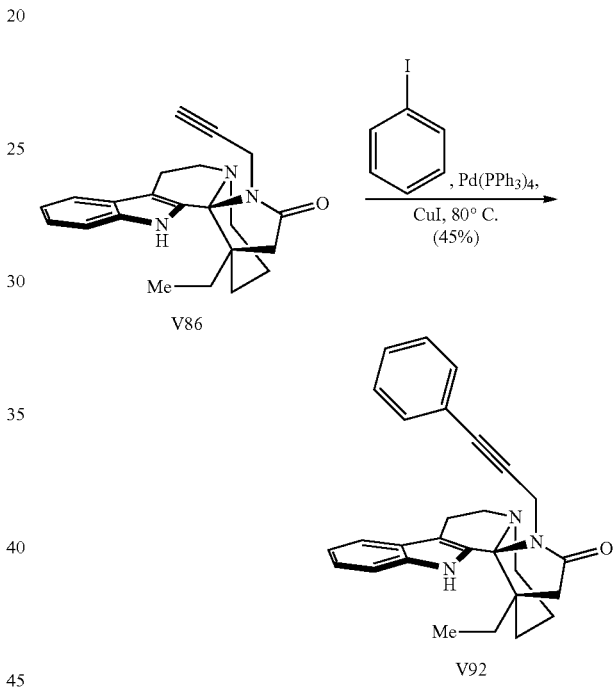

Procedure for the synthesis of V92: To a flame-dried round-bottom flask was added Tetrakis(triphenlyphosphine) palladium(0) (10.3 mg, 0.0089 mmol), copper(I) iodide (3.4 mg, 0.018 mmol), and iodobenzene (20.0 µL, 0.177 mmol). The resulting starting materials were dissolved in anhydrous N,N-dimethylformamide (2.0 mL), then triethylamine (22.0 µL, 0.160 mmol) was added dropwise. V86 (30.8 mg, 0.089 mmol) as a 0.6 M solution in anhydrous N,N-dimethylformamide was added and the reaction proceeded at room temperature for 4 hours. The reaction was heated to 80° C. for another 3 hours, upon completion, the reaction was quenched with deionized water. The crude reaction mixture was extracted with ethyl acetate, washed with brine, and the organic layer was dried with sodium sulfate. The organic layer was filtered, concentrated in vacuo, and the crude product was purified via column chromatography using a gradient of 100% hexanes to 4:1 hexanes:ethyl acetate with 1% triethylamine throughout to afford V92 (17.0 mg, 45%) as a brown residue.

$^1$H NMR: (400 MHz, CDCl$_3$) δ 9.11 (s, 1H), 7.56-7.47 (m, 2H), 7.17 (dd, J=8.2, 7.3 Hz, 1H), 7.12-7.04 (m, 3H), 6.78 (d, J=7.5 Hz, 2H), 4.05 (d, J=17.4 Hz, 1H), 3.82 (d, J=17.4 Hz, 1H), 3.41-3.22 (m, 3H), 3.11-2.93 (m, 2H), 2.90-2.75 (m, 2H), 2.28 (d, J=17.1 Hz, 1H), 2.07-1.96 (m, 1H), 1.83 (d, J=12.0 Hz, 1H), 1.64-1.40 (m, 3H), 1.36-1.12 (m, 2H), 0.82 (t, J=7.5 Hz, 3H). $^{13}$C NMR: (100 MHz, CDCl$_3$) δ 174.1, 137.6, 132.1, 131.8, 128.1, 128.0, 126.4, 122.9, 122.6, 119.4, 118.4, 114.6, 112.4, 84.3, 83.4, 82.5, 50.1, 50.0, 44.2, 43.9, 32.8, 30.4, 26.9, 22.3, 18.4, 9.5. HRMS (ESI): calc. for C$_{28}$H$_{30}$N$_3$O [M+H]$^+$: 424.2383, found: 424.2380.

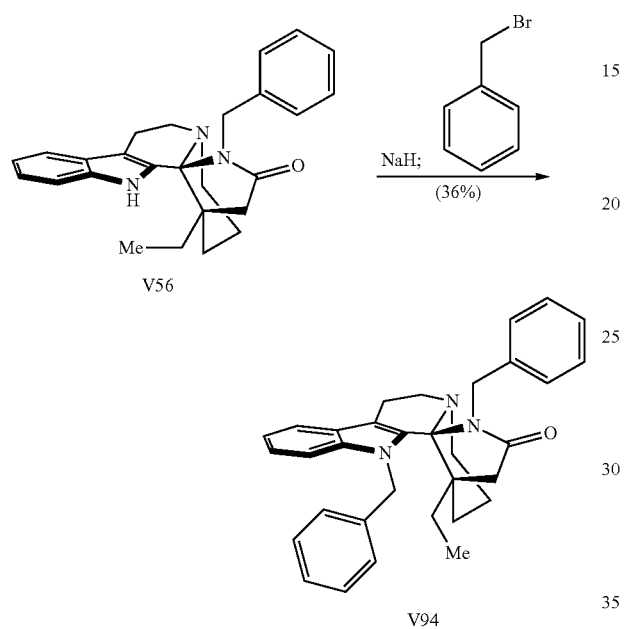

V56

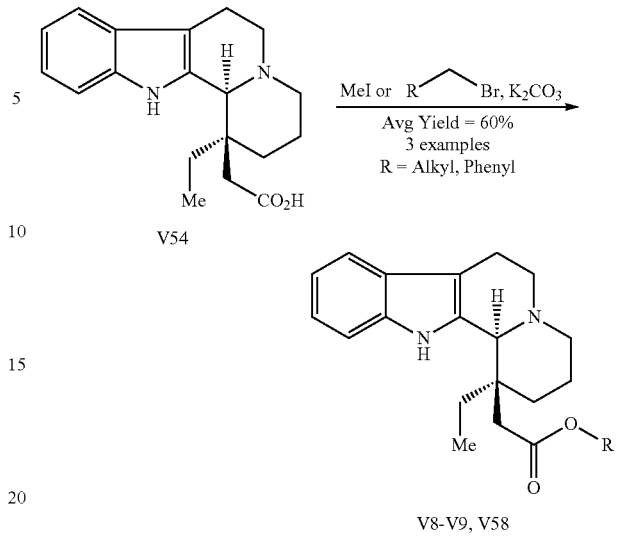

V54

V8-V9, V58

General Procedure for the synthesis of V8-V9 & V58: V54 (1.51 g, 4.84 mmol) was added to a round-bottom flask and dissolved in anhydrous N,N-dimethylformamide (48.4 mL). The solution was cooled to 0° C., then anhydrous potassium carbonate (1.34 g, 9.69 mmol) and iodomethane (0.362 mL, 5.81 mmol) were added sequentially. The resulting reaction mixture warmed slowly to room temperature and reacted for 3 hours. Upon completion, the reaction was quenched with brine, extracted with ethyl acetate, and the organic layer was washed with deionized water three times (~1 L). The organic layer was dried with sodium sulfate, filtered, concentrated in vacuo, and crude product purified via column chromatography using a gradient of 100% hexanes to 5:1 hexanes:ethyl acetate with 1% triethylamine throughout to afford V58 (1.18 g, 75%) as a brownish solid.

V94

Procedure for the synthesis of V94: To a flame-dried round-bottom flask containing anhydrous tetrahydrofuran (2.0 mL), was added sodium hydride (8.0 mg, 0.19 mmol, 60% dispersion in mineral oil). V56 (38.0 mg, 0.095 mmol) as a 0.2 M solution in anhydrous tetrahydrofuran was added at 0° C., and the reaction was warmed to room temperature over 12 hours. After this time, two equivalents of sodium hydride (16.0 mg, 0.38 mmol, 60% dispersion in mineral oil) was added and the reaction was heated to 66° C. for 6 hours. Once complete, the reaction was quenched with brine, extracted with ethyl acetate, and the organic layer dried with sodium sulfate. Organics were filtered, concentrated in vacuo, and purified via column chromatography using a gradient of 100% hexanes to 3:1 hexanes:ethyl acetate with 1% triethylamine throughout to afford V94 (19.0 mg, 36%) as a brown residue. $^1$H NMR: (400 MHz, CDCl$_3$) δ 7.62 (m, 1H), 7.23-7.13 (m, 5H), 7.10 (m, 1H), 7.04-6.95 (m, 4H), 6.88 (d, J=7.6 Hz, 3H), 4.77 (d, J=18.3 Hz, 1H), 4.31 (d, J=18.3 Hz, 1H), 4.12 (s, 2H), 3.27 (ddd, J=11.6, 8.2, 4.5 Hz, 1H), 3.19 (m, 1H), 2.99 (m, 1H), 2.87-2.69 (m, 2H), 2.61 (td, J=11.2, 1.8 Hz, 1H), 2.37 (d, J=17.9 Hz, 1H), 2.21 (d, J=17.9 Hz, 1H), 1.79-1.63 (m, 2H), 1.48 (m, 1H), 1.34 (dd, J=7.3 Hz, 1H), 1.24 (m, 1H), 1.08 (sextet, J=7.4 Hz, 1H), 0.42 (t, J=7.4 Hz, 3H). $^{13}$C NMR: (100 MHz, CDCl$_3$) δ 174.6, 138.9, 137.0, 136.7, 132.6, 129.8, 128.6, 128.1, 127.3, 127.2, 126.5, 125.8, 123.0, 119.8, 118.7, 116.1, 111.2, 85.1, 50.2, 47.7, 47.5, 45.7, 44.4, 42.5, 34.0, 31.5, 23.0, 17.6, 8.6. HRMS (ESI): calc. for C$_{33}$H$_{36}$N$_3$O [M+H]$^+$: 490.2853, found: 490.2856.

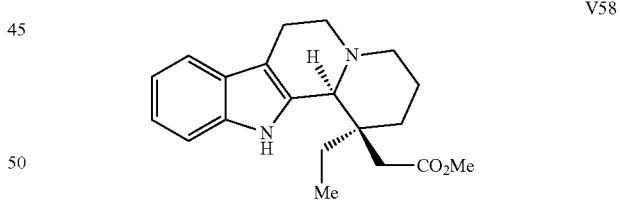

V58

Yield: 75%; 1.180 g of V58 as a brownish solid. $^1$H NMR: (400 MHz, CDCl$_3$) δ 7.83 (s, 1H), 7.47 (d, J=7.8 Hz, 1H), 7.32 (d, J=8.0 Hz, 1H), 7.15 (ddd, J=8.0, 7.1, 1.3 Hz, 1H), 7.09 (td, J=8.0, 1.1 Hz, 1H), 3.49 (s, 3H), 3.38 (t, J=1.9 Hz, 1H), 3.09-2.97 (m, 3H), 2.84 (m, 1H), 2.68-2.53 (m, 2H), 2.40 (ddd, J=12.5, 11.2, 2.8 Hz, 1H), 2.11-1.86 (m, 3H), 1.82 (m, 1H), 1.67-1.55 (m, 3H), 1.18 (t, J=7.7 Hz, 3H). $^{13}$C NMR: (100 MHz, CDCl$_3$) δ 173.7, 136.1, 132.6, 126.8, 121.7, 119.4, 117.9, 112.4, 110.9, 66.3, 56.9, 54.0, 51.2, 40.4, 38.1, 32.3, 31.4, 22.2, 22.1, 8.2. HRMS (ESI): calc. for C$_{20}$H$_{27}$N$_2$O$_2$[M+H]$^+$: 327.2067, found: 327.2074. MP: 127-129° C.

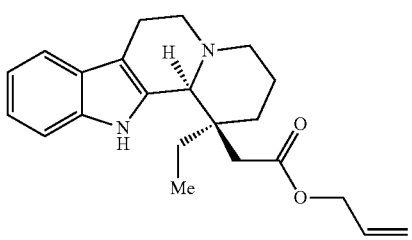

V9

Yield: 56%; 85.0 mg of V9 as a white-brown solid. $^1$H NMR: (400 MHz, CDCl$_3$) δ 7.85 (s, 1H), 7.48 (d, J=7.7 Hz, 1H), 7.33 (d, J=8.0 Hz, 1H), 7.16 (td, J=7.1, 1.0 Hz, 1H), 7.10 (td, J=7.4, 1.1 Hz, 1H), 5.83 (dddd, J=17.1, 10.4, 5.8, 5.0 Hz, 1H), 5.24 (dq, J=17.2, 1.4 Hz, 1H), 5.18 (dq, J=10.7, 1.4 Hz, 1H), 4.45 (ddd, J=13.2, 5.7, 1.2 Hz, 1H), 4.37 (ddd, J=13.2, 5.7, 1.2 Hz, 1H), 3.39 (s, 1H), 3.11 (d, J=14.1 Hz, 1H), 3.07-2.97 (m, 2H), 2.91 (m, 1H), 2.68-2.55 (m, 2H), 2.41 (td, J=12.6, 2.2 Hz, 1H), 2.12-1.90 (m, 4H), 1.86 (m, 1H), 1.68-1.55 (m, 2H), 1.19 (t, J=7.7 Hz, 3H). $^{13}$C NMR: (100 MHz, CDCl$_3$) δ 173.0, 136.2, 132.7, 132.5, 126.9, 121.8, 119.5, 118.3, 118.1, 112.6, 111.0, 66.3, 64.9, 57.0, 54.1, 40.6, 38.4, 32.4, 31.6, 22.3, 22.2, 8.3. HRMS (ESI): calc. for C$_{22}$H$_{29}$N$_2$O$_2$ [M+H]$^+$: 353.2224, found: 353.2214.

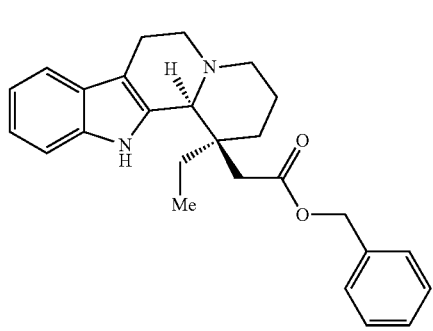

V8

MP: 81-83° C. Yield: 49%; 26.0 mg of V8 as a yellow-brown residue. $^1$H NMR: (400 MHz, CDCl$_3$) δ 7.88 (s, 1H), 7.51 (d, J=7.6 Hz, 1H), 7.40-7.28 (m, 6H), 7.19 (td, J=7.6, 1.3 Hz, 1H), 7.13 (td, J=7.3, 1.1 Hz, 1H), 5.04 (d, J=12.6 Hz, 1H), 4.92 (d, J=12.6 Hz, 1H), 3.41 (s, 1H), 3.18 (d, J=14.1 Hz, 1H), 3.01-2.99 (m, 2H), 2.93 (m, 1H), 2.70-2.57 (m, 2H), 2.43 (ddd, J=12.0, 2.4 Hz, 1H), 2.14-1.91 (m, 4H), 1.85 (m, 1H), 1.70-1.56 (m, 2H), 1.19 (t, J=7.7 Hz, 3H). $^{13}$C NMR: (100 MHz, CDCl$_3$) δ 173.2, 136.2, 136.2, 132.7, 128.6, 128.4, 128.2, 126.8, 121.8, 119.5, 118.1, 112.5, 111.0, 66.3, 66.0, 57.0, 54.0, 40.6, 38.4, 32.4, 31.6, 22.3, 22.1, 8.2. HRMS (ESI): calc. for C$_{26}$H$_{31}$N$_2$O$_2$ [M+H]$^+$: 403.2380, found: 403.2392.

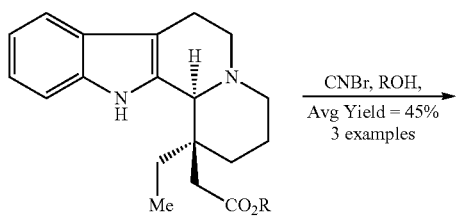

V9 or V58

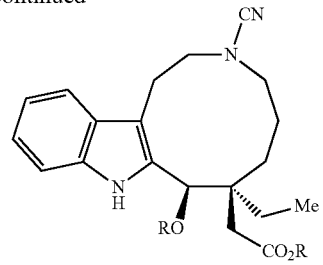

V7, V55, V79

General Procedure for the synthesis of V7, V55, & V79: V58 (44.8 mg, 0.137 mmol) was added to a round-bottom flask and dissolved in (3:1) chloroform:methanol (3.0 mL). To the resulting solution was added a 3M solution of cyanogen bromide (0.137 mL, 0.412 mmol) in dichloromethane at room temperature. The reaction proceeded for 24 hours, upon completion, quenched with brine, extracted with dichloromethane, and the organic layer was dried with sodium sulfate. The organic layer was filtered, concentrated in vacuo, and purified via column chromatography 100% hexanes to 3:1 hexanes:ethyl acetate to afford V55 (33.0 mg, 62%) as a brown residue.

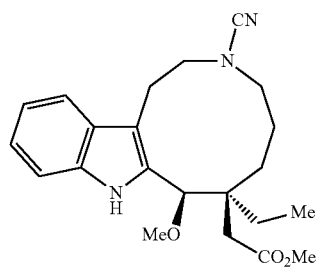

V55

Yield: 62%; 33.0 mg of V55 as brown residue. $^1$H NMR: (400 MHz, CDCl$_3$ at 50° C.) δ 9.86 (s, 1H), 7.49 (d, J=7.9 1H), 7.44 (dt, J=8.1, 0.8 Hz, 1H), 7.22 (ddd, J=7.9, 7.1, 1.1 Hz, 1H), 7.11 (ddd, J=8.0, 7.1, 1.1 Hz, 1H), 4.31 (s, 1H), 3.77 (s, 3H), 3.70-3.54 (m, 2H), 3.23-3.11 (m, 2H), 3.04 (s, 3H), 3.03-2.91 (m, 2H), 2.42 (d, J=13.4 Hz, 1H), 2.32-2.19 (m 2H), 1.66-1.40 (m, 3H), 1.38-1.25 (m, 2H), 1.03 (t, J=7.4 Hz, 3H). $^{13}$C NMR: (100 MHz, CDCl$_3$ at 50° C.) δ 174.6, 136.3, 133.3, 127.4, 122.7, 119.6, 118.2, 112.2, 111.8, 111.4, 81.1, 57.3, 53.6, 53.0, 51.9, 45.8, 38.1, 30.7, 26.8, 26.0, 23.7, 8.2. HRMS (ESI): calc. for C$_{22}$H$_{30}$N$_3$O$_3$ [M+H]$^+$: 384.2282, found: 384.2281.

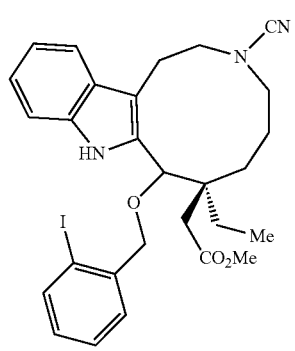

V79

Yield: 37%; 33.0 mg of V79 as a yellow-brown residue. ¹H NMR: (400 MHz, CDCl₃ at 50° C.) δ 10.08 (s, 1H), 7.80 (dd, J=8.2, 1.2 Hz, 1H), 7.52 (d, J=8.0 Hz, 1H), 7.49 (d, J=8.0 Hz, 1H), 7.29 (td, J=7.4, 1.0 Hz, 1H), 7.25-7.19 (m, 2H), 7.14 (ddd, J=7.9, 7.1, 0.9 Hz, 1H), 6.96 (td, J=7.6, 1.5 Hz, 1H), 4.54 (s, 1H), 4.24 (d, J=11.6 Hz, 1H), 4.13 (d, J=11.6 Hz, 1H), 3.79-3.67 (m, 1H), 3.53 (s, 3H), 3.26-3.09 (m, 2H), 2.96 (m, 1H), 2.49-2.36 (m, 2H), 2.32 (d, J=13.3 Hz, 1H), 1.65-1.48 (m, 2H), 1.47-1.40 (m, 2H), 1.39-1.24 (s, 2H), 1.00 (t, J=7.4 Hz, 3H). ¹³C NMR: (100 MHz, CDCl₃ at 50° C.) 174.7, 140.3, 139.6, 136.4, 132.9, 130.4, 129.7, 128.2, 127.4, 122.8, 119.7, 119.6, 118.4, 112.2, 111.9, 99.3, 78.8, 75.2, 53.6, 53.0, 51.8, 46.0, 38.3, 30.7, 26.9, 26.2, 23.7, 8.2. HRMS (ESI): calc. for C₂₈H₃₂IN₃O₃Na [M+Na]⁺: 608.1381, found: 608.1405.

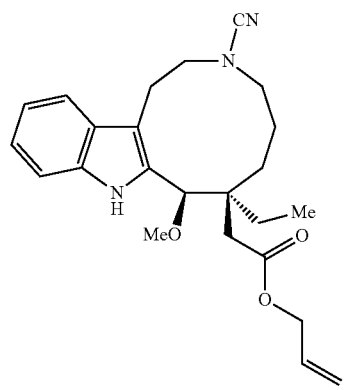

V7

Yield: 37%; 33.0 mg of V7 as a yellow-brown residue. ¹H NMR: (400 MHz, CDCl₃ at 50° C.) δ 9.83 (s, 1H), 7.48 (d, J=8.1 Hz, 1H), 7.42 (d, J=8.3 Hz, 1H), 7.21 (dd, J=7.3 Hz, 1H), 7.11 (ddd, J=8.1, 7.1, 1.0 Hz, 1H), 6.02 (ddd, J=17.4, 10.9, 6.0 Hz, 1H), 5.42 (dd, J=17.4, 1.3 Hz, 1H), 5.31 (d, J=10.4 Hz, 1H), 4.75-4.61 (m, 2H), 4.31 (s, 1H), 3.74-3.53 (m, 2H), 3.22-3.08 (m, 2H), 3.03 (s, 3H), 3.02-2.91 (m, 2H), 2.44 (d, J=13.4 Hz, 1H), 2.34-2.23 (m, 2H), 1.69-1.40 (m, 3H), 1.37-1.22 (m, 2H), 1.04 (t, J=7.4 Hz, 3H). ¹³C NMR: (100 MHz, CDCl₃ at 50° C.) δ 173.5, 136.3, 133.3, 132.5, 127.4, 122.7, 119.7, 119.6, 118.6, 118.3, 112.2, 111.8, 81.3, 65.8, 57.3, 53.6, 53.1, 45.9, 38.2, 30.7, 26.7, 26.0, 23.8, 8.2. HRMS (ESI): calc. for C₂₄H₃₁N₃O₃Na [M+Na]⁺: 432.2258, found: 432.2261.

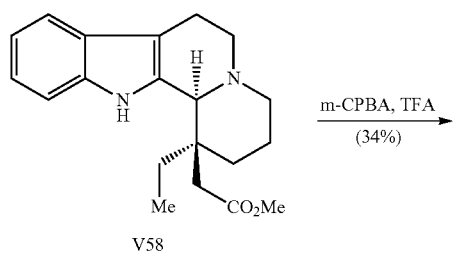

V58

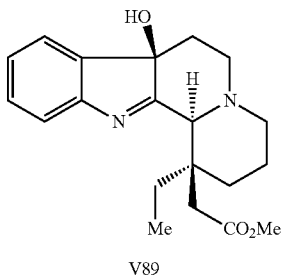

V89

Procedure for the synthesis of V89: V58 (1.180 g, 3.61 mmol) was added to a round-bottom flask and dissolved in anhydrous dichloromethane (132.4 mL). The resulting solution was cooled to −41° C., and trifluoroacetic acid (5.0 mL, 61.5 mmol) was added and stirred for 5 minutes. m-Chloroperbenzoic acid (623.0 mg, 3.61 mmol) was added as a 0.3 M solution in anhydrous dichloromethane (12.0 mL). The reaction stirred for 12 hours at −41° C., upon completion, the reaction was quenched with 3 M aqueous ammonium hydroxide. Crude reaction was extracted with dichloromethane, washed with brine, and dried with sodium sulfate. Crude extract filtered, concentrated in vacuo, and purified via column chromatography using a gradient of 99:1 hexanes:triethylamine to 4.9:0.9:1.0 hexanes:ethyl acetate: triethylamine to afford V89 (294.3 mg, 34%) as a white-crystalline solid. ¹H NMR: (400 MHz, CDCl₃) δ 7.49 (d, J=7.6 Hz, 1H), 7.41 (d, J=7.0 Hz, 1H), 7.31 (dd, J=8.2, 7.0 Hz, 1H), 7.18 (dd, J=8.2, 7.5 Hz, 1H), 4.48 (s, 1H), 3.55 (s, 3H), 3.12 (s, 1H), 3.06-2.97 (m, 2H), 2.88 (d, J=13.5 Hz, 1H), 2.62 (ddd, J=14.4, 9.8, 6.4 Hz, 1H), 2.39 (d, J=13.5 Hz, 1H), 2.27 (ddd, J=12.2, 7.8, 6.4 Hz, 1H), 2.10-1.95 (m, 3H), 1.92 (m, 1H), 1.74 (dq, J=14.6, 7.4 Hz, 1H), 1.63 (m, 1H), 1.60-1.42 (m, 2H), 1.05 (t, J=7.5 Hz, 3H). ¹³C NMR: (100 MHz, CDCl₃) δ 183.8, 173.6, 154.1, 139.9, 129.3, 126.2, 122.3, 121.0, 82.5, 71.5, 55.6, 51.5, 50.8, 40.7, 38.9, 32.2, 31.3, 29.7, 21.4, 8.1. HRMS (ESI): calc. for C₂₀H₂₇N₂O₃ [M+H]⁺: 343.2046, found: 343.2036. MP: 122-124° C.

TABLE 3

| Crystal data and structure refinement for V#. | |
|---|---|
| Identification code | chip4 |
| Empirical formula | C20H26N2O3 |
| Formula weight | 342.43 |
| Temperature | 100(2) K |
| Wavelength | 1.54178 Å |
| Crystal system | Orthorhombic |
| Space group | P2₁2₁2₁ |
| Unit cell dimensions | a = 11.3809(3) Å   α = 90°. |
| | b = 11.7902(3) Å   β = 90°. |
| | c = 12.9504(4) Å   γ = 90°. |
| Volume | 1737.72(8) Å³ |
| Z | 4 |
| Density (calculated) | 1.309 Mg/m³ |
| Absorption coefficient | 0.707 mm⁻¹ |
| F(000) | 736 |
| Crystal size | 0.221 × 0.166 × 0.126 mm³ |
| Theta range for data collection | 5.073 to 66.480°. |
| Index ranges | −13 ≤ h ≤ 12, −13 ≤ k ≤ 14, −15 ≤ l ≤ 15 |
| Reflections collected | 14635 |
| Independent reflections | 3042 [R(int) = 0.0149] |
| Completeness to theta = 66.480° | 99.9% |
| Absorption correction | Empirical |
| Max. and min. transmission | 0.9398 and 0.8883 |

TABLE 3-continued

Crystal data and structure refinement for V#.

| | |
|---|---|
| Refinement method | Full-matrix least-squares on $F^2$ |
| Data/restraints/parameters | 3042/0/231 |
| Goodness-of-fit on $F^2$ | 1.088 |
| Final R indices [I > 2sigma(I)] | R1 = 0.0254, wR2 = 0.0642 [3015] |
| R indices (all data) | R1 = 0.0256, wR2 = 0.0644 |
| Absolute structure parameter | 0.02(3) |
| Largest diff. peak and hole | 0.160 and −0.157 e · Å$^{-3}$ |

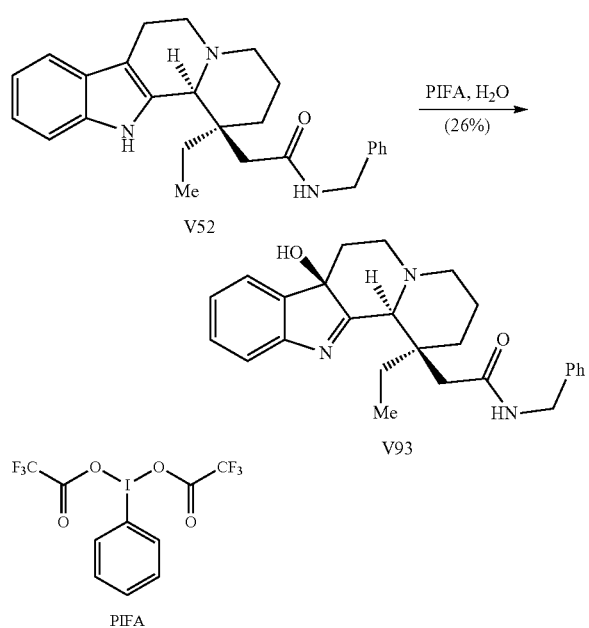

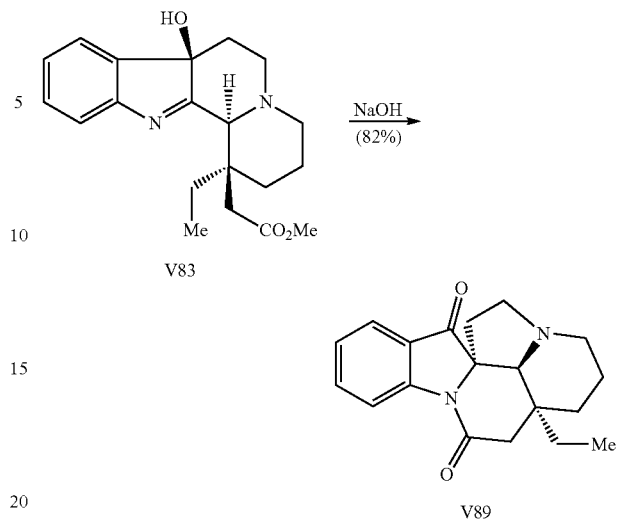

Procedure for the synthesis of V93: V52 (403.0 mg, 1.00 mmol) was added to a round-bottom flask and dissolved in a acetonitrile:water solution (2:1) (30.0 mL). The resulting solution was cooled to 0° C., and a 0.3 M solution of PIFA in acetonitrile was added slowly over 5 minutes. The reaction stirred for 3 hours at 0° C., upon completion, the reaction was quenched with cold saturated aqueous sodium bicarbonate. Crude reaction was extracted with dichloromethane, washed with brine, and the organic layer was dried with sodium sulfate. The organic layer was filtered, concentrated in vacuo, and purified via column chromatography using a gradient of 100% hexanes to 1:1 hexanes:ethyl acetate with 1% triethylamine throughout to afford V93 (108.7 mg, 26%) as a brown residue. $^1$H NMR: (400 MHz, CDCl$_3$) δ 7.48 (d, J=7.7 Hz, 1H), 7.40 (d, J=7.3 Hz, 1H), 7.31 (td, J=7.6, 1.3 Hz, 1H), 7.25-7.15 (m, 4H), 7.13-7.09 (m, 2H), 6.23 (t, J=5.6 Hz, 1H), 5.09 (s, 1H), 4.32 (dd, J=14.7, 5.6 Hz, 1H), 3.86 (dd, J=14.7, 5.6 Hz, 1H), 3.10 (s, 1H), 3.06-2.97 (m, 3H), 2.70-2.54 (m, 2H), 2.40 (d, J=13.7 Hz, 1H), 2.28 (ddd, J=12.2, 7.8, 2.2 Hz, 1H), 2.10-1.96 (m, 2H), 1.96-1.80 (m, 2H), 1.67-1.40 (m, 3H), 1.08 (t, J=7.4 Hz, 3H). $^{13}$C NMR: (100 MHz, CDCl$_3$) δ 184.1, 171.9, 154.1, 139.9, 138.3, 129.3, 128.7, 128.0, 127.4, 126.2, 122.3, 121.0, 82.6, 72.0, 55.7, 50.9, 43.6, 41.0, 40.8, 32.9, 32.2, 29.9, 21.4, 8.3. HRMS (ESI): calc. for C$_{26}$H$_{32}$N$_3$O$_2$ [M+H]$^+$: 418.2489, found: 418.2484.

Procedure for the synthesis of V83: V89 (12.9 mg, 0.038 mmol) was added to a round-bottom flask and dissolved in methanol (1.5 mL). Sodium hydroxide (8.0 mg, 0.19 mmol) was added and the reaction was heated to 64° C. after being equipped with a reflux condenser. The reaction was quenched with brine, extracted with chloroform, and the organic layer was dried with sodium sulfate. The organic layer was filtered, concentrated in vacuo, and purified via column chromatography 100% hexanes to 3:1 hexanes:ethyl acetate with 1% triethylamine throughout to afford V83 (9.7 mg, 82%) as a white-brown solid. $^1$H NMR: (400 MHz, CDCl$_3$) δ 8.29 (d, J=8.2 Hz, 1H), 7.75 (d, J=7.7 Hz, 1H), 7.66 (td, J=7.8, 1.4 Hz, 1H), 7.24 (dd, J=7.8, 7.5 Hz, 1H), 3.44 (d, J=15.6 Hz, 1H), 3.11 (m, 1H), 3.03 (dd, J=8.8, 7.4 Hz, 1H), 2.53 (s, 1H), 2.49 (m, 1H), 2.30 (td, J=11.4, 3.1 Hz, 1H), 2.17 (dd, J=12.4, 5.5 Hz, 1H), 2.11 (dd, J=15.6, 2.1 Hz, 1H), 1.95 (td, J=11.3, 7.8 Hz, 1H), 1.79-1.67 (m, 2H), 1.61 (m, 1H), 1.21 (m, 1H), 0.91 (m, 1H), 0.78-0.69 (m, 4H). $^{13}$C NMR: (100 MHz, CDCl$_3$) δ 200.9, 170.9, 152.3, 136.9, 125.0, 124.5, 122.7, 119.9, 75.5, 68.8, 51.6, 51.0, 40.9, 38.4, 38.3, 32.3, 30.1, 22.3, 7.1. HRMS (ESI): calc. for C$_{19}$H$_{23}$N$_2$O$_2$ [M+H]$^+$: 311.1754, found: 311.1756. MP: 115-117° C.

Example 2. Biological Assays

Biological Methods
ARE Luciferase Assay in LNCaP and MDA-MB-231-ARE-Luc Cells

The antioxidant response element (ARE) expression induction assay with LNCaP cells was performed as previously described.[10] The ARE expression inhibition assay was performed with MDA-MB-231-ARE-Luc cells that stably express the ARE reporter construct.[11] MDA-MB-231-ARE-Luc cells were seeded in 96 well plates at 1.5×10$^4$ cells/well in DMEM medium (GIBCO) containing 10% FCS and 1% antibiotic-antimycotic (GIBCO), and allowed to attach overnight. Test compounds were screened in triplicate at three concentrations (100, 10 and 1 μM) and ARE expression was quantified on the EnVision plate reader (Perkin-Elmer) using the BriteLite plus luciferase reporter assay system (Perkin-Elmer) after 24 h exposure in a humidified incubator at 37° C. with 5% CO$_2$. In both cell line assays the luciferase expression for compound-treated wells was expressed relative the 0.5% DMSO carrier solvent control. A parallel viability assay was performed with the Cell Titer 96 Non-radioactive Cell Proliferation Assay (Promega) and the data expressed in the same manner as above. Compounds that inhibited ARE expression 20% more than viability, or induced ARE expression more than three-fold were re-tested in a seven-point, two-fold serial dilution dose-response assay (100-1.56 µM). Compounds that displayed activity comparable to the primary screen were assessed for their effect on the expression of Nqo1 by RT-qPCR.

RT-qPCR Validation

In order to validate the ARE modulatory effects of compounds from the primary screen, the expression of the target Nrf2 target gene, Nqo1, was quantified by RT-PCR. LNCaP and MDA-MB-231-ARE-Luc cells were seeded in 6 well plates at 5×10$^5$ and 7×10$^5$ cells per well, in EMEM and DMEM media containing 10% FCS and 1% antibiotic-antimycotic (GIBCO) respectively. Cells were allowed to attach overnight before the addition of test compounds. After 24 h exposure in a humidified incubator at 37° C. with 5% CO$_2$, RNA was isolated using the RNeasy kit (Qiagen) and quantified using a NanoDrop spectrophotometer (Thermo Fisher Scientific). cDNA was synthesized from 2 µg of RNA using Oligo(dT)12-18 (Life Technologies) primer and SuperScript II (Thermo Fisher Scientific) on the Mastercycler Gradient PCR machine (Eppendorf) for 1 h at 42° C. following a 10 min denaturation at 65° C. Gene expression was quantified on the 7300 Real Time PCR machine (Applied Biosystems) using TaqMan Gene Expression Master Mix (Thermo Fisher Scientific) and probes for the target gene Nqo1 (Hs02512143_s1, Thermo Fisher Scientific) and reference gene ActB (Hs99999903_m1, Thermo Fisher Scientific). Real time PCR was performed with the following thermal cycle: 1. 50° C. for 2 min; 2. 95° C. for 10 min; 3. 40 cycles of 95° C. for 15 sec followed by 60° C. for 1 min.

REFERENCES

1. Lancefield et al., *Org. Lett.* 2012, 14, 6166-6169.
2. Moldvai et al., *Synthetic Comm.* 1991, 21, 965-967.
3. Voskressensky et al., *Russ. Chem. Bull.* 2012, 61, 1231-1241.
4. Ma et al., *J. Mol. Struct.* 2015, 1097, 87-97.
5. Nemes et al., *Heterocycles* 2007, 71, 2347-2362.
6. Honty et al., *Tetrahedron*, 1993, 49, 10421-10426.
7. Goh et al., *Tetrahedron*, 1989, 45, 7899-7920.
8. Kalaus et al., *Heterocycles* 1988, 27, 1179-1190.
9. Hu et al., *J. Org. Chem.* 2012, 77, 5198-5202.
10. Ratnayake et al., *Cancer Prev. Res.* 2013, 6, 989-999.
11. Du et al., *Environ. Health Perspect.* 2008, 116, 1154-1161.

What is claimed is:

1. A compound of Formula (VII):

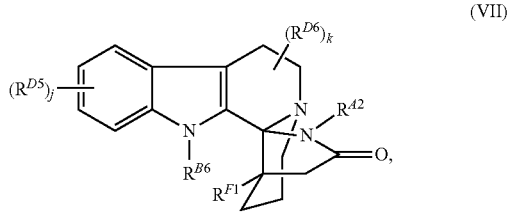

(VII)

or a pharmaceutically acceptable salt thereof, wherein:

$R^{A2}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^{B6}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^{D5}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of $R^{D6}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

$R^{F1}$ is hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^a$, —N(R$^b$)$_2$, or —SR$^a$;

each instance of R$^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of R$^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R$^b$ are joined together with the intervening atoms to form optionally substituted heterocyclyl or optionally substituted heteroaryl;

j is 1, 2, 3, or 4; and k is 1, 2, 3, or 4.

2. The compound of claim 1, wherein $R^{A2}$ is optionally substituted C$_{1-6}$ alkyl, optionally substituted alkynyl, optionally substituted carbocyclyl, or optionally substituted aryl.

3. The compound of claim 2, wherein $R^{A2}$ is n-butyl.

4. The compound of claim 2, wherein $R^{A2}$ is of the formula:

—(CH$_2$)$_x$R$^{A2b}$, wherein:

x is 1, 2, 3, or 4; and $R^{A2b}$ is optionally substituted alkynyl, optionally substituted carbocyclyl, of optionally substituted aryl, or optionally substituted heteroaryl.

5. The compound of claim 2, wherein $R^{A2}$ is of the formula:

[chemical structures]

, , ,

, or .

6. The compound of claim 1, wherein $R^{F1}$ is optionally substituted $C_{1-6}$ alkyl.

7. The compound of claim 6, wherein $R^{F1}$ is ethyl.

8. The compound of claim 1, wherein j is 1 and k is 1.

9. The compound of claim 1, wherein $R^{D5}$ and $R^{D6}$ are both hydrogen.

10. The compound of claim 2, wherein $R^2$ is optionally substituted 3- to 7-membered, monocyclic carbocyclyl comprising zero double bonds in the carbocyclic ring system.

11. The compound of claim 2, wherein $R^{A2}$ is optionally substituted alkynyl.

12. The compound of claim 1, wherein $R^{F1}$ is optionally substituted alkyl.

13. The compound of claim 1, wherein $R^{B6}$ is hydrogen.

14. The compound of claim 1, wherein $R^{A2}$ is optionally substituted 6- to 10-membered aryl.

15. The compound of claim 1, wherein $R^{A2}$ is optionally substituted $C_{2-6}$ alkynyl.

16. The compound of claim 1, wherein $R^{A2}$ is optionally substituted $C_{1-6}$ alkyl.

17. The compound of claim 1, wherein $R^{A2}$ is of the formula:

[chemical structure]

.

18. The compound of claim 1, wherein the compound is of formula:

[chemical structures continuing]

or a pharmaceutically acceptable salt thereof.

19. A pharmaceutical composition comprising a compound of claim 1, or a pharmaceutically acceptable salt thereof, and optionally a pharmaceutically acceptable excipient.

20. A method of treating a proliferative disease, a metabolic disorder, drug addiction, or an infectious disease in a subject in need thereof, the method comprising administering to the subject an effective amount of a compound of claim 1, or a pharmaceutically acceptable salt thereof.

21. The method of claim 20, wherein the method is for treating a proliferative disease.

22. The method of claim 20, wherein the drug addiction is addiction to an opioid.

23. The method of claim 20, wherein the method is for treating a metabolic disorder.

24. The method of claim 20, wherein the method is for treating a drug addiction.

25. The method of claim 20, wherein the method is for treating an infectious disease.

\* \* \* \* \*

UNITED STATES PATENT AND TRADEMARK OFFICE
CERTIFICATE OF CORRECTION

PATENT NO. : 11,130,764 B2
APPLICATION NO. : 16/486814
DATED : September 28, 2021
INVENTOR(S) : Huigens, III et al.

Page 1 of 1

It is certified that error appears in the above-identified patent and that said Letters Patent is hereby corrected as shown below:

In the Claims

In Claim 4, at Column 218, Lines 65-67, the text: "$R^{A2b}$ is optionally substituted alkynyl, optionally substituted carbocyclyl, of optionally substituted aryl, or optionally substituted heteroaryl." should be replaced with: --$R^{A2b}$ is optionally substituted alkynyl, optionally substituted carbocyclyl, optionally substituted aryl, or optionally substituted heteroaryl.--

Signed and Sealed this
Seventh Day of December, 2021

Drew Hirshfeld
*Performing the Functions and Duties of the
Under Secretary of Commerce for Intellectual Property and
Director of the United States Patent and Trademark Office*